(12) United States Patent
Yao et al.

(10) Patent No.: US 7,998,733 B2
(45) Date of Patent: Aug. 16, 2011

(54) CHIMERIC VECTORS

(75) Inventors: Jiansheng Yao, North York (CA);
Sheena May Loosmore, Aurora (CA);
Jean-Christophe Francis Audonnet,
Lyons (FR)

(73) Assignee: Merial Limited, Duluth, GA (US)

( * ) Notice: Subject to any disclaimer, the term of this patent is extended or adjusted under 35 U.S.C. 154(b) by 1120 days.

(21) Appl. No.: 10/958,267

(22) Filed: Oct. 5, 2004

(65) Prior Publication Data
US 2006/0073594 A1  Apr. 6, 2006

(51) Int. Cl.
*C12N 15/63* (2006.01)
*C12N 15/11* (2006.01)
*C07K 14/00* (2006.01)

(52) U.S. Cl. ............. 435/320.1; 530/350; 536/23.1
(58) Field of Classification Search .......... None
See application file for complete search history.

(56) References Cited

U.S. PATENT DOCUMENTS

| 5,174,993 | A  | * | 12/1992 | Paoletti ............... 424/199.1 |
| 5,833,975 | A  | * | 11/1998 | Paoletti et al. .......... 424/93.2 |
| 7,034,141 | B2 | * | 4/2006  | Kovacs et al. .......... 536/23.72 |
| 7,045,335 | B2 | * | 5/2006  | Smith et al. ........... 435/235.1 |
| 2004/0110295 | A1 | * | 6/2004 | Punnonen et al. ........ 435/455 |

OTHER PUBLICATIONS

Sawicki et al. A second nonstructural protein functions in the regulation of alphavirus negative-strand RNA synthesis. J Virol. Jun. 1993;67(6):3605-10.*

* cited by examiner

*Primary Examiner* — Michele K Joike
(74) *Attorney, Agent, or Firm* — Judy Jarecki-Black; Ruoying Chen; Merial Limited

(57) ABSTRACT

The present invention relates to chimeric vectors. More specifically, the invention relates to recombinant poxvirus vectors and viruses that are capable of expressing an alphaviral RNA replicon expressing a heterologous sequence of interest.

28 Claims, 89 Drawing Sheets

FIG. 1.
A schematic illustration of an ALVAC-SFV chimera

ALVAC and C6 locus

SFV replicon

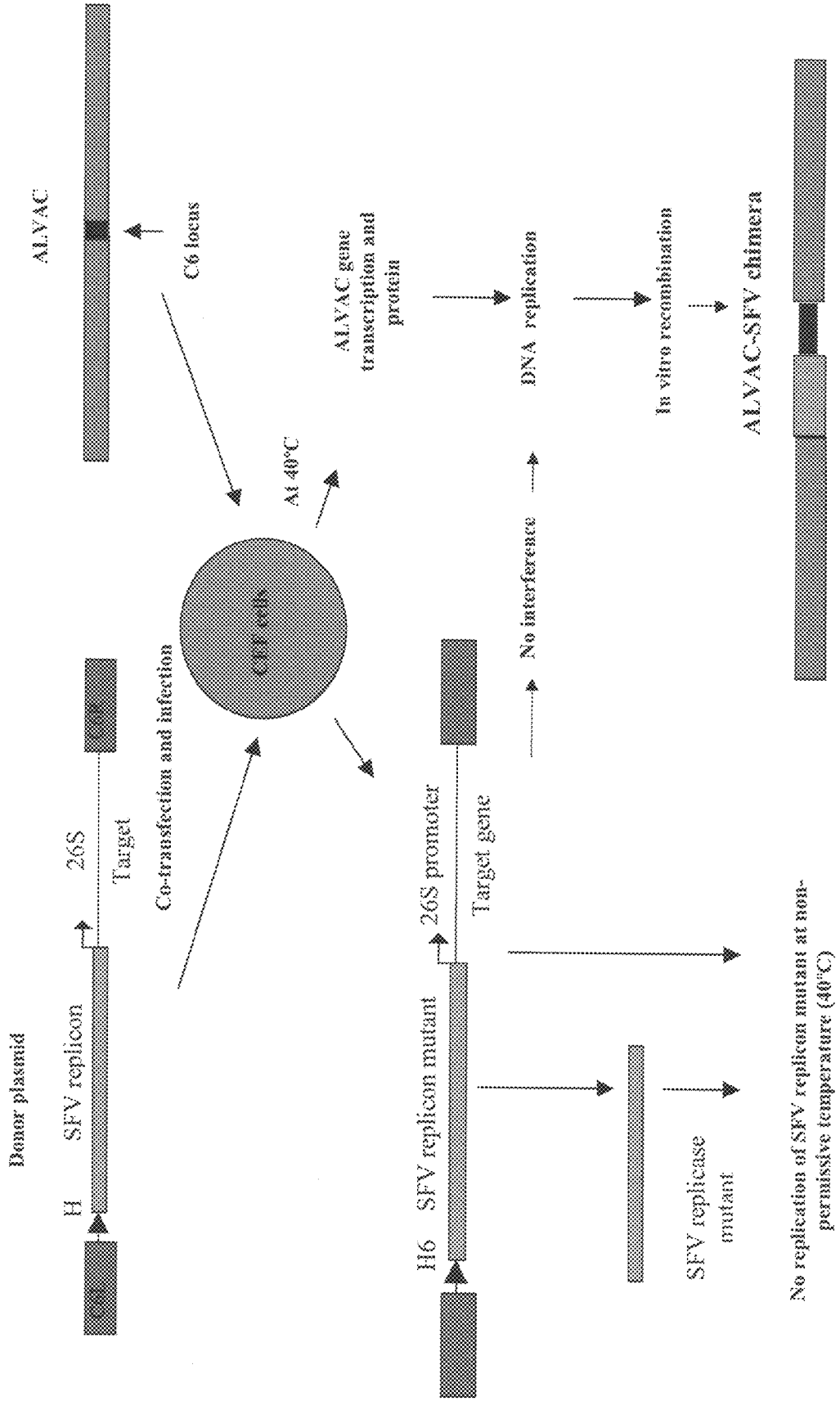
FIG. 4. A schematic illustration of the ALVAC-SFV chimera generation

FIG. 5A.
Construction of SFV nsP2 Leu 713Ala mutant

FIG. 5B.
Construction of SFV nsP2 Leu 713 Ala mutant

FIG. 6.
SFV nsP2 mutant GFP expression in BHK-21 cells (western blot)

GFP-Blasticidin⇒

1. BHK-21 mock transfection.
2. SFV-Leu713Ala/GFP-Blasticidin
3. SFV-Leu713Arg/GFP-Blasticidin
4. SFV-Leu713Phe/GFP-Blasticidin
5. SFV-Leu713Thr/GFP-Blasticidin
6. SFV-Leu713Gln/GFP-Blasticidin
7. SFV wild type/GFP-Blasticidin SFV nsP2 mutant GFP expression in BHK-21 cells at 37C and 40C (western blot)

8. BHK-21 mock transfection.
9. SFV-Leu713Ala/GFP-Blasticidin
10. SFV-Leu713Thr/GFP-Blasticidin
11. SFV wild type/GFP-Blasticidin
12. No loading
13. SFV-Leu713Ala/GFP-Blasticidin
14. SFV-Leu713Thr/GFP-Blasticidin
15. SFV wild type/GFP-Blasticidin

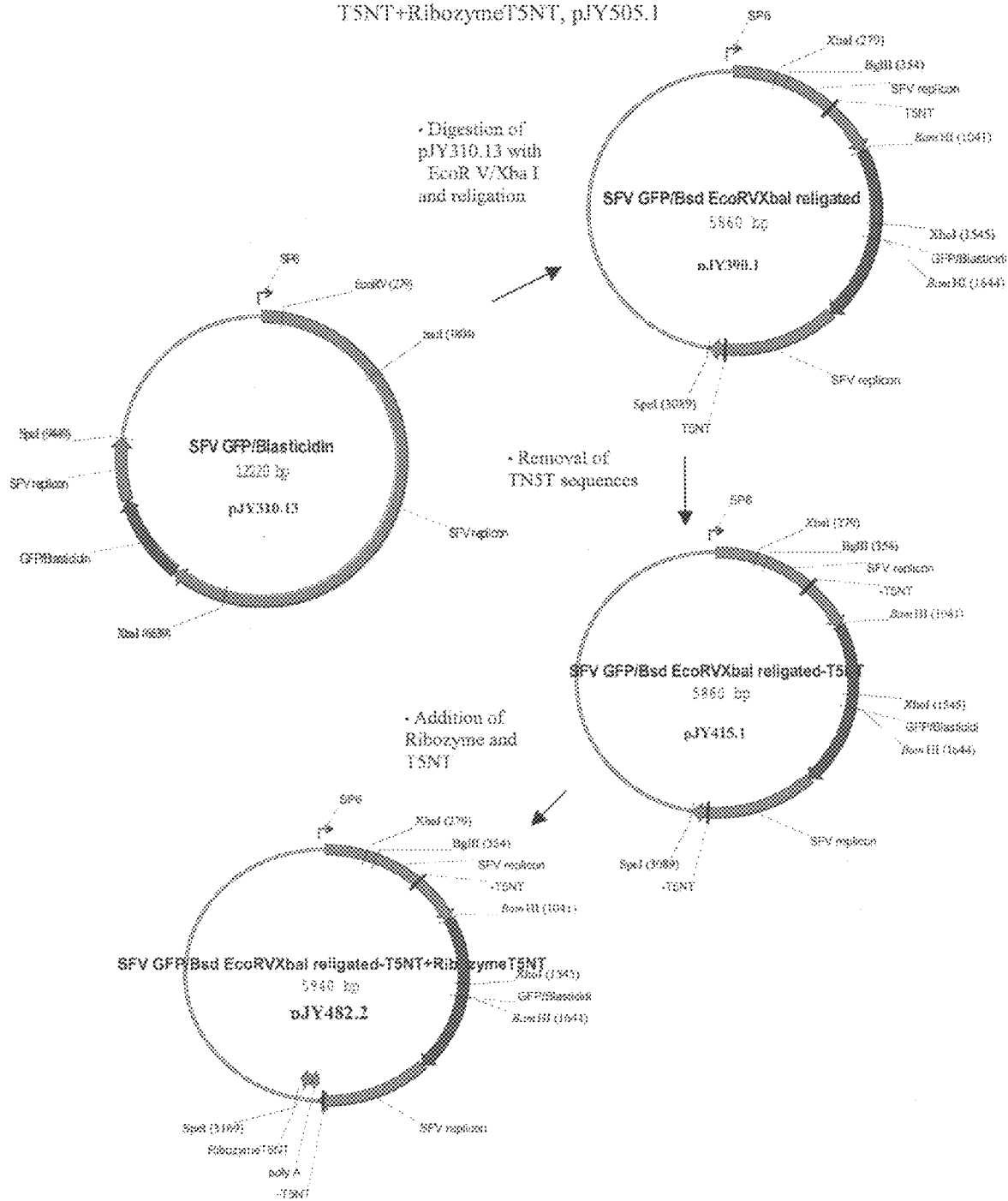

Construction of C6 donor plasmid containing SFV GFP/Bsd Leu713Ala-T5NT+RibozymeT5NT, pJY505.1

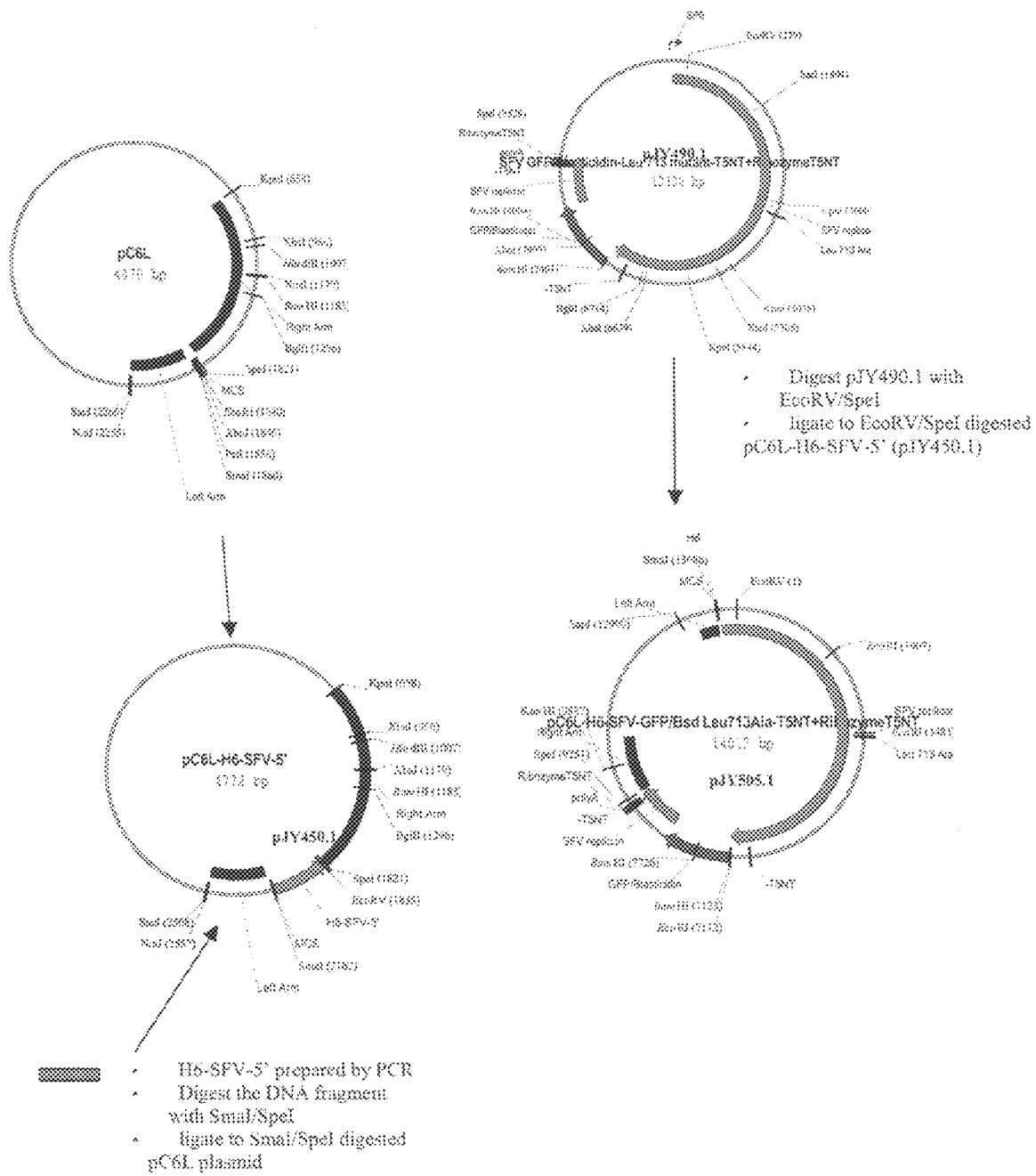

pC6L-H6-SFV-Leu713Ala-GFP/Blasticidin

FIG. 10A.
Nucleotide sequence and translation of C6-H6-SFV Leu713Ala GFP/Blasticidin

```
        NotI
        ---------C6 Left arm =>
   1    GCGGCCGCCTAT CAAAAGTCTTAA TGAGTTAGGTGT AGATAGTATAGA TATTACTACAAA
        CGCCGGCGGATA GTTTTCAGAATT ACTCAATCCACA TCTATCATATCT ATAATGATGTTT
  61    GGTATTCATATT TTCTATCAATTC TAAAGTAGATGA TATTAATAACTC AAAGATGATGAT
        CCATAAGTATAA AGATAGTTAAG ATTTCATCTACT ATAATTATTGAG TTTCTACTACTA
 121    AGTAGATAATAG ATACGCTCATAT AATGACTGCAAA TTTGGACGGTTC ACATTTAATCA
        TCATCTATTATC TATGCGAGTATA TTACTGACGTTT AAACCTGCCAAG TGTAAATTAGT
 181    TCACGCGTTCAT AAGTTTCAACTG CATAGATCAAAA TCTCACTAAAAA GATAGCCGATGT
        AGTGCGCAAGTA TTCAAAGTTGAC GTATCTAGTTTT AGAGTGATTTTT CTATCGGCTACA
 241    ATTGAGAGAGA TTGGACATCTAA CTACGCTAAAGA AATTACAGTTAT AAATAATACATA
        TAACTCTCTCT AACCTGTAGATT GATGCGATTTCT TTAATGTCAATA TTTATTATGTAT
 301    ATGGATTTGTT ATCATCAGTTAT ATTAACATAAG TACAATAAAAG TATTAAATAAAA
        TACCTAAACAA TAGTAGTCAATA TAATTGTATTC ATGTTATTTTC ATAATTTATTTT
                                                    SmaI
                                                    --------H6=>
 361    ATACTTACTTAC GAAAAAATGACT AATAGCTATAA AAACCCGGGTTT TTTATTCATAC
        TATGAATGAATG CTTTTTTACTGA TTAATCGATATT TTTGGGCCCAAA AAATAAGTATG
                                   SFV=>
 421    TTAAAAGTGAA AATAATACAAA GGTCTTGATG CGATGTGTCAC ATACACGACGCC
        AATTTTCACTT TTATTATGTTT CCAGAACTACC GCTACACACTG TATGTGCTGCGG
                                                                        M
 481    AAAAGATTTGT TCCAGCTCCTGC CACCTCCGCTAC GCGAGAGATTAA CCACCCACGATG
        TTTTCTAAACA AGGTCGAGGACG GTGGAGGCGATG CGCTCTCTAATT GGTGGGTGCTAC
         A   A   K   V   H   V   D   I   E   A   D   S   P   P   I   K   S   L   Q   K
 541    GCCGCCAAAGTG CATGTTGATATT GAGGCTGACAGC CCATTCATCAAG TCTTTGCAGAAG
        CGGCGGTTTCAC GTACAACTATAA CTCCGACTGTCG GGTAAGTAGTTC AGAAACGTCTTC
         A   F   P   S   F   E   V   E   S   L   Q   V   T   P   N   D   H   A   N   A
 601    GCATTCCGTCG TTCGAGGTGGAG TCATTGCAGGTC ACACCAAATGAC CATGCAAATGCC
        CGTAAGGCAGC AAGCTCCACCTC AGTAACGTCCAG TGTGGTTTACTG GTACGTTTACGG
         R   A   F   S   H   L   A   T   K   L   I   E   Q   E   T   D   K   D   T   L
 661    AGAGCATTTTCG CACCTGGCTACC AAATTGATCGAG CAGGAGACTGAC AAAGACACACTC
        TCTCGTAAAAGC GTGGACCGATGG TTTAACTAGCTC GTCCTCTGACTG TTTCTGTGTGAG
         I   L   D   I   G   S   A   P   S   R   R   M   M   S   T   H   K   Y   H   C
 721    ATCTTGGATATC GGCAGTGCGCCT TCCAGGAGAATG ATGTCTACGCAC AAATACCACTGC
        TAGAACCTATAG CCGTCACGCGGA AGGTCCTCTTAC TACAGATGCGTG TTTATGGTGACG
         V   C   P   M   R   S   A   E   D   P   E   R   L   D   S   Y   A   K   K   L
 781    GTATGCCCTATG CGCAGCGCAGAA GACCCCGAAAGG CTCGATAGCTAC GCAAAGAAACTG
        CATACGGGATAC GCGTCGCGTCTT CTGGGGCTTTCC GAGCTATCGATG CGTTTCTTTGAC
         A   A   A   S   G   K   V   L   D   R   E   I   A   G   K   I   T   D   L   Q
 841    GCAGCGGCCTCC GGGAAGGTGCTG GATAGAGAGATC GCAGGAAAAATC ACCGACCTGCAG
        CGTCGCCGGAGG CCCTTCCACGAC CTATCTCTCTAG CGTCCTTTTTAG TGGCTGGACGTC
         T   V   M   A   T   P   D   A   E   S   P   T   F   C   L   H   T   D   V   T
 901    ACCGTCATGGCT ACGCCAGACGCT GAATCTCCTACC TTTTGCCTGCAT ACAGACGTCACG
        TGGCAGTACCGA TGCGGTCTGCGA CTTAGAGGATGG AAAACGGACGTA TGTCTGCAGTGC
         C   R   T   A   A   E   V   A   V   Y   Q   D   V   Y   A   V   H   A   P   T
 961    TGTCGTACGGCA GCCGAAGTGGCC GTATACCAGGAC GTGTATGCTGTA CATGCACCAACA
        ACAGCATGCCGT CGGCTTCACCGG CATATGGTCCTG CACATACGACAT GTACGTGGTTGT
         S   L   Y   H   Q   A   M   K   G   V   R   T   A   Y   W   I   G   F   D   T
1021    TCGCTGTACCAT CAGGCGATGAAA GGTGTCAGAACG GCGTATTGGATT GGGTTTGACACC
        AGCGACATGGTA GTCCGCTACTTT CCACAGTCTTGC CGCATAACCTAA CCCAAACTGTGG
         T   P   F   M   F   D   A   L   A   G   A   Y   P   T   Y   A   T   N   W   A
1081    ACCCCGTTTATG TTTGACGCGCTA GCAGGCGCGTAT CCAACCTACGCC ACAAACTGGGCC
```

FIG. 10B.

```
            TGGGGCAAATAC AAACTGCGCGAT CGTCCGCGCATA GGTTGGATGCGG TGTTTGACCCGG
             D  E  Q  V   L  Q  A  R    N  I  G  L    C  A  A  S   L  T  E  G
1141  GACGAGCAGGTG TTACAGGCCAGG AACATAGGACTG TGTGCAGCATCC TTGACTGAGGGA
      CTGCTCGTCCAC AATGTCCGGTCC TTGTATCCTGAC ACACGTCGTAGG AACTGACTCCCT
       R  L  G  K   L  S  I  L    R  K  K  Q    L  K  P  C   D  T  V  M
1201  AGACTCGGCAAA CTGTCCATTCTC CGCAAGAAGCAA TTGAAACCTTGC GACACAGTCATG
      TCTGAGCCGTTT GACAGGTAAGAG GCGTTCTTCGTT AACTTTGGAACG CTGTGTCAGTAC
       F  S  V  G   S  T  L  Y    T  E  S  R    K  L  L  R   S  W  H  L
1261  TTCTCGGTAGGA TCTACATTGTAC ACTGAGAGCAGA AAGCTACTGAGG AGCTGGCACTTA
      AAGAGCCATCCT AGATGTAACATG TGACTCTCGTCT TTCGATGACTCC TCGACCGTGAAT
       P  S  V  F   H  L  K  G    K  Q  S  F    T  C  R  C   D  T  I  V
1321  CCCTCCGTATTC CACCTGAAAGGT AAACAATCCTTT ACCTGTAGGTGC GATACCATCGTA
      GGGAGGCATAAG GTGGACTTTCCA TTTGTTAGGAAA TGGACATCCACG CTATGGTAGCAT
       S  C  E  G   Y  V  V  K    K  I  T  M    C  P  G  L   Y  G  K  T
1381  TCATGTGAAGGG TACGTAGTTAAG AAAATCACTATG TGCCCCGGCCTG TACGGTAAAACG
      AGTACACTTCCC ATGCATCAATTC TTTTAGTGATAC ACGGGGCCGGAC ATGCCATTTTGC
       V  G  Y  A   V  T  Y  H    A  E  G  F    L  V  C  K   T  T  D  T
1441  GTAGGGTACGCC GTGACGTATCAC GCGGAGGGATTC CTAGTGTGCAAG ACCACAGACACT
      CATCCCATGCGG CACTGCATAGTG CGCCTCCCTAAG GATCACACGTTC TGGTGTCTGTGA
       V  K  G  E   R  V  S  F    P  V  C  T    Y  V  P  S   T  I  C  D
1501  GTCAAAGGAGAA AGAGTCTCATTC CCTGTATGCACC TACGTCCCCTCA ACCATCTGTGAT
      CAGTTTCCTCTT TCTCAGAGTAAG GGACATACGTGG ATGCAGGGGAGT TGGTAGACACTA
       Q  M  T  G   I  L  A  T    D  V  T  P    E  D  A  Q   K  L  L  V
1561  CAAATGACTGGC ATACTAGCGACC GACGTCACACCG GAGGACGCACAG AAGTTGTTAGTG
      GTTTACTGACCG TATGATCGCTGG CTGCAGTGTGGC CTCCTGCGTGTC TTCAACAATCAC
       G  L  N  Q   R  I  V  V    N  G  R  T    Q  R  N  T   N  T  M  K
1621  GGATTGAATCAG AGGATAGTTGTG AACGGAAGAACA CAGCGAAACACT AACACGATGAAG
      CCTAACTTAGTC TCCTATCAACAC TTGCCTTCTTGT GTCGCTTTGTGA TTGTGCTACTTC
       N  Y  L  L   P  I  V  A    V  A  F  S    K  W  A  R   E  Y  K  A
1681  AACTATCTGCTT CCGATTGTGGCC GTCGCATTTAGC AAGTGGGCGAGG GAATACAAGGCA
      TTGATAGACGAA GGCTAACACCGG CAGCGTAAATCG TTCACCCGCTCC CTTATGTTCCGT
       D  L  D  D   E  K  P  L    G  V  R  E    R  S  L  T   C  C  C  L
1741  GACCTTGATGAT GAAAAACCTCTG GGTGTCCGAGAG AGGTCACTTACT TGCTGCTGCTTG
      CTGGAACTACTA CTTTTTGGAGAC CCACAGGCTCTC TCCAGTGAATGA ACGACGACGAAC
       W  A  F  K   T  R  K  M    H  T  M  Y    K  K  P  D   T  Q  T  I
1801  TGGGCATTTAAA ACGAGGAAGATG CACACCATGTAC AAGAAACCAGAC ACCCAGACAATA
      ACCCGTAAATTT TGCTCCTTCTAC GTGTGGTACATG TTCTTTGGTCTG TGGGTCTGTTAT
       V  K  V  P   S  E  F  N    S  F  V  I    P  S  L  W   S  T  G  L
1861  GTGAAGGTGCCT TCAGAGTTTAAC TCGTTCGTCATC CCGAGCCTATGG TCTACAGGCCTC
      CACTTCCACGGA AGTCTCAAATTG AGCAAGCAGTAG GGCTCGGATACC AGATGTCCGGAG
       A  I  P  V   R  S  R  I    K  M  L  L    A  K  K  T   K  R  E  L
1921  GCAATCCCAGTC AGATCACGCATT AAGATGCTTTTG GCCAAGAAGACC AAGCGAGAGTTA
      CGTTAGGGTCAG TCTAGTGCGTAA TTCTACGAAAAC CGGTTCTTCTGG TTCGCTCTCAAT
       I  P  V  L   D  A  S  S    A  R  D  A    E  Q  E  E   K  E  R  L
1981  ATACCTGTTCTC GACGCGTCGTCA GCCAGGGATGCT GAACAAGAGGAG AAGGAGAGGTTG
      TATGGACAAGAG CTGCGCAGCAGT CGGTCCCTACGA CTTGTTCTCCTC TTCCTCTCCAAC
       E  A  E  L   T  R  E  A    L  P  P  L    V  P  I  A   P  A  E  T
2041  GAGGCCGAGCTG ACTAGAGAAGCC TTACCACCCCTC GTCCCATCGCG CCGGCGGAGACG
      CTCCGGCTCGAC TGATCTCTTCGG AATGGTGGGGAG CAGGGGTAGCGC GGCCGCCTCTGC
       G  V  V  D   V  D  V  E    E  L  E  Y    H  A  G  A   G  V  V  E
2101  GGAGTCGTCGAC GTCGACGTTGAA GAACTAGAGTAT CACGCAGGTGCA GGGGTCGTGGAA
      CCTCAGCAGCTG CAGCTGCAACTT CTTGATCTCATA GTGCGTCCACGT CCCCAGCACCTT
       T  P  R  S   A  L  K  V    T  A  Q  P    N  D  V  L   L  G  N  Y
2161  ACACCTCGCAGC GCGTTGAAAGTC ACCGCACAGCCG AACGACGTACTA CTAGGAAATTAC
      TGTGGAGCGTCG CGCAACTTTCAG TGGCGTGTCGGC TTGCTGCATGAT GATCCTTTAATG
       V  V  L  S   P  Q  T  V    L  K  S  S    K  L  A  P   V  H  P  L
2221  GTAGTTCTGTCC CCGCAGACCGTG CTCAAGAGCTCC AAGTTGGCCCCC GTGCACCCTCTA
      CATCAAGACAGG GGCGTCTGGCAC GAGTTCTCGAGG TTCAACCGGGGG CACGTGGGAGAT
       A  E  Q  V   K  I  I  T    H  N  G  R    A  G  G  Y   Q  V  D  G
2281  GCAGAGCAGGTG AAAATAATAACA CATAACGGGAGG GCCGGCGGTTAC CAGGTCGACGGA
      CGTCTCGTCCAC TTTTATTATTGT GTATTGCCCTCC CGGCCGCCAATG GTCCAGCTGCCT
```

FIG. 10C.

```
           Y  D  G  R     V  L  L  P     C  G  S  A     I  P  V  P     E  F  Q  A
2341   TATGACGGCAGG GTCCTACTACCA TGTGGATCGGCC ATTCCGGTCCCT GAGTTTCAAGCT
       ATACTGCCGTCC CAGGATGATGGT ACACCTAGCCGG TAAGGCCAGGGA CTCAAAGTTCGA
           L  S  E  S     A  T  M  V     Y  N  E  R     E  F  V  N     R  K  L  Y
2401   TTGAGCGAGAGC GCCACTATGGTG TACAACGAAAGG GAGTTCGTCAAC AGGAAACTATAC
       AACTCGCTCTCG CGGTGATACCAC ATGTTGCTTTCC CTCAAGCAGTTG TCCTTTGATATG
           H  I  A  V     H  G  P  S     L  N  T  D     E  E  N  Y     E  K  V  R
2461   CATATTGCCGTT CACGGACCGTCG CTGAACACCGAC GAGGAGAACTAC GAGAAAGTCAGA
       GTATAACGGCAA GTGCCTGGCAGC GACTTGTGGCTG CTCCTCTTGATG CTCTTTCAGTCT
           A  E  R  T     D  A  E  Y     V  F  D  V     D  K  K  C     C  V  K  R
2521   GCTGAAAGAACT GACGCCGAGTAC GTGTTCGACGTA GATAAAAAATGC TGCGTCAAGAGA
       CGACTTTCTTGA CTGCGGCTCATG CACAAGCTGCAT CTATTTTTTACG ACGCAGTTCTCT
           E  E  A  S     G  L  V  L     V  G  E  L     T  N  P  P     F  H  E  F
2581   GAGGAAGCGTCG GGTTTGGTGTTG GTGGGAGAGCTA ACCAACCCCCCG TTCCATGAATTC
       CTCCTTCGCAGC CCAAACCACAAC CACCCTCTCGAT TGGTTGGGGGGC AAGGTACTTAAG
           A  Y  E  G     L  K  I  R     P  S  A  P     Y  K  T  T     V  V  G  V
2641   GCCTACGAAGGG CTGAAGATCAGG CCGTCGGCACCA TATAAGACTACA GTAGTAGGAGTC
       CGGATGCTTCCC GACTTCTAGTCC GGCAGCCGTGGT ATATTCTGATGT CATCATCCTCAG
           F  G  V  P     G  S  G  K     S  A  I  I     K  S  L  V     T  K  H  D
2701   TTTGGGGTTCCG GGATCAGGCAAG TCTGCTATTATT AAGAGCCTCGTG ACCAAACACGAT
       AAACCCCAAGGC CCTAGTCCGTTC AGACGATAATAA TTCTCGGAGCAC TGGTTTGTGCTA
           L  V  T  S     G  K  K  E     N  C  Q  E     I  V  N  D     V  K  K  H
2761   CTGGTCACCAGC GGCAAGAAGGAG AACTGCCAGGAA ATAGTTAACGAC GTGAAGAAGCAC
       GACCAGTGGTCG CCGTTCTTCCTC TTGACGGTCCTT TATCAATTGCTG CACTTCTTCGTG
           R  G  K  G     T  S  R  E     N  S  D  S     I  L  L  N     G  C  R  R
2821   CGCGGGAAGGGG ACAAGTAGGGAA AACAGTGACTCC ATCCTGCTAAAC GGGTGTCGTCGT
       GCGCCCTTCCCC TGTTCATCCCTT TTGTCACTGAGG TAGGACGATTTG CCCACAGCAGCA
           A  V  D  I     L  Y  V  D     E  A  F  A     C  H  S  G     T  L  L  A
2881   GCCGTGGACATC CTATATGTGGAC GAGGCTTTCGCT TGCCATTCCGGT ACTCTGCTGGCC
       CGGCACCTGTAG GATATACACCTG CTCCGAAAGCGA ACGGTAAGGCCA TGAGACGACCGG
           L  I  A  L     V  K  P  R     S  K  V  L     C  G  D     P  K  Q  C
2941   CTAATTGCTCTT GTTAAACCTCGG AGCAAAGTGGTG TTATGCGGAGAC CCCAAGCAATGC
       GATTAACGAGAA CAATTTGGAGCC TCGTTTCACCAC AATACGCCTCTG GGGTTCGTTACG
           G  F  F  N     M  M  Q  L     K  V  N  F     N  H  N  I     C  T  E  V
3001   GGATTCTTCAAT ATGATGCAGCTT AAGGTAAACTTC AACCACAACATC TGCACTGAAGTA
       CCTAAGAAGTTA TACTACGTCGAA TTCCATTTGAAG TTGGTGTTGTAG ACGTGACTTCAT
           C  H  K  S     I  S  R  R     C  T  R  P     V  T  A  I     V  S  T  L
3061   TGTCATAAAAGT ATATCCAGACGT TGCACGCGTCCA GTCACGGCCATC GTGTCTACGTTG
       ACAGTATTTTCA TATAGGTCTGCA ACGTGCGCAGGT CAGTGCCGGTAG CACAGATGCAAC
           H  Y  G  G     K  M  R  T     T  N  P  C     N  K  P  I     I  I  D  T
3121   CACTACGGAGGC AAGATGCGCACG ACCAACCCGTGC AACAAACCCATA ATCATAGACACC
       GTGATGCCTCCG TTCTACGCGTGC TGGTTGGGCACG TTGTTTGGGTAT TAGTATCTGTGG
           T  G  Q  T     K  P  K  P     G  D  I  V     L  T  C  F     R  G  W  A
3181   ACAGGACAGACC AAGCCCAAGCCA GGAGACATCGTG TTAACATGCTTC CGAGGCTGGGCA
       TGTCCTGTCTGG TTCGGGTTCGGT CCTCTGTAGCAC AATTGTACGAAG GCTCCGACCCGT
           K  Q  L  Q     L  D  Y  R     G  H  E  V     M  T  A  A     A  S  Q  G
3241   AAGCAGCTGCAG TTGGACTACCGT GGACACGAAGTC ATGACAGCAGCA GCATCTCAGGGC
       TTCGTCGACGTC AACCTGATGGCA CCTGTGCTTCAG TACTGTCGTCGT CGTAGAGTCCCG
           L  T  R  K     G  V  Y  A     V  R  Q  K     V  N  E  N     P  L  Y  A
3301   CTCACCCGCAAA GGGGTATACGCC GTAAGGCAGAAG GTGAATGAAAAT CCCTTGTATGCC
       GAGTGGGCGTTT CCCCATATGCGG CATTCCGTCTTC CACTTACTTTTA GGGAACATACGG
           P  A  S  E     H  V  N  V     L  L  T  R     T  E  D  R     L  V  W  K
3361   CCTGCGTCGGAG CACGTGAATGTA CTGCTGACGCGC ACTGAGGATAGG CTGGTGTGGAAA
       GGACGCAGCCTC GTGCACTTACAT GACGACTGCGCG TGACTCCTATCC GACCACACCTTT
           T  L  A  G     D  P  W  I     K  V  L  S     N  I  P  Q     G  N  F  T
3421   ACGCTGGCCGGC GATCCCTGGATT AAGGTCCTATCA AACATTCCACAG GGTAACTTTACG
       TGCGACCGGCCG CTAGGGACCTAA TTCCAGGATAGT TTGTAAGGTGTC CCATTGAAATGC
           A  T  L  E     E  W  Q  E     E  H  D  K     I  M  K  V     I  E  G  P
3481   GCCACATTGGAA GAATGGCAAGAA GAACACGACAAA ATAATGAAGGTG ATTGAAGGACCG
       CGGTGTAACCTT CTTACCGTTCTT CTTGTGCTGTTT TATTACTTCCAC TAACTTCCTGGC
           A  A  P  V     D  A  F  Q     N  K  A  N     V  C  W  A     K  S  L  V
```

```
            H   A   V   A       P   N   F   S       A   T   T   E       A   E   G   D       R   E   L   A
4741        CACGCTGTAGCG        CCTAATTTCTCT        GCCACGACTGAA        GCGGAAGGGGAC        CGCGAATTGGCC
            GTGCGACATCGC        GGATTAAAGAGA        CGGTGCTGACTT        CGCCTTCCCCTG        GCGCTTAACCGG
            A   V   Y   R       A   V   A   A       E   V   N   R       L   S   L   S       S   V   A   I
4801        GCTGTCTACCGG        GCAGTGGCCGCC        GAAGTAAACAGA        CTGTCACTGAGC        AGCGTAGCCATC
            CGACAGATGGCC        CGTCACCGGCGG        CTTCATTTGTCT        GACAGTGACTCG        TCGCATCGGTAG
            P   L   L   S       T   G   V   F       S   G   G   R       D   R   L   Q       Q   S   L   N
4861        CCGCTGCTGTCC        ACAGGAGTGTTC        AGCGGCGGAAGA        GATAGGCTGCAG        CAATCCCTCAAC
            GGCGACGACAGG        TGTCCTCACAAG        TCGCCGCCTTCT        CTATCCGACGTC        GTTAGGGAGTTG
            H   L   F   T       A   M   D   A       T   D   A   D       V   T   I   Y       C   R   D   K
4921        CATCTATTCACA        GCAATGGACGCC        ACGGACGCTGAC        GTGACCATCTAC        TGCAGAGACAAA
            GTAGATAAGTGT        CGTTACCTGCGG        TGCCTGCGACTG        CACTGGTAGATG        ACGTCTCTGTTT
            S   W   E   K       K   I   Q   E       A   I   D   M       R   T   A   V       E   L   L   N
4981        AGTTGGGAGAAG        AAAATCCAGGAA        GCCATTGACATG        AGGACGGCTGTG        GAGTTGCTCAAT
            TCAACCCTCTTC        TTTTAGGTCCTT        CGGTAACTGTAC        TCCTGCCGACAC        CTCAACGAGTTA
            D   D   V   E       L   T   T   D       L   V   R   V       H   P   D   S       S   L   V   G
5041        GATGACGTGGAG        CTGACCACAGAC        TTGGTGAGAGTG        CACCCGGACAGC        AGCCTGGTGGGT
            CTACTGCACCTC        GACTGGTGTCTG        AACCACTCTCAC        GTGGGCCTGTCG        TCGGACCACCCA
            R   K   G   Y       S   T   T   D       G   S   L   Y       S   Y   F   E       G   T   K   F
5101        CGTAAGGGCTAC        AGTACCACTGAC        GGGTCGCTGTAC        TCGTACTTTGAA        GGTACGAAATTC
            GCATTCCCGATG        TCATGGTGACTG        CCCAGCGACATG        AGCATGAAACTT        CCATGCTTTAAG
            N   Q   A   A       I   D   M   A       E   I   L   T       L   W   P   R       L   Q   E   A
5161        AACCAGGCTGCT        ATTGATATGGCA        GAGATACTGACG        TTGTGGCCCAGA        CTGCAAGAGGCA
            TTGGTCCGACGA        TAACTATACCGT        CTCTATGACTGC        AACACCGGGTCT        GACGTTCTCCGT
            N   E   Q   I       C   L   Y   A       L   G   E   T       M   D   N   I       R   S   K   C
5221        AACGAACAGATA        TGCCTATACGCG        CTGGGCGAAACA        ATGGACAACATC        AGATCCAAATGT
            TTGCTTGTCTAT        ACGGATATGCGC        GACCCGCTTTGT        TACCTGTTGTAG        TCTAGGTTTACA
            P   V   N   D       S   D   S   S       T   P   P   R       T   V   P   C       L   C   R   Y
5281        CCGGTGAACGAT        TCCGATTCATCA        ACACCTCCCAGG        ACAGTGCCCTGC        CTGTGCCGCTAC
            GGCCACTTGCTA        AGGCTAAGTAGT        TGTGGAGGGTCC        TGTCACGGGACG        GACACGGCGATG
            A   M   T   A       E   R   I   A       R   L   R   S       H   Q   V   K       S   M   V   V
5341        GCAATGACAGCA        GAACGGATCGCC        CGCCTTAGGTCA        CACCAAGTTAAA        AGCATGGTGGTT
            CGTTACTGTCGT        CTTGCCTAGCGG        GCGGAATCCAGT        GTGGTTCAATTT        TCGTACCACCAA
            C   S   S   F       P   L   P   K       Y   H   V   D       G   V   Q   K       V   K   C   E
5401        TGCTCATCTTTT        CCCCTCCCGAAA        TACCATGTAGAT        GGGGTGCAGAAG        GTAAAGTGCGAG
            ACGAGTAGAAAA        GGGGAGGGCTTT        ATGGTACATCTA        CCCCACGTCTTC        CATTTCACGCTC
                                                                KpnI
                                                                ~~~~~~~
            K   V   L   L       F   D   P   T       V   P   S   V       V   S   P   R       K   Y   A   A
5461        AAGGTTCTCCTG        TTCGACCCGACG        GTACCTTCAGTG        GTTAGTCCGCGG        AAGTATGCCGCA
            TTCCAAGAGGAC        AAGCTGGGCTGC        CATGGAAGTCAC        CAATCAGGCGCC        TTCATACGGCGT
            S   T   T   D       H   S   D   R       S   L   R   G       F   D   L   D       W   T   T   D
5521        TCTACGACGGAC        CACTCAGATCGG        TCGTTACGAGGG        TTTGACTTGGAC        TGGACCACCGAC
            AGATGCTGCCTG        GTGAGTCTAGCC        AGCAATGCTCCC        AAACTGAACCTG        ACCTGGTGGCTG
            S   S   S   T       A   S   D   T       M   S   L   P       S   L   Q   S       C   D   I   D
5581        TCGTCTTCCACT        GCCAGCGATACC        ATGTCGCTACCC        AGTTTGCAGTCG        TGTGACATCGAC
            AGCAGAAGGTGA        CGGTCGCTATGG        TACAGCGATGGG        TCAAACGTCAGC        ACACTGTAGCTG
            S   I   Y   E       P   M   A   P       I   V   V   T       A   D   V   H       P   E   P   A
5641        TCGATCTACGAG        CCAATGGCTCCC        ATAGTAGTGACG        GCTGACGTACAC        CCTGAACCCGCA
            AGCTAGATGCTC        GGTTACCGAGGG        TATCATCACTGC        CGACTGCATGTG        GGACTTGGGCGT
            G   I   A   D       L   A   A   D       V   H   P   E       P   A   D   H       V   D   L   E
5701        GGCATCGCGGAC        CTGGCGGCAGAT        GTGCACCCTGAA        CCCGCAGACCAT        GTGGACCTCGAG
            CCGTAGCGCCTG        GACCGCCGTCTA        CACGTGGGACTT        GGGCGTCTGGTA        CACCTGGAGCTC
            N   P   I   P       P   P   R   P       K   R   A   A       Y   L   A   S       R   A   A   E
5761        AACCCGATTCCT        CCACCGCGCCCG        AAGAGAGCTGCA        TACCTTGCCTCC        CGCGCGGCGGAG
            TTGGGCTAAGGA        GGTGGCGCGGGC        TTCTCTCGACGT        ATGGAACGGAGG        GCGCGCCGCCTC
            R   P   V   P       A   P   R   K       P   T   P   A       P   R   T   A       F   R   N   K
5821        CGACCGGTGCCG        GCGCCGAGAAAG        CCGACGCCTGCC        CCAAGGACTGCG        TTTAGGAACAAG
            GCTGGCCACGGC        CGCGGCTCTTTC        GGCTGCGGACGG        GGTTCCTGACGC        AAATCCTTGTTC
            L   P   L   T       F   G   D   F       D   E   H   E       V   D   A   L       A   S   G   I
5881        CTGCCTTTGACG        TTCGGCGACTTT        GACGAGCACGAG        GTCGATGCGTTG        GCCTCCGGGATT
```

FIG. 10F.

```
           GACGGAAACTGC AAGCCGCTGAAA CTGCTCGTGCTC CAGCTACGCAAC CGGAGGCCCTAA
            T  F  G  D   F  D  D  V   L  R  L  G   R  A  G  A   Y  I  F  S
     5941  ACTTTCGGAGAC TTCGACGACGTC CTGCGACTAGGC CGCGCGGGTGCA TATATTTTCTCC
           TGAAAGCCTCTG AAGCTGCTGCAG GACGCTGATCCG GCGCGCCCACGT ATATAAAAGAGG
            S  D  T  G   S  G  H  L   Q  Q  K  S   V  R  Q  H   N  L  Q  C
     6001  TCGGACACTGGC AGCGGACATTTA CAACAAAAATCC GTTAGGCAGCAC AATCTCCAGTGC
           AGCCTGTGACCG TCGCCTGTAAAT GTTGTTTTTAGG CAATCCGTCGTG TTAGAGGTCACG
            A  Q  L  D   A  V  Q  E   E  K  M  Y   P  P  K  L   D  T  E  R
     6061  GCACAACTGGAT GCGGTCCAGGAG GAGAAAATGTAC CCGCCAAAATTG GATACTGAGAGG
           CGTGTTGACCTA CGCCAGGTCCTC CTCTTTTACATG GGCGGTTTTAAC CTATGACTCTCC
            E  K  L  L   L  L  K  M   Q  M  H  P   S  E  A  N   K  S  R  Y
     6121  GAGAAGCTGTTG CTGCTGAAAATG CAGATGCACCCA TCGGAGGCTAAT AAGAGTCGATAC
           CTCTTCGACAAC GACGACTTTTAC GTCTACGTGGGT AGCCTCCGATTA TTCTCAGCTATG
            Q  S  R  K   V  E  N  M   K  A  T  V   V  D  R  L   T  S  G  A
     6181  CAGTCTCGCAAA GTGGAGAACATG AAAGCCACGGTG GTGGACAGGCTC ACATCGGGGGCC
           GTCAGAGCGTTT CACCTCTTGTAC TTTCGGTGCCAC CACCTGTCCGAG TGTAGCCCCCGG
                                                                 KpnI
                                                                ------
            R  L  Y  T   G  A  D  V   G  R  I  P   T  Y  A  V   R  Y  P  R
     6241  AGATTGTACACG GGAGCGGACGTA GGCCGCATACCA ACATACGCGGTT CGGTACCCCCGC
           TCTAACATGTGC CCTCGCCTGCAT CCGGCGTATGGT TGTATGCGCCAA GCCATGGGGGCG
            P  V  Y  S   P  T  V  I   E  R  F  S   P  D  V  A   I  A  A
     6301  CCCGTGTACTCC CCTACCGTGATC GAAAGATTCTCA AGCCCCGATGTA GCAATCGCAGCG
           GGGCACATGAGG GGATGGCACTAG CTTTCTAAGAGT TCGGGGCTACAT CGTTAGCGTCGC
            C  N  E  Y   L  S  R  N   Y  P  T  V   A  S  Y  Q   I  T  D  E
     6361  TGCAACGAATAC CTATCCAGAAAT TACCCAACAGTG GCGTCGTACCAG ATAACAGATGAA
           ACGTTGCTTATG GATAGGTCTTTA ATGGGTTGTCAC CGCAGCATGGTC TATTGTCTACTT
            Y  D  A  Y   L  D  M  V   D  G  S  C   L  D  R  A   T  F
     6421  TACGACGCATAC TTGGACATGGTT GACGGGTCGGAT AGTTGCTTGAC AGAGCGACATTC
           ATGCTGCGTATG AACCTGTACCAA CTGCCCAGCCTA TCAACGAACCTG TCTCGCTGTAAG
            C  P  A  K   L  R  C  Y   P  K  H  H   A  Y  H  Q   P  T  V  R
     6481  TGCCCGGCAAG CTCCGGTGCTAC CCGAAACATCAT GCGTACCACCAG CCGACTGTACGC
           ACGGGCCGCTTC GAGGCCACGATG GGCTTTGTAGTA CGCATGGTGGTC GGCTGACATGCG
                                                                 NotI
                                                                --------
            S  A  V  P   S  P  F  Q   N  T  L  Q   N  V  L  A   A  A  T  K
     6541  AGTGCCGTCCCG TCACCCTTTCAG AACACACTACAG AACGTGCTAGCG GCCGCCACCAAG
           TCACGGCAGGGC AGTGGGAAAGTC TTGTGTGATGTC TTGCACGATCGC CGGCGGTGGTTC
            R  N  C  N   V  T  Q  M   R  E  L  P   T  M  D  S   A  V  F  N
     6601  AGAAACTGCAAC GTCACGCAAATG CGAGAACTACCC ACCATGGACTCG GCAGTGTTCAAC
           TCTTTGACGTTG CAGTGCGTTTAC GCTCTTGATGGG TGGTACCTGAGC CGTCACAAGTTG
            V  E  C  F   K  R  Y  A   C  S  G  E   Y  W  E  E   Y  A  K  Q
     6661  GTGGAGTGCTTC AAGCGCTATGCC TGCTCCGGAGAA TATTGGGAAGAA TATGCTAAACAA
           CACCTCACGAAG TTCGCGATACGG ACGAGGCCTCTT ATAACCCTTCTT ATACGATTTGTT
            P  I  R  I   T  T  E  N   I  T  T  Y   V  T  K  L   K  G  P  K
     6721  CCTATCCGGATA ACCACTGAGAAC ATCACTACCTAT GTGACCAAATTG AAAGGCCCGAAA
           GGATAGGCCTAT TGGTGACTCTTG TAGTGATGGATA CACTGGTTTAAC TTTCCGGGCTTT
            A  A  A  L   F  A  K  T   H  N  L  V   P  L  Q  E   V  P  M  D
     6781  GCTGCTGCCTTG TTCGCTAAGACC CACAACTTGGTT CCGCTGCAGGAG GTTCCCATGGAC
           CGACGACGGAAC AAGCGATTCTGG GTGTTGAACCAA GGCGACGTCCTC CAAGGGTACCTG
            R  F  T  V   D  M  K  R   D  V  K  V   T  P  G  T   K  H  T  E
     6841  AGATTCACGGTC GACATGAAACGA GATGTCAAAGTC ACTCCAGGGACG AAACACACAGAG
           TCTAAGTGCCAG CTGTACTTTGCT CTACAGTTTCAG TGAGGTCCCTGC TTTGTGTGTCTC
            E  R  P  K   V  Q  V  I   Q  A  A  E   P  L  A  T   A  Y  L  C
     6901  GAAAGACCCAAA GTCCAGGTAATT CAAGCAGCGGAG CCATTGGCGACC GCTTACCTGTGC
           CTTTCTGGGTTT CAGGTCCATTAA GTTCGTCGCCTC GGTAACCGCTGG CGAATGGACACG
            G  I  H  R   E  L  V  R   R  L  N  A   V  L  R  P   N  V  H  T
     6961  GGCATCCACAGG GAATTAGTAAGG AGACTAAATGCT GTGTTACGCCCT AACGTGCACACA
           CCGTAGGTGTCC CTTAATCATTCC TCTGATTTACGA CACAATGCGGGA TTGCACGTGTGT
            L  F  D  M   S  A  E  D   F  D  A  I   I  A  S  H   F  H  P  G
     7021  TTGTTTGATATG TCGGCCGAAGAC TTTGACGCGATC ATCGCCTCTCAC TTCCACCCAGGA
```

```
            ..T  I  S  F  K  D  D  G  N  Y  K  T  R  A  E  V  K  F  E  G ·
     8221   GCACTATATCTT TCAAAGATGACG GGAACTACAAGA CGCGTGCTGAAG TCAAGTTTGAAG
            CGTGATATAGAA AGTTTCTACTGC CCTTGATGTTCT GCGCACGACTTC AGTTCAAACTTC
            ..D  T  L  V  N  R  I  E  L  K  G  I  D  F  K  E  D  G  N  I ·
     8281   GTGATACCCTTG TTAATCGTATCG AGTTAAAAGGTA TTGATTTTAAAG AAGATGGAAACA
            CACTATGGGAAC AATTAGCATAGC TCAATTTTCCAT AACTAAAATTTC TTCTACCTTTGT
            ..L  G  H  K  L  E  Y  N  Y  N  S  H  N  V  Y  I  T  A  D  K ·
     8341   TTCTCGGACACA AACTCGAGTACA ACTATAACTCAC ACAATGTATACA TCACGGCAGACA
            AAGAGCCTGTGT TTGAGCTCATGT TGATATTGAGTG TGTTACATATGT AGTGCCGTCTGT
                                                                    BamHI
                                                                    ---
            ..Q  K  N  G  I  K  A  N  F  K  I  R  H  N  I  E  D  G  S  V ·
     8401   AACAAAAGAATG GAATCAAAGCTA ACTTCAAAATTC GTCACAACATTG AAGATGGATCCG
            TTGTTTTCTTAC CTTAGTTTCGAT TGAAGTTTTAAG CAGTGTTGTAAC TTCTACCTAGGC
            ..Q  L  A  D  H  Y  Q  Q  N  T  P  I  G  D  G  P  V  L  L  P ·
     8461   TTCAACTAGCAG ACCATTATCAAC AAAATACTCCAA TTGGCGATGGCC CTGTCCTTTTAC
            AAGTTGATCGTC TGGTAATAGTTG TTTTATGAGGTT AACCGCTACCGG GACAGGAAATG
            ..D  N  H  Y  L  S  T  Q  S  A  L  S  K  D  P  N  E  K  R  D ·
     8521   CAGACAACCATT ACCTGTCGACAC AATCTGCCCTTT CGAAAGATCCCA ACGAAAAGCGTG
            GTCTGTTGGTAA TGGACAGCTGTG TTAGACGGGAAA GCTTTCTAGGGT TGCTTTTCGCAC
            ..H  M  V  L  E  F  V  T  A  A  G  I  T  H  G  M  D  Q  A ·
     8581   ACCACATGGTCC TTCTTGAGTTTG TAACTGCTGCTG GGATTACACATG GCATGGATCAGG
            TGGTGTACCAGG AAGAACTCAAAC ATTGACGACGAC CCTAATGTGTAC CGTACCTAGTCC
            ..K  P  L  S  Q  E  E  S  T  L  I  E  R  A  T  A  T  I  N  S ·
     8641   CCAAGCCTTTGT CTCAAGAAGAAT CCACCCTCATTG AAAGAGCAACGG CTACAATCAACA
            GGTTCGGAAACA GAGTTCTTCTTA GGTGGGAGTAAC TTTCTCGTTGCC GATGTTAGTTGT
            ..I  P  I  S  E  D  Y  S  V  A  S  A  A  L  S  S  D  G  R  I ·
     8701   GCATCCCCATCT CTGAAGACTACA GCGTCGCCAGCG CAGCTCTCTCTA GCGACGGCCGCA
            CGTAGGGGTAGA GACTTCTGATGT CGCAGCGGTCGC GTCGAGAGAGAT CGCTGCCGGCGT
            ..F  T  G  V  N  V  Y  H  F  T  G  G  P  C  A  E  L  V  V  L ·
     8761   TCTTCACTGGTG TCAATGTATATC ATTTTACTGGGG GACCTTGTGCAG AACTCGTGGTGC
            AGAAGTGACCAC AGTTACATATAG TAAAATGACCCC CTGGAACACGTC TTGAGCACCACG
            ..G  T  A  A  A  A  A  G  N  L  T  C  I  V  A  I  G  N  E ·
     8821   TGGGCACTGCTG CTGCTGCGGCAG CTGGCAACCTGA CTTGTATCGTCG CGATCGGAAATG
            ACCCGTGACGAC GACGACGCCGTC GACCGTTGGACT GAACATAGCAGC GCTAGCCTTTAC
            ..N  R  G  I  L  S  P  C  G  R  C  R  Q  V  L  L  D  L  H  P ·
     8881   AGAACAGGGCA TCTTGAGCCCCT GCGGACGGTGCC GACAGGTGCTTC TCGATCTGCATC
            TCTTGTCCCCGT AGAACTCGGGGA CGCCTGCCACGG CTGTCCACGAAG AGCTAGACGTAG
            ..G  I  K  A  I  V  K  D  S  D  G  Q  P  T  A  V  G  I  R  E ·
     8941   CTGGGATCAAAG CCATAGTGAAGG ACAGTGATGGAC AGCCGACGGCAG TTGGGATTCGTG
            GACCCTAGTTTC GGTATCACTTCC TGTCACTACCTG TCGGCTGCCGTC AACCCTAAGCAC
            ..L  L  P  S  G  Y  V  W  E  G  *
     9001   AATTGCTGCCCT CTGGTTATGTGT GGGAGGGCTAAG CACTTCGTGGGT AATTAATTGAAT
            TTAACGACGGGA GACCAATACACA CCCTCCCGATTC GTGAAGCACCCA TTAATTAACTTA
     9061   TACATCCCTACG CAAACGTTTTAC GGCCGCCGGTGG CGCCCGCGCCCG GCGGCCCGTCCT
            ATGTAGGGATGC GTTTGCAAAATG CCGGCGGCCACC GCGGGCGCGGGC CGCCGGGCAGGA
     9121   TGGCCGTTGCAG GCCACTCCGGTG GCTCCCGTCGTC CCCGACTTCCAG GCCCAGCAGATG
            ACCGGCAACGTC CGGTGAGGCCAC CGAGGGCAGCAG GGGCTGAAGGTC CGGGTCGTCTAC
     9181   CAGCAACTCATC AGCGCCGTAAAT GCGCTGACAATG AGACAGAACGCA ATTGCTCCTGCT
            GTCGTTGAGTAG TCGCGGCATTTA CGCGACTGTTAC TCTGTCTTGCGT TAACGAGGACGA
     9241   AGGCCTCCCAAA CCAAAGAAGAAG AAGACAACCAAA CCAAAGCCGAAA ACGCAGCCCAAG
            TCCGGAGGGTTT GGTTTCTTCTTC TTCTGTTGGTTT GGTTTCGGCTTT TGCGTCGGGTTC
     9301   AAGATCAACGGA AAAACGCAGCAG CAAAAGAAGAAA GACAAGCAAGCC GACAAGAAGAAG
            TTCTAGTTGCCT TTTTGCGTCGTC GTTTTCTTCTTT CTGTTCGTTCGG CTGTTCTTCTTC
     9361   AAGAAACCCGGA AAAAGAGAAAGA ATGTGCATGAAG ATTGAAAATGAC TGTATCTTCGTA
            TTCTTTGGGCCT TTTTCTCTTTCT TACACGTACTTC TAACTTTTACTG ACATAGAAGCAT
     9421   TGCGGCTAGCCA CAGTAACGTAGT GTTTCCAGACAT GTCGGGCACCGC ACTATCATGGGT
            ACGCCGATCGT GTCATTGCATCA CAAAGGTCTGTA CAGCCCGTGGCG TGATAGTACCCA
     9481   GCAGAAAATCTC GGGTGGTCTGGG GGCCTTCGCAAT CGGCGCTATCCT GGTGCTGGTTGT
            CGTCTTTTAGAG CCCACCAGACCC CCGGAAGCGTTA GCCGCGATAGGA CCACGACCAACA
     9541   GGTCACTTGCAT TGGGCTCCGCAG ATAAGTTAGGGT AGGCAATGGCAT TGATATAGCAAG
```

FIG. 10I.

```
         CCAGTGAACGTA ACCCGAGGCGTC TATTCAATCCCA TCCGTTACCGTA ACTATATCGTTC
  9601   AAAATTGAAAAC AGAAAAGTTAG GGTAAGCAATGG CATATAACCATA ACTGTATAACTT
         TTTTAACTTTTG TCTTTTTCAATC CCATTCGTTACC GTATATTGGTAT TGACATATTGAA
  9661   GTAACAAAGCGC AACAAGACCTGC GCAATTGGCCCC GTGGTCCGCCTC ACGGAAACTCGG
         CATTGTTTCGCG TTGTTCTGGACG CGTTAACCGGGG CACCAGGCGGAG TGCCTTTGAGCC
  9721   GGCAACTCATAT TGACACATTAAT TGGCAATAATTG GAAGCTTACATA AGCTTAATTCGA
         CCGTTGAGTATA ACTGTGTAATTA ACCGTTATTAAC CTTCGAATGTAT TCGAATTAAGCT
  9781   CGAATAATTGGA TTTATATTTTAT TTTGCAATTGGT TTTTAATATTTC CAAAAAAAAAAA
         GCTTATTAACCT AAATATAAAATA AAACGTTAACCA AAAATTATAAAG GTTTTTTTTTT
  9841   AAAAAAAAAAAA AAAAAAAAAAAA AAAAAAAAAAAA AAAAAAAAAACG GGTCGGCATGGC
         TTTTTTTTTTTT TTTTTTTTTTTT TTTTTTTTTTTT TTTTTTTTTGC CCAGCCGTACCG
  9901   ATCTCCACCTCC TCGCGGTCCGAC CTGGGCATCCGA AGGAGGACGCAC GTCCACTCGGAT
         TAGAGGTGGAGG AGCGCCAGGCTG GACCCGTAGGCT TCCTCCTGCGTG CAGGTGAGCCTA
                                   SpeI
                             ~~~~~~~ C6 Right arm ⇒
  9961   GGCTAAGGGAGT TTTTCTACTAGT CAAATGAGTATA TATAATTGAAAA AGTAAAATATAA
         CCGATTCCCTCA AAAAGATGATCA GTTTACTCATAT ATATTAACTTTT TCATTTTATATT
 10021   ATCATATAATAA TGAAACGAAATA TCAGTAATAGAC AGGAACTGGCAG ATTCTTCTTCTA
         TAGTATATTATT ACTTGCTTTAT AGTCATTATCTG TCCTTGACCGTC TAAGAAGAAGAT
 10081   ATGAAGTAAGTA CTGCTAAATCTC CAAAATTAGATA AAAATGATACAG CAAATACAGCTT
         TACTTCATTCAT GACGATTTAGAG GTTTTAATCTAT TTTTACTATGTC GTTTATGTCGAA
 10141   CATTCAACGAAT TACCTTTTAATT TTTTCAGACACA CCTTATTACAAA CTAACTAAGTCA
         GTAAGTTGCTTA ATGGAAAATTAA AAAAGTCTGTGT GGAATAATGTTT GATTGATTCAGT
 10201   GATGATGAGAAA GTAAATATAAAT TTAACTTATGGG TATAATATAATA AAGATTCATGAT
         CTACTACTCTTT CATTTATATTTA AATTGAATACCC ATATTATATTAT TTCTAAGTACTA
 10261   ATTAATAATTTA CTTAACGATGTT AATAGACTTATT CCATCAACCCCT TCAAACCTTTCT
         TAATTATTAAAT GAATTGCTACAA TTATCTGAATAA GGTAGTTGGGGA AGTTTGGAAAGA
 10321   GGATATTATAAA ATACCAGTTAAT GATATTAAAATA GATTGTTTAAGA GATGTAAATAAT
         CCTATAATATTT TATGGTCAATTA CTATAATTTTAT CTAACAAATTCT CTACATTTATTA
 10381   TATTTGGAGGTA AAGGATATAAAA TTAGTCTATCTT TCACATGGAAAT GAATTACCTAAT
         ATAAACCTCCAT TTCCTATATTTT AATCAGATAGAA AGTGTACCTTTA CTTAATGGATTA
 10441   ATTAATAATTAT GATAGGAATTTT TTAGGATTTACA GCTGTTATATGT ATCAACAATACA
         TAATTATTAATA CTATCCTTAAAA AATCCTAAATGT CGACAATATACA TAGTTGTTATGT
 10501   GGCAGATCTATG GTTATGGTAAAA CACTGTAACGGG AAGCAGCATTCT ATGGTAACTGGC
         CCGTCTAGATAC CAATACCATTTT GTGACATTGCCC TTCGTCGTAAGA TACCATTGACCG
 10561   CTATGTTTAATA GCCAGATCATTT TACTCTATAAAC ATTTTACCACAA ATAATAGGATCC
         GATACAAATTAT CGGTCTAGTAAA ATGAGATATTTG TAAAATGGTGTT TATTATCCTAGG
 10621   TCTAGATATTTA ATATTATATCTA ACAACAACAAAA AAATTTAACGAT GTATGGCCAGAA
         AGATCTATAAAT TATAATATAGAT TGTTGTTGTTTT TTTAAATTGCTA CATACCGGTCTT
 10681   GTATTTCTACT AATAAAGATAAA GATAGTCTATCT TATCTACAAGAT ATGAAAGAAGAT
         CATAAAAGATGA TTATTTCTATTT CTATCAGATAGA ATAGATGTTCTA TACTTCTTCTA
 10741   AATCATTTAGTA GTAGCTACTAAT ATGGAAGAAAT GTATACAAAAAC GTGGAAGCTTTT
         TTAGTAAATCAT CATCGATGATTA TACCTTTCTTTA CATATGTTTTTG CACCTTCGAAAA
 10801   ATATTAAATAGC ATATTACTAGAA GATTTAAAATCT AGACTTAGTATA ACAAAACAGTTA
         TATAATTTATCG TATAATGATCTT CTAAATTTTAGA TCTGAATCATAT TGTTTTGTCAAT
 10861   AATGCCAATATC GATTCTATATTT CATCATAACAGT AGTACATTAATC AGTGATATACTG
         TTACGGTTATAG CTAAGATATAAA GTAGTATTGTCA TCATGTAATTAG TCACTATATGAC
 10921   AAACGATCTACA GACTCAACTATG CAAGGAATAAGC AAATATGCCAATT ATGTCTAATATT
         TTTGCTAGATGT CTGAGTTGATAC GTTCCTTATTCG TTATACGGTTAA TACAGATTATAA
 10981   TTAACTTTAGAA CTAAAACGTTCT ACCAATACTAAA AATAGGATACGT GATAGGCTGTTA
         AATTGAAATCTT GATTTTGCAAGA TGGTTATGATTT TTATCCTATGCA CTATCCGACAAT
 11041   AAAGCTGCAATA AATAGTAAGGAT GTAGAAGAAATA CTTTGTTCTATA CCTTCGGAGGAA
         TTTCGACGTTAT TTATCATTCCTA CATCTTCTTTAT GAAACAAGATAT GGAAGCCTCCTT
 11101   AGAACTTTAGAA CAACTTAAGTTT AATCAAACTTGT ATTTATGAAGGT AC
         TCTTGAAATCTT GTTGAATTCAAA TTAGTTTGAACA TAAATACTTCCA TG
```

FIG. 11.
An illustration of the generation of an ALVAC-SFV chimera using a C6 donor plasmid containing SFV-GFP/Bsd Leu713Ala, pJY505.1

FIG. 12.
Immunoplaque Assay of ALVAC-SFV GFP/Bsd Leu 713 Ala chimera
ALVAC-SFV
A mixture of plaques incubated at
40C for 4 days and then at 37C for 1
day
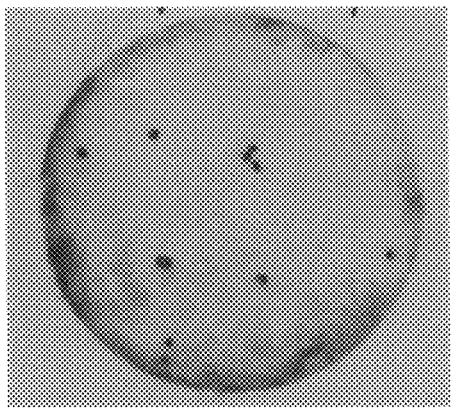
ALVAC-SFV
A mixture of plaques incubated at
40C for 5 days
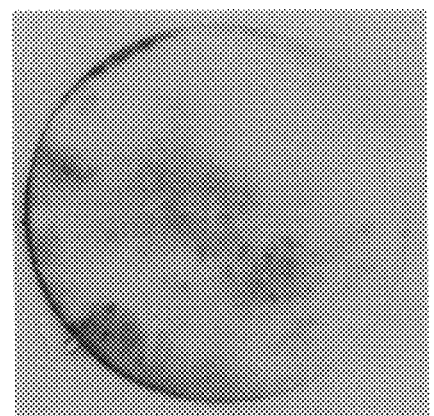
Note: A mixture of plaques consists of ALVAC-SFV and
parental ALVAC viruses.
These are duplicates from same dilution.

Protein expression of ALVAC-SFV (GFP/Blasticidin) chimera in BHK cells

Lane 1. BHK cell mock infection
Lane 2. BHK cell infected with ALVAC-SFV-GFP/Bsd and incubated at 37C
Lane 3. BHK cell infected with ALVAC-SFV-GFP/Bsd and incubated at 38C FIG. 14A.
Construction scheme for an ALVAC-SFV Leu713Ala C6 donor plasmid containing multiple cloning sites FIG 14B.
Construction scheme for an ALVAC-SFV Leu713Ala C6 donor plasmid containing multiple cloning sites FIG. 14C.
Construction scheme for an ALVAC-SFV Leu713Ala C6 donor plasmid containing two 26S promoters.

FIG. 14D.
Construction scheme for an ALVAC-SFV Leu713Ala C6 donor plasmid containing two 26S promoters

FIG.15.

Oligonucleotide primers used for construction of an ALVAC-SFV C6 donor plasmid containing a multiple cloning site and or two 26S promoters Primers:

*Spe* I                Hepatitis delta ribozyme sequence
8284JY   5' CG|ACTAGT| *AGAAAAA* <u>CTCCCTTAGCCAT CCGAGTGGAC</u>

*Eco*RI         *Pac*I        *Sbf*I       *Pme*I
8314JY   5' G|GAATTC|TGATT |TTAATTAA| |CCTGCAGG| |GTTTAAAC| TAATTA
ATTGAATTACATCCCTACGCAAAC

*Eco*RI        *Pac*I       *Sbf*I               26S promoter
8315JY   5' G|GAATTC|TGATT |TTAATTAA| |CCTGCAGG| <u>ACCTC TAC GGC GGT</u>
                                                *Pme* I
<u>CCT AGA TTG GTG CGT TAA TAC ACA</u> |GTTTAAAC| TAATTAATTGAA
TTACATCCCTACGCAAAC

FIG. 16.

An illustration of the ALVAC-SFV Leu713Ala C6 donor plasmid containing a multiple cloning sites, pJY C6 SFV L713A 1

FIG. 17A.

Nucleotide sequence and translation of pJYC6SFVL713A1

C6L⇒
1 CTATCAAAAGTC TTAATGAGTTAG GTGTAGATAGTA TAGATATTACTA CAAAGGTATTCA
GATAGTTTTCAG AATTACTCAATC CACATCTATCAT ATCTATAATGAT GTTTCCATAAGT
61 TATTTCCTATCA ATTCTAAAGTAG ATGATATTAATA ACTCAAAGATGA TGATAGTAGATA
ATAAAGGATAGT TAAGATTTCATC TACTATAATTAT TGAGTTTCTACT ACTATCATCTAT
121 ATAGATACGCTC ATATAATGACTG CAAATTTGGACG GTTCACATTTTA ATCATCACGCGT
TATCTATGCGAG TATATTACTGAC GTTTAAACCTGC CAAGTGTAAAAT TAGTAGTGCGCA
181 TCATAAGTTTCA ACTGCATAGATC AAAATCTCACTA AAAAGATAGCCG ATGTATTTGAGA
AGTATTCAAAGT TGACGTATCTAG TTTTAGAGTGAT TTTTCTATCGGC TACATAAACTCT
241 GAGATTGGACAT CTAACTACGCTA AAGAAATTACAG TTATAAATAATA CATAATGGATTT
CTCTAACCTGTA GATTGATGCGAT TTCTTTAATGTC AATATTTATTAT GTATTACCTAAA
301 TGTTATCATCAG TTATATTTAACA TAAGTACAATAA AAAGTATTAAAT AAAAATACTTAC
ACAATAGTAGTC AATATAAATTGT ATTCATGTTATT TTTCATAATTTA TTTTTATGAATG
H6⇒
361 TTACGAAAAAAT GACTAATTAGCT ATAAAAACCCGG GTTCTTTATTCT ATACTTAAAAAG
AATGCTTTTTTA CTGATTAATCGA TATTTTTGGGCC CAAGAAATAAGA TATGAATTTTTC
SFV ⇒
421 TGAAAATAAATA CAAAGGTTCTTG ATGGCGGATGTG TGACATACACGA CGCCAAAAGATT
ACTTTTATTTAT GTTTCCAAGAAC TACCGCCTACAC ACTGTATGTGCT GCGGTTTTCTAA
M A A K ·
481 TTGTTCCAGCTC CTGCCACCTCCG CTACGCGAGAGA TTAACCACCCAC GATGGCCGCCAA
AACAAGGTCGAG GACGGTGGAGGC GATGCGCTCTCT AATTGGTGGGTG CTACCGGCGGTT
. V H V D I E A D S P F I K S L Q K A F P ·
541 AGTGCATGTTGA TATTGAGGCTGA CAGCCCATTCAT CAAGTCTTTGCA GAAGGCATTTCC
TCACGTACAACT ATAACTCCGACT GTCGGGTAAGTA GTTCAGAAACGT CTTCCGTAAAGG
. S F E V E S L Q V T P N D H A N A R A F ·
601 GTCGTTCGAGGT GGAGTCATTGCA GGTCACACCAAA TGACCATGCAAA TGCCAGAGCATT
CAGCAAGCTCCA CCTCAGTAACGT CCAGTGTGGTTT ACTGGTACGTTT ACGGTCTCGTAA
. S H L A T K L I E Q E T D K D T L I L D ·
661 TTCGCACCTGGC TACCAAATTGAT CGAGCAGGAGAC TGACAAAGACAC ACTCATCTTGGA
AAGCGTGGACCG ATGGTTTAACTA GCTCGTCCTCTG ACTGTTTCTGTG TGAGTAGAACCT
. I G S A P S R R M M S T H K Y H C V C P ·
721 TATCGGCAGTGC GCCTTCCAGGAG AATGATGTCTAC GCACAAATACCA CTGCGTATGCCC
ATAGCCGTCACG CGGAAGGTCCTC TTACTACAGATG CGTGTTTATGGT GACGCATACGGG
. M R S A E D P E R L D S Y A K K L A A A ·
781 TATGCGCAGCGC AGAAGACCCCGA AAGGCTCGATAG CTACGCAAAGAA ACTGGCAGCGGC
ATACGCGTCGCG TCTTCTGGGGCT TTCCGAGCTATC GATGCGTTTCTT TGACCGTCGCCG
. S G K V L D R E I A G K I T D L Q T V M ·
841 CTCCGGGAAGGT GCTGGATAGAGA GATCGCAGGAAA AATCACCGACCT GCAGACCGTCAT
GAGGCCCTTCCA CGACCTATCTCT CTAGCGTCCTTT TTAGTGGCTGGA CGTCTGGCAGTA
. A T P D A E S P T F C L H T D V T C R T ·
901 GGCTACGCCAGA CGCTGAATCTCC TACCTTTTGCCT GCATACAGACGT CACGTGTCGTAC
CCGATGCGGTCT GCGACTTAGAGG ATGGAAAACGGA CGTATGTCTGCA GTGCACAGCATG
. A A E V A V Y Q D V Y A V H A P T S L Y ·
961 GGCAGCCGAAGT GGCCGTATACCA GGACGTGTATGC TGTACATGCACC AACATCGCTGTA
CCGTCGGCTTCA CCGGCATATGGT CCTGCACATACG ACATGTACGTGG TTGTAGCGACAT
. H Q A M K G V R T A Y W I G F D T T P F ·
1021 CCATCAGGCGAT GAAAGGTGTCAG AACGGCGTATTG GATTGGGTTTGA CACCACCCCGTT
GGTAGTCCGCTA CTTTCCACAGTC TTGCCGCATAAC CTAACCCAAACT GTGGTGGGGCAA
. M F D A L A G A Y P T Y A T N W A D E Q ·
1081 TATGTTTGACGC GCTAGCAGGCGC GTATCCAACCTA CGCCACAAACTG GGCCGACGAGCA
ATACAAACTGCG CGATCGTCCGCG CATAGGTTGGAT GCGGTGTTTGAC CCGGCTGCTCGT
. V L Q A R N I G L C A A S L T E G R L G ·
1141 GGTGTTACAGGC CAGGAACATAGG ACTGTGTGCAGC ATCCTTGACTGA GGGAAGACTCGG
CCACAATGTCCG GTCCTTGTATCC TGACACACGTCG TAGGAACTGACT CCCTTCTGAGCC
. K L S I L R K K Q L K P C D T V M F S V ·
1201 CAAACTGTCCAT TCTCCGCAAGAA GCAATTGAAACC TTGCGACACAGT CATGTTCTCGGT
GTTTGACAGGTA AGAGGCGTTCTT CGTTAACTTTGG AACGCTGTGTCA GTACAAGAGCCA

FIG. 17B.

```
       . G   S   T   L     Y   T   E   S     R   K   L   L     R   S   W   H     L   P   S   V  ·
1261   AGGATCTACATT GTACACTGAGAG CAGAAAGCTACT GAGGAGCTGGCA CTTACCCTCCGT
       TCCTAGATGTAA CATGTGACTCTC GTCTTTCGATGA CTCCTCGACCGT GAATGGGAGGCA
       . F   H   L   K     G   K   Q   S     F   T   C   R     C   D   T   I     V   S   C   E  ·
1321   ATTCCACCTGAA AGGTAAACAATC CTTTACCTGTAG GTGCGATACCAT CGTATCATGTGA
       TAAGGTGGACTT TCCATTTGTTAG GAAATGGACATC CACGCTATGGTA GCATAGTACACT
       . G   Y   V   V     K   K   I   T     M   C   P   G     L   Y   G   K     T   V   G   Y  ·
1381   AGGGTACGTAGT TAAGAAAATCAC TATGTGCCCCGG CCTGTACGGTAA AACGGTAGGGTA
       TCCCATGCATCA ATTCTTTTAGTG ATACACGGGGCC GGACATGCCATT TTGCCATCCCAT
       . A   V   T   Y     H   A   E   G     F   L   V   C     K   T   T   D     T   V   K   G  ·
1441   CGCCGTGACGTA TCACGCGGAGGG ATTCCTAGTGTG CAAGACCACAGA CACTGTCAAAGG
       GCGGCACTGCAT AGTGCGCCTCCC TAAGGATCACAC GTTCTGGTGTCT GTGACAGTTTCC
       . E   R   V   S     F   P   V   C     T   Y   V   P     S   T   I   C     D   Q   M   T  ·
1501   AGAAAGAGTCTC ATTCCCTGTATG CACCTACGTCCC CTCAACCATCTG TGATCAAATGAC
       TCTTTCTCAGAG TAAGGGACATAC GTGGATGCAGGG GAGTTGGTAGAC ACTAGTTTACTG
       . G   I   L   A     T   D   V   T     P   E   D   A     Q   K   L   L     V   G   L   N  ·
1561   TGGCATACTAGC GACCGACGTCAC ACCGGAGGACGC ACAGAAGTTGTT AGTGGGATTGAA
       ACCGTATGATCG CTGGCTGCAGTG TGGCCTCCTGCG TGTCTTCAACAA TCACCCTAACTT
       . Q   R   I   V     V   N   G   R     T   Q   R   N     T   N   T   M     K   N   Y   L  ·
1621   TCAGAGGATAGT TGTGAACGGAAG AACACAGCGAAA CACTAACACGAT GAAGAACTATCT
       AGTCTCCTATCA ACACTTGCCTTC TTGTGTCGCTTT GTGATTGTGCTA CTTCTTGATAGA
       . L   P   I   V     A   V   A   F     S   K   W   A     R   E   Y   K     A   D   L   D  ·
1681   GCTTCCGATTGT GGCCGTCGCATT TAGCAAGTGGGC GAGGGAATACAA GGCAGACCTTGA
       CGAAGGCTAACA CCGGCAGCGTAA ATCGTTCACCCG CTCCCTTATGTT CCGTCTGGAACT
       . D   E   K   P     L   G   V   R     E   R   S   L     T   C   C   C     L   W   A   F  ·
1741   TGATGAAAAACC TCTGGGTGTCCG AGAGAGGTCACT TACTTGCTGCTG CTTGTGGCATT
       ACTACTTTTTGG AGACCACAGGC TCTCTCCAGTGA ATGAACGACGAC GAACACCCGTAA
       . K   T   R   K     M   H   T   M     Y   K   K   P     D   T   Q   T     I   V   K   V  ·
1801   TAAAACGAGGAA GATGCACACCAT GTACAAGAAACC AGACACCCAGAC AATAGTGAAGGT
       ATTTTGCTCCTT CTACGTGTGGTA CATGTTCTTTGG TCTGTGGGTCTG TTATCACTTCCA
       . P   S   E   F     N   S   F   V     I   P   S   L     W   S   T   G     L   A   I   P  ·
1861   GCCTTCAGAGTT TAACTCGTTCGT CATCCCGAGCCT ATGGTCTACAGG CCTCGCAATCCC
       CGGAAGTCTCAA ATTGAGCAAGCA GTAGGGCTCGGA TACCAGATGTCC GGAGCGTTAGGG
       . V   R   S   R     I   K   M   L     L   A   K   K     T   K   R   E     L   I   P   V  ·
1921   AGTCAGATCACG CATTAAGATGCT TTTGGCCAAGAA GACCAAGCGAGA GTTAATACCTGT
       TCAGTCTAGTGC GTAATTCTACGA AAACCGGTTCTT CTGGTTCGCTCT CAATTATGGACA
       . L   D   A   S     S   A   R   D     A   E   Q   E     E   K   E   R     L   E   A   E  ·
1981   TCTCGACGCGTC GTCAGCCAGGGA TGCTGAACAAGA GGAGAAGGAGAG GTTGGAGGCCGA
       AGAGCTGCGCAG CAGTCGGTCCCT ACGACTTGTTCT CCTCTTCCTCTC CAACCTCCGGCT
       . L   T   R   E     A   L   P   P     L   V   P   I     A   P   A   E     T   G   V   V  ·
2041   GCTGACTAGAGA AGCCTTACCACC CCTCGTCCCCAT CGCGCCGGCGGA GACGGGAGTCGT
       CGACTGATCTCT TCGGAATGGTGG GGAGCAGGGGTA GCGCGGCCGCCT CTGCCCTCAGCA
       . D   V   D   V     E   E   L   E     Y   H   A   G     A   G   V   V     E   T   P   R  ·
2101   CGACGTCGACGT TGAAGAACTAGA GTATCACGCAGG TGCAGGGGTCGT GGAAACACCTCG
       GCTGCAGCTGCA ACTTCTTGATCT CATAGTGCGTCC ACGTCCCCAGCA CCTTTGTGGAGC
       . S   A   L   K     V   T   A   Q     P   N   D   V     L   L   G   N     Y   V   V   L  ·
2161   CAGCGCGTTGAA AGTCACCGCACA GCCGAACGACGT ACTACTAGGAAA TTACGTAGTTCT
       GTCGCGCAACTT TCAGTGGCGTGT CGGCTTGCTGCA TGATGATCCTTT AATGCATCAAGA
       . S   P   Q   T     V   L   K   S     S   K   L   A     P   V   H   P     L   A   E   Q  ·
2221   GTCCCCGCAGAC CGTGCTCAAGAG CTCCAAGTTGGC CCCCGTGCACCC TCTAGCAGAGCA
       CAGGGGCGTCTG GCACGAGTTCTC GAGGTTCAACCG GGGGCACGTGGG AGATCGTCTCGT
       . V   K   I   I     T   H   N   G     R   A   G   G     Y   Q   V   D     G   Y   D   G  ·
2281   GGTGAAAATAAT AACACATAACGG GAGGGCCGGCGG TTACCAGGTCGA CGGATATGACGG
       CCACTTTTATTA TTGTGTATTGCC CTCCCGGCCGCC AATGGTCCAGCT GCCTATACTGCC
       . R   V   L   L     P   C   G   S     A   I   P   V     P   E   F   Q     A   L   S   E  ·
2341   CAGGGTCCTACT ACCATGTGGATC GGCCATTCCGGT CCCTGAGTTTCA AGCTTTGAGCGA
       GTCCCAGGATGA TGGTACACCTAG CCGGTAAGGCCA GGGACTCAAAGT TCGAAACTCGCT
       . S   A   T   M     V   Y   N   E     R   E   F   V     N   R   K   L     Y   H   I   A  ·
2401   GAGCGCCACTAT GGTGTACAACGA AAGGGAGTTCGT CAACAGGAAACT ATACCATATTGC
       CTCGCGGTGATA CCACATGTTGCT TTCCCTCAAGCA GTTGTCCTTTGA TATGGTATAACG
       . V   H   G   P     S   L   N   T     D   E   E   N     Y   E   K   V     R   A   E   R  ·
```

FIG. 17C.

```
2461  CGTTCACGGACC GTCGCTGAACAC CGACGAGGAGAA CTACGAGAAAGT CAGAGCTGAAAG
      GCAAGTGCCTGG CAGCGACTTGTG GCTGCTCCTCTT GATGCTCTTTCA GTCTCGACTTTC
      . T  D  A  E    Y  V  F  D    V  D  K  K    C  C  V  K    R  E  E  A .
2521  AACTGACGCCGA GTACGTGTTCGA CGTAGATAAAAA ATGCTGCGTCAA GAGAGAGGAAGC
      TTGACTGCGGCT CATGCACAAGCT GCATCTATTTTT TACGACGCAGTT CTCTCTCCTTCG
      . S  G  L  V    L  V  G  E    L  T  N  P    P  F  H  E    F  A  Y  E .
2581  GTCGGGTTTGGT GTTGGTGGGAGA GCTAACCAACCC CCCGTTCCATGA ATTCGCCTACGA
      CAGCCCAAACCA CAACCACCCTCT CGATTGGTTGGG GGGCAAGGTACT TAAGCGGATGCT
      . G  L  K  I    R  P  S  A    P  Y  K  T    T  V  V  G    V  F  G  V .
2641  AGGGCTGAAGAT CAGGCCGTCGGC ACCATATAAGAC TACAGTAGTAGG AGTCTTTGGGGT
      TCCCGACTTCTA GTCCGGCAGCCG TGGTATATTCTG ATGTCATCATCC TCAGAAACCCCA
      . P  G  S  G    K  S  A  I    I  K  S  L    V  T  K  H    D  L  V  T .
2701  TCCGGGATCAGG CAAGTCTGCTAT TATTAAGAGCCT CGTGACCAAACA CGATCTGGTCAC
      AGGCCCTAGTCC GTTCAGACGATA ATAATTCTCGGA GCACTGGTTTGT GCTAGACCAGTG
      . S  G  K  K    E  N  C  Q    E  I  V  N    D  V  K  K    H  R  G  K .
2761  CAGCGGCAAGAA GGAGAACTGCCA GGAAATAGTTAA CGACGTGAAGAA GCACCGCGGGAA
      GTCGCCGTTCTT CCTCTTGACGGT CCTTTATCAATT GCTGCACTTCTT CGTGGCGCCCTT
      . G  T  S  R    E  N  S  D    S  I  L  L    N  G  C  R    R  A  V  D .
2821  GGGGACAAGTAG GGAAAACAGTGA CTCCATCCTGCT AAACGGGTGTCG TCGTGCCGTGGA
      CCCCTGTTCATC CCTTTTGTCACT GAGGTAGGACGA TTTGCCCACAGC AGCACGGCACCT
      . I  L  Y  V    D  E  A  F    A  C  H  S    G  T  L  L    A  L  I  A .
2881  CATCCTATATGT GGACGAGGCTTT CGCTTGCCATTC CGGTACTCTGCT GGCCCTAATTGC
      GTAGGATATACA CCTGCTCCGAAA GCGAACGGTAAG GCCATGAGACGA CCGGGATTAACG
      . L  V  K  P    R  S  K  V    V  L  C  G    D  P  K  Q    C  G  F  F .
2941  TCTTGTTAAACC TCGGAGCAAAGT GGTGTTATGCGG AGACCCCAAGCA ATGCGGATTCTT
      AGAACAATTTGG AGCCTCGTTTCA CCACAATACGCC TCTGGGGTTCGT TACGCCTAAGAA
      . N  M  M  Q    L  K  V  N    F  N  H  N    I  C  T  E    V  C  H  K .
3001  CAATATGATGCA GCTTAAGGTGAA CTTCAACCACAA CATCTGCACTGA AGTATGTCATAA
      GTTATACTACGT CGAATTCCACTT GAAGTTGGTGTT GTAGACGTGACT TCATACAGTATT
      . S  I  S  R    R  C  T  R    P  V  T  A    I  V  S  T    L  H  Y  G .
3061  AAGTATATCCAG ACGTTGCACGCG TCCAGTCACGGC CATCGTGTCTAC GTTGCACTACGG
      TTCATATAGGTC TGCAACGTGCGC AGGTCAGTGCCG GTAGCACAGATG CAACGTGATGCC
      . G  K  M  R    T  T  N  P    C  N  K  P    I  I  I  D    T  T  G  Q .
3121  AGGCAAGATGCG CACGACCAACCC GTGCAACAAACC CATAATCATAGA CACCACAGGACA
      TCCGTTCTACGC GTGCTGGTTGGG CACGTTGTTTGG GTATTAGTATCT GTGGTGTCCTGT
      . T  K  P  K    P  G  D  I    V  L  T  C    F  R  G  W    A  K  Q  L .
3181  GACCAAGCCCAA GCCAGGAGACAT CGTGTTAACATG CTTCCGAGGCTG GGCAAAGCAGCT
      CTGGTTCGGGTT CGGTCCTCTGTA GCACAATTGTAC GAAGGCTCCGAC CCGTTTCGTCGA
      . Q  L  D  Y    R  G  H  E    V  M  T  A    A  A  S  Q    G  L  T  R .
3241  GCAGTTGGACTA CCGGGACACGA AGTCATGACAGC AGCAGCATCTCA GGGCCTCACCCG
      CGTCAACCTGAT GGCACCTGTGCT TCAGTACTGTCG TCGTCGTAGAGT CCCGGAGTGGGC
      . K  G  V  Y    A  V  R  Q    K  V  N  E    N  P  L  Y    A  P  A  S .
3301  CAAAGGGGTATA CGCCGTAAGGCA GAAGGTGAATGA AAATCCCTTGTA TGCCCCTGCGTC
      GTTTCCCCATAT GCGGCATTCCGT CTTCCACTTACT TTTAGGGAACAT ACGGGGACGCAG
      . E  H  V  N    V  L  L  T    R  T  E  D    R  L  V  W    K  T  L  A .
3361  GGAGCACGTGAA TGTACTGCTGAC GCGCACTGAGGA TAGGCTGGTGTG GAAAACGCTGGC
      CCTCGTGCACTT ACATGACGACTG CGCGTGACTCCT ATCCGACCACAC CTTTTGCGACCG
      . G  D  P  W    I  K  V  L    S  N  I  P    Q  G  N  F    T  A  T  L .
3421  CGGCGATCCCTG GATTAAGGTCCT ATCAAACATTCC ACAGGGTAACTT TACGGCCACATT
      GCCGCTAGGGAC CTAATTCCAGGA TAGTTTGTAAGG TGTCCCATTGAA ATGCCGGTGTAA
      . E  E  W  Q    E  E  H  D    K  I  M  K    V  I  E  G    P  A  A  P .
3481  GGAAGAATGGCA AGAAGAACACGA CAAAATAATGAA GGTGATTGAAGG ACCGGCTGCGCC
      CCTTCTTACCGT TCTTCTTGTGCT GTTTTATTACTT CCACTAACTTCC TGGCCGACGCGG
      . V  D  A  F    Q  N  K  A    N  V  C  W    A  K  S  L    V  P  V  L .
3541  TGTGGACGCGTT CCAGAACAAAGC GAACGTGTGTTG GGCGAAAAGCCT GGTGCCTGTCCT
      ACACCTGCGCAA GGTCTTGTTTCG CTTGCACACAAC CCGCTTTTCGGA CCACGGACAGGA
      . D  T  A  G    I  R  L  T    A  E  E  W    S  T  I  I    T  A  F  K .
3601  GGACACTGCCGG AATCAGATTGAC AGCAGAGGAGTG GAGCACCATAAT TACAGCATTTAA
      CCTGTGACGGCC TTAGTCTAACTG TCGTCTCCTCAC CTCGTGGTATTA ATGTCGTAAATT
      . E  D  R  A    Y  S  P  V    V  A  L  N    E  I  C  T    K  Y  Y  G .
3661  GGAGGACAGAGC TTACTCTCCAGT GGTGGCCTTGAA TGAAATTTGCAC CAAGTACTATGG
```

FIG. 17D.

```
         CCTCCTGTCTCG AATGAGAGGTCA CCACCGGAACTT ACTTTAAACGTG GTTCATGATACC
        . V  D  L  D    S  G  L  F    S  A  P  K    V  S  L  Y    Y  E  N  N ·
3721    AGTTGACCTGGA CAGTGGCCTGTT TTCTGCCCCGAA GGTGTCCCTGTA TTACGAGAACAA
        TCAACTGGACCT GTCACCGGACAA AAGACGGGGCTT CCACAGGGACAT AATGCTCTTGTT
        . H  W  D  N    R  P  G  G    R  M  Y  G    F  N  A  A    T  A  A  R ·
3781    CCACTGGGATAA CAGACCTGGTGG AAGGATGTATGG ATTCAATGCCGC AACAGCTGCCAG
        GGTGACCCTATT GTCTGGACCACC TTCCTACATACC TAAGTTACGGCG TTGTCGACGGTC
        . L  E  A  R    H  T  F  L    K  G  Q  W    H  T  G  K    Q  A  V  I ·
3841    GCTGGAAGCTAG ACATACCTTCCT GAAGGGGCAGTG GCATACGGGCAA GCAGGCAGTTAT
        CGACCTTCGATC TGTATGGAAGGA CTTCCCCGTCAC CGTATGCCCGTT CGTCCGTCAATA
        . A  E  R  K    I  Q  P  L    S  V  L  D    N  V  I  P    I  N  R  R ·
3901    CGCAGAAAGAAA AATCCAACCGCT TTCTGTGCTGGA CAATGTAATTCC TATCAACCGCAG
        GCGTCTTTCTTT TTAGGTTGGCGA AAGACACGACCT GTTACATTAAGG ATAGTTGGCGTC
        . L  P  H  A    L  V  A  E    Y  K  T  V    K  G  S  R    V  E  W  L ·
3961    GCTGCCGCACGC CCTGGTGGCTGA GTACAAGACGGT TAAAGGCAGTAG GGTTGAGTGGCT
        CGACGGCGTGCG GGACCACCGACT CATGTTCTGCCA ATTTCCGTCATC CCAACTCACCGA
        . V  N  K  V    R  G  Y  H    V  L  L  V    S  E  Y  N    L  A  L  P ·
4021    GGTCAATAAAGT AAGAGGGTACCA CGTCCTGCTGGT GAGTGAGTACAA CCTGGCTTTGCC
        CCAGTTATTTCA TTCTCCCATGGT GCAGGACGACCA CTCACTCATGTT GGACCGAAACGG
        . R  R  R  V    T  W  L  S    P  L  N  V    T  G  A  D    R  C  Y  D ·
4081    TCGACGCAGGGT CACTTGGTTGTC ACCGCTGAATGT CACAGGCGCCGA TAGGTGCTACGA
        AGCTGCGTCCCA GTGAACCAACAG TGGCGACTTACA GTGTCCGCGGCT ATCCACGATGCT
        . L  S  L  G    L  P  A  D    A  G  R  F    D  L  V  F    V  N  I  H ·
4141    CCTAAGTTTAGG ACTGCCGGCTGA CGCCGGCAGGTT CGACTTGGTCTT TGTGAACATTCA
        GGATTCAAATCC TGACGGCCGACT GCGGCCGTCCAA GCTGAACCAGAA ACACTTGTAAGT
        . T  E  F  R    I  H  H  Y    Q  Q  C  V    D  H  A  M    K  L  Q  M ·
4201    CACGGAATTCAG AATCCACCACTA CCAGCAGTGTGT CGACCACGCCAT GAAGCTGCAGAT
        GTGCCTTAAGTC TTAGGTGGTGAT GGTCGTCACACA GCTGGTGCGGTA CTTCGACGTCTA
        . L  G  G  D    A  A  R  L    L  K  P  G    G  I  L  M    R  A  Y  G ·
4261    GCTTGGGGGAGA TGCGGCACGACT GCTAAAACCCGG CGGCATCTTGAT GAGAGCTTACGG
        CGAACCCCCTCT ACGCCGTGCTGA CGATTTTGGGCC GCCGTAGAACTA CTCTCGAATGCC
        . Y  A  D  K    I  S  E  A    V  V  S  S    L  S  R  K    F  S  S  A ·
4321    ATACGCCGATAA AATCAGCGAAGC CGTTGTTTCCTC CTTAAGCAGAAA GTTCTCGTCTGC
        TATGCGGCTATT TTAGTCGCTTCG GCAACAAAGGAG GAATTCGTCTTT CAAGAGCAGACG
        . R  V  L  R    P  D  C  V    T  S  N  T    E  V  F  L    L  F  S  N ·
4381    AAGAGTGTTGCG CCCGGATTGTGT CACCAGCAATAC AGAAGTGTTCTT GCTGTTCTCCAA
        TTCTCACAACGC GGGCCTAACACA GTGGTCGTTATG TCTTCACAAGAA CGACAAGAGGTT
        . F  D  N  G    K  R  P  S    T  L  H  Q    M  N  T  K    L  S  A  V ·
4441    CTTTGACAACGG AAAGAGACCCTC TACGCTACACCA GATGAATACCAA GCTGAGTGCCGT
        GAAACTGTTGCC TTTCTCTGGGAG ATGCGATGTGGT CTACTTATGGTT CGACTCACGGCA
        . Y  A  G  E    A  M  H  T    A  G  C  A    P  S  Y  R    V  K  R  A ·
4501    GTATGCCGGAGA AGCCATGCACAC GGCCGGGTGTGC ACCATCCTACAG AGTTAAGAGAGC
        CATACGGCCTCT TCGGTACGTGTG CCGGCCCACACG TGGTAGGATGTC TCAATTCTCTCG
        . D  I  A  T    C  T  E  A    A  V  V  N    A  A  N  A    R  G  T  V ·
4561    AGACATAGCCAC GTGCACAGAAGC GGCTGTGGTTAA CGCAGCTAACGC CCGTGGAACTGT
        TCTGTATCGGTG CACGTGTCTTCG CCGACACCAATT GCGTCGATTGCG GGCACCTTGACA
        . G  D  G  V    C  R  A  V    A  K  K  W    P  S  A  F    K  G  A  A ·
4621    AGGGGATGGCGT ATGCAGGGCCGT GGCGAAGAAATG GCCGTCAGCCTT TAAGGGAGCAGC
        TCCCCTACCGCA TACGTCCCGGCA CCGCTTCTTTAC CGGCAGTCGGAA ATTCCCTCGTCG
        . T  P  V  G    T  I  K  T    V  M  C  G    S  Y  P  V    I  H  A  V ·
4681    AACACCAGTGGG CACAATTAAAAC AGTCATGTGCGG CTCGTACCCCGT CATCCACGCTGT
        TTGTGGTCACCC GTGTTAATTTTG TCAGTACACGCC GAGCATGGGCA GTAGGTGCGACA
        . A  P  N  F    S  A  T  T    E  A  E  G    D  R  E  L    A  A  V  Y ·
4741    AGCGCCTAATTT CTCTGCCACGAC TGAAGCGGAAGG GGACCGCGAATT GGCCGCTGTCTA
        TCGCGGATTAAA GAGACGGTGCTG ACTTCGCCTTCC CCTGGCGCTTAA CCGGCGACAGAT
        . R  A  V  A    A  E  V  N    R  L  S  L    S  S  V  A    I  P  L  L ·
4801    CCGGGCAGTGGC CGCCGAAGTAAA CAGACTGTCACT GAGCAGCGTAGC CATCCCGCTGCT
        GGCCCGTCACCG GCGGCTTCATTT GTCTGACAGTGA CTCGTCGCATCG GTAGGCGACGA
        . S  T  G  V    F  S  G  G    R  D  R  L    Q  Q  S  L    N  H  L  F ·
4861    GTCCACAGGAGT GTTCAGCGGCGG AAGAGATAGGCT GCAGCAATCCCT CAACCATCTATT
        CAGGTGTCCTCA CAAGTCGCCGCC TTCTCTATCCGA CGTCGTTAGGGA GTTGGTAGATAA
```

FIG. 17E.

```
           .  T  A  M  D     A  T  D  A     D  V  T  I     Y  C  R  D     K  S  W  E  .
     4921  CACAGCAATGGA CGCCACGGACGC TGACGTGACCAT CTACTGCAGAGA CAAAAGTTGGGA
           GTGTCGTTACCT GCGGTGCCTGCG ACTGCACTGGTA GATGACGTCTCT GTTTTCAACCCT
           .  K  K  I  Q     E  A  I  D     M  R  T  A     V  E  L  L     N  D  D  V  .
     4981  GAAGAAAATCCA GGAAGCCATTGA CATGAGGACGGC TGTGGAGTTGCT CAATGATGACGT
           CTTCTTTTAGGT CCTTCGGTAACT GTACTCCTGCCG ACACCTCAACGA GTTACTACTGCA
           .  E  L  T  T     D  L  V  R     V  H  P  D     S  S  L  V     G  R  K  G  .
     5041  GGAGCTGACCAC AGACTTGGTGAG AGTGCACCCGGA CAGCAGCCTGGT GGGTCGTAAGGG
           CCTCGACTGGTG TCTGAACCACTC TCACGTGGGCCT GTCGTCGGACCA CCCAGCATTCCC
           .  Y  S  T  T     D  G  S  L     Y  S  Y  F     E  G  T  K     F  N  Q  A  .
     5101  CTACAGTACCAC TGACGGGTCGCT GTACTCGTACTT TGAAGGTACGAA ATTCAACCAGGC
           GATGTCATGGTG ACTGCCCAGCGA CATGAGCATGAA ACTTCCATGCTT TAAGTTGGTCCG
           .  A  I  D  M     A  E  I  L     T  L  W  P     R  L  Q  E     A  N  E  Q  .
     5161  TGCTATTGATAT GGCAGAGATACT GACGTTGTGGCC CAGACTGCAAGA GGCAAACGAACA
           ACGATAACTATA CCGTCTCTATGA CTGCAACACCGG GTCTGACGTTCT CCGTTTGCTTGT
           .  I  C  L  Y     A  L  G  E     T  M  D  N     I  R  S  K     C  P  V  N  .
     5221  GATATGCCTATA CGCGCTGGGCGA AACAATGGACAA CATCAGATCCAA ATGTCCGGTGAA
           CTATACGGATAT GCGCGACCCGCT TTGTTACCTGTT GTAGTCTAGGTT TACAGGCCACTT
           .  D  S  D  S     S  T  P  P     R  T  V  P     C  L  C  R     Y  A  M  T  .
     5281  CGATTCCGATTC ATCAACACCTCC CAGGACAGTGCC CTGCCTGTGCCG CTACGCAATGAC
           GCTAAGGCTAAG TAGTTGTGGAGG GTCCTGTCACGG GACGGACACGGC GATGCGTTACTG
           .  A  E  R  I     A  R  L  R     S  H  Q  V     K  S  M  V     C  S  S  .
     5341  AGCAGAACGGAT CGCCCGCCTTAG GTCACACCAAGT TAAAAGCATGGT GGTTTGCTCATC
           TCGTCTTGCCTA GCGGGCGGAATC CAGTGTGGTTCA ATTTTCGTACCA CCAAACGAGTAG
           .  F  P  L  P     K  Y  H  V     D  G  V  Q     K  V  K  C     E  K  V  L  .
     5401  TTTTCCCCTCCC GAAATACCATGT AGATGGGGTGCA GAAGGTAAAGTG CGAGAAGGTTCT
           AAAAGGGGAGGG CTTTATGGTACA TCTACCCCACGT CTTCCATTTCAC GCTCTTCCAAGA
           .  L  F  D  P     T  V  P  S     V  V  S  P     R  K  Y  A     S  T  T  .
     5461  CCTGTTCGACCC GACGGTACCTTC AGTGGTTAGTCC GCGGAAGTATGC CGCATCTACGAC
           GGACAAGCTGGG CTGCCATGGAAG TCACCAATCAGG CGCCTTCATACG GCGTAGATGCTG
           .  D  H  S  D     R  S  L  R     G  F  D  L     D  W  T  T     D  S  S  S  .
     5521  GGACCACTCAGA TCGGTCGTTACG AGGGTTTGACTT GGACTGGACCAC CGACTCGTCTTC
           CCTGGTGAGTCT AGCCAGCAATGC TCCCAAACTGAA CCTGACCTGGTG GCTGAGCAGAAG
           .  T  A  S  D     T  M  S  L     P  S  L  Q     S  C  D  I     D  S  I  Y  .
     5581  CACTGCCAGCGA TACCATGTCGCT ACCCAGTTTGCA GTCGTGTGACAT CGACTCGATCTA
           GTGACGGTCGCT ATGGTACAGCGA TGGGTCAAACGT CAGCACACTGTA GCTGAGCTAGAT
           .  E  P  M  A     P  I  V  V     T  A  D  V     H  P  E  P     A  G  I  A  .
     5641  CGAGCCAATGGC TCCCATAGTAGT GACGGCTGACGT ACACCCTGAACC CGCAGGCATCGC
           GCTCGGTTACCG AGGGTATCATCA CTGCCGACTGCA TGTGGGACTTGG GCGTCCGTAGCG
           .  D  L  A  A     D  V  H  P     E  P  A  D     H  V  D  L     E  N  P  I  .
     5701  GGACCTGGCGGC AGATGTGCACCC TGAACCCGCAGA CCATGTGGACCT CGAGAACCCGAT
           CCTGGACCGCCG TCTACACGTGGG ACTTGGGCGTCT GGTACACCTGGA GCTCTTGGGCTA
           .  P  P  P  R     P  K  R  A     A  Y  L  A     S  R  A  A     E  R  P  V  .
     5761  TCCTCCACCGCG CCCGAAGAGAGC TGCATACCTTGC CTCCCGCGCGGC GGAGCGACCGGT
           AGGAGGTGGCGC GGGCTTCTCTCG ACGTATGGAACG GAGGGCGCGCCG CCTCGCTGGCCA
           .  P  A  P  R     K  P  T  P     A  P  R  T     A  F  R  N     K  L  P  L  .
     5821  GCCGGCGCCGAG AAAGCCGACGCC TGCCCCAAGGAC TGCGTTTAGGAA CAAGCTGCCTTT
           CGGCCGCGGCTC TTTCGGCTGCGG ACGGGGTTCCTG ACGCAAATCCTT GTTCGACGGAAA
           .  T  F  G  D     F  D  E  H     E  V  D  A     L  A  S  G     I  T  F  G  .
     5881  GACGTTCGGCGA CTTTGACGAGCA CGAGGTCGATGC GTTGGCCTCCGG GATTACTTTCGG
           CTGCAAGCCGCT GAAACTGCTCGT GCTCCAGCTACG CAACCGGAGGCC CTAATGAAAGCC
           .  D  F  D  D     V  L  R  L     G  R  A  G     A  Y  I  F     S  S  D  T  .
     5941  AGACTTCGACGA CGTCCTGCGACT AGGCCGCGCGGG TGCATATATTTT CTCCTCGGACAC
           TCTGAAGCTGCT GCAGGACGCTGA TCCGGCGCGCCC ACGTATATAAAA GAGGAGCCTGTG
           .  G  S  G  H     L  Q  Q  K     S  V  R  Q     H  N  L  Q     C  A  Q  L  .
     6001  TGGCAGCGGACA TTTACAACAAAA ATCCGTTAGGCA GCACAATCTCCA GTGCGCACAACT
           ACCGTCGCCTGT AAATGTTGTTTT TAGGCAATCCGT CGTGTTAGAGGT CACGCGTGTTGA
           .  D  A  V  Q     E  E  K  M     Y  P  P  K     L  D  T  E     R  E  K  L  .
     6061  GGATGCGGTCCA GGAGGAGAAAAT GTACCCGCCAAA ATTGGATACTGA GAGGGAGAAGCT
           CCTACGCCAGGT CCTCCTCTTTTA CATGGGCGGTTT TAACCTATGACT CTCCCTCTTCGA
           .  L  L  L  K     M  Q  M  H     P  S  E  A     N  K  S  R     Y  Q  S  R  .
```

FIG. 17F.

```
6121  GTTGCTGCTGAA AATGCAGATGCA CCCATCGGAGGC TAATAAGAGTCG ATACCAGTCTCG
      CAACGACGACTT TTACGTCTACGT GGGTAGCCTCCG ATTATTCTCAGC TATGGTCAGAGC
      . K  V  E  N    M  K  A  T    V  V  D  R    L  T  S  G    A  R  L  Y .
6181  CAAAGTGGAGAA CATGAAAGCCAC GGTGGTGGACAG GCTCACATCGGG GGCCAGATTGTA
      GTTTCACCTCTT GTACTTTCGGTG CCACCACCTGTC CGAGTGTAGCCC CCGGTCTAACAT
      . T  G  A  D    V  G  R  I    P  T  Y  A    V  R  Y  P    R  P  V  Y .
6241  CACGGGAGCGGA CGTAGGCCGCAT ACCAACATACGC GGTTCGGTACCC CCGCCCCGTGTA
      GTGCCCTCGCCT GCATCCGGCGTA TGGTTGTATGCG CCAAGCCATGGG GGCGGGGCACAT
      . S  P  T  V    I  E  R  F    S  S  P  D    V  A  I  A    A  C  N  E .
6301  CTCCCCTACCGT GATCGAAAGATT CTCAAGCCCCGA TGTAGCAATCGC AGCGTGCAACGA
      GAGGGGATGGCA CTAGCTTTCTAA GAGTTCGGGGCT ACATCGTTAGCG TCGCACGTTGCT
      . Y  L  S  R    N  Y  P  T    V  A  S  Y    Q  I  T  D    E  Y  D  A .
6361  ATACCTATCCAG AAATTACCCAAC AGTGGCGTCGTA CCAGATAACAGA TGAATACGACGC
      TATGGATAGGTC TTTAATGGGTTG TCACCGCAGCAT GGTCTATTGTCT ACTTATGCTGCG
      . Y  L  D  M    V  D  G  S    D  S  C  L    D  R  A  T    F  C  P  A .
6421  ATACTTGGACAT GGTTGACGGGTC GGATAGTTGCTT GGACAGAGCGAC ATTCTGCCCGGC
      TATGAACCTGTA CCAACTGCCCAG CCTATCAACGAA CCTGTCTCGCTG TAAGACGGGCCG
      . K  L  R  C    Y  P  K  H    H  A  Y  H    Q  P  T  V    R  S  A  V .
6481  GAAGCTCCGGTG CTACCCGAAACA TCATGCGTACCA CCAGCCGACTGT ACGCAGTGCCGT
      CTTCGAGGCCAC GATGGGCTTTGT AGTACGCATGGT GGTCGGCTGACA TGCGTCACGGCA
      . P  S  P  F    Q  N  T  L    Q  N  V  L    A  A  A  T    K  R  N  C .
6541  CCCGTCACCCTT TCAGAACACACT ACAGAACGTGCT AGCGGCCGCCAC CAAGAGAAACTG
      GGGCAGTGGGAA AGTCTTGTGTGA TGTCTTGCACGA TCGCCGGCGGTG GTTCTCTTTGAC
      . N  V  T  Q    M  R  E  L    P  T  M  D    S  A  V  F    N  V  E  C .
6601  CAACGTCACGCA AATGCGAGAACT ACCCACCATGGA CTCGGCAGTGTT CAACGTGGAGTG
      GTTGCAGTGCGT TTACGCTCTTGA TGGGTGGTACCT GAGCCGTCACAA GTTGCACCTCAC
      . F  K  R  Y    A  C  S  G    E  Y  W  E    E  Y  A  K    Q  P  I  R .
6661  CTTCAAGCGCTA TGCCTGCTCCGG AGAATATTGGGA AGAATATGCTAA ACAACCTATCCG
      GAAGTTCGCGAT ACGGACGAGGCC TCTTATAACCCT TCTTATACGATT TGTTGGATAGGC
      . I  T  T  E    N  I  T  T    Y  V  T  L    K  G  P    K  A  A  A .
6721  GATAACCACTGA GAACATCACTAC CTATGTGACCAA ATTGAAAGGCCC GAAAGCTGCTGC
      CTATTGGTGACT CTTGTAGTGATG GATACACTGGTT TAACTTTCCGGG CTTTCGACGACG
      . L  F  A  K    T  H  N  L    V  P  L  Q    E  V  P  M    D  R  F  T .
6781  CTTGTTCGCTAA GACCCACAACTT GGTTCCGCTGCA GGAGGTTCCCAT GGACAGATTCAC
      GAACAAGCGATT CTGGGTGTTGAA CCAAGGCGACGT CCTCCAAGGGTA CCTGTCTAAGTG
      . V  D  M  K    R  D  V  K    V  T  P  G    T  K  H  T    E  E  R  P .
6841  GGTCGACATGAA ACGAGATGTCAA AGTCACTCCAGG GACGAAACACAC AGAGGAAAGACC
      CCAGCTGTACTT TGCTCTACAGTT TCAGTGAGGTCC CTGCTTTGTGT TCTCCTTTCTGG
      . K  V  Q  V    I  Q  A  A    E  P  L  A    T  A  Y  L    C  G  I  H .
6901  CAAAGTCCAGGT AATTCAAGCAGC GGAGCCATTGGC GACCGCTTACCT GTGCGGCATCCA
      GTTTCAGGTCCA TTAAGTTCGTCG CCTCGGTAACCG CTGGCGAATGGA CACGCCGTAGGT
      . R  E  L  V    R  R  L  N    A  V  L  R    P  N  V  H    T  L  F  D .
6961  CAGGGAATTAGT AAGGAGACTAAA TGCTGTGTTACG CCCTAACGTGCA CACATTGTTTGA
      GTCCCTTAATCA TTCCTCTGATTT ACGACACAATGC GGGATTGCACGT GTGTAACAAACT
      . M  S  A  E    D  F  D  A    I  I  A  S    H  F  H  P    G  D  P  V .
7021  TATGTCGGCCGA AGACTTTGACGC GATCATCGCCTC TCACTTCCACCC AGGAGACCCGGT
      ATACAGCCGGCT TCTGAAACTGCG CTAGTAGCGGAG AGTGAAGGTGGG TCCTCTGGGCCA
      . L  E  T  D    I  A  S  F    D  K  S  Q    D  D  S  L    A  L  T  G .
7081  TCTAGAGACGGA CATTGCATCATT CGACAAAGCCA GGACGACTCCTT GGCTCTTACAGG
      AGATCTCTGCCT GTAACGTAGTAA GCTGTTTCGGT CCTGCTGAGGAA CCGAGAATGTCC
      . L  M  I  L    E  D  L  G    V  D  Q  Y    L  L  D  L    I  E  A  A .
7141  TTTAATGATCCT CGAAGATCTAGG GGTGGATCAGTA CCTGCTGGACTT GATCGAGGCAGC
      AAATTACTAGGA GCTTCTAGATCC CCACCTAGTCAT GGACGACCTGAA CTAGCTCCGTCG
      . F  G  E  I    S  S  C  H    L  P  T  G    T  R  F  K    F  G  A  M .
7201  CTTTGGGGAAAT ATCCAGCTGTCA CCTACCAACTGG CACGCGCTTCAA GTTCGGAGCTAT
      GAAACCCCTTTA TAGGTCGACAGT GGATGGTTGACC GTGCGCGAAGTT CAAGCCTCGATA
      . M  K  S  G    M  F  L  T    L  F  I  N    T  V  L  N    I  T  I  A .
7261  GATGAAATCGGG CATGTTTCTGAC TTTGTTTATTAA CACTGTTTTGAA CATCACCATAGC
      CTACTTTAGCCC GTACAAAGACTG AAACAAATAATT GTGACAAAACTT GTAGTGGTATCG
      . S  R  V  L    E  Q  R  L    T  D  S  A    C  A  A  F    I  G  D  D .
7321  AAGCAGGGTACT GGAGCAGAGACT CACTGACTCCGC CTGTGCGGCCTT CATCGGCGACGA
```

FIG. 17G.

```
             TTCGTCCCATGA CCTCGTCTCTGA GTGACTGAGGCG GACACGCCGGAA GTAGCCGCTGCT
            .  N   I   V   H     G   V   I   S     D   K   L   M     A   E   R   C     A   S   W   V  ·
      7381   CAACATCGTTCA CGGAGTGATCTC CGACAAGCTGAT GGCGGAGAGGTG CGCGTCGTGGGT
             GTTGTAGCAAGT GCCTCACTAGAG GCTGTTCGACTA CCGCCTCTCCAC GCGCAGCACCCA
            .  N   M   E   V     K   I   I   D     A   V   M   G     E   K   P   P     Y   F   C   G  ·
      7441   CAACATGGAGGT GAAGATCATTGA CGCTGTCATGGG CGAAAAACCCCC ATATTTCTGTGG
             GTTGTACCTCCA CTTCTAGTAACT GCGACAGTACCC GCTTTTTGGGGG TATAAAGACACC
            .  G   F   I   V     F   D   S   V     T   Q   T   A     C   R   V   S     D   P   L   K  ·
      7501   GGGATTCATAGT TTTTGACAGCGT CACACAGACCGC CTGCCGTGTTTC AGACCCACTTAA
             CCCTAAGTATCA AAAACTGTCGCA GTGTGTCTGGCG GACGGCACAAAG TCTGGGTGAATT
            .  R   L   F   K     L   G   K   P     L   T   A   E     D   K   Q   D     E   D   R   R  ·
      7561   GCGCCTGTTCAA GTTGGGTAAGCC GCTAACAGCTGA AGACAAGCAGGA CGAAGACAGGCG
             CGCGGACAAGTT CAACCCATTCGG CGATTGTCGACT TCTGTTCGTCCT GCTTCTGTCCGC
            .  R   A   L   S     D   E   V   S     K   W   F   R     T   G   L     A   E   L   E  ·
      7621   ACGAGCACTGAG TGACGAGGTTAG CAAGTGGTTCCG GACAGGCTTGGG GGCCGAACTGGA
             TGCTCGTGACTC ACTGCTCCAATC GTTCACCAAGGC CTGTCCGAACCC CCGGCTTGACCT
            .  V   A   L   T     S   R   Y   E     V   E   G   C     K   S   I   L     I   A   M  A  ·
      7681   GGTGGCACTAAC ATCTAGGTATGA GGTAGAGGGCTG CAAAAGTATCCT CATAGCCATGGC
             CCACCGTGATTG TAGATCCATACT CCATCTCCCGAC GTTTTCATAGGA GTATCGGTACCG
            .  T   L   A   R     D   I   K     A     F   K   K   L     R   G   P   V     I   H   L   Y  ·
      7741   CACCTTGGCGAG GGACATTAAGGC GTTTAAGAAATT GAGAGGACCTGT TATACACCTCTA
             GTGGAACCGCTC CCTGTAATTCCG CAAATTCTTTAA CTCTCCTGGACA ATATGTGGAGAT
```

```
                                                                   PacI          PmeI
                                                                  ~~~~~~~~~
            .  G   G   P   R     L   V   R   *
      7801   CGGCGGTCCTAG ATTGGTGCGTTA ATACACAGAATT CTGATTTTAATT AACCTGCAGGGT
             GCCGCCAGGATC TAACCACGCAAT TATGTGTCTTAA GACTAAAATTAA TTGGACGTCCCA
             PmeI
             ~~~~~~
      7861   TTAAACTAATTA ATTGAATTACAT CCCTACGCAAAC GTTTTACGGCCG CCGGTGGCGCCC
             AATTTGATTAAT TAACTTAATGTA GGGATGCGTTTG CAAAATGCCGGC GGCCACCGCGGG
      7921   GCGCCCGGCGGC CCGTCCTTGGCC GTTGCAGGCCAC TCCGGTGGCTCC CGTCGTCCCCGA
             CGCGGGCCGCCG GGCAGGAACCGG CAACGTCCGGTG AGGCCACCGAGG GCAGCAGGGGCT
      7981   CTTCCAGGCCCA GCAGATGCAGCA ACTCATCAGCGC CGTAAATGCGCT GACAATGAGACA
             GAAGGTCCGGGT CGTCTACGTCGT TGAGTAGTCGCG GCATTTACGCGA CTGTTACTCTGT
      8041   GAACGCAATTGC TCCTGCTAGGCC TCCCAAACCAAA GAAGAAGAAGAC AACCAAACCAAA
             CTTGCGTTAACG AGGACGATCCGG AGGGTTTGGTTT CTTCTTCTTCTG TTGGTTTGGTTT
      8101   GCCGAAAACGCA GCCCAAGAAGAT CAACGGAAAAAC GCAGCAGCAAAA GAAGAAAGACAA
             CGGCTTTTGCGT CGGGTTCTTCTA GTTGCCTTTTTG CGTCGTCGTTTT CTTCTTTCTGTT
      8161   GCAAGCCGACAA GAAGAAGAAGAA ACCCGGAAAAAG AGAAAGAATGTG CATGAAGATTGA
             CGTTCGGCTGTT CTTCTTCTTCTT TGGGCCTTTTTC TCTTTCTTACAC GTACTTCTAACT
      8221   AAATGACTGTAT CTTCGTATGCGC CTAGCCACAGTA ACGTAGTGTTTC CAGACATGTCAGG
             TTTACTGACATA GAAGCATACGCC GATCGGTGTCAT TGCATCACAAAG GTCTGTACAGCC
      8281   GCACCGCACTAT CATGGGTGCAGA AAATCTCGGGTG GTCTGGGGGCCT TCGCAATCGGCG
             CGTGGCGTGATA GTACCCACGTCT TTTAGAGCCCAC CAGACCCCCGGA AGCGTTAGCCGC
      8341   CTATCCTGGTGC TGGTTGTGGTCA CTTGCATTGGGC TCCGCAGATAAG TTAGGGTAGGCA
             GATAGGACCACG ACCAACACCAGT GAACGTAACCCG AGGCGTCTATTC AATCCCATCCGT
      8401   ATGGCATTGATA TAGCAAGAAAAT TGAAAACAGAAA AAGTTAGGGTAA GCAATGGCATAT
             TACCGTAACTAT ATCGTTCTTTTA ACTTTTGTCTTT TTCAATCCCATT CGTTACCGTATA
      8461   AACCATAACTGT ATAACTTGTAAC AAAGCGCAACAA GACCTGCGCAAT TGGCCCCGTGGT
             TTGGTATTGACA TATTGAACATTG TTTCGCGTTGTT CTGGACGCGTTA ACCGGGGCACCA
      8521   CCGCCTCACGGA AACTCGGGGCAA CTCATATTGACA CATTAATTGGCA ATAATTGGAAGC
             GGCGGAGTGCCT TTGAGCCCCGTT GAGTATAACTGT GTAATTAACCGT TATTAACCTTCG
      8581   TTACATAAGCTT AATTCGACGAAT AATTGGATTTAT ATTTTATTTTGC AATTGGTTTTTA
             AATGTATTCGAA TTAAGCTGCTTA TTAACCTAAATA TAAAATAAAACG TTAACCAAAAAT
      8641   ATATTTCCAAAA AAAAAAAAAAAA AAAAAAAAAAAA AAAAAAAAAAAA AAAAAAAAAAAA
```

FIG. 17H.

```
          TATAAAGGTTTT TTTTTTTTTTTT TTTTTTTTTTTT TTTTTTTTTTTT TTTTTTTTTTTT
8701      AAAAAAAAAAAA AAAAACGGGTCG GCATGGCATCTC CACCTCCTCGCG GTCCGACCTGGG
          TTTTTTTTTTTT TTTTGCCCAGC CGTACCGTAGAG GTGGAGGAGCGC CAGGCTGGACCC
                                                              C6R⇒
8761      CATCCGAAGGAG GACGCACGTCCA CTCGGATGGCTA AGGGAGTTTTTC TACTAGTCAAAT
          GTAGGCTTCCTC CTGCGTGCAGGT GAGCCTACCGAT TCCCTCAAAAAG ATGATCAGTTTA
8821      GAGTATATATAA TTGAAAAGTAA AATATAAATCAT ATAATAATGAAA CGAAATATCAGT
          CTCATATATATT AACTTTTTCATT TTATATTTAGTA TATTATTACTTT GCTTTATAGTCA
8881      AATAGACAGGAA CTGGCAGATTCT TCTTCTAATGAA GTAAGTACTGCT AAATCTCCAAAA
          TTATCTGTCCTT GACCGTCTAAGA AGAAGATTACTT CATTCATGACGA TTTAGAGGTTTT
8941      TTAGATAAAAAT GATACAGCAAAT ACAGCTTCATTC AACGAATTACCT TTTAATTTTTC
          AATCTATTTTA CTATGTCGTTTA TGTCGAAGTAAG TTGCTTAATGGA AAATTAAAAAG
9001      AGACACACCTTA TTACAAACTAAC TAAGTCAGATGA TGAGAAAGTAAA TATAAATTTAAC
          TCTGTGTGGAAT AATGTTTGATTG ATTCAGTCTACT ACTCTTTCATTT ATATTTAAATTG
9061      TTATGGGTAAA TATAATAAAGAT TCATGATATTAA TAATTTACTTAA CGATGTTAATAG
          AATACCCATATT ATATTATTTCTA AGTACTATAATT ATTAAATGAATT GCTACAATTATC
9121      ACTTATTCCATC AACCCCTTCAAA CCTTTCTGGATA TTATAAAATACC AGTTAATGATAT
          TGAATAAGGTAG TTGGGGAAGTTT GGAAAGACCTAT AATATTTTATGG TCAATTACTATA
9181      TAAAATAGATTG TTTAAGAGATGT AAATAATTATTT GGAGGTAAAGGA TATAAAATTAGT
          ATTTTATCTAAC AAATTCTCTACA TTTATTAATAAA CCTCCATTTCCT ATATTTAATCA
9241      CTATCTTTCACA TGGAAATGAATT ACCTAATATTAA TAATTATGATAG GAATTTTTTAGG
          GATAGAAAGTGT ACCTTTACTTAA TGGATTATAATT ATTAATACTATC CTTAAAAAATCC
9301      ATTTACAGCTGT TATATGTATCAA CAATACAGGCAG ATCTATGGTTAT GGTAAAACACTG
          TAAATGTCGACA ATATACATAGTT GTTATGTCCGTC TAGATACCAATA CCATTTTGTGAC
9361      TAACGGGAAGCA GCATTCTATGGT AACTGGCCTATG TTTAATAGCCAG ATCATTTTACTC
          ATTGCCCTTCGT CGTAAGATACCA TTGACCGGATAC AAATTATCGGTC TAGTAAAATGAG
9421      TATAAACATTTT ACCACAAATAAT AGGATCCTCTAG ATATTTAATATT ATATCTAACAAC
          ATATTTGTAAAA TGGTGTTTATTA TCCTAGGAGATC TATAAATTATAA TATAGATTGTTG
9481      AACAAAAAATT TAACGATGTATG GCCAGAAGTATT TTCTACTAATAA AGATAAAGATAG
          TTGTTTTTTAA ATTGCTACATAC CGGTCTTCATAA AAGATGATTATT TCTATTTCTATC
9541      TCTATCTTATCT ACAAGATATGAA AGAAGATAATCA TTTAGTAGTAGC TACTAATATGGA
          AGATAGAATAGA TGTTCTATACTT TCTTCTATTAGT AAATCATCATCG ATGATTATACCT
9601      AAGAAATGTATA CAAAAACGTGGA AGCTTTTATATT AAATAGCATATT ACTAGAAGATTT
          TTCTTTACATAT GTTTTTGCACCT TCGAAATATAAA TTTATCGTATAA TGATCTTCTAAA
9661      AAAATCTAGACT TAGTATAACAAA ACAGTTAAATGC CAATATCGATTC TATATTTCATCA
          TTTTAGATCTGA ATCATATTGTTT TGTCAATTTACG GTTATAGCTAAG ATATAAAGTAGT
9721      TAACAGTAGTAC ATTAATCAGTGA TATACTGAAACG ATCTACAGACTC AACTATGCAAGG
          ATTGTCATCATG TAATTAGTCACT ATATGACTTTGC TAGATGTCTGAG TTGATACGTTCC
9781      AATAAGCAATAT GCCAATTATGTC TAATATTTTAAC TTTAGAACTAAA ACGTTCTACCAA
          TTATTCGTTATA CGGTTAATACAG ATTATAAAATTG AAATCTTGATTT TGCAAGATGGTT
9841      TACTAAAAATAG GATACGTGATAG GCTGTTAAAAGC TGCAATAAATAG TAAGGATGTAGA
          ATGATTTTTATC CTATGCACTATC CGACAATTTTCG ACGTTATTTATC ATTCCTACATCT
9901      AGAAATACTTTG TTCTATACCTTC GGAGGAAAGAAC TTTAGAACAACT TAAGTTTAATCA
          TCTTTATGAAAC AAGATATGGAAG CCTCCTTTCTTG AAATCTTGTTGA ATTCAAATTAGT
9961      AACTTGTATTTA TGAAGGTAC
          TTGAACATAAAT ACTTCCATG
```

FIG. 18.
An illustration of the ALVAC-SFV Leu713Ala C6 donor plasmid containing two 26S promoters.
pJY C6 SFV L713A 2

Construction scheme for an ALVAC C6 donor plasmid containing SFV Leu713Ala/FIV gag-pro under the control of H6 promoter FIG. 19B.
Construction scheme for an ALVAC C6 donor plasmid containing
SFV Leu713Ala/FIV gag-pro under the control of H6 promoter FIG. 19C.
Oligonucleotide primers for construction of an ALAVC C6 donor
plasmid containing SFV Leu713Ala/FIV gag-pro

```
Primers for amplification of FIV gag-pro

Pac 1         FIV gag
8330JY  5'  GG TTAATTAA  ATG GGG AAT GGA CAG GGG CGA
                          M   G   N   G   Q   G   R Pme I         FIV pro
8331JY  5'  GG GTTTAAAC  TTA CAT TAC TAA CCT AAT ATT GAA
                         AAT GTA ATG ATT GGA TTA TAA CTT   5'
                          *   M   V   L   R   I   N   F Primer for mutation of T5NT located at FIV pro TTTTTAT
              EcoRV                         ▼
8332JY  5'  AAT GGATATC CT ATA AAA   TTCTTAT   TA GAT ACA GGA

GCA
```

A schematic illustration of pC6 ALVAC H6p-SFV Leu713Ala/FIV gag-pro donor plasmid (pJY654.1).

FIG. 21.
Generation of an ALVAC-SFV Leu713Ala chimera expressing FIV gag-pro (vCP2092)

Construction scheme for SFV nsP2 Arg650Asp/FIV gag-pro

FIG. 22B.
Construction scheme for SFV nsP2 Arg650Asp/FIV gag-pro

Construction scheme for SFV nsP2 Ser259Pro/FIV gag-pro

Construction scheme for SFV nsP2 Ser259Pro/FIV gag-pro

FIG. 22E.
Oligonucleotide primers for construction of SFV nsP2 Arg650Asp/FIV gag-pro
and SFV nsP2 Ser259Pro/FIV gag-pro.

Primers for PCR amplification of a Kpn I DNA fragment containing Arg650Asp mutation

```
                    Kpn I  H   V   L   L   V   S   E   Y   N
8267JY  5' AGA G GGTACC AC GTC CTG CTG GTG AGT GAG TAC AAC

L   A   L   P   R   R   D   V   T   W   L   S
  CTG GCT TTG CCT CGA CGC GAC GTC ACT TGG TTG TCA

8286JY  5' TCG TAA CGA CCG ATC TGA GTG GTC CGT CGT AGA TGC
```

Primers for site-directed mutagenesis to change Ser259 to Pro

```
                V   D   E   A   F   A   C   H   P   G   T   L
8265JY  5' GTG GAC GAG GCT TTC GCT TGC CAT CCC GGT ACT CTG
           CAC CTG CTC CGA AAG CGA ACG GTA GGG CCA TGA GAC

L   A   L   I   A
  CTG GCC CTA ATT GCT
  GAC CGG GAT TAA CGA  5'  8266JY
```

FIG. 23.

Immunoblot analysis of the protein expression from SFV Arg650Asp mutant and SFV Ser259Pro mutant in BHK-21 cells.

1. nsP2 SFV Arg650Asp-FIV gag-pro
2. nsP2 SFV Ser259Pro-FIV gag-pro
3. Wild type SFV-FIV gag-pro FIG. 24A.
Construction scheme for an ALVAC C6 donor plasmid containing SFV Arg650Asp/FIV gag-pro or SFV Ser259Pro/FIV gag-pro under the control of H6 promoter.

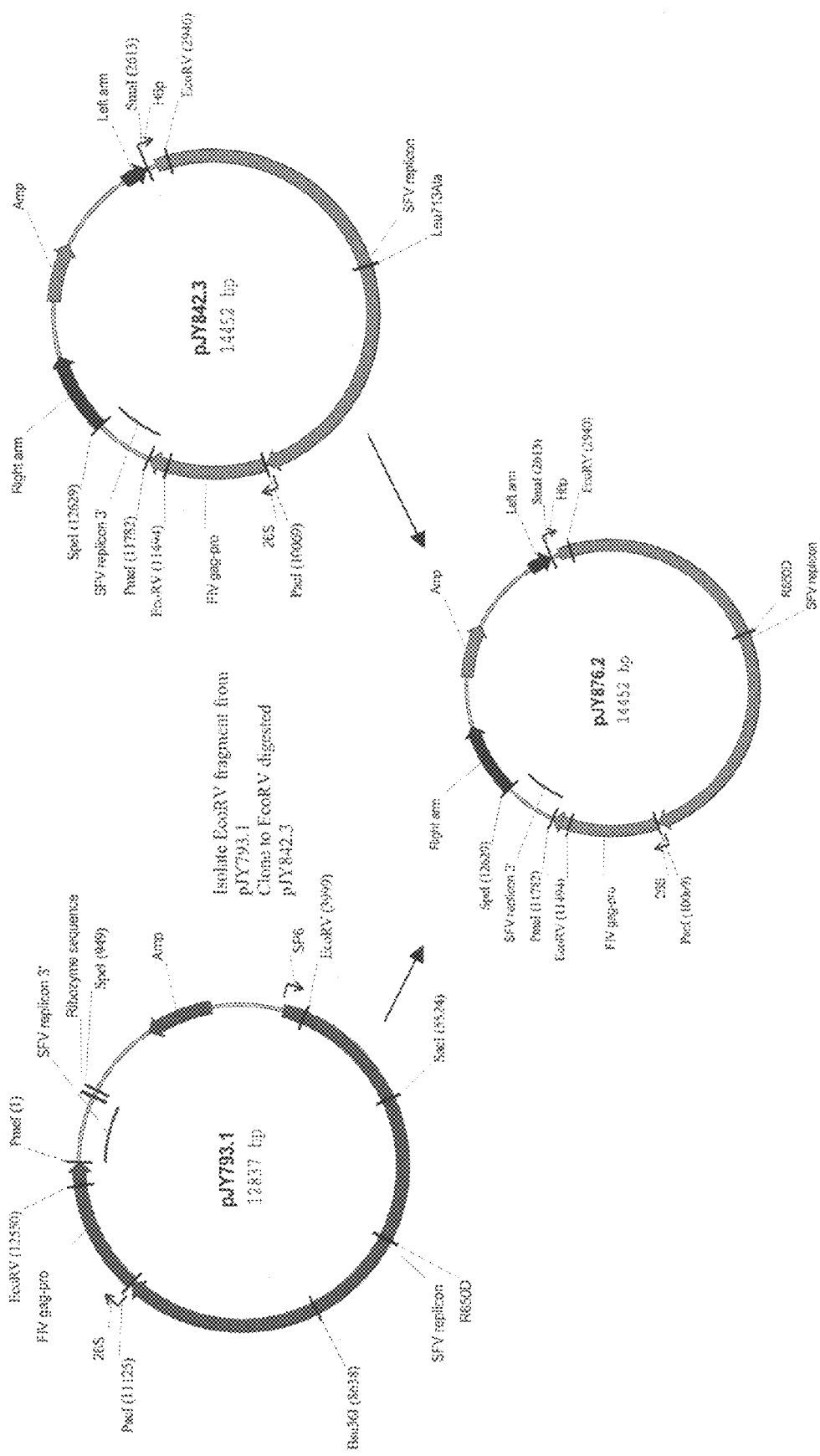
FIG. 24B. Construction scheme for an ALVAC C6 donor plasmid containing SFV Arg650Asp/FIV gag-pro or SFV Ser25s Construction scheme for an ALVAC C6 donor plasmid containing SFV Arg650Asp/FIV g

FIG. 24D.

Oligonucleotide primers for construction of an ALVAC C6 donor plasmid containing SFV Arg650Asp/FIV gag-pro or SFV Ser259Pro/FIV gag-pro under the control of H6 promoter.

```
8281JY  5'  TAA TAC ACA GAA TTC TGA TTG

SpeI
8260JY  5'  CAG ACTAGT AGA AAA ATTTTTTTTTTTTTTTT
```

Construction scheme for an ALVAC C6 donor plasmid containing SFV Arg650Asp/FIV gag-pro under the control of a mutant H6 promoter.

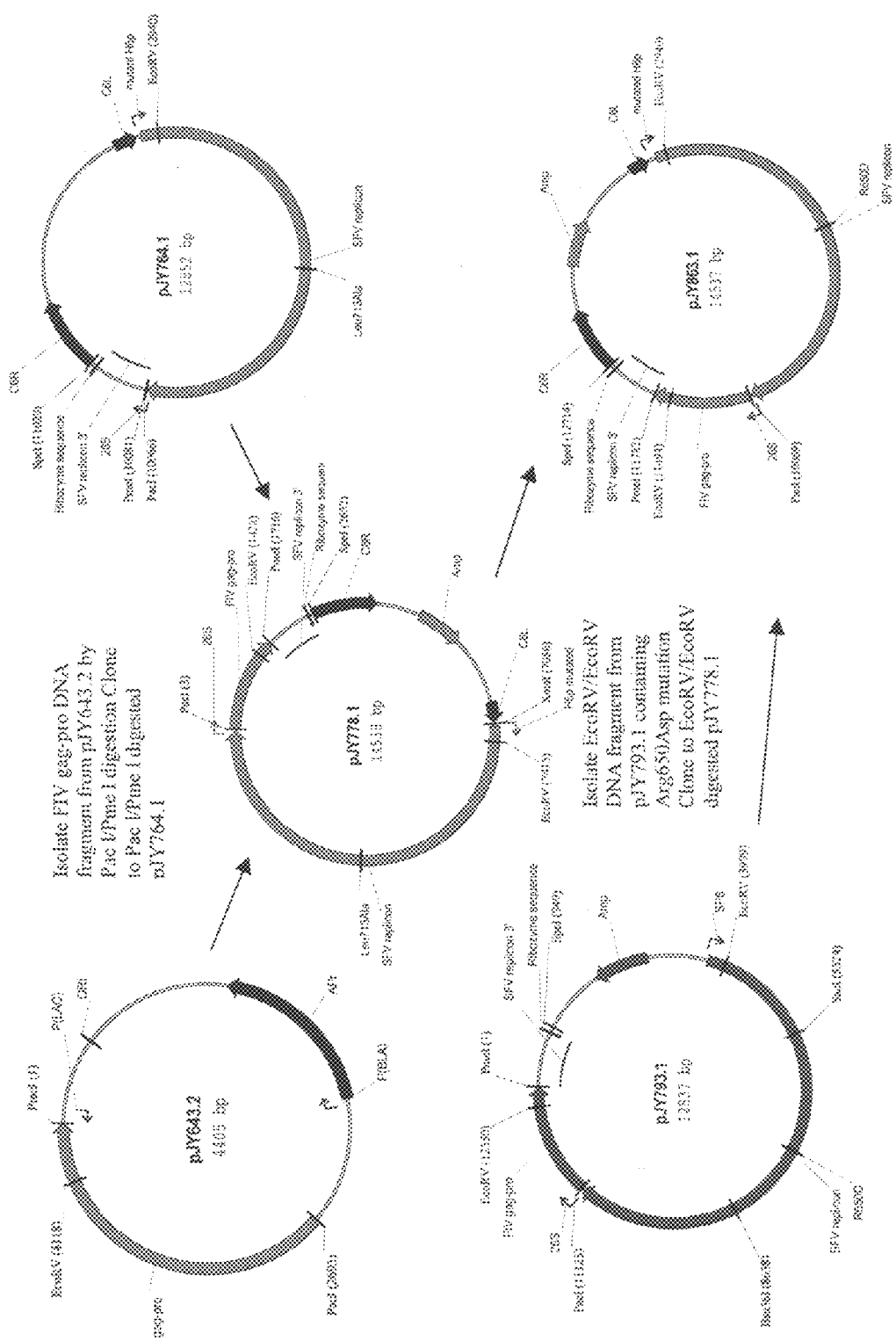
Construction scheme for an ALVAC C6 donor plasmid containing SFV Arg650Asp/FIV gag-pro under the control of a mutant H6 promoter.

FIG. 25C.
Oligonucleotide primers for construction of an ALVAC C6 donor plasmid containing SFV Arg650Asp/FIV gag-pro under the control of a mutant H6 promoter.

H6 early promoter    5' AAAAAGTG A AAATAAATACAAAGGTTCTTGA
                                 ↓
Mutant H6 promoter   5' AAAAAGTG C AAATAAATACAAAGGTTCTTGA SmaI                    mutated H6 promoter
        8424JY   5' AA CCC GGG TTCTTTATTCTATACTTAAAAAGTG c
                             AAATAAATACAAAggt EcoRV
        8280JY   5' GCG TAC ACT AGT GCC GAT ATC CAA GAT GAG TGT GTC TTT GTC FIG. 26A.
Construction scheme for an ALVAC C6 donor plasmid containing SFV Arg650Asp + Ser259Pro/FIV gag-pro under the control of a mutant H6 promoter.

Construction scheme for an ALVAC C6 donor plasmid containing SFV Arg650Asp+Ser259P A schematic illustration of pC6 ALVAC mutant H6p-SFV R650D+S259P/FIV gag-pro donor plasmid (pJY1099.1)

FIG. 28A.
Nucleotide sequences of pC6 mutant H6p-SFV R650D+S259P/FIV gag-pro (pJY1099.1)

```
                                      C6 left arm
   1    CTATCAAAAG TCTTAATGAG TTAGGTGTAG ATAGTATAGA TATTACTACA AAGGTATTCA
        GATAGTTTTC AGAATTACTC AATCCACATC TATCATATCT ATAATGATGT TTCCATAAGT
  61    TATTTCCTAT CAATTCTAAA GTAGATGATA TTAATAACTC AAAGATGATG ATAGTAGATA
        ATAAAGGATA GTTAAGATTT CATCTACTAT AATTATTGAG TTTCTACTAC TATCATCTAT
 121    ATAGATACGC TCATATAATG ACTGCAAATT GGACGGTTC ACATTTTAAT CATCACGCGT
        TATCTATGCG AGTATATTAC TGACGTTTAA ACCTGCCAAG TGTAAAATTA GTAGTGCGCA
 181    TCATAAGTTT CAACTGCATA GATCAAAATC TCACTAAAAA GATAGCCGAT GTATTTGAGA
        AGTATTCAAA GTTGACGTAT CTAGTTTTAG AGTGATTTTT CTATCGGCTA CATAAACTCT
 241    GAGATTGGAC ATCTAACTAC GCTAAAGAAA TTACAGTTAT AAATAATACA TAATGGATTT
        CTCTAACCTG TAGATTGATG CGATTTCTTT AATGTCAATA TTTATTATGT ATTACCTAAA
 301    TGTTATCATC AGTTATATTT AACATAAGTA CAATAAAAAG TATTAAATAA AAATACTTAC
        ACAATAGTAG TCAATATAAA TTGTATTCAT GTTATTTTTC ATAATTTATT TTTATGAATG
                                                Mutant H6 promoter
 361    TTACGAAAAA ATGACTAATT AGCTATAAAA ACCCGGGTTC TTTATTCTAT ACTTAAAAAG
        AATGCTTTTT TACTGATTAA TCGATATTTT TGGGCCCAAG AAATAAGATA TGAATTTTTC
                                      SFV replicon
 421    TGCAAATAAA TACAAAGGTT CTTGATGGCG GATGTGTGAC ATACACGACG CCAAAAGATT
        ACGTTTATTT ATGTTTCCAA GAACTACCGC CTACACACTG TATGTGCTGC GGTTTTCTAA
                                                                       M  A  A  K ·
 481    TTGTTCCAGC TCCTGCCACC TCCGCTACGC GAGAGATTAA CCACCCACGA TGGCCGCCAA
        AACAAGGTCG AGGACGGTGG AGGCGATGCG CTCTCTAATT GGTGGGTGCT ACCGGCGGTT
        · V  H  V   D  I  E    A  D  S    P  F  I   K  S  L    Q  K  A   F  P  ·
 541    AGTGCATGTT GATATTGAGG CTGACAGCCC ATTCATCAAG TCTTTGCAGA AGGCATTTCC
        TCACGTACAA CTATAACTCC GACTGTCGGG TAAGTAGTTC AGAAACGTCT TCCGTAAAGG
        · S  F  E   V  E  S    L  Q  V    T  P  N   D  H  A    N  A  R   A  F  ·
 601    GTCGTTCGAG GTGGAGTCAT TGCAGGTCAC ACCAAATGAC CATGCAAATG CCAGAGCATT
        CAGCAAGCTC CACCTCAGTA ACGTCCAGTG TGGTTTACTG GTACGTTTAC GGTCTCGTAA
        · S  H  L   A  T  K    L  I  E    Q  E  T   D  K  D    T  L  I   L  D  ·
 661    TTCGCACCTG GCTACCAAAT TGATCGAGCA GGAGACTGAC AAAGACACAC TCATCTTGGA
        AAGCGTGGAC CGATGGTTTA ACTAGCTCGT CCTCTGACTG TTTCTGTGTG AGTAGAACCT
        · I  G  S   A  P  S    R  R  M    M  S  T   H  K  Y    H  C  V   C  P  ·
 721    TATCGGCAGT GCGCCTTCCA GGAGAATGAT GTCTACGCAC AAATACCACT GCGTATGCCC
        ATAGCCGTCA CGCGGAAGGT CCTCTTACTA CAGATGCGTG TTTATGGTGA CGCATACGGG
        · M  R  S   A  E  D    P  E  R    L  V  C   Y  A  K    K  L  A   A  A  ·
 781    TATGCGCAGC GCAGAAGACC CCGAAAGGCT CGTATGCTAC GCAAAGAAAC TGGCAGCGGC
        ATACGCGTCG CGTCTTCTGG GGCTTTCCGA GCATACGATG CGTTTCTTTG ACCGTCGCCG
        · S  G  K   V  L  D    R  E  I    A  G  K   I  T  D    L  Q  T   V  M  ·
 841    CTCCGGGAAG GTGCTGGATA GAGAGATCGC AGGAAAAATC ACCGACCTGC AGACCGTCAT
        GAGGCCCTTC CACGACCTAT CTCTCTAGCG TCCTTTTTAG TGGCTGGACG TCTGGCAGTA
        · A  T  P   D  A  E    S  P  T    F  C  L   H  T  D    V  T  C   R  T  ·
 901    GGCTACGCCA GACGCTGAAT CTCCTACCTT TTGCCTGCAT ACAGACGTCA CGTGTCGTAC
        CCGATGCGGT CTGCGACTTA GAGGATGGAA AACGGACGTA TGTCTGCAGT GCACAGCATG
        · A  A  E   V  A  V    Y  Q  D    V  Y  A   V  H  A    P  T  S   L  Y  ·
 961    GGCAGCCGAA GTGGCCGTAT ACCAGGACGT GTATGCTGTA CATGCACCAA CATCGCTGTA
        CCGTCGGCTT CACCGGCATA TGGTCCTGCA CATACGACAT GTACGTGGTT GTAGCGACAT
        · H  Q  A   M  K  G    V  R  T    A  Y  W   I  G  F    D  T  T   P  F  ·
1021    CCATCAGGCA ATGAAAGGTG TCAGAACGGC TTATTGGATT GGGTTTGACA CCACCCCGTT
        GGTAGTCCGT TACTTTCCAC AGTCTTGCCG AATAACCTAA CCCAAACTGT GGTGGGGCAA
        · M  F  D   A  L  A    G  A  Y    P  T  Y   A  T  N    W  A  D   E  Q  ·
1081    TATGTTTGAC GCGCTAGCAG GCGCGTATCC AACCTACGCC ACAAACTGGG CCGACGAGCA
        ATACAAACTG CGCGATCGTC CGCGCATAGG TTGGATGCGG TGTTTGACCC GGCTGCTCGT
        · V  L  Q   A  R  N    I  G  L    C  A  A   S  L  T    E  G  R   L  G  ·
1141    GGTGTTACAG GCCAGGAACA TAGGACTGTG TGCAGCATCC TTGACTGAGG GAAGACTCGG
        CCACAATGTC CGGTCCTTGT ATCCTGACAC ACGTCGTAGG AACTGACTCC CTTCTGAGCC
        · K  L  S   I  L  R    K  K  Q    L  K  P   C  D  T    V  M  F   S  V  ·
```

FIG. 28B.

```
1201   CAAACTGTCC ATTCTCCGCA AGAAGCAATT GAAACCTTGC GACACAGTCA TGTTCTCGGT
       GTTTGACAGG TAAGAGGCGT TCTTCGTTAA CTTTGGAACG CTGTGTCAGT ACAAGAGCCA
       . G  S  T    L  Y  T  E    S  R  K    L  L  R    S  W  H    P  S  V  ·
1261   AGGATCTACA TTGTACACTG AGAGCAGAAA GCTACTGAGG AGCTGGCACT TACCCTCCGT
       TCCTAGATGT AACATGTGAC TCTCGTCTTT CGATGACTCC TCGACCGTGA ATGGGAGGCA
       . F  H  L    K  G  K  Q    S  F  T    C  R  C    D  T  I  V    S  C  E  ·
1321   ATTCCACCTG AAAGGTAAAC AATCCTTTAC CTGTAGGTGC GATACCATCG TATCATGTGA
       TAAGGTGGAC TTTCCATTTG TTAGGAAATG GACATCCACG CTATGGTAGC ATAGTACACT
       . G  Y  V    V  K  K  I    T  M  C    P  G  L    Y  G  K    T  V  G  Y ·
1381   AGGGTACGTA GTTAAGAAAA TCACTATGTG CCCCGGCCTG TACGGTAAAA CGGTAGGGTA
       TCCCATGCAT CAATTCTTTT AGTGATACAC GGGGCCGGAC ATGCCATTTT GCCATCCCAT
       . A  V  T    Y  H  A  E    G  F  L    V  C  K    T  T  D  T    V  K  G ·
1441   CGCCGTGACG TATCACGCGG AGGGATTCCT AGTGTGCAAG ACCACAGACA CTGTCAAAGG
       GCGGCACTGC ATAGTGCGCC TCCCTAAGGA TCACACGTTC TGGTGTCTGT GACAGTTTCC
       . E  R  V    S  F  P  V    C  T  Y    V  P  S    T  I  C  D    Q  M  T ·
1501   AGAAAGAGTC TCATTCCCTG TATGCACCTA CGTCCCCTCA ACCATCTGTG ATCAAATGAC
       TCTTTCTCAG AGTAAGGGAC ATACGTGGAT GCAGGGGAGT TGGTAGACAC TAGTTTACTG
       . G  I  L    A  T  D  V    T  P  E    D  A  Q    K  L  L  V    G  L  N ·
1561   TGGCATACTA GCGACCGACG TCACACCGGA GGACGCACAG AAGTTGTTAG TGGGATTGAA
       ACCGTATGAT CGCTGGCTGC AGTGTGGCCT CCTGCGTGTC TTCAACAATC ACCCTAACTT
       . Q  R  I    V  V  N  G    R  T  Q    R  N  T    N  T  M  K    N  Y  L ·
1621   TCAGAGGATA GTTGTGAACG GAAGAACACA GCGAAACACT AACACGATGA AGAACTATCT
       AGTCTCCTAT CAACACTTGC CTTCTTGTGT CGCTTTGTGA TTGTGCTACT TCTTGATAGA
       . L  P  I    V  A  V  A    F  S  K    W  A  R    E  Y  K  A    D  L  D ·
1681   GCTTCCGATT GTGGCCGTCG CATTTAGCAA GTGGGCGAGG GAATACAAGG CAGACCTTGA
       CGAAGGCTAA CACCGGCAGC GTAAATCGTT CACCCGCTCC CTTATGTTCC GTCTGGAACT
       . D  E  K    P  L  G  V    R  E  R    S  L  T    C  C  C  L    W  A  F ·
1741   TGATGAAAAA CCTCTGGGTG TCCGAGAGAG GTCACTTACT TGCTGCTGCT TGTGGGCATT
       ACTACTTTTT GGAGACCCAC AGGCTCTCTC CAGTGAATGA ACGACGACGA ACACCCGTAA
       . K  T  R    K  M  H  T    M  Y  K    K  P  D    T  Q  T  I    V  K  V ·
1801   TAAAACGAGG AAGATGCACA CCATGTACAA GAAACCAGAC ACCCAGACAA TAGTGAAGGT
       ATTTTGCTCC TTCTACGTGT GGTACATGTT CTTTGGTCTG TGGGTCTGTT ATCACTTCCA
       . P  S  E    F  N  S  F    V  I  P    S  L  W    S  T  G    L  A  I  P ·
1861   GCCTTCAGAG TTTAACTCGT TCGTCATCCC GAGCCTATGG TCTACAGGCC TCGCAATCCC
       CGGAAGTCTC AAATTGAGCA AGCAGTAGGG CTCGGATACC AGATGTCCGG AGCGTTAGGG
       . V  R  S    R  I  K  M    L  L  A    K  K  T    K  R  E  L    I  P  V ·
1921   AGTCAGATCA CGCATTAAGA TGCTTTTGGC CAAGAAGACC AAGCGAGAGT TAATACCTGT
       TCAGTCTAGT GCGTAATTCT ACGAAAACCG GTTCTTCTGG TTCGCTCTCA ATTATGGACA
       . L  D  A    S  S  A  R    D  A  E    Q  E  E    K  E  R  L    E  A  E ·
1981   TCTCGACGCG TCGTCAGCCA GGGATGCTGA ACAAGAGGAG AAGGAGAGGT TGGAGGCCGA
       AGAGCTGCGC AGCAGTCGGT CCCTACGACT TGTTCTCCTC TTCCTCTCCA ACCTCCGGCT
       . L  T  R    E  A  L  P    P  L  V    P  I  A    P  A  E  T    G  V  V ·
2041   GCTGACTAGA GAAGCCTTAC CACCCCTCGT CCCCATCGCG CCGGCGGAGA CGGGAGTCGT
       CGACTGATCT CTTCGGAATG GTGGGGAGCA GGGGTAGCGC GGCCGCCTCT GCCCTCAGCA
       . D  V  D    V  E  E  L    E  Y  H    A  G  A    G  V  V  E    T  P  R ·
2101   CGACGTCGAC GTTGAAGAAC TAGAGTATCA CGCAGGTGCA GGGGTCGTGG AAACACCTCG
       GCTGCAGCTG CAACTTCTTG ATCTCATAGT GCGTCCACGT CCCCAGCACC TTTGTGGAGC
       . S  A  L    K  V  T  A    Q  P  N    D  V  L    G  N  Y    V  V  L  ·
2161   CAGCGCGTTG AAAGTCACCG CACAGCCGAA CGACGTACTA CTAGGAAATT ACGTAGTTCT
       GTCGCGCAAC TTTCAGTGGC GTGTCGGCTT GCTGCATGAT GATCCTTTAA TGCATCAAGA
       . S  P  Q    T  V  L  K    S  S  K    L  A  P    V  H  P  L    A  E  Q ·
2221   GTCCCCGCAG ACCGTGCTCA AGAGCTCCAA GTTGGCCCCC GTGCACCCTC TAGCAGAGCA
       CAGGGGCGTC TGGCACGAGT TCTCGAGGTT CAACCGGGGG CACGTGGGAG ATCGTCTCGT
       . V  K  I    I  T  H  N    G  R  A    G  R  Y    Q  V  D  G    Y  D  G ·
2281   GGTGAAAATA ATAACACATA ACGGGAGGGC CGGCCGTTAC CAGGTCGACG GATATGACGG
       CCACTTTTAT TATTGTGTAT TGCCCTCCCG GCCGGCAATG GTCCAGCTGC CTATACTGCC
       . R  V  L    L  P  C  G    S  A  I    P  V  P    E  F  Q  A    L  S  E ·
2341   CAGGGTCCTA CTACCATGTG GATCGGCCAT TCCGGTCCCT GAGTTTCAAG CTTTGAGCGA
       GTCCCAGGAT GATGGTACAC CTAGCCGGTA AGGCCAGGGA CTCAAAGTTC GAAACTCGCT
```

FIG. 28C.

```
          .  S   A   T    M   V   Y   N    E   R   E    F   V   N    R   K   L    Y   H   I   A  .
2401      GAGCGCCACT ATGGTGTACA ACGAAAGGGA GTTCGTCAAC AGGAAACTAT ACCATATTGC
          CTCGCGGTGA TACCACATGT TGCTTTCCCT CAAGCAGTTG TCCTTTGATA TGGTATAACG
          .  V   H   G    P   S   L   N    T   D   E    E   N   Y    E   K   V    R   A   E   R  .
2461      CGTTCACGGA CCGTCGCTGA ACACCGACGA GGAGAACTAC GAGAAAGTCA GAGCTGAAAG
          GCAAGTGCCT GGCAGCGACT TGTGGCTGCT CCTCTTGATG CTCTTTCAGT CTCGACTTTC
          .  T   D   A    E   Y   V   F    D   V   D    K   K   C    C   V   K    R   E   E   A  .
2521      AACTGACGCC GAGTACGTGT TCGACGTAGA TAAAAAATGC TGCGTCAAGA GAGAGGAAGC
          TTGACTGCGG CTCATGCACA AGCTGCATCT ATTTTTTACG ACGCAGTTCT CTCTCCTTCG
          .  S   G   L    V   L   V   G    E   L   T    N   P   P    P   H   E    F   A   Y   E  .
2581      GTCGGGTTTG GTGTTGGTGG AGAGCTAAC CAACCCCCCG TTCCATGAAT TCGCCTACGA
          CAGCCCAAAC CACAACCACC CTCTCGATTG GTTGGGGGGC AAGGTACTTA AGCGGATGCT
          .  G   L   K    I   R   P   S    A   P   Y    K   T   T    V   V   G    V   F   G   V  .
2641      AGGGCTGAAG ATCAGGCCGT CGGCACCATA TAAGACTACA GTAGTAGGAG TCTTTGGGGT
          TCCCGACTTC TAGTCCGGCA GCCGTGGTAT ATTCTGATGT CATCATCCTC AGAAACCCCA
          .  P   G   S    G   K   S   A    I   I   K    S   L   V    T   K   H    D   L   V   T  .
2701      TCCGGGATCA GGCAAGTCTG CTATTATTAA GAGCCTCGTG ACCAAACACG ATCTGGTCAC
          AGGCCCTAGT CCGTTCAGAC GATAATAATT CTCGGAGCAC TGGTTTGTGC TAGACCAGTG
          .  S   G   K    K   E   N   C    Q   E   I    V   N   D    V   K   K    H   R   G   L  .
2761      CAGCGGCAAG AAGGAGAACT GCCAGGAAAT AGTCAACGAC GTGAAGAAGC ACCGCGGACT
          GTCGCCGTTC TTCCTCTTGA CGGTCCTTTA TCAGTTGCTG CACTTCTTCG TGGCGCCTGA
          .  D   I   Q    A   K   T   V    D   S   I    L   L   N    G   C   R    R   A   V   D  .
2821      GGACATCCAG GCAAAAACAG TGGACTCCAT CCTGCTAAAC GGGTGTCGTC GTGCCGTGGA
          CCTGTAGGTC CGTTTTTGTC ACCTGAGGTA GGACGATTTG CCCACAGCAG CACGGCACCT
                                                S239P
          .  I   L   Y    V   D   E   A    F   A   C    H   P   G    T   L   A    L   I   A  .
2881      CATCCTATAT GTGGACGAGG CTTTCGCTTG CCATCCCGGT ACTCTGCTAG CCCTAATTGC
          GTAGGATATA CACCTGCTCC GAAAGCGAAC GGTAGGGCCA TGAGACGATC GGGATTAACG
          .  L   V   K    P   R   S   K    V   V   L    C   G   D    P   K   Q    C   G   F   F  .
2941      TCTTGTTAAA CCTCGGAGCA AAGTGGTGTT ATGCGGAGAC CCCAAGCAAT GCGGATTCTT
          AGAACAATTT GGAGCCTCGT TTCACCACAA TACGCCTCTG GGGTTCGTTA CGCCTAAGAA
          .  N   M   M    Q   L   K   V    N   F   N    H   N   I    C   T   E    V   C   H   K  .
3001      CAATATGATG CAGCTTAAGG TGAACTTCAA CCACAACATC TGCACTGAAG TATGTCATAA
          GTTATACTAC GTCGAATTCC ACTTGAAGTT GGTGTTGTAG ACGTGACTTC ATACAGTATT
          .  S   I   S    R   R   C   T    R   P   V    T   A   I    V   S   T    L   H   Y   G  .
3061      AAGTATATCC AGACGTTGCA CGCGTCCAGT CACGGCCATC GTGTCTACGT TGCACTACGG
          TTCATATAGG TCTGCAACGT GCGCAGGTCA GTGCCGGTAG CACAGATGCA ACGTGATGCC
          .  G   K   M    R   T   T   N    P   C   N    K   P   I    I   I   D    T   T   G   Q  .
3121      AGGCAAGATG CGCACGACCA ACCCGTGCAA CAAACCCATA ATCATAGACA CCACAGGACA
          TCCGTTCTAC GCGTGCTGGT TGGGCACGTT GTTTGGGTAT TAGTATCTGT GGTGTCCTGT
          .  T   K   P    K   P   G   D    I   V   L    T   C   F    R   G   W    V   K   Q   L  .
3181      GACCAAGCCC AAGCCAGGAG ACATCGTGTT AACATGCTTC CGAGGCTGGG TAAAGCAGCT
          CTGGTTCGGG TTCGGTCCTC TGTAGCACAA TTGTACGAAG GCTCCGACCC ATTTCGTCGA
          .  Q   L   D    Y   R   G   H    E   V   M    T   A   A    A   S   Q    G   L   T   R  .
3241      GCAGTTGGAC TACCGTGGAC ACGAAGTCAT GACAGCAGCA GCATCTCAGG GCCTCACCCG
          CGTCAACCTG ATGGCACCTG TGCTTCAGTA CTGTCGTCGT CGTAGAGTCC CGGAGTGGGC
          .  K   G   V    Y   A   V   R    Q   K   V    N   E   N    P   L   Y    A   P   A   S  .
3301      CAAAGGGGTA TACGCCGTAA GGCAGAAGGT GAATGAAAAT CCCTTGTATG CCCCTGCGTC
          GTTTCCCCAT ATGCGGCATT CCGTCTTCCA CTTACTTTTA GGGAACATAC GGGGACGCAG
          .  E   H   V    N   V   L   L    T   R   T    E   D   R    L   V   W    K   T   L   A  .
3361      GGAGCACGTG AATGTACTGC TGACGCGCAC TGAGGATAGG CTGGTGTGGA AAACGCTGGC
          CCTCGTGCAC TTACATGACG ACTGCGCGTG ACTCCTATCC GACCACACCT TTTGCGACCG
          .  G   D   P    W   I   K   V    L   S   N    I   P   Q    G   N   F    T   A   T   L  .
3421      CGGCGATCCC TGGATTAAGG TCCTATCAAA CATTCCACAG GGTAACTTTA CGGCCACATT
          GCCGCTAGGG ACCTAATTCC AGGATAGTTT GTAAGGTGTC CCATTGAAAT GCCGGTGTAA
          .  E   E   W    Q   E   E   H    D   K   I    M   K   V    I   E   G    P   A   A   P  .
3481      GGAAGAATGG CAAGAAGAAC ACGACAAAAT AATGAAGGTG ATTGAAGGAC CGGCTGCGCC
          CCTTCTTACC GTTCTTCTTG TGCTGTTTTA TTACTTCCAC TAACTTCCTG GCCGACGCGG
          .  V   D   A    F   Q   N   K    A   N   V    C   W   A    K   S   L    V   P   V   L  .
```

FIG. 28D.

```
3541  TGTGGACGCG TTCCAGAACA AAGCGAACGT GTGTTGGGCG AAAAGCCTGG TGCCTGTCCT
      ACACCTGCGC AAGGTCTTGT TTCGCTTGCA CACAACCCGC TTTTCGGACC ACGGACAGGA
       . D T A     G I R L     T A E     W S     T I I T     A F K .
3601  GGACACTGCC GGAATCAGAT TGACAGCAGA GGAGTGGAGC ACCATAATTA CAGCATTTAA
      CCTGTGACGG CCTTAGTCTA ACTGTCGTCT CCTCACCTCG TGGTATTAAT GTCGTAAATT
       . E D R     A Y S P     V V A     L N E     I C T K     Y Y G .
3661  GGAGGACAGA GCTTACTCTC CAGTGGTGGC CTTGAATGAA ATTTGCACCA AGTACTATGG
      CCTCCTGTCT CGAATGAGAG GTCACCACCG GAACTTACTT TAAACGTGGT TCATGATACC
       . V D L     D S G L     F S A     P K V     S L Y Y     E N N .
3721  AGTTGACCTG GACAGTGGCC TGTTTTCTGC CCCGAAGGTG TCCCTGTATT ACGAGAACAA
      TCAACTGGAC CTGTCACCGG ACAAAAGACG GGGCTTCCAC AGGGACATAA TGCTCTTGTT
       . H W D     N R P G     G R M     Y G F     N A A T     A A R .
3781  CCACTGGGAT AACAGACCTG GTGGAAGGAT GTATGGATTC AATGCCGCAA CAGCTGCCAG
      GGTGACCCTA TTGTCTGGAC CACCTTCCTA CATACCTAAG TTACGGCGTT GTCGACGGTC
       . L E A     R H T F     L K G     Q W H     T G K Q     A V I .
3841  GCTGGAAGCT AGACATACCT TCCTGAAGGG GCAGTGGCAT ACGGGCAAGC AGGCAGTTAT
      CGACCTTCGA TCTGTATGGA AGGACTTCCC CGTCACCGTA TGCCCGTTCG TCCGTCAATA
       . A E R     K I Q P     L S V     L D N     V I P I     N R R .
3901  CGCAGAAAGA AAAATCCAAC CGCTTTCTGT GCTGGACAAT GTAATTCCTA TCAACCGCAG
      GCGTCTTTCT TTTTAGGTTG GCGAAAGACA CGACCTGTTA CATTAAGGAT AGTTGGCGTC
       . L P H     A L V A     E Y K     T V K     G S R V     E W L .
3961  GCTGCCGCAC GCCCTGGTGG CTGAGTACAA GACGGTTAAA GGCAGTAGGG TTGAGTGGCT
      CGACGGCGTG CGGGACCACC GACTCATGTT CTGCCAATTT CCGTCATCCC AACTCACCGA
       . V N K     V R G Y     H V L     L V S     E Y N L     A L P .
4021  GGTCAATAAA GTAAGAGGGT ACCACGTCCT GCTGGTGAGT GAGTACAACC TGGCTTTGCC
      CCAGTTATTT CATTCTCCCA TGGTGCAGGA CGACCACTCA CTCATGTTGG ACCGAAACGG
                   R650D
       . R R D     V T W L     S P L     N V T     G A D R     C Y D .
4081  TCGACGCGAC GTCACTTGGT TGTCACCGCT GAATGTCACA GGCGCCGATA GGTGCTACGA
      AGCTGCGCTG CAGTGAACCA ACAGTGGCGA CTTACAGTGT CCGCGGCTAT CCACGATGCT
       . L S L     G L P A     D A G     R F D     L V F V     N I H .
4141  CCTAAGTTTA GGACTGCCGG CTGACGCCGG CAGGTTCGAC TTGGTCTTTG TGAACATTCA
      GGATTCAAAT CCTGACGGCC GACTGCGGCC GTCCAAGCTG AACCAGAAAC ACTTGTAAGT
       . T E F     R I H H     Y Q Q     C V D     H A M K     L Q M .
4201  CACGGAATTC AGAATCCACC ACTACCAGCA GTGTGTCGAC CACGCCATGA AGCTGCAGAT
      GTGCCTTAAG TCTTAGGTGG TGATGGTCGT CACACAGCTG GTGCGGTACT TCGACGTCTA
       . L G G     D A L R     L L K     P G G     S L L M     R A Y .
4261  GCTTGGGGGA GATGCGCTAC GACTGCTAAA ACCCGGCGGC AGCCTCTTGA TGAGAGCTTA
      CGAACCCCCT CTACGCGATG CTGACGATTT TGGGCCGCCG TCGAGAACT ACTCTCGAAT
       . G Y A     D K I S     E A V     V S S     L S R K     F S S .
4321  CGGATACGCC GATAAAATCA GCGAAGCCGT TGTTTCCTCC TTAAGCAGAA AGTTCTCGTC
      GCCTATGCGG CTATTTTAGT CGCTTCGGCA ACAAAGGAGG AATTCGTCTT TCAAGAGCAG
       . A R V     L R P D     C V T     S N T     E V F L     L F S .
4381  TGCAAGAGTG TTGCGCCCGG ATTGTGTCAC CAGCAATACA GAAGTGTTCT TGCTGTTCTC
      ACGTTCTCAC AACGCGGGCC TAACACAGTG GTCGTTATGT CTTCACAAGA ACGACAAGAG
       . N F D     N G K R     P S T     L H Q     M N T K     L S A .
4441  CAACTTTGAC AACGGAAAGA GACCCTCTAC GCTACACCAG ATGAATACCA AGCTGAGTGC
      GTTGAAACTG TTGCCTTTCT CTGGGAGATG CGATGTGGTC TACTTATGGT TCGACTCACG
       . V Y A     G E A M     H T A     G C A     P S Y R     V K R .
4501  CGTGTATGCC GGAGAAGCCA TGCACACGGC CGGGTGTGCA CCATCCTACA GAGTTAAGAG
      GCACATACGG CCTCTTCGGT ACGTGTGCCG GCCCACACGT GGTAGGATGT CTCAATTCTC
       . A D I     A T C T     E A A     V N A     A N A R     G T .
4561  AGCAGACATA GCCACGTGCA CAGAAGCGGC TGTGGTTAAC GCAGCTAACG CCCGTGGAAC
      TCGTCTGTAT CGGTGCACGT GTCTTCGCCG ACACCAATTG CGTCGATTGC GGGCACCTTG
       . V G D     G V C R     A V A     K K W     P S A F     K G E .
4621  TGTAGGGGAT GGCGTATGCA GGGCCGTGGC GAAGAAATGG CCGTCAGCCT TAAGGGAGA
      ACATCCCCTA CCGCATACGT CCCGGCACCG CTTCTTTACC GGCAGTCGGA AATTCCCTCT
       . A T P     V G T I     K T V     M C G     S Y P V     I H A .
4681  AGCAACACCA GTGGGCACAA TTAAAACAGT CATGTGCGGC TCGTACCCCG TCATCCACGC
```

FIG. 28E.

```
           TCGTTGTGGT CACCCGTGTT AATTTTGTCA GTACACGCCG AGCATGGGGC AGTAGGTGCG
           . V  A  P   N  F  S  A   T  T  E    A  E  G    D  R  E  L   A  A  V  ·
 4741      TGTAGCGCCT AATTTCTCTG CCACGACTGA AGCGGAAGGG GACCGCGAAT TGGCCGCTGT
           ACATCGCGGA TTAAAGAGAC GGTGCTGACT TCGCCTTCCC CTGGCGCTTA ACCGGCGACA
           . Y  R  A   V  A  A  E   V  N  R    L  S  L    S  S  V  A   I  P  L  ·
 4801      CTACCGGGCA GTGGCCGCCG AAGTAAACAG ACTGTCACTG AGCAGCGTAG CCATCCCGCT
           GATGGCCCGT CACCGGCGGC TTCATTTGTC TGACAGTGAC TCGTCGCATC GGTAGGGCGA
           . L  S  T   G  V  F  S   G  G  R    D  R  L    Q  Q  S  L   N  H  L  ·
 4861      GCTGTCCACA GGAGTGTTCA GCGGCGGAAG AGATAGGCTG CAGCAATCCC TCAACCATCT
           CGACAGGTGT CCTCACAAGT CGCCGCCTTC TCTATCCGAC GTCGTTAGGG AGTTGGTAGA
           . F  T  A   M  D  A  T   D  A  D    V  T  I    Y  C  R  D   K  S  W  ·
 4921      ATTCACAGCA ATGGACGCCA CGGACGCTGA CGTGACCATC TACTGCAGAG ACAAAAGTTG
           TAAGTGTCGT TACCTGCGGT GCCTGCGACT GCACTGGTAG ATGACGTCTC TGTTTTCAAC
           . E  K  K   I  Q  E  A   I  D  M    R  T  A    V  E  L  L   N  D  D  ·
 4981      GGAGAAGAAA ATCCAGGAAG CCATAGACAT GAGGACGGCT GTGGAGTTGC TCAATGATGA
           CCTCTTCTTT TAGGTCCTTC GGTATCTGTA CTCCTGCCGA CACCTCAACG AGTTACTACT
           . V  E  L   T  T  D  L   V  R  V    H  P  D    S  S  L  V   G  R  K  ·
 5041      CGTGGAGCTG ACCACAGACT TGGTGAGAGT GCACCCGGAC AGCAGCCTGG TGGGTCGTAA
           GCACCTCGAC TGGTGTCTGA ACCACTCTCA CGTGGGCCTG TCGTCGGACC ACCCAGCATT
           . G  Y  S   T  T  D  G   S  L  Y    S  Y  F    E  G  T  K   F  N  Q  ·
 5101      GGGCTACAGT ACCACTGACG GGTCGCTGTA CTCGTACTTT GAAGGTACGA AATTCAACCA
           CCCGATGTCA TGGTGACTGC CCAGCGACAT GAGCATGAAA CTTCCATGCT TTAAGTTGGT
           . A  A  I   D  M  A  E   I  L  T    L  W  P    R  L  Q  E   A  N  E  ·
 5161      GGCTGCTATT GATATGGCAG AGATACTGAC GTTGTGGCCC AGACTGCAAG AGGCAAACGA
           CCGACGATAA CTATACCGTC TCTATGACTG CAACACCGGG TCTGACGTTC TCCGTTTGCT
           . Q  I  C   L  Y  A  L   G  E  T    M  D  N    I  R  S  K   C  P  V  ·
 5221      ACAGATATGC CTATACGCGC TGGGCGAAAC AATGGACAAC ATCAGATCCA AATGTCCGGT
           TGTCTATACG GATATGCGCG ACCCGCTTTG TTACCTGTTG TAGTCTAGGT TTACAGGCCA
           . N  D  S   D  S  T  P   P  R  T    V  P  C    L  C  R  Y   A  M  ·
 5281      GAACGATTCC GATTCATCAA CACCTCCCAG GACAGTGCCC TGCCTGTGCC GCTACGCAAT
           CTTGCTAAGG CTAAGTAGTT GTGGAGGGTC CTGTCACGGG ACGGACACGG CGATGCGTTA
           . T  A  E   R  I  A  R   L  R  S    H  Q  V    K  S  M  V   V  C  S  ·
 5341      GACAGCAGAA CGGATCGCCC GCCTTAGGTC ACACCAAGTT AAAAGCATGG TGGTTTGCTC
           CTGTCGTCTT GCCTAGCGGG CGGAATCCAG TGTGGTTCAA TTTTCGTACC ACCAAACGAG
           . S  F  P   L  P  K  Y   H  V  D    G  V  Q    K  V  K  C   E  K  V  ·
 5401      ATCTTTTCCC CTCCCGAAAT ACCATGTAGA TGGGGTGCAG AAGGTAAAGT GCGAGAAGGT
           TAGAAAAGGG GAGGGCTTTA TGGTACATCT ACCCCACGTC TTCCATTTCA CGCTCTTCCA
           . L  L  F   D  P  T  V   P  S  V    V  S  P    R  K  Y  A   A  S  T  ·
 5461      TCTCCTGTTC GACCCGACGG TACCTTCAGT GGTTAGTCCG CGGAAGTATG CCGCATCTAC
           AGAGGACAAG CTGGGCTGCC ATGGAAGTCA CCAATCAGGC GCCTTCATAC GGCGTAGATG
           . T  D  H   S  D  R  S   L  R  G    F  D  L    D  W  T  T   D  S  S  ·
 5521      GACGGACCAC TCAGATCGGT CGTTACGAGG GTTTGACTTG GACTGGACCA CCGACTCGTC
           CTGCCTGGTG AGTCTAGCCA GCAATGCTCC CAAACTGAAC CTGACCTGGT GGCTGAGCAG
           . S  T  A   S  D  T  M   S  L  P    S  L  Q    S  C  D  I   D  S  I  ·
 5581      TTCCACTGCC AGCGATACCA TGTCGCTACC CAGTTTGCAG TCGTGTGACA TCGACTCGAT
           AAGGTGACGG TCGCTATGGT ACAGCGATGG GTCAAACGTC AGCACACTGT AGCTGAGCTA
           . Y  E  P   M  A  P  I   V  V  T    A  D  V    H  P  E  P   A  G  I  ·
 5641      CTACGAGCCA ATGGCTCCCA TAGTAGTGAC GGCTGACGTA CACCCTGAAC CCGCAGGCAT
           GATGCTCGGT TACCGAGGGT ATCATCACTG CCGACTGCAT GTGGGACTTG GGCGTCCGTA
           . A  D  L   A  A  D  V   H  P  E    P  A  D    H  V  D  L   E  N  P  ·
 5701      CGCGGACCTG GCGGCAGATG TGCATCCTGA ACCCGCAGAC CATGTGGACC TCGAGAACCC
           GCGCCTGGAC CGCCGTCTAC ACGTAGGACT TGGGCGTCTG GTACACCTGG AGCTCTTGGG
           . I  P  P   P  R  P  K   R  A  A    Y  L  A    S  R  A  A   E  R  P  ·
 5761      GATTCCTCCA CCGCGCCCGA AGAGAGCTGC ATACCTTGCC TCCCGCGCGG CGGAGCGACC
           CTAAGGAGGT GGCGCGGGCT TCTCTCGACG TATGGAACGG AGGGCGCGCC GCCTCGCTGG
           . V  P  A   P  R  K  P   T  P  A    P  R  T    A  F  R  N   K  L  P  ·
 5821      GGTGCCGGCG CCGAGAAAGC CGACGCCTGC CCCAAGGACT GCGTTTAGGA ACAAGCTGCC
           CCACGGCCGC GGCTCTTTCG GCTGCGGACG GGGTTCCTGA CGCAAATCCT TGTTCGACGG
           . L  T  F   G  D  F  D   E  H  E    V  D  A    L  A  S  G   I  T  F  ·
```

FIG. 28F.

```
5881    TTTGACGTTC GGCGACTTTG ACGAGCACGA GGTCGATGCG TTGGCCTCCG GGATTACTTT
        AAACTGCAAG CCGCTGAAAC TGCTCGTGCT CCAGCTACGC AACCGGAGGC CCTAATGAAA
        . G  D  F   D  D  V   L  R  G   R  A  G   A  Y  I   F  S  S  D  .
5941    CGGAGACTTC GACGACGTCC TGCGACTAGG CCGCGCGGGT GCATATATTT TCTCCTCGGA
        GCCTCTGAAG CTGCTGCAGG ACGCTGATCC GGCGCGCCCA CGTATATAAA AGAGGAGCCT
        . T  G  S   G  H  L   Q  Q  K   S  V  R   Q  H  N   L  Q  C  A  Q  .
6001    CACTGGCAGC GGACATTTAC AACAAAAATC CGTTAGGCAG CACAATCTCC AGTGCGCACA
        GTGACCGTCG CCTGTAAATG TTGTTTTTAG GCAATCCGTC GTGTTAGAGG TCACGCGTGT
        . L  D  A   V  E  E   K  M  Y   P  P  K   L  D  T   E  R  E  K  .
6061    ACTGGATGCG GTCGAGGAGG AGAAAATGTA CCCGCCAAAA TTGGATACTG AGAGGGAGAA
        TGACCTACGC CAGCTCCTCC TCTTTTACAT GGGCGGTTTT AACCTATGAC TCTCCCTCTT
        . L  L  L   L  K  M   Q  M  H   P  S  E   A  N  K   S  R  Y  Q  S  .
6121    GCTGTTGCTG CTGAAAATGC AGATGCACCC ATCGGAGGCT AATAAGAGTC GATACCAGTC
        CGACAACGAC GACTTTTACG TCTACGTGGG TAGCCTCCGA TTATTCTCAG CTATGGTCAG
        . R  K  V   E  N  M  K   A  T  V   V  D  R   L  T  S   G  A  R  L  .
6181    TCGCAAAGTG GAGAACATGA AGCCACGGT GGTGGACAGG CTCACATCGG GGCCAGATT
        AGCGTTTCAC CTCTTGTACT TCGGTGCCA CCACCTGTCC GAGTGTAGCC CCCGGTCTAA
        . Y  T  G   A  D  V   G  R  I  P   T  Y  A   V  R  Y   P  R  P  V  .
6241    GTACACGGGA GCGGACGTAG GCCGCATACC AACATACGGA GTTCGGTACC CCCGCCCCGT
        CATGTGCCCT CGCCTGCATC CGGCGTATGG TTGTATGCGC CAAGCCATGG GGGCGGGGCA
        . Y  S  P   T  V  I   E  R  F   S  P  D   V  A  I   A  A  C  N  .
6301    GTACTCCCCT ACCGTGATCG AAAGATTCTC AAGCCCCGAT GTAGCAATCG CAGCGTGCAA
        CATGAGGGGA TGGCACTAGC TTTCTAAGAG TTCGGGGCTA CATCGTTAGC GTCGCACGTT
        . E  Y  L   S  R  N   Y  P  T   V  A  S   Y  Q  I   T  D  E  Y  D  .
6361    CGAATACCTA TCCAGAAATT ACCCAACAGT GGCGTCGTAC CAGATAACAG ATGAATACGA
        GCTTATGGAT AGGTCTTTAA TGGGTTGTCA CCGCAGCATG GTCTATTGTC TACTTATGCT
        . A  Y  L   D  M  V   D  G  S   D  S  C   L  D  R   A  T  F  C  P  .
6421    CGCATACTTG GACATGGTTG ACGGGTCGGA TAGTTGCTTG GACAGAGCGA CATTCTGCCC
        GCGTATGAAC CTGTACCAAC TGCCCAGCCT ATCAACGAAC CTGTCTCGCT GTAAGACGGG
        . A  K  L   R  C  Y  P   K  H  H   A  Y  H   Q  P  T   V  R  S  A  .
6481    GGCGAAGCTC CGGTGCTACC CGAAACATCA TGCGTACCAC CAGCCGACTG TACGCAGTGC
        CCGCTTCGAG GCCACGATGG GCTTTGTAGT ACGCATGGTG GTCGGCTGAC ATGCGTCACG
        . V  P  S   P  F  Q   N  T  L   Q  N  V   L  A  A   A  T  K  R  N  .
6541    CGTCCCGTCA CCCTTTCAGA ACACACTACA GAACGTGCTA GCGGCCGCCA CCAAGAGAAA
        GCAGGGCAGT GGGAAAGTCT TGTGTGATGT CTTGCACGAT CGCCGGCGGT GGTTCTCTTT
        . C  N  V   T  Q  M   R  E  L  P   T  M  D   S  A  V   F  N  V  E  .
6601    CTGCAACGTC ACGCAAATGC GAGAACTACC CACCATGGAC TCGGCAGTGT TCAACGTGGA
        GACGTTGCAG TGCGTTTACG CTCTTGATGG GTGGTACCTG AGCCGTCACA AGTTGCACCT
        . C  F  K   R  Y  A   C  S  G  E   Y  W  E   E  Y  A   K  Q  P  I  .
6661    GTGCTTCAAG CGCTATGCCT GCTCCGGAGA ATATTGGGAA GAATATGCTA AACAACCTAT
        CACGAAGTTC GCGATACGGA CGAGGCCTCT TATAACCCTT CTTATACGAT TTGTTGGATA
        . R  I  T   T  E  N  I   T  T  Y   V  T  K   L  K  G   P  K  A  A  .
6721    CCGGATAACC ACTGAGAACA TCACTACCTA TGTGACCAAA TTGAAAGGCC CGAAAGCTGC
        GGCCTATTGG TGACTCTTGT AGTGATGGAT ACACTGGTTT AACTTTCCGG GCTTTCGACG
        . A  L  F   A  K  T  H   N  L  V   P  L  Q   E  V  P   M  D  R  F  .
6781    TGCCTTGTTC GCTAAGACCC ACAACTTGGT TCCGCTGCAG GAGGTTCCCA TGGACAGATT
        ACGGAACAAG CGATTCTGGG TGTTGAACCA AGGCGACGTC CTCCAAGGGT ACCTGTCTAA
        . T  V  D   M  K  R  D   V  K  V   T  P  G   T  K  H  T   E  E  R  .
6841    CACGGTCGAC ATGAAACGAG ATGTCAAAGT CACTCCAGGG ACGAAACACA CAGAGGAAAG
        GTGCCAGCTG TACTTTGCTC TACAGTTTCA GTGAGGTCCC TGCTTTGTGT GTCTCCTTTC
        . P  K  V   Q  V  I   Q  A  A  E   P  L  A   T  A  Y  L   C  G  I  .
6901    ACCCAAAGTC CAGGTAATTC AAGCAGCGGA GCCATTGGCG ACCGCTTACC TGTGCGGCAT
        TGGGTTTCAG GTCCATTAAG TTCGTCGCCT CGGTAACCGC TGGCGAATGG ACACGCCGTA
        . H  R  E   L  V  R  R   L  N  A   V  L  R   P  N  V   H  T  L  F  .
6961    CCACAGGGAA TTAGTAAGGA GACTAAATGC TGTGTTACGC CCTAACGTGC ACACATTGTT
        GGTGTCCCTT AATCATTCCT CTGATTTACG ACACAATGCG GGATTGCACG TGTGTAACAA
        . D  M  S   A  E  D  F   D  A  I   I  A  S   H  F  H   P  G  D  P  .
7021    TGATATGTCG GCCGAAGACT TTGACGCGAT CATCGCCTCT CACTTCCACC CAGGAGACCC
        ACTATACAGC CGGCTTCTGA AACTGCGCTA GTAGCGGAGA GTGAAGGTGG GTCCTCTGGG
```

FIG. 28G.

```
             . V  L  E   T  D  I  A   S  F  D   K  S  Q   D  D  S   L  A  L  T  ·
      7081   GGTTCTAGAG ACGGACATTG CATCATTCGA CAAAAGCCAG GACGACTCCT TGGCTCTTAC
             CCAAGATCTC TGCCTGTAAC GTAGTAAGCT GTTTTCGGTC CTGCTGAGGA ACCGAGAATG
             . G  L  M   I  L  E  D   L  G  V   D  Q  Y   L  L  D  L   I  E  A  ·
      7141   AGGTTTAATG ATCCTCGAAG ATCTAGGGGT GGATCAGTAC CTGCTGGACT TGATCGAGGC
             TCCAAATTAC TAGGAGCTTC TAGATCCCCA CCTAGTCATG GACGACCTGA ACTAGCTCCG
             . A  F  G   E  I  S  S   C  H  L   P  T  G   T  R  F  K   F  G  A  ·
      7201   AGCCTTTGGG GAAATATCCA GCTGTCACCT ACCAACTGGC ACGCGCTTCA AGTTCGGAGC
             TCGGAAACCC CTTTATAGGT CGACAGTGGA TGGTTGACCG TGCGCGAAGT TCAAGCCTCG
             . M  M  K   S  G  M  F   L  T  L   F  I  N   T  V  L  N   I  T  I  ·
      7261   TATGATGAAA TCGGGCATGT TTCTGACTTT GTTTATTAAC ACTGTTTTGA ACATCACCAT
             ATACTACTTT AGCCCGTACA AAGACTGAAA CAAATAATTG TGACAAAACT TGTAGTGGTA
             . A  S  R   V  L  E  Q   R  L  T   D  S  A   C  A  A  F   I  G  D  ·
      7321   AGCAAGCAGG GTACTGGAGC AGAGACTCAC TGACTCCGCC TGTGCGGCCT TCATCGGCGA
             TCGTTCGTCC CATGACCTCG TCTCTGAGTG ACTGAGGCGG ACACGCCGGA AGTAGCCGCT
             . D  N  I   V  H  G  V   I  S  D   K  L  M   A  E  R  C   A  S  W  ·
      7381   CGACAACATC GTTCACGGAG TGATCTCCGA CAAGCTGATG GCGGAGAGGT GCGCGTCGTG
             GCTGTTGTAG CAAGTGCCTC ACTAGAGGCT GTTCGACTAC CGCCTCTCCA CGCGCAGCAC
             . V  N  M   E  V  K  I   I  D  A   V  M  G   E  K  P  P   Y  F  C  ·
      7441   GGTCAACATG GAGGTGAAGA TCATTGACGC TGTCATGGGC GAAAAACCCC CATATTTCTG
             CCAGTTGTAC CTCCACTTCT AGTAACTGCG ACAGTACCCG CTTTTTGGGG GTATAAAGAC
             . G  G  F   I  V  F  D   S  V  T   Q  T  A   C  R  V  S   D  P  L  ·
      7501   TGGGGGATTC ATAGTTTTTG ACAGCGTCAC ACAGACCGCC TGCCGTGTTT CAGACCCACT
             ACCCCCTAAG TATCAAAAAC TGTCGCAGTG TGTCTGGCGG ACGGCACAAA GTCTGGGTGA
             . K  R  L   F  K  L  G   K  P  L   T  A  E   D  K  Q  D   E  D  R  ·
      7561   TAAGCGCCTG TTCAAGTTGG GTAAGCCGCT AACAGCTGAA GACAAGCAGG ACGAAGACAG
             ATTCGCGGAC AAGTTCAACC CATTCGGCGA TTGTCGACTT CTGTTCGTCC TGCTTCTGTC
             . R  R  A   L  S  D  E   V  S  K   W  F  R   T  G  L  G   A  E  L  ·
      7621   GCGACGAGCA CTGAGTGACG AGGTTAGCAA GTGGTTCCGG ACAGGCTTGG GGGCCGAACT
             CGCTGCTCGT GACTCACTGC TCCAATCGTT CACCAAGGCC TGTCCGAACC CCCGGCTTGA
             . E  V  A   L  T  S  R   Y  E  V   E  G  C   K  S  I  L   I  A  M  ·
      7681   GGAGGTGGCA CTAACATCTA GGTATGAGGT AGAGGGCTGC AAAAGTATCC TCATAGCCAT
             CCTCCACCGT GATTGTAGAT CCATACTCCA TCTCCCGACG TTTTCATAGG AGTATCGGTA
                                                                           26S
             . A  T  L   A  R  D  I   K  A  F   K  K  L   R  G  P  V   I  H  L  ·
      7741   GGCCACCTTG GCGAGGACA TTAAGGCGTT TAAGAAATTG AGAGGACCTG TTATACACCT
             CCGGTGGAAC CGCTCCCTGT AATTCCGCAA ATTCTTTAAC TCTCCTGGAC AATATGTGGA
                              26S promoter                              FIV gag
             . Y  G  G   P  R  L  V   R                                 M  G  N
      7801   CTACGGCGGT CCTAGATTGG TGCGTTAATA CACAGAATTC TGATTTTAAT TAAATGGGGA
             GATGCCGCCA GGATCTAACC ACGCAATTAT GTGTCTTAAG ACTAAAATTA ATTTACCCCT
             .. G  Q  G   R  D  W   K  M  A  I   K  R  C   S  N  V   A  V  G  V  ·
      7861   ATGGACAGGG GCGAGATTGG AAAATGGCCA TTAAGAGATG TAGTAATGTT GCTGTAGGAG
             TACCTGTCCC CGCTCTAACC TTTTACCGGT AATTCTCTAC ATCATTACAA CGACATCCTC
             .. G  G  K   S  K  K   F  G  E  G   N  F  R   W  A  I   R  M  A  N  ·
      7921   TAGGGGGGAA GAGTAAAAAA TTTGGAGAAG GAATTTCAG ATGGGCCATT AGAATGGCTA
             ATCCCCCCTT CTCATTTTTT AAACCTCTTC CCTTAAAGTC TACCCGGTAA TCTTACCGAT
             .. V  S  T   G  R  E   P  G  D  I   P  E  T   L  D  Q   L  R  L  V  ·
      7981   ATGTATCTAC AGGACGAGAA CCTGGTGATA TACCAGAGAC TTTAGATCAA CTAAGGTTGG
             TACATAGATG TCCTGCTCTT GGACCACTAT ATGGTCTCTG AAATCTAGTT GATTCCAACC
             .. I  C  D   L  Q  E   R  R  E  K   F  G  S   K  E  I   D  M  A  ·
      8041   TTATTTGCGA TTTACAAGAA AGAAGAGAAA AATTTGGATC TAGCAAAGAA ATTGATATGG
             AATAAACGCT AAATGTTCTT TCTTCTCTTT TTAAACCTAG ATCGTTTCTT TAACTATACC
             .. I  V  T   L  K  V   F  A  V  A   G  L  L   N  M  T   V  S  T  A  ·
      8101   CAATTGTGAC ATTAAAAGTC TTTGCGGTAG CAGGACTTTT GAATATGACG GTGTCTACTG
             GTTAACACTG TAATTTTCAG AAACGCCATC GTCCTGAAAA CTTATACTGC CACAGATGAC
             .. A  A  A   E  N  M   Y  S  Q  M   G  L  D   T  R  P   S  M  K  E  ·
      8161   CTGCTGCAGC TGAAAATATG TATTCTCAAA TGGGATTAGA CACTAGGCCA TCTATGAAAG
             GACGACGTCG ACTTTTATAC ATAAGAGTTT ACCCTAATCT GTGATCCGGT AGATACTTTC
```

FIG. 28H.

```
           .. A   G   G      K   E   E      G   P   P      Q   A   Y   P      I   Q   T      V   N   G   V  ·
8221       AAGCAGGTGG      AAAAGAGGAA      GGCCCTCCAC      AGGCATATCC      TATTCAAACA      GTAAATGGAG
           TTCGTCCACC      TTTTCTCCTT      CCGGGAGGTG      TCCGTATAGG      ATAAGTTTGT      CATTTACCTC
           .. P   Q   Y      V   A   L      D   P   K   M      V   S   I      F   M   E      K   A   R   E  ·
8281       TACCACAATA      TGTAGCACTT      GACCCAAAAA      TGGTGTCCAT      TTTCATGAA       AAGGCAAGAG
           ATGGTGTTAT      ACATCGTGAA      CTGGGTTTTT      ACCACAGGTA      AAAGTACCTT      TTCCGTTCTC
           .. G   L   G      G   E   E      V   Q   L   W      F   T   A      F   S   A      N   L   T   P  ·
8341       AAGGACTAGG      AGGGGAGGAA      GTTCAACTAT      GGTTTACTGC      CTTCTCTGCA      AATTTAACAC
           TTCCTGATCC      TCCCCTCCTT      CAAGTTGATA      CCAAATGACG      GAAGAGACGT      TTAAATTGTG
           .. T   D   M      A   T   L      I   M   A   A      P   G   C      A   A   D      K   E   I   L  ·
8401       CTACTGACAT      GGCCACATTA      ATAATGGCCG      CACCAGGGTG      CGCTGCAGAT      AAAGAAATAT
           GATGACTGTA      CCGGTGTAAT      TATTACCGGC      GTGGTCCCAC      GCGACGTCTA      TTTCTTTATA
           .. D   E   S      L   K   Q      L   T   A   E      Y   D   R      T   H   P      P   D   A   P  ·
8461       TGGATGAAAG      CTTAAAGCAA      CTGACAGCAG      AATATGATCG      CACACATCCC      CCTGATGCTC
           ACCTACTTTC      GAATTTCGTT      GACTGTCGTC      TTATACTAGC      GTGTGTAGGG      GGACTACGAG
           .. R   P   L      P   Y   F      T   A   A   E      I   M   G      I   G   L      T   Q   E   Q  ·
8521       CCAGACCATT      ACCCTATTTT      ACTGCAGCAG      AAATTATGGG      TATAGGATTA      ACTCAAGAAC
           GGTCTGGTAA      TGGGATAAAA      TGACGTCGTC      TTTAATACCC      ATATCCTAAT      TGAGTTCTTG
           .. Q   A   E      A   R   F      A   P   A   R      M   Q   C      R   A   W      Y   L   E   A  ·
8581       AACAAGCAGA      AGCAAGATTT      GCACCAGCTA      GGATGCAGTG      TAGAGCATGG      TATCTCGAGG
           TTGTTCGTCT      TCGTTCTAAA      CGTGGTCGAT      CCTACGTCAC      ATCTCGTACC      ATAGAGCTCC
           .. L   G   K      L   A   A      I   K   A   K      S   P   R      A   V   Q      L   R   Q   G  ·
8641       CATTAGGAAA      ATTGGCTGCC      ATAAAAGCTA      AGTCTCCTCG      AGCTGTGCAG      TTAAGACAAG
           GTAATCCTTT      TAACCGACGG      TATTTTCGAT      TCAGAGGAGC      TCGACACGTC      AATTCTGTTC
           .. A   K   E      D   Y   S      F   I   D   R      L   F      A   Q   I      D   Q   E   Q  ·
8701       GAGCTAAGGA      AGATTATTCA      TCCTTTATAG      ACAGATTGTT      TGCCCAAATA      GATCAAGAAC
           CTCGATTCCT      TCTAATAAGT      AGGAAATATC      TGTCTAACAA      ACGGGTTTAT      CTAGTTCTTG
           .. N   T   A      E   V   K      L   Y   L   K      Q   S   L      S   I   A      N   A   N   A  ·
8761       AAAATACAGC      TGAAGTTAAG      TTATATTTAA      AACAGTCATT      AAGCATAGCT      AATGCTAATG
           TTTTATGTCG      ACTTCAATTC      AATATAAATT      TTGTCAGTAA      TTCGTATCGA      TTACGATTAC
           .. D   C   K      K   A   M      S   H   L   K      P   E   S      T   L   E      E   K   L   R  ·
8821       CAGACTGTAA      AAAGGCAATG      AGCCACCTTA      AGCCAGAAAG      TACCCTAGAA      GAAAAGTTGA
           GTCTGACATT      TTTCCGTTAC      TCGGTGGAAT      TCGGTCTTTC      ATGGGATCTT      CTTTTCAACT
           .. A   C   Q      E   I   G      S   P   G   Y      K   M   Q      L   L   A      E   A   L   T  ·
8881       GAGCTTGTCA      AGAAATAGGC      TCACCAGGAT      ATAAAATGCA      ACTCTTGGCA      GAAGCTCTTA
           CTCGAACAGT      TCTTTATCCG      AGTGGTCCTA      TATTTTACGT      TGAGAACCGT      CTTCGAGAAT
           .. K   V   Q      V   V   Q      S   K   G   S      G   P   V      C   F   N      C   K   K   P  ·
8941       CAAAAGTTCA      AGTAGTGCAA      TCAAAAGGAT      CAGGACCAGT      GTGTTTTAAT      TGTAAAAAAC
           GTTTTCAAGT      TCATCACGTT      AGTTTTCCTA      GTCCTGGTCA      CACAAAATTA      ACATTTTTTG
           .. G   H   L      A   R   Q      C   R   E   V      K   K   C      N   K   C      G   K   P   G  ·
9001       CAGGACATCT      AGCAAGACAA      TGTAGAGAAG      TGAAAAAATG      TAATAAATGT      GGAAAACCTG
           GTCCTGTAGA      TCGTTCTGTT      ACATCTCTTC      ACTTTTTTAC      ATTATTTACA      CCTTTTGGAC
           .. H   L   A      A   K   C      W   Q   G   N      R   K   N      S   G   N      W   K   A   G  ·
                                                                  FIV pro      L   E   G   G  ·
9061       GTCATCTAGC      TGCCAAATGT      TGGCAAGGAA      ATAGAAAGAA      TTCGGGAAAC      TGGAAGGCGG
           CAGTAGATCG      ACGGTTTACA      ACCGTTCCTT      TATCTTTCTT      AAGCCCTTTG      ACCTTCCGCC
           .. R   A   A      A   P   V      N   Q   M   Q      Q   A   V      M   P   S      A   P   P   M  ·
            . A   S   C      S   P   S   E      S   N   A      A   S   S      N   A   I   C      T   S   N  ·
9121       GGCGAGCTGC      AGCCCCAGTG      AATCAAATGC      AGCAAGCAGT      AATGCCATCT      GCACCTCCAA
           CCGCTCGACG      TCGGGGTCAC      TTAGTTTACG      TCGTTCGTCA      TTACGGTAGA      CGTGGAGGTT
           .. E   E   K      L   L   D   L
            . G   G   E      T   I   G   F      I   N   Y      N   K   V      G   T   T   T      T   L   E  ·
9181       TGGAGGAGAA      ACTATTGGAT      TTATAAATTA      TAATAAAGTA      GGTACGACTA      CAACATTAGA
           ACCTCCTCTT      TGATAACCTA      AATATTTAAT      ATTATTTCAT      CCATGCTGAT      GTTGTAATCT
            . K   R   P      E   I   L   I      F   V   N      G   Y   P      I   K   F   L      L   D   T  ·
9241       AAAGAGGCCA      GAAATACTTA      TATTTGTAAA      TGGATATCCT      ATAAAATTCT      TATTAGATAC
           TTTCTCCGGT      CTTTATGAAT      ATAAACATTT      ACCTATAGGA      TATTTTAAGA      ATAATCTATG
            . G   A   D      I   T   I   L      N   R   R      D   F   Q      V   K   N   S      I   E   N  ·
9301       AGGAGCAGAT      ATAACAATTT      TAAATAGGAG      AGATTTTCAA      GTAAAAAATT      CTATAGAAAA
```

FIG. 28I.

```
           TCCTCGTCTA TATTGTTAAA ATTTATCCTC TCTAAAAGTT CATTTTTTAA GATATCTTTT
           . G  R  Q   N  M  I   G  V  G  G    G  K  R    G  T  N    Y  I  N  V .
    9361   TGGAAGGCAA AATATGATTG GAGTAGGAGG AGGAAAGAGA GGAACAAATT ATATTAATGT
           ACCTTCCGTT TTATACTAAC CTCATCCTCC TCCTTTCTCT CCTTGTTTAA TATAATTACA
           . H  L  E   I  R  D   E  N  Y  K    T  Q  C    I  F  G    N  V  C  V .
    9421   ACATTTAGAG ATTAGAGATG AAAATTATAA GACACAATGT ATATTTGGTA ATGTTTGTGT
           TGTAAATCTC TAATCTCTAC TTTTAATATT CTGTGTTACA TATAAACCAT TACAAACACA
           . L  E  D   N  S  L   I  Q  P  L    L  G  R    D  N  M    I  K  F  N .
    9481   CTTAGAAGAT AACTCATTAA TACAACCATT ATTGGGAGA GATAATATGA TTAAATTCAA
           GAATCTTCTA TTGAGTAATT ATGTTGGTAA TAACCCCTCT CTATTATACT AATTTAAGTT
           . I  R  L   V  M  *                  SFV replicon 3'
    9541   TATTAGGTTA GTAATGTAAG TTTAAACTAA TTAATTGAAT TACATCCCTA CGCAAACGTT
           ATAATCCAAT CATTACATTC AAATTTGATT AATTAACTTA ATGTAGGGAT GCGTTTGCAA
    9601   TTACGGCCGC CGGTGGCGCC CGCGCCCGGC GGCCCGTCCT TGGCCGTTGC AGGCCACTCC
           AATGCCGGCG GCCACCGCGG GCGCGGGCCG CCGGGCAGGA ACCGGCAACG TCCGGTGAGG
    9661   GGTGGCTCCC GTCGTCCCCG ACTTCCAGGC CCAGCAGATG CAGCAACTCA TCAGCGCCGT
           CCACCGAGGG CAGCAGGGGC TGAAGGTCCG GGTCGTCTAC GTCGTTGAGT AGTCGCGGCA
    9721   AAATGCGCTG ACAATGAGAC AGAACGCAAT TGCTCCTGCT AGGCCTCCCA AACCAAAGAA
           TTTACGCGAC TGTTACTCTG TCTTGCGTTA ACGAGGACGA TCCGGAGGGT TTGGTTTCTT
    9781   GAAGAAGACA ACCAAACCAA AGCCGAAAAC GCAGCCCAAG AAGATCAACG GAAAACGCA
           CTTCTTCTGT TGGTTTGGTT TCGGCTTTTG CGTCGGGTTC TTCTAGTTGC CTTTTTGCGT
    9841   GCAGCAAAAG AAGAAAGACA AGCAAGCCGA CAAGAAGAAG AAGAAACCCG GAAAAAGAGA
           CGTCGTTTTC TTCTTTCTGT TCGTTCGGCT GTTCTTCTTC TTCTTTGGGC CTTTTTCTCT
    9901   AAGAATGTGC ATGAAGATTG AAAATGACTG TATCTATGCG GCTAGCCACA GTAACGTAGT
           TTCTTACACG TACTTCTAAC TTTTACTGAC ATAGATACGC CGATCGGTGT CATTGCATCA
    9961   GTTTCCAGAC ATGTCGGGCA CCGCACTATC ATGGGTGCAG AAAATCTCGG GTGGTCTGGG
           CAAAGGTCTG TACAGCCCGT GGCGTGATAG TACCCACGTC TTTTAGAGCC CACCAGACCC
   10021   GGCCTTCGCA ATCGGCGCTA TCCTGGTGCT GGTTGTGGTC ACTTGCATTG GCTCCGCAG
           CCGGAAGCGT TAGCCGCGAT AGGACCACGA CCAACACCAG TGAACGTAAC CCGAGGCGTC
   10081   ATAAGTTAGG GTAGGCAATG GCATTGATAT AGCAAGAAAA TTGAAAACAG AAAAAGTTAG
           TATTCAATCC CATCCGTTAC CGTAACTATA TCGTTCTTTT AACTTTTGTC TTTTTCAATC
   10141   GGTAAGCAAT GGCATATAAC CATAACTGTA TAACTTGTAA CAAAGCGCAA CAAGACCTGC
           CCATTCGTTA CCGTATATTG GTATTGACAT ATTGAACATT GTTTCGCGTT GTTCTGGACG
   10201   GCAATTGGCC CCGTGGTCCG CCTCACGGAA ACTCGGGCA ACTCATATTG ACACATTAAT
           CGTTAACCGG GGCACCAGGC GGAGTGCCTT TGAGCCCGT TGAGTATAAC TGTGTAATTA
   10261   TGGCAATAAT TGGAAGCTTA CATAAGCTTA ATTCGACGAA TAATTGGATT TATATTTTAT
           ACCGTTATTA ACCTTCGAAT GTATTCGAAT TAAGCTGCTT ATTAACCTAA ATATAAAATA
   10321   TTTGCAATTG GTTTTTAATA TTTCCAAAAA AAAAAAAAAA AAAAAAAAAA AAAAAAAAA
           AAACGTTAAC CAAAAATTAT AAAGGTTTTT TTTTTTTTTT TTTTTTTTTT TTTTTTTTT
                                             Ribozyme sequence
   10381   AAAAAAAAAA AAAAAAAAAA AACGGGTCGG CATGGCATCT CCACCTCCTC GCGGTCCGAC
           TTTTTTTTTT TTTTTTTTTT TTGCCCAGCC GTACCGTAGA GGTGGAGGAG CGCCAGGCTG
   10441   CTGGGCATCC GAAGGAGGAC GCACGTCCAC TCGGATGGCT AAGGGAGTTT TTCTACTAGT
           GACCCGTAGG CTTCCTCCTG CGTGCAGGTG AGCCTACCGA TTCCCTCAAA AAGATGATCA
                        C6 right arm
   10501   CAAATGAGTA TATATAATTG AAAAAGTAAA ATATAAATCA TATAATAATG AAACGAAATA
           GTTTACTCAT ATATATTAAC TTTTTCATTT TATATTTAGT ATATTATTAC TTTGCTTTAT
   10561   TCAGTAATAG ACAGGAACTG GCAGATTCTT CTTCTAATGA AGTAAGTACT GCTAAATCTC
           AGTCATTATC TGTCCTTGAC CGTCTAAGAA GAAGATTACT TCATTCATGA CGATTTAGAG
   10621   CAAAATTAGA TAAAAATGAT ACAGCAAATA CAGCTTCATT CAACGAATTA CCTTTTAATT
           GTTTTAATCT ATTTTTACTA TGTCGTTTAT GTCGAAGTAA GTTGCTTAAT GGAAAATTAA
   10681   TTTTCAGACA CACCTTATTA CAAACTAACT AAGTCAGATG ATGAGAAAGT AAATATAAAT
           AAAAGTCTGT GTGGAATAAT GTTTGATTGA TTCAGTCTAC TACTCTTTCA TTTATATTTA
   10741   TTAACTTATG GGTATAATAT AATAAAGATT CATGATATTA ATAATTTACT TAACGATGTT
           AATTGAATAC CCATATTATA TTATTTCTAA GTACTATAAT TATTAAATGA ATTGCTACAA
   10801   AATAGACTTA TTCCATCAAC CCCTTCAAAC CTTTCTGGAT ATTATAAAAT ACCAGTTAAT
           TTATCTGAAT AAGGTAGTTG GGGAAGTTTG GAAAGACCTA TAATATTTTA TGGTCAATTA
   10861   GATATTAAAA TAGATTGTTT AAGAGATGTA ATAATTATT TGGAGGTAAA GGATATAAAA
           CTATAATTTT ATCTAACAAA TTCTCTACAT TTATTAATAA ACCTCCATTT CCTATATTTT
```

FIG. 28J.

```
10921   TTAGTCTATC TTTCACATGG AAATGAATTA CCTAATATTA ATAATTATGA TAGGAATTTT
        AATCAGATAG AAAGTGTACC TTTACTTAAT GGATTATAAT TATTAATACT ATCCTTAAAA
10981   TTAGGATTTA CAGCTGTTAT ATGTATCAAC AATACAGGCA GATCTATGGT TATGGTAAAA
        AATCCTAAAT GTCGACAATA TACATAGTTG TTATGTCCGT CTAGATACCA ATACCATTTT
11041   CACTGTAACG GGAAGCAGCA TTCTATGGTA ACTGGCCTAT GTTTAATAGC CAGATCATTT
        GTGACATTGC CCTTCGTCGT AAGATACCAT TGACCGGATA CAAATTATCG GTCTAGTAAA
11101   TACTCTATAA ACATTTTACC ACAAATAATA GGATCCTCTA GATATTTAAT ATTATATCTA
        ATGAGATATT TGTAAAATGG TGTTTATTAT CCTAGGAGAT CTATAAATTA TAATATAGAT
11161   ACAACAACAA AAAAATTTAA CGATGTATGG CCAGAAGTAT TTTCTACTAA TAAAGATAAA
        TGTTGTTGTT TTTTTAAATT GCTACATACC GGTCTTCATA AAAGATGATT ATTTCTATTT
11221   GATAGTCTAT CTTATCTACA AGATATGAAA GAAGATAATC ATTTAGTAGT AGCTACTAAT
        CTATCAGATA GAATAGATGT TCTATACTTT CTTCTATTAG TAAATCATCA TCGATGATTA
11281   ATGGAAAGAA ATGTATACAA AAACGTGGAA GCTTTTATAT TAAATAGCAT ATTACTAGAA
        TACCTTTCTT TACATATGTT TTTGCACCTT CGAAAATATA ATTTATCGTA TAATGATCTT
11341   GATTTAAAAT CTAGACTTAG TATAACAAAA CAGTTAAATG CCAATATCGA TTCTATATTT
        CTAAATTTTA GATCTGAATC ATATTGTTTT GTCAATTTAC GGTTATAGCT AAGATATAAA
11401   CATCATAACA GTAGTACATT AATCAGTGAT ATACTGAAAC GATCTACAGA CTCAACTATG
        GTAGTATTGT CATCATGTAA TTAGTCACTA TATGACTTTG CTAGATGTCT GAGTTGATAC
11461   CAAGGAATAA GCAATATGCC AATTATGTCT AATATTTTAA CTTTAGAACT AAAACGTTCT
        GTTCCTTATT CGTTATACGG TTAATACAGA TTATAAAATT GAAATCTTGA TTTTGCAAGA
11521   ACCAATACTA AAAATAGGAT ACGTGATAGG CTGTTAAAAG CTGCAATAAA TAGTAAGGAT
        TGGTTATGAT TTTTATCCTA TGCACTATCC GACAATTTTC GACGTTATTT ATCATTCCTA
11581   GTAGAAGAAA TACTTTGTTC TATACCTTCG GAGGAAAGAA CTTTAGAACA ACTTAAGTTT
        CATCTTCTTT ATGAAACAAG ATATGGAAGC CTCCTTTCTT GAAATCTTGT TGAATTCAAA
11641   AATCAAACTT GTATTTATGA A
        TTAGTTTGAA CATAAATACT T
```

FIG. 29.

A schematic illustration of the generation of an ALVAC-SFV Arg650Asp+Ser259Pro chimera expressing FIV gag-pro (vCP2161)

FIG. 30.

Construction scheme for a fowlpox F8 donor plasmid containing SFV Arg650Asp+Ser259Pro/FIV gag-pro under the control of a mutant H6 promoter

FIG. 31.

A schematic illustration of pF8 mutant H6p-SFV R650D+S259P/FIV gag-pro donor plasmid (pJY1302.4)

FIG. 32A.

Nucleotide sequences of pF8 mutant H6p-SFV Arg650Asp+Ser259Pro/FIV gag-pro (pJY1302.4)

```
                                                                F8 left arm
   1    GACCCTTTAC AAGAATAAAA GAAGAAACAA CTGTGAAATA GTTTATAAAT GTAATTCGTA
        CTGGGAAATG TTCTTATTTT CTTCTTTGTT GACACTTTAT CAAATATTTA CATTAAGCAT
  61    TGCAGAAAAC GATAATATAT TTTGGTATGA GAAATCTAAA GGAGACATAG TTTGTATAGA
        ACGTCTTTTG CTATTATATA AAACCATACT CTTTAGATTT CCTCTGTATC AAACATATCT
 121    CATGCGCTCT TCCGATGAGA TATTCGATGC TTTTCTAATG TATCATATAG CTACAAGATA
        GTACGCGAGA AGGCTACTCT ATAAGCTACG AAAAGATTAC ATAGTATATC GATGTTCTAT
 181    TGCCTATCAT GATGATGATA TATATCTACA AATAGTGTTA TATTATTCTA ATAATCAAAA
        ACGGATAGTA CTACTACTAT ATATAGATGT TTATCACAAT ATAATAAGAT TATTAGTTTT
 241    TGTTATATCT TATATTACGA AAAATAAATA CGTTAAGTAT ATAAGAAATA AACTAGAGA
        ACAATATAGA ATATAATGCT TTTTATTTAT GCAATTCATA TATTCTTTAT TTTGATCTCT
 301    CGATATTCAT AAAGTAAAAA TATTAGCTCT AGAAGACTTT ACAACGGAAG AAATATATTG
        GCTATAAGTA TTTCATTTTT ATAATCGAGA TCTTCTGAAA TGTTGCCTTC TTTATATAAC
 361    TTGGATTAGT AATATATAAC AGCGTAGCTG CACGGTTTTG ATCATTTTCC AACAATATAA
        AACCTAATCA TTATATATTG TCGCATCGAC GTGCCAAAAC TAGTAAAAGG TTGTTATATT
 421    ACCAATGAAG GAGGACGACT CATCAAACAT AAATAACATT CACGGAAAAT ATTCAGTATC
        TGGTTACTTC CTCCTGCTGA GTAGTTTGTA TTTATTGTAA GTGCCTTTTA TAAGTCATAG
 481    AGATTTATCA CAAGATGATT ATGTTATTGA ATGTATAGAC GGATCTTTTG ATTCGATCAA
        TCTAAATAGT GTTCTACTAA TACAATAACT TACATATCTG CCTAGAAAAC TAAGCTAGTT
 541    GTATAGAGAT ATAAAGGTTA TAATAATGAA GAATAACGGT TACGTTAATT GTAGTAAATT
        CATATCTCTA TATTTCCAAT ATTATTACTT CTTATTGCCA ATGCAATTAA CATCATTTAA
 601    ATGTAAAATG CGGAATAAAT ACTTTTCTAG ATGGTTGCGT CTTTCTACTT CTAAAGCATT
        TACATTTTAC GCCTTATTTA TGAAAAGATC TACCAACGCA GAAAGATGAA GATTTCGTAA
 661    ATTAGACATT TACAATAATA AGTCAGTAGA TAATGCTATT GTTAAAGTCT ATGGTAAAGG
        TAATCTGTAA ATGTTATTAT TCAGTCATCT ATTACGATAA CAATTTCAGA TACCATTTCC
 721    TAAGAAACTT ATTATAACAG GATTTTATCT CAAACAAAAT ATGATACGTT ATGTTATTGA
        ATTCTTTGAA TAATATTGTC CTAAAATAGA GTTTGTTTTA TACTATGCAA TACAATAACT
 781    GTGGATAGGG GATGATTTTA CAAACGATAT ATACAAATG ATTAATTTCT ATAATGCGTT
        CACCTATCCC CTACTAAAAT GTTTGCTATA TATGTTTTAC TAATTAAAGA TATTACGCAA
 841    ATTCGGTAAC GATGAATTAA AAATAGTATC CTGTGAAAAC ACTCTATGCC CGTTTATAGA
        TAAGCCATTG CTACTTAATT TTTATCATAG GACACTTTTG TGAGATACGG GCAAATATCT
 901    ACTTGGTAGA TGCTATTATG GTAAAAAATG TAAGTACATA CACGGAAGCA AATGTGATAT
        TGAACCATCT ACGATAATAC CATTTTTTAC ATTCATATAT GTGCCTCTAG TTACACTATA
 961    CTGTGGTCTA TATATACTAC ACCCTACCGA TATTAACCAA CGAGTTTCTC ACAAGAAAAC
        GACACCAGAT ATATATGATG TGGGATGGCT ATAATTGGTT GCTCAAAGAG TGTTCTTTTG
1021    TTGTTTAGTA GATAGAGATT CTTTGATTGT GTTTAAAAGA AGTACCAGTA AAAAGTGTGG
        AACAAATCAT CTATCTCTAA GAAACTAACA CAAATTTTCT TCATGGTCAT TTTTCACACC
1081    CATATGCATA GAAGAAATAA ACAAAAAACA TATTTCCGAA CAGTATTTTG GAATTCTCCC
        GTATACGTAT CTTCTTTATT TGTTTTTTGT ATAAAGGCTT GTCATAAAAC CTTAAGAGGG
1141    AAGTTGTAAA CATATTTTTT GCCTATCATG TATAAGACGT TGGGCAGATA CTACCAGAAA
        TTCAACATTT GTATAAAAAA CGGATAGTAC ATATTCTGCA ACCCGTCTAT GATGGTCTTT
1201    TACAGATACT GAAAATACGT GTCCTGAATG TAGAATAGTT TTTCCTTTCA TAATACCCAG
        ATGTCTATGA CTTTTATGCA CAGGACTTAC ATCTTATCAA AAAGGAAAGT ATTATGGGTC
1261    TAGGTATTGG ATAGATAATA AATATGATAA AAAAATATTA TATAATAGAT ATAAGAAAAT
        ATCCATAACC TATCTATTAT TTATACTATT TTTTTATAAT ATATTATCTA TATTCTTTTA
1321    GATTTTTACA AAAATACCTA TAAGAACAAT AAAAATATAA TTACATTTAC GGAAAATAGC
        CTAAAAATGT TTTTATGGAT ATTCTTGTTA TTTTTATATT AATGTAAATG CCTTTTATCG
1381    TGGTTTTAGT TTACCAACTT AGAGTAATTA TCATATTGAA TCTATATTGC TAATTAGCTA
        ACCAAAATCA AATGGTTGAA TCTCATTAAT AGTATAACTT AGATATAACG ATTAATCGAT
                            Mutant H6 promoter
1441    ATAAAACCCC GGGTTCTTTA TTCTATACTT AAAAAGTGCA AATAAATACA AAGGTTCTTG
        TATTTTTGGG CCCAAGAAAT AAGATATGAA TTTTTCACGT TTATTTATGT TTCCAAGAAC
         SFV replicon
1501    ATGGCGGATG TGTGACATAC ACGACGCCAA AAGATTTTGT TCCAGCTCCT GCCACCTCCG
        TACCGCCTAC ACACTGTATG TGCTGCGGTT TTCTAAAACA AGGTCGAGGA CGGTGGAGGC
           M    A    A    K    V    H    V    D    I    E    A    D  ·
```

FIG. 32B.

```
1561   CTACGCGAGA GATTAACCAC CCACGATGGC CGCCAAAGTG CATGTTGATA TTGAGGCTGA
       GATGCGCTCT CTAATTGGTG GGTGCTACCG GCGGTTTCAC GTACAACTAT AACTCCGACT
       . S  P  F   I  K  S  L   Q  K  A   F  P  S   F  E  V   S  L  Q .
1621   CAGCCCATTC ATCAAGTCTT TGCAGAAGGC ATTTCCGTCG TTCGAGGTGG AGTCATTGCA
       GTCGGGTAAG TAGTTCAGAA ACGTCTTCCG TAAAGGCAGC AAGCTCCACC TCAGTAACGT
       . V  T  P   N  D  H   A  N  A  R   A  F  S   H  L  A  T   K  L  I .
1681   GGTCACACCA AATGACCATG CAAATGCCAG AGCATTTTCG CACCTGGCTA CCAAATTGAT
       CCAGTGTGGT TTACTGGTAC GTTTACGGTC TCGTAAAAGC GTGGACCGAT GGTTTAACTA
       . E  Q  E   T  D  K  D   T  L  I   L  D  I   G  S  A  P   S  R  R .
1741   CGAGCAGGAG ACTGACAAAG ACACACTCAT CTTGGATATC GGCAGTGCGC CTTCCAGGAG
       GCTCGTCCTC TGACTGTTTC TGTGTGAGTA GAACCTATAG CCGTCACGCG GAAGGTCCTC
       . M  M  S   T  K  Y   H  C  V   C  P  M   R  S  A  E   D  P  E .
1801   AATGATGTCT ACGCACAAAT ACCACTGCGT ATGCCCTATG CGCAGCGCAG AAGACCCCGA
       TTACTACAGA TGCGTGTTTA TGGTGACGCA TACGGGATAC GCGTCGCGTC TTCTGGGGCT
       . R  L  V   C  Y  A  K   K  L  A   A  A  S   G  K  V   L  D  R  E .
1861   AAGGCTCGTA TGCTACGCAA AGAAACTGGC AGCGGCCTCC GGGAAGGTGC TGGATAGAGA
       TTCCGAGCAT ACGATGCGTT TCTTTGACCG TCGCCGGAGG CCCTTCCACG ACCTATCTCT
       . I  A  G   K  I  T  D   L  Q  T   V  M  A   T  P  D   A  E  S  P .
1921   GATCGCAGGA AAAATCACCG ACCTGCAGAC CGTCATGGCT ACGCCAGACG CTGAATCTCC
       CTAGCGTCCT TTTTAGTGGC TGGACGTCTG GCAGTACCGA TGCGGTCTGC GACTTAGAGG
       . T  F  C   L  H  T  D   V  T  C   R  T  A   A  E  V  A   V  Y  Q .
1981   TACCTTTTGC CTGCATACAG ACGTCACGTG TCGTACGGCA GCCGAAGTGG CCGTATACCA
       ATGGAAAACG GACGTATGTC TGCAGTGCAC AGCATGCCGT CGGCTTCACC GGCATATGGT
       . D  V  Y   A  V  H   A  P  T  S   L  Y  H   Q  A  M  K   G  V  R .
2041   GGACGTGTAT GCTGTACATG CACCAACATC GCTGTACCAT CAGGCGATGA AAGGTGTCAG
       CCTGCACATA CGACATGTAC GTGGTTGTAG CGACATGGTA GTCCGCTACT TTCCACAGTC
       . T  A  Y   W  I  G  F   D  T  T   P  F  M   F  D  A  L   A  G  A .
2101   AACGGCGTAT TGGATTGGGT TTGACACCAC CCCGTTTATG TTTGACGCGC TAGCAGGCGC
       TTGCCGCATA ACCTAACCCA AACTGTGGTG GGGCAAATAC AAACTGCGCG ATCGTCCGCG
       . Y  P  T   Y  A  T  N   W  A  D   E  Q  V   L  Q  A   R  N  I  G .
2161   GTATCCAACC TACGCCACAA ACTGGGCCGA CGAGCAGGTG TTACAGGCCA GGAACATAGG
       CATAGGTTGG ATGCGGTGTT TGACCCGGCT GCTCGTCCAC AATGTCCGGT CCTTGTATCC
       . L  C  A   A  S  L  T   E  G  R   L  G  K   L  S  I   L  R  K  K .
2221   ACTGTGTGCA GCATCCTTGA CTGAGGGAAG ACTCGGCAAA CTGTCCATTC TCCGCAAGAA
       TGACACACGT CGTAGGAACT GACTCCCTTC TGAGCCGTTT GACAGGTAAG AGGCGTTCTT
       . Q  L  K   P  C  D  T   V  M  F   S  V  G   S  T  L   Y  T  E  S .
2281   GCAATTGAAA CCTTGCGACA CAGTCATGTT CTCGGTAGGA TCTACATTGT ACACTGAGAG
       CGTTAACTTT GGAACGCTGT GTCAGTACAA GAGCCATCCT AGATGTAACA TGTGACTCTC
       . R  K  L   L  R  S  W   H  L  P   S  V  F   H  L  K   G  K  Q  S .
2341   CAGAAAGCTA CTGAGGAGCT GGCACTTACC CTCCGTATTC CACCTGAAAG GTAAACAATC
       GTCTTTCGAT GACTCCTCGA CCGTGAATGG GAGGCATAAG GTGGACTTTC CATTTGTTAG
       . F  T  C   R  C  D  T   I  V  S   C  E  G   Y  V  V   K  I  T .
2401   CTTTACCTGT AGGTGCGATA CCATCGTATC ATGTGAAGGG TACGTAGTTA AGAAAATCAC
       GAAATGGACA TCCACGCTAT GGTAGCATAG TACACTTCCC ATGCATCAAT TCTTTTAGTG
       . M  C  P   G  L  Y  G   K  T  V   G  Y  A   V  T  Y   H  A  E  G .
2461   TATGTGCCCC GGCCTGTACG GTAAAACGGT AGGGTACGCC GTGACGTATC ACGCGGAGGG
       ATACACGGGG CCGGACATGC CATTTTGCCA TCCCATGCGG CACTGCATAG TGCGCCTCCC
       . F  L  V   C  K  T  T   D  T  V   K  G  E   R  V  S  F   P  V  C .
2521   ATTCCTAGTG TGCAAGACCA CAGACACTGT CAAAGGAGAA AGAGTCTCAT TCCCTGTATG
       TAAGGATCAC ACGTTCTGGT GTCTGTGACA GTTTCCTCTT TCTCAGAGTA AGGGACATAC
       . T  Y  V   P  S  T  I   C  D  Q   M  T  G   I  L  A  T   D  V  T .
2581   CACCTACGTC CCCTCAACCA TCTGTGATCA AATGACTGGC ATACTAGCGA CCGACGTCAC
       GTGGATGCAG GGGAGTTGGT AGACACTAGT TTACTGACCG TATGATCGCT GGCTGCAGTG
       . P  E  D   A  Q  K  L   L  V  G   L  N  Q   R  I  V  V   N  G  R .
2641   ACCGGAGGAC GCACAGAAGT TGTTAGTGGG ATTGAATCAG AGGATAGTTG TGAACGGAAG
       TGGCCTCCTG CGTGTCTTCA ACAATCACCC TAACTTAGTC TCCTATCAAC ACTTGCCTTC
       . T  Q  R   N  T  N  T   M  K  N   Y  L  L   P  I  V  A   V  A  F .
2701   AACACAGCGA AACACTAACA CGATGAAGAA CTATCTGCTT CCGATTGTGG CCGTCGCATT
       TTGTGTCGCT TTGTGATTGT GCTACTTCTT GATAGACGAA GGCTAACACC GGCAGCGTAA
```

FIG. 32C.

```
             .  S   K   W       A   R   E   Y       K   A   D       L   D   D       E   K   P       L   G   V   R  .
      2761    TAGCAAGTGG  GCGAGGGAAT  ACAAGGCAGA  CCTTGATGAT  GAAAAACCTC  TGGGTGTCCG
              ATCGTTCACC  CGCTCCCTTA  TGTTCCGTCT  GGAACTACTA  CTTTTTGGAG  ACCCACAGGC
             .  E   R   S       L   T   C   C       L   W       A   F   K       T   R   K   M       H   T   M  .
      2821    AGAGAGGTCA  CTTACTTGCT  GCTGCTTGTG  GGCATTTAAA  ACGAGGAAGA  TGCACACCAT
              TCTCTCCAGT  GAATGAACGA  CGACGAACAC  CCGTAAATTT  TGCTCCTTCT  ACGTGTGGTA
             .  Y   K   K       P   D   T   Q       T   I   V       K   V   P       S   E   F   N       S   F   V  .
      2881    GTACAAGAAA  CCAGACACCC  AGACAATAGT  GAAGGTGCCT  TCAGAGTTTA  ACTCGTTCGT
              CATGTTCTTT  GGTCTGTGGG  TCTGTTATCA  CTTCCACGGA  AGTCTCAAAT  TGAGCAAGCA
             .  I   P   S       L   W   S   T       G   L   A       I   P   V       R   S   R   I       K   M   L  .
      2941    CATCCCGAGC  CTATGGTCTA  CAGGCCTCGC  AATCCCAGTC  AGATCACGCA  TTAAGATGCT
              GTAGGGCTCG  GATACCAGAT  GTCCGGAGCG  TTAGGGTCAG  TCTAGTGCGT  AATTCTACGA
             .  L   A   K       K   T   K   R       E   L   I       P   V   L       D   A   S   S       A   R   D  .
      3001    TTTGGCCAAG  AAGACCAAGC  GAGAGTTAAT  ACCTGTTCTC  GACGCGTCGT  CAGCCAGGGA
              AAACCGGTTC  TTCTGGTTCG  CTCTCAATTA  TGGACAAGAG  CTGCGCAGCA  GTCGGTCCCT
             .  A   E   Q       E   E   K   E       R   L   E       A   E   L       T   R   E   A       L   P   P  .
      3061    TGCTGAACAA  GAGGAGAAGG  AGAGGTTGGA  GGCCGAGCTG  ACTAGAGAAG  CCTTACCACC
              ACGACTTGTT  CTCCTCTTCC  TCTCCAACCT  CCGGCTCGAC  TGATCTCTTC  GGAATGGTGG
             .  L   V   P       I   A   P   A       E   T   G       V   V   D       V   D   V   E       E   L   E  .
      3121    CCTCGTCCCC  ATCGCGCCGG  CGGAGACGGG  AGTCGTCGAC  GTCGACGTTG  AAGAACTAGA
              GGAGCAGGGG  TAGCGCGGCC  GCCTCTGCCC  TCAGCAGCTG  CAGCTGCAAC  TTCTTGATCT
             .  Y   H   A       G   A   G   V       V   E   T       P   R   S       A   L   K   V       T   A   Q  .
      3181    GTATCACGCA  GGTGCAGGGG  TCGTGGAAAC  ACCTCGCAGC  GCGTTGAAAG  TCACCGCACA
              CATAGTGCGT  CCACGTCCCC  AGCACCTTTG  TGGAGCGTCG  CGCAACTTTC  AGTGGCGTGT
             .  P   N   D       V   L   L   G       N   Y   V       V   L   S       P   Q   T   V       L   K   S  .
      3241    GCCGAACGAC  GTACTACTAG  GAAATTACGT  AGTTCTGTCC  CCGCAGACCG  TGCTCAAGAG
              CGGCTTGCTG  CATGATGATC  CTTTAATGCA  TCAAGACAGG  GGCGTCTGGC  ACGAGTTCTC
             .  S   K   L       A   P   V   H       P   L   A       E   Q   V       K   I   I   T       H   N   G  .
      3301    CTCCAAGTTG  GCCCCCGTGC  ACCCTCTAGC  AGAGCAGGTG  AAAATAATAA  CACATAACGG
              GAGGTTCAAC  CGGGGGCACG  TGGGAGATCG  TCTCGTCCAC  TTTTATTATT  GTGTATTGCC
             .  R   A   G       R   Y   Q   V       D   G   Y       D   G   R       V   L   L   P       C   G   S  .
      3361    GAGGGCCGGC  CGTTACCAGG  TCGACGGATA  TGACGGCAGG  GTCCTACTAC  CATGTGGATC
              CTCCCGGCCG  GCAATGGTCC  AGCTGCCTAT  ACTGCCGTCC  CAGGATGATG  GTACACCTAG
             .  A   I   P       V   P   E   F       Q   A   L       S   E   S       A   T   M   V       Y   N   E  .
      3421    GGCCATTCCG  GTCCCTGAGT  TTCAAGCTTT  AGCGAGAGC  GCCACTATGG  TGTACAACGA
              CCGGTAAGGC  CAGGGACTCA  AAGTTCGAAA  CTCGCTCTCG  CGGTGATACC  ACATGTTGCT
             .  R   E   F       V   N   R   K       L   Y   H       I   A   V       H   G   P   S       L   N   T  .
      3481    AAGGGAGTTC  GTCAACAGGA  AACTATACCA  TATTGCCGTT  CACGGACCGT  CGCTGAACAC
              TTCCCTCAAG  CAGTTGTCCT  TTGATATGGT  ATAACGGCAA  GTGCCTGGCA  GCGACTTGTG
             .  D   E   E       N   Y   E   K       V   R   A       E   R   T       D   A   E   Y       V   F   D  .
      3541    CGACGAGGAG  AACTACGAGA  AAGTCAGAGC  TGAAAGAACT  GACGCCGAGT  ACGTGTTCGA
              GCTGCTCCTC  TTGATGCTCT  TTCAGTCTCG  ACTTTCTTGA  CTGCGGCTCA  TGCACAAGCT
             .  V   D   K       K   C   C   V       K   R   E       E   A   S       G   L   V   L       V   G   E  .
      3601    CGTAGATAAA  AAATGCTGCG  TCAAGAGAGA  GGAAGCGTCG  GGTTTGGTGT  TGGTGGGAGA
              GCATCTATTT  TTTACGACGC  AGTTCTCTCT  CCTTCGCAGC  CCAAACCACA  ACCACCCTCT
             .  L   T   N       P   P   F   H       E   F   A       Y   E   G       L   K   I   R       P   S   A  .
      3661    GCTAACCAAC  CCCCCGTTCC  ATGAATTCGC  CTACGAAGGG  CTGAAGATCA  GGCCGTCGGC
              CGATTGGTTG  GGGGGCAAGG  TACTTAAGCG  GATGCTTCCC  GACTTCTAGT  CCGGCAGCCG
             .  P   Y   K       T   T   V   V       G   V   F       G   V   P       G   S   G   K       S   A   I  .
      3721    ACCATATAAG  ACTACAGTAG  TAGGAGTCTT  TGGGGTTCCG  GGATCAGGCA  AGTCTGCTAT
              TGGTATATTC  TGATGTCATC  ATCCTCAGAA  ACCCCAAGGC  CCTAGTCCGT  TCAGACGATA
             .  I   K   S       L   V   T   K       H   D   L       V   T   S       G   K   K   E       N   C   Q  .
      3781    TATTAAGAGC  CTCGTGACCA  AACACGATCT  GGTCACCAGC  GGCAAGAAGG  AGAACTGCCA
              ATAATTCTCG  GAGCACTGGT  TTGTGCTAGA  CCAGTGGTCG  CCGTTCTTCC  TCTTGACGGT
             .  E   I   V       N   D   V   K       K   H   R       G   L   D       I   Q   A   K       T   V   D  .
      3841    GGAAATAGTC  AACGACGTGA  AGAAGCACCG  CGGACTGGAC  ATCCAGGCAA  AAACAGTGGA
              CCTTTATCAG  TTGCTGCACT  TCTTCGTGGC  GCCTGACCTG  TAGGTCCGTT  TTTGTCACCT
             .  S   I   L       L   N   G   C       R   R   A       V   D   I       L   Y   V   D       E   A   F  .
      3901    CTCCATCCTG  CTAAACGGGT  GTCGTCGTGC  CGTGGACATC  CTATATGTGG  ACGAGGCTTT
```

FIG. 32D.

```
         GAGGTAGGAC GATTTGCCCA CAGCAGCACG GCACCTGTAG GATATACACC TGCTCCGAAA
                    S239P
       .  A  C  H   P  G  T   L     L  A  L    I  A  L    V  K  P    S  K  V  .
3961     CGCTTGCCAT CCCGGTACTC TGCTAGCCCT AATTGCTCTT GTTAAACCTC GGAGCAAAGT
         GCGAACGGTA GGGCCATGAG ACGATCGGGA TTAACGAGAA CAATTTGGAG CCTCGTTTCA
       .  V  L  C   G  D  P   K  Q  C     F  F  N    M  M  Q    L  K  V  N  .
4021     GGTGTTATGC GGAGACCCCA AGCAATGCGG ATTCTTCAAT ATGATGCAGC TTAAGGTGAA
         CCACAATACG CCTCTGGGGT TCGTTACGCC TAAGAAGTTA TACTACGTCG AATTCCACTT
       .  F  N  H   N  I  C   T  E  V    H  K  S    I  S  R  R    C  T  R  .
4081     CTTCAACCAC AACATCTGCA CTGAAGTATG TCATAAAAGT ATATCCAGAC GTTGCACGCG
         GAAGTTGGTG TTGTAGACGT GACTTCATAC AGTATTTTCA TATAGGTCTG CAACGTGCGC
       .  P  V  T   A  I  V   S  T  L    H  Y  G  G    K  M  R  T    T  N  P  .
4141     TCCAGTCACG GCCATCGTGT CTACGTTGCA CTACGGAGGC AAGATGCGCA CGACCAACCC
         AGGTCAGTGC CGGTAGCACA GATGCAACGT GATGCCTCCG TTCTACGCGT GCTGGTTGGG
       .  C  N  K   P  I  I   I  D  T  T    G  Q  T    K  P  K  P    G  D  I  .
4201     GTGCAACAAA CCCATAATCA TAGACACCAC AGGACAGACC AAGCCCAAGC CAGGAGACAT
         CACGTTGTTT GGGTATTAGT ATCTGTGGTG TCCTGTCTGG TTCGGGTTCG GTCCTCTGTA
       .  V  L  T   C  F  R   G  W  V  K    Q  L  Q    L  D  Y  R    G  H  E  .
4261     CGTGTTAACA TGCTTCCGAG GCTGGGTAAA GCAGCTGCAG TTGGACTACC GTGGACACGA
         GCACAATTGT ACGAAGGCTC CGACCCATTT CGTCGACGTC AACCTGATGG CACCTGTGCT
       .  V  M  T   A  A  A   S  Q  G  L    T  R  K    G  V  Y  A    V  R  Q  .
4321     AGTCATGACA GCAGCAGCAT CTCAGGGCCT CACCCGCAAA GGGGTATACG CCGTAAGGCA
         TCAGTACTGT CGTCGTCGTA GAGTCCCGGA GTGGGCGTTT CCCCATATGC GGCATTCCGT
       .  K  V  N   E  N  P   L  Y  A  P    A  S  E    H  V  N  V    L  L  T  .
4381     GAAGGTGAAT GAAAATCCCT TGTATGCCCC TGCGTCGGAG CACGTGAATG TACTGCTGAC
         CTTCCACTTA CTTTTAGGGA ACATACGGGG ACGCAGCCTC GTGCACTTAC ATGACGACTG
       .  R  T  E   D  R  L   V  W  K  T    L  A  G    D  P  W  I    K  V  L  .
4441     GCGCACTGAG GATAGGCTGG TGTGGAAAAC GCTGGCCGGC GATCCCTGGA TTAAGGTCCT
         CGCGTGACTC CTATCCGACC ACACCTTTTG CGACCGGCCG CTAGGGACCT AATTCCAGGA
       .  S  N  I   P  Q  G   N  F  T  A    T  L  E    E  W  Q    E  H  D  .
4501     ATCAAACATT CCACAGGGTA ACTTTACGGC CACATTGGAA GAATGGCAAG AAGAACACGA
         TAGTTTGTAA GGTGTCCCAT TGAAATGCCG GTGTAACCTT CTTACCGTTC TTCTTGTGCT
       .  K  I  M   K  V  I   E  G  P  A    A  P  V    D  A  F  Q    N  K  A  .
4561     CAAAATAATG AAGGTGATTG AAGGACCGGC TGCGCCTGTG GACGCGTTCC AGAACAAAGC
         GTTTTATTAC TTCCACTAAC TTCCTGGCCG ACGCGGACAC CTGCGCAAGG TCTTGTTTCG
       .  N  V  C   W  A  K   S  L  V  P    V  L  D    T  A  G  I    R  L  T  .
4621     GAACGTGTGT TGGGCGAAAA GCCTGGTGCC TGTCCTGGAC ACTGCCGGAA TCAGATTGAC
         CTTGCACACA ACCCGCTTTT CGGACCACGG ACAGGACCTG TGACGGCCTT AGTCTAACTG
       .  A  E  E   W  S  T   I  I  T  A    F  K  E    D  R  A  Y    S  P  V  .
4681     AGCAGAGGAG TGGAGCACCA TAATTACAGC ATTTAAGGAG GACAGAGCTT ACTCTCCAGT
         TCGTCTCCTC ACCTCGTGGT ATTAATGTCG TAAATTCCTC CTGTCTCGAA TGAGAGGTCA
       .  V  A  L   N  E  I   C  T  K  Y    G  V    D  L  D  S    G  L  F  .
4741     GGTGGCCTTG AATGAAATTT GCACCAAGTA CTATGGAGTT GACCTGGACA GTGGCCTGTT
         CCACCGGAAC TTACTTTAAA CGTGGTTCAT GATACCTCAA CTGGACCTGT CACCGGACAA
       .  S  A  P   K  V  S   L  Y  Y  E    N  N  H    W  D  N  R    P  G  G  .
4801     TTCTGCCCCG AAGGTGTCCC TGTATTACGA GAACAACCAC TGGGATAACA GACCTGGTGG
         AAGACGGGGC TTCCACAGGG ACATAATGCT CTTGTTGGTG ACCCTATTGT CTGGACCACC
       .  R  M  Y   G  F  N   A  A  T  A    A  R  L    E  A  R  H    T  F  L  .
4861     AAGGATGTAT GGATTCAATG CCGCAACAGC TGCCAGGCTG GAAGCTAGAC ATACCTTCCT
         TTCCTACATA CCTAAGTTAC GGCGTTGTCG ACGGTCCGAC CTTCGATCTG TATGGAAGGA
       .  K  G  Q   W  H  T   G  K  Q  A    V  I  A    E  R  K  I    Q  P  L  .
4921     GAAGGGGCAG TGGCATACGG GCAAGCAGGC AGTTATCGCA GAAAGAAAAA TCCAACCGCT
         CTTCCCCGTC ACCGTATGCC CGTTCGTCCG TCAATAGCGT CTTTCTTTTT AGGTTGGCGA
       .  S  V  L   D  N  V   I  P  I  N    R  R  L    P  H  A  L    V  A  E  .
4981     TTCTGTGCTG GACAATGTAA TTCCTATCAA CCGCAGGCTG CCGCACGCCC TGGTGGCTGA
         AAGACACGAC CTGTTACATT AAGGATAGTT GGCGTCCGAC GGCGTGCGGG ACCACCGACT
       .  Y  K  T   V  K  G   S  R  V  E    W  L  V    N  K  V  R    G  Y  H  .
5041     GTACAAGACG GTTAAAGGCA GTAGGGTTGA GTGGCTGGTC AATAAAGTAA GAGGGTACCA
         CATGTTCTGC CAATTTCCGT CATCCCAACT CACCGACCAG TTATTTCATT CTCCCATGGT
```

FIG. 32E.

```
                                                      R650D
         . V   L   L     V   S   E   Y     N   L   A     L   P   R     R   D   V     T   W   L   S .
5101     CGTCCTGCTG    GTGAGTGAGT    ACAACCTGGC    TTTGCCTCGA    CGCGACGTCA    CTTGGTTGTC
         GCAGGACGAC    CACTCACTCA    TGTTGGACCG    AAACGGAGCT    GCGCTGCAGT    GAACCAACAG
         . P   L   N     V   T   G     A   D   R     C   Y   D     L   S   L     G   L   P   A   D .
5161     ACCGCTGAAT    GTCACAGGCG    CCGATAGGTG    CTACGACCTA    AGTTTAGGAC    TGCCGGCTGA
         TGGCGACTTA    CAGTGTCCGC    GGCTATCCAC    GATGCTGGAT    TCAAATCCTG    ACGGCCGACT
         . A   G   R     F   D   L     V   F   V     N   I   H     T   E   F     R   I   H   H   Y .
5221     CGCCGGCAGG    TTCGACTTGG    TCTTTGTGAA    CATTCACACG    GAATTCAGAA    TCCACCACTA
         GCGGCCGTCC    AAGCTGAACC    AGAAACACTT    GTAAGTGTGC    CTTAAGTCTT    AGGTGGTGAT
         . Q   Q   C     V   D   H     A   M   K     L   Q   M     L   G   G     D   A   L   R   L .
5281     CCAGCAGTGT    GTCGACCACG    CCATGAAGCT    GCAGATGCTT    GGGGGAGATG    CGCTACGACT
         GGTCGTCACA    CAGCTGGTGC    GGTACTTCGA    CGTCTACGAA    CCCCCTCTAC    GCGATGCTGA
         . L   K   P     G   G   S     L   L   M     R   A   Y     G   Y   A     D   K   I   S   E .
5341     GCTAAAACCC    GGCGGCAGCC    TCTTGATGAG    AGCTTACGGA    TACGCCGATA    AAATCAGCGA
         CGATTTTGGG    CCGCCGTCGG    AGAACTACTC    TCGAATGCCT    ATGCGGCTAT    TTTAGTCGCT
         . A   V   V     S   S   L     S   R   K     F   S   S     A   R   V     L   R   P   D   C .
5401     AGCCGTTGTT    TCCTCCTTAA    GCAGAAAGTT    CTCGTCTGCA    AGAGTGTTGC    GCCCGGATTG
         TCGGCAACAA    AGGAGGAATT    CGTCTTTCAA    GAGCAGACGT    TCTCACAACG    CGGGCCTAAC
         . V   T   S     N   T   E     V   F   L     L   F   S     N   F   D     N   G   K   R   P .
5461     TGTCACCAGC    AATACAGAAG    TGTTCTTGCT    GTTCTCCAAC    TTTGACAACG    GAAAGAGACC
         ACAGTGGTCG    TTATGTCTTC    ACAAGAACGA    CAAGAGGTTG    AAACTGTTGC    CTTTCTCTGG
         . S   T   L     H   Q   M     N   T   K     L   S   A   V     Y   A   G     E   A   M   H .
5521     CTCTACGCTA    CACCAGATGA    ATACCAAGCT    GAGTGCCGTG    TATGCCGGAG    AAGCCATGCA
         GAGATGCGAT    GTGGTCTACT    TATGGTTCGA    CTCACGGCAC    ATACGGCCTC    TTCGGTACGT
         . T   A   G     C   A   P   S     Y   R   V     K   R   A     D   I   A     T   C   T   E .
5581     CACGGCCGGG    TGTGCACCAT    CCTACAGAGT    TAAGAGAGCA    GACATAGCCA    CGTGCACAGA
         GTGCCGGCCC    ACACGTGGTA    GGATGTCTCA    ATTCTCTCGT    CTGTATCGGT    GCACGTGTCT
         . A   A   V     V   N   A   A     N   A   R     G   T   V     G   D   G     V   C   R   A .
5641     AGCGGCTGTG    GTTAACGCAG    CTAACGCCCG    TGGAACTGTA    GGGGATGGCG    TATGCAGGGC
         TCGCCGACAC    CAATTGCGTC    GATTGCGGGC    ACCTTGACAT    CCCCTACCGC    ATACGTCCCG
         . V   A   K     K   W   P     S   A   F   K     G   E   A     T   P   V     G   T   I   K .
5701     CGTGGCGAAG    AAATGGCCGT    CAGCCTTTAA    GGGAGAAGCA    ACACCAGTGG    GCACAATTAA
         GCACCGCTTC    TTTACCGGCA    GTCGGAAATT    CCCTCTTCGT    TGTGGTCACC    CGTGTTAATT
         . T   V   M     C   G   S   Y     P   V   I     H   A   V     A   P   N     F   S   A   T .
5761     AACAGTCATG    TGCGGCTCGT    ACCCCGTCAT    CCACGCTGTA    GCGCCTAATT    TCTCTGCCAC
         TTGTCAGTAC    ACGCCGAGCA    TGGGGCAGTA    GGTGCGACAT    CGCGGATTAA    AGAGACGGTG
         . T   E   A     E   G   D     R   E   L     A   V   Y     R   A   V     A   A   E   V .
5821     GACTGAAGCG    GAAGGGGACC    GCGAATTGGC    CGCTGTCTAC    CGGGCAGTGG    CCGCCGAAGT
         CTGACTTCGC    CTTCCCCTGG    CGCTTAACCG    GCGACAGATG    GCCCGTCACC    GGCGGCTTCA
         . N   R   L     S   L   S   S     V   A   I     P   L   L     S   T   G     V   F   S   G .
5881     AAACAGACTG    TCACTGAGCA    GCGTAGCCAT    CCCGCTGCTG    TCCACAGGAG    TGTTCAGCGG
         TTTGTCTGAC    AGTGACTCGT    CGCATCGGTA    GGGCGACGAC    AGGTGTCCTC    ACAAGTCGCC
         . G   R   D     R   L   Q   Q     S   L   N     H   L   F     T   A   M     D   A   T   D .
5941     CGGAAGAGAT    AGGCTGCAGC    AATCCCTCAA    CCATCTATTC    ACAGCAATGG    ACGCCACGGA
         GCCTTCTCTA    TCCGACGTCG    TTAGGGAGTT    GGTAGATAAG    TGTCGTTACC    TGCGGTGCCT
         . A   D   V     T   I   Y     C   R   D   K     S   W   E     K   K   I     Q   E   A   I .
6001     CGCTGACGTG    ACCATCTACT    GCAGAGACAA    AAGTTGGGAG    AAGAAAATCC    AGGAAGCCAT
         GCGACTGCAC    TGGTAGATGA    CGTCTCTGTT    TTCAACCCTC    TTCTTTTAGG    TCCTTCGGTA
         . D   M   R     T   A   V   E     L   L   N     D   D   V     E   L   T   T     D   L   V .
6061     AGACATGAGG    ACGGCTGTGG    AGTTGCTCAA    TGATGACGTG    GAGCTGACCA    CAGACTTGGT
         TCTGTACTCC    TGCCGACACC    TCAACGAGTT    ACTACTGCAC    CTCGACTGGT    GTCTGAACCA
         . R   V   H     P   D   S   S     L   V   G     R   K   G     Y   S   T   T     D   G   S .
6121     GAGAGTGCAC    CCGGACAGCA    GCCTGGTGGG    TCGTAAGGGC    TACAGTACCA    CTGACGGGTC
         CTCTCACGTG    GGCCTGTCGT    CGGACCACCC    AGCATTCCCG    ATGTCATGGT    GACTGCCCAG
         . L   Y   S     Y   F   E     G   T   K   F     N   Q   A     A   I   D     M   A   E   I .
6181     GCTGTACTCG    TACTTTGAAG    GTACGAAATT    CAACCAGGCT    GCTATTGATA    TGGCAGAGAT
         CGACATGAGC    ATGAAACTTC    CATGCTTTAA    GTTGGTCCGA    CGATAACTAT    ACCGTCTCTA
         . L   T   L     W   P   R   L     Q   E   A     N   E   Q     I   C   L   Y     A   L   G .
```

FIG. 32F.

```
6241  ACTGACGTTG TGGCCCAGAC TGCAAGAGGC AAACGAACAG ATATGCCTAT ACGCGCTGGG
      TGACTGCAAC ACCGGGTCTG ACGTTCTCCG TTTGCTTGTC TATACGGATA TGCGCGACCC
      . E  T  M    D  N  I  R   S  K  C    P  V  N    D  S  D  S    T  P   ·
6301  CGAAACAATG GACAACATCA GATCCAAATG TCCGGTGAAC GATTCCGATT CATCAACACC
      GCTTTGTTAC CTGTTGTAGT CTAGGTTTAC AGGCCACTTG CTAAGGCTAA GTAGTTGTGG
      . P  R  T    V  P  C  L   C  R  Y    A  M  T    A  E  R  I    A  R  L  ·
6361  TCCCAGGACA GTGCCCTGCC TGTGCCGCTA CGCAATGACA GCAGAACGGA TCGCCCGCCT
      AGGGTCCTGT CACGGGACGG ACACGGCGAT GCGTTACTGT CGTCTTGCCT AGCGGGCGGA
      . R  S  H    Q  V  K  S   M  V  V    C  S  S    F  P  L  P    K  Y  H  ·
6421  TAGGTCACAC CAAGTTAAAA GCATGGTGGT TTGCTCATCT TTTCCCCTCC CGAAATACCA
      ATCCAGTGTG GTTCAATTTT CGTACCACCA AACGAGTAGA AAAGGGGAGG GCTTTATGGT
      . V  D  G    V  Q  K  V   K  C  E    K  V  L    L  F  D  P    T  V  P  ·
6481  TGTAGATGGG GTGCAGAAGG TAAAGTGCGA GAAGGTTCTC CTGTTCGACC CGACGGTACC
      ACATCTACCC CACGTCTTCC ATTTCACGCT CTTCCAAGAG GACAAGCTGG GCTGCCATGG
      . S  V  V    S  P  R  K   Y  A  A    S  T  T    D  H  S  D    R  S  L  ·
6541  TTCAGTGGTT AGTCCGCGGA AGTATGCCGC ATCTACGACG GACCACTCAG ATCGGTCGTT
      AAGTCACCAA TCAGGCGCCT TCATACGGCG TAGATGCTGC CTGGTGAGTC TAGCCAGCAA
      . R  G  F    D  L  D  W   T  T  D    S  S  S    T  A  S  D    T  M  S  ·
6601  ACGAGGGTTT GACTTGGACT GGACCACCGA CTCGTCTTCC ACTGCCAGCG ATACCATGTC
      TGCTCCCAAA CTGAACCTGA CCTGGTGGCT GAGCAGAAGG TGACGGTCGC TATGGTACAG
      . L  P  S    L  Q  S  C   D  I  D    S  I  Y    E  P  M  A    P  I  V  ·
6661  GCTACCCAGT TTGCAGTCGT GTGACATCGA CTCGATCTAC GAGCCAATGG CTCCCATAGT
      CGATGGGTCA AACGTCAGCA CACTGTAGCT GAGCTAGATG CTCGGTTACC GAGGGTATCA
      . V  T  A    D  V  H  P   E  P  A    G  I  A    D  L  A  A    D  V  H  ·
6721  AGTGACGGCT GACGTACACC CTGAACCCGC AGGCATCGCG GACCTGGCGG CAGATGTGCA
      TCACTGCCGA CTGCATGTGG GACTTGGGCG TCCGTAGCGC CTGGACCGCC GTCTACACGT
      . P  E  P    A  D  H  V   D  L  E    N  P  I    P  P  P  R    P  K  R  ·
6781  TCCTGAACCC GCAGACCATG TGGACCTCGA GAACCCGATT CCTCCACCGC GCCCGAAGAG
      AGGACTTGGG CGTCTGGTAC ACCTGGAGCT CTTGGGCTAA GGAGGTGGCG CGGGCTTCTC
      . A  A  Y    L  A  S  R   A  A  E    R  P  V    P  A  P  R    K  P  T  ·
6841  AGCTGCATAC CTTGCCTCCC GCGCGGCGGA GCGACCGGTG CCGGCGCCGA AAAGCCGAC
      TCGACGTATG GAACGGAGGG CGCGCCGCCT CGCTGGCCAC GGCCGCGGCT CTTTCGGCTG
      . P  A  P    R  T  A  F   R  N  K    L  P  L    T  F  G  D    F  D  E  ·
6901  GCCTGCCCCA AGGACTGCGT TTAGGAACAA GCTGCCTTTG ACGTTCGGCG ACTTTGACGA
      CGGACGGGGT TCCTGACGCA AATCCTTGTT CGACGGAAAC TGCAAGCCGC TGAAACTGCT
      . H  E  V    D  A  L  A   S  G  I    T  F  G    D  F  D  D    V  L  R  ·
6961  GCACGAGGTC GATGCGTTGG CCTCCGGGAT TACTTTCGGA GACTTCGACG ACGTCCTGCG
      CGTGCTCCAG CTACGCAACC GGAGGCCCTA ATGAAAGCCT CTGAAGCTGC TGCAGGACGC
      . L  G  R    A  G  A  Y   I  F  S    S  D  T    G  S  G  H    L  Q  Q  ·
7021  ACTAGGCCGC GCGGGTGCAT ATATTTTCTC CTCGGACACT GGCAGCGGAC ATTTACAACA
      TGATCCGGCG CGCCCACGTA TATAAAAGAG GAGCCTGTGA CCGTCGCCTG TAAATGTTGT
      . K  S  V    R  Q  H  N   L  Q  C    A  Q  L    D  A  V  E    E  E  K  ·
7081  AAAATCCGTT AGGCAGCACA ATCTCCAGTG CGCACAACTG GATGCGGTCG AGGAGGAGAA
      TTTTAGGCAA TCCGTCGTGT TAGAGGTCAC GCGTGTTGAC CTACGCCAGC TCCTCCTCTT
      . M  Y  P    P  K  L  D   T  E  R    E  K  L    L  L  L  K    M  Q  M  ·
7141  AATGTACCCG CCAAAATTGG ATACTGAGAG GGAGAAGCTG TTGCTGCTGA AAATGCAGAT
      TTACATGGGC GGTTTTAACC TATGACTCTC CCTCTTCGAC AACGACGACT TTTACGTCTA
      . H  P  S    E  A  N  K   S  R  Y    Q  S  R    K  V  E  N    M  K  A  ·
7201  GCACCCATCG GAGGCTAATA AGAGTCGATA CCAGTCTCGC AAAGTGGAGA ACATGAAAGC
      CGTGGGTAGC CTCCGATTAT TCTCAGCTAT GGTCAGAGCG TTTCACCTCT TGTACTTTCG
      . T  V  V    D  R  L  T   S  G  A    R  L  Y    T  G  A  D    V  G  R  ·
7261  CACGGTGGTG GACAGGCTCA CATCGGGGGC CAGATTGTAC ACGGGAGCGG ACGTAGGCCG
      GTGCCACCAC CTGTCCGAGT GTAGCCCCCG GTCTAACATG TGCCCTCGCC TGCATCCGGC
      . I  P  T    Y  A  V  R   Y  P  R    P  V  Y    S  P  T  V    I  E  R  ·
7321  CATACCAACA TACGCGGTTC GGTACCCCCG CCCCGTGTAC TCCCCTACCG TGATCGAAAG
      GTATGGTTGT ATGCGCCAAG CCATGGGGGC GGGGCACATG AGGGGATGGC ACTAGCTTTC
      . F  S  S    P  D  V  A   I  A  A    C  N  E    Y  L  S  R    N  Y  P  ·
7381  ATTCTCAAGC CCCGATGTAG CAATCGCAGC GTGCAACGAA TACCTATCCA GAAATTACCC
      TAAGAGTTCG GGGCTACATC GTTAGCGTCG CACGTTGCTT ATGGATAGGT CTTTAATGGG
```

FIG. 32G.

```
            .  T  V  A     S  Y  Q  I     T  D  E     Y  D  A     Y  L  D  M     V  D  G  .
    7441    AACAGTGGCG TCGTACCAGA TAACAGATGA ATACGACGCA TACTTGGACA TGGTTGACGG
            TTGTCACCGC AGCATGGTCT ATTGTCTACT TATGCTGCGT ATGAACCTGT ACCAACTGCC
            .  S  D  S     C  L  D  R     A  T  F     C  P  A     K  L  R  C     Y  P  K  .
    7501    GTCGGATAGT TGCTTGGACA GAGCGACATT CTGCCCGGCG AAGCTCCGGT GCTACCCGAA
            CAGCCTATCA ACGAACCTGT CTCGCTGTAA GACGGGCCGC TTCGAGGCCA CGATGGGCTT
            .  H  H  A     Y  H  Q  P     T  V  R     S  A  V     P  S  P  F     Q  N  T  .
    7561    ACATCATGCG TACCACCAGC CGACTGTACG CAGTGCCGTC CCGTCACCCT TTCAGAACAC
            TGTAGTACGC ATGGTGGTCG GCTGACATGC GTCACGGCAG GGCAGTGGGA AAGTCTTGTG
            .  L  Q  N     V  L  A  A     A  T  K     R  N  C     N  V  T  Q     M  R  E  .
    7621    ACTACAGAAC GTGCTAGCGG CCGCCACCAA GAGAAACTGC AACGTCACGC AAATGCGAGA
            TGATGTCTTG CACGATCGCC GGCGGTGGTT CTCTTTGACG TTGCAGTGCG TTTACGCTCT
            .  L  P  T     M  D  S  A     V  F  N     V  E  C     F  K  R  Y     A  C  S  .
    7681    ACTACCCACC ATGGACTCGG CAGTGTTCAA CGTGGAGTGC TTCAAGCGCT ATGCCTGCTC
            TGATGGGTGG TACCTGAGCC GTCACAAGTT GCACCTCACG AAGTTCGCGA TACGGACGAG
            .  G  E  Y     W  E  E  Y     A  K  Q     P  I  R     I  T  T  E     N  I  T  .
    7741    CGGAGAATAT TGGGAAGAAT ATGCTAAACA ACCTATCCGG ATAACCACTG AGAACATCAC
            GCCTCTTATA ACCCTTCTTA TACGATTTGT TGGATAGGCC TATTGGTGAC TCTTGTAGTG
            .  T  Y  V     T  K  L  K     G  P  K     A  A  A     L  F  A  K     T  H  N  .
    7801    TACCTATGTG ACCAAATTGA AAGGCCCGAA AGCTGCTGCC TTGTTCGCTA AGACCCACAA
            ATGGATACAC TGGTTTAACT TTCCGGGCTT TCGACGACGG AACAAGCGAT TCTGGGTGTT
            .  L  V  P     L  Q  E  V     P  M  D     R  F  T     V  D  M  K     R  D  V  .
    7861    CTTGGTTCCG CTGCAGGAGG TTCCCATGGA CAGATTCACG GTCGACATGA AACGAGATGT
            GAACCAAGGC GACGTCCTCC AAGGGTACCT GTCTAAGTGC CAGCTGTACT TTGCTCTACA
            .  K  V  T     P  G  T  K     H  T  E     E  R  P     K  V  Q  V     I  Q  A  .
    7921    CAAAGTCACT CCAGGGACGA AACACACAGA GGAAAGACCC AAAGTCCAGG TAATTCAAGC
            GTTTCAGTGA GGTCCCTGCT TTGTGTGTCT CCTTTCTGGG TTTCAGGTCC ATTAAGTTCG
            .  A  E  P     L  A  T  A     Y  L  C     G  I  H     R  E  L  V     R  R  L  .
    7981    AGCGGAGCCA TTGGCGACCG CTTACCTGTG CGGCATCCAC AGGGAATTAG TAAGGAGACT
            TCGCCTCGGT AACCGCTGGC GAATGGACAC GCCGTAGGTG TCCCTTAATC ATTCCTCTGA
            .  N  A  V     L  R  P  N     V  H  T     L  F  D     M  S  A  E     D  F  D  .
    8041    AAATGCTGTG TTACGCCCTA ACGTGCACAC ATTGTTTGAT ATGTCGGCCG AAGACTTTGA
            TTTACGACAC AATGCGGGAT TGCACGTGTG TAACAAACTA TACAGCCGGC TTCTGAAACT
            .  A  I  I     A  S  H  F     H  P  G     D  P  V     L  E  T  D     I  A  S  .
    8101    CGCGATCATC GCCTCTCACT TCCACCCAGG ACCCTGTTCT CTAGAGACAG ACATTGCATC
            GCGCTAGTAG CGGAGAGTGA AGGTGGGTCC TCTGGGCCAA GATCTCTGCC TGTAACGTAG
            .  F  D  K     S  Q  D  D     S  L  A     L  T  G     L  M  I  L     E  D  L  .
    8161    ATTCGACAAA AGCCAGGACG ACTCCTTGGC TCTTACAGGT TTAATGATCC TCGAAGATCT
            TAAGCTGTTT TCGGTCCTGC TGAGGAACCG AGAATGTCCA AATTACTAGG AGCTTCTAGA
            .  G  V  D     Q  Y  L  L     D  L  I     E  A  A     F  G  E  I     S  S  C  .
    8221    AGGGGTGGAT CAGTACCTGC TGGACTTGAT CGAGGCAGCC TTTGGGGAAA TATCCAGCTG
            TCCCCACCTA GTCATGGACG ACCTGAACTA GCTCCGTCGG AAACCCCTTT ATAGGTCGAC
            .  H  L  P     T  G  T  R     F  K  F     G  A  M     M  K  S  G     M  F  L  .
    8281    TCACCTACCA ACTGGCACGC GCTTCAAGTT CGGAGCTATG ATGAAATCGG CATGTTTCT
            AGTGGATGGT TGACCGTGCG CGAAGTTCAA GCCTCGATAC TACTTTAGCC CGTACAAAGA
            .  T  L  F     I  N  T  V     L  N  I     T  I  A     S  R  V  L     E  Q  R  .
    8341    GACTTTGTTT ATTAACACTG TTTTGAACAT CACCATAGCA AGCAGGGTAC TGGAGCAGAG
            CTGAAACAAA TAATTGTGAC AAAACTTGTA GTGGTATCGT TCGTCCCATG ACCTCGTCTC
            .  L  T  D     S  A  C  A     A  F  I     G  D  D     N  I  V  H     G  V  I  .
    8401    ACTCACTGAC TCCGCCTGTG CGGCCTTCAT CGGCGACGAC AACATCGTTC ACGGAGTGAT
            TGAGTGACTG AGGCGGACAC GCCGGAAGTA GCCGCTGCTG TTGTAGCAAG TGCCTCACTA
            .  S  D  K     L  M  A  E     R  C  A     S  W  V     N  M  E  V     K  I  I  .
    8461    CTCCGACAAG CTGATGGCGG AGAGGTGCGC GTCGTGGGTC AACATGGAGG TGAAGATCAT
            GAGGCTGTTC GACTACCGCC TCTCCACGCG CAGCACCCAG TTGTACCTCC ACTTCTAGTA
            .  D  A  V     M  G  E  K     P  P  Y     F  C  G     G  F  I  V     F  D  S  .
    8521    TGACGCTGTC ATGGGCGAAA AACCCCCATA TTTCTGTGGG GGATTCATAG TTTTTGACAG
            ACTGCGACAG TACCCGCTTT TTGGGGGTAT AAAGACACCC CCTAAGTATC AAAAACTGTC
            .  V  T  Q     T  A  C  R     V  S  D     P  L  K     R  L  F  K     L  G  K  .
    8581    CGTCACACAG ACCGCCTGCC GTGTTTCAGA CCCACTTAAG CGCCTGTTCA AGTTGGGTAA
```

FIG. 32H.

```
           GCAGTGTGTC TGGCGGACGG CACAAAGTCT GGGTGAATTC GCGGACAAGT TCAACCCATT
            . P L T    A E D K    Q D E    D R R    R A L S    D E V  ·
    8641   GCCGCTAACA GCTGAAGACA AGCAGGACGA AGACAGGCGA CGAGCACTGA GTGACGAGGT
           CGGCGATTGT CGACTTCTGT TCGTCCTGCT TCTGTCCGCT GCTCGTGACT CACTGCTCCA
            . S K W    F R T G    L G A    E L E    V A L T    S R Y  ·
    8701   TAGCAAGTGG TTCCGGACAG GCTTGGGGGC CGAACTGGAG GTGGCACTAA CATCTAGGTA
           ATCGTTCACC AAGGCCTGTC CGAACCCCCG GCTTGACCTC CACCGTGATT GTAGATCCAT
            . E V E    G C K S    I L I    A M A    T L A R    D I K  ·
    8761   TGAGGTAGAG GGCTGCAAAA GTATCCTCAT AGCCATGGCC ACCTTGGCGA GGGACATTAA
           ACTCCATCTC CCGACGTTTT CATAGGAGTA TCGGTACCGG TGGAACCGCT CCCTGTAATT
                                                      26S promoter
            . A F K    K L R G    P V I    H L Y    G G P R    L V R  ·
    8821   GGCGTTTAAG AAATTGAGAG GACCTGTTAT ACACCTCTAC GGCGGTCCTA GATTGGTGCG
           CCGCAAATTC TTTAACTCTC CTGGACAATA TGTGGAGATG CCGCCAGGAT CTAACCACGC
                                    FIV gag
                                       M    G N G    Q G R    D W K M  ·
    8881   TTAATACACA GAATTCTGAT TTTAATTAAA TGGGGAATGG ACAGGGGCGA GATTGGAAAA
           AATTATGTGT CTTAAGACTA AAATTAATTT ACCCCTTACC TGTCCCCGCT CTAACCTTTT
            .. A I K    R C S    N V A V    G V G    G K S    K K F G  ·
    8941   TGGCCATTAA GAGATGTAGT AATGTTGCTG TAGGAGTAGG GGGGAAGAGT AAAAAATTTG
           ACCGGTAATT CTCTACATCA TTACAACGAC ATCCTCATCC CCCCTTCTCA TTTTTTAAAC
            .. E G N    F R W    A I R M    A N V    S T G    R E P G  ·
    9001   GAGAAGGGAA TTTCAGATGG GCCATTAGAA TGGCTAATGT ATCTACAGGA CGAGAACCTG
           CTCTTCCCTT AAAGTCTACC CGGTAATCTT ACCGATTACA TAGATGTCCT GCTCTTGGAC
            .. D I P    E T L    D Q L R    L V I    C D L    Q E R R  ·
    9061   GTGATATACC AGAGACTTTA GATCAACTAA GGTTGGTTAT TTGCGATTTA CAAGAAAGAA
           CACTATATGG TCTCTGAAAT CTAGTTGATT CCAACCAATA AACGCTAAAT GTTCTTTCTT
            .. E K F    G S S    K E I D    M A I    V T L    K V F A  ·
    9121   GAGAAAAATT TGGATCTAGC AAAGAAATTG ATATGGCAAT TGTGACATTA AAAGTCTTTG
           CTCTTTTTAA ACCTAGATCG TTTCTTTAAC TATACCGTTA ACACTGTAAT TTTCAGAAAC
            .. V A G    L L N    M T V S    T A A    A E N    M Y S  ·
    9181   CGGTAGCAGG ACTTTTGAAT ATGACGGTGT CTACTGCTGC TGCAGCTGAA AATATGTATT
           GCCATCGTCC TGAAAACTTA TACTGCCACA GATGACGACG ACGTCGACTT TTATACATAA
            .. Q M G    L D T    R P S M    K E A    G G K    E E G P  ·
    9241   CTCAAATGGG ATTAGACACT AGGCCATCTA TGAAAGAAGC AGGTGGAAAA GAGGAAGGCC
           GAGTTTACCC TAATCTGTGA TCCGGTAGAT ACTTTCTTCG TCCACCTTTT CTCCTTCCGG
            .. P Q A    Y P I    Q T V N    G V P    Q Y V    A L D P  ·
    9301   CTCCACAGGC ATATCCTATT CAAACAGTAA ATGGAGTACC ACAATATGTA GCACTTGACC
           GAGGTGTCCG TATAGGATAA GTTTGTCATT TACCTCATGG TGTTATACAT CGTGAACTGG
            .. K M V    S I F    M E K A    R E G    L G G    E E V Q  ·
    9361   CAAAAATGGT GTCCATTTTC ATGGAAAAGG CAAGAGAAGG ACTAGGAGGG GAGGAAGTTC
           GTTTTTACCA CAGGTAAAAG TACCTTTTCC GTTCTCTTCC TGATCCTCCC CTCCTTCAAG
            .. L W F    T A F    S A N L    T P T    D M A    T L I M  ·
    9421   AACTATGGTT TACTGCCTTC TCTGCAAATT TAACACCTAC TGACATGGCC ACATTAATAA
           TTGATACCAA ATGACGGAAG AGACGTTTAA ATTGTGGATG ACTGTACCGG TGTAATTATT
            .. A A P    G C A    A D K E    I L D    E S L    K Q L T  ·
    9481   TGGCCGCACC AGGGTGCGCT GCAGATAAAG AAATATTGGA TGAAAGCTTA AAGCAACTGA
           ACCGGCGTGG TCCCACGCGA CGTCTATTTC TTTATAACCT ACTTTCGAAT TTCGTTGACT
            .. A E Y    D R T    H P P D    A P R    P L P    Y F T A  ·
    9541   CAGCAGAATA TGATCGCACA CATCCCCCTG ATGCTCCCAG ACCATTACCC TATTTTACTG
           GTCGTCTTAT ACTAGCGTGT GTAGGGGGAC TACGAGGGTC TGGTAATGGG ATAAAATGAC
            .. A E I    M G I    G L T Q    E Q Q    A E A    R F A P  ·
    9601   CAGCAGAAAT TATGGGTATA GGATTAACTC AAGAACAACA AGCAGAAGCA AGATTTGCAC
           GTCGTCTTTA ATACCCATAT CCTAATTGAG TTCTTGTTGT TCGTCTTCGT TCTAAACGTG
            .. A R M    Q C R    A W Y L    E A L    G K L    A A I K  ·
    9661   CAGCTAGGAT GCAGTGTAGA GCATGGTATC TCGAGGCATT AGGAAAATTG GCTGCCATAA
           GTCGATCCTA CGTCACATCT CGTACCATAG AGCTCCGTAA TCCTTTTAAC CGACGGTATT
            .. A K S    P R A    V Q L R    Q G A    K E D    Y S S F  ·
    9721   AAGCTAAGTC TCCTCGAGCT GTGCAGTTAA GACAAGGAGC TAAGGAAGAT TATTCATCCT
```

FIG. 32I.

```
         TTCGATTCAG AGGAGCTCGA CACGTCAATT CTGTTCCTCG ATTCCTTCTA ATAAGTAGGA
         .. I  D  R   L  F  A   Q  I  D  Q   E  Q  N    T  A  E   V  K  L  Y .
  9781   TTATAGACAG ATTGTTTGCC CAAATAGATC AAGAACAAAA TACAGCTGAA GTTAAGTTAT
         AATATCTGTC TAACAAACGG GTTTATCTAG TTCTTGTTTT ATGTCGACTT CAATTCAATA
         .. L  K  Q   S  L  S   I  A  N  A  N  A  D    C  K  K    A  M  S  H .
  9841   ATTTAAAACA GTCATTAAGC ATAGCTAATG CTAATGCAGA CTGTAAAAAG GCAATGAGCC
         TAAATTTTGT CAGTAATTCG TATCGATTAC GATTACGTCT GACATTTTTC CGTTACTCGG
         .. L  K  P   E  S  T   L  E  E  K   L  R  A   C  Q  E   I  G  S  P .
  9901   ACCTTAAGCC AGAAAGTACC CTAGAAGAAA AGTTGAGAGC TTGTCAAGAA ATAGGCTCAC
         TGGAATTCGG TCTTTCATGG GATCTTCTTT TCAACTCTCG AACAGTTCTT TATCCGAGTG
         .. G  Y  K   M  Q  L   L  A  E  A   L  T  K    V  Q  V   V  Q  S  K .
  9961   CAGGATATAA AATGCAACTC TTGGCAGAAG CTCTTACAAA AGTTCAAGTA GTGCAATCAA
         GTCCTATATT TTACGTTGAG AACCGTCTTC GAGAATGTTT TCAAGTTCAT CACGTTAGTT
         .. G  S  G   P  V  C   F  N  C  K   K  P  G    H  L  A   R  Q  C  R .
 10021   AAGGATCAGG ACCAGTGTGT TTTAATTGTA AAAAACCAGG ACATCTAGCA AGACAATGTA
         TTCCTAGTCC TGGTCACACA AAATTAACAT TTTTTGGTCC TGTAGATCGT TCTGTTACAT
         .. E  V  K   K  C  N   K  C  G  K   P  G  H    L  A  A   K  C  W  Q .
 10081   GAGAAGTGAA AAAATGTAAT AAATGTGGAA AACCTGGTCA TCTAGCTGCC AAATGTTGGC
         CTCTTCACTT TTTTACATTA TTTACACCTT TTGGACCAGT AGATCGACGG TTTACAACCG
         .. G  N  R   K  N  S   G  N  W  K   A  G  R    A  A  A   P  V  N  Q .
                             FIV pro L  E   G  G  A    S  C  S   P  S  E  S .
 10141   AAGGAAATAG AAAGAATTCG GGAAACTGGA AGGCGGGGCG AGCTGCAGCC CCAGTGAATC
         TTCCTTTATC TTTCTTAAGC CCTTTGACCT TCCGCCCCGC TCGACGTCGG GGTCACTTAG
         .. M  Q  Q   A  V  M   P  S  A  P   P  M  E   K  L  L  D  L
         . N  A  A   S  S  N  A   I  C  T   S  N  G    E  T  I    G  F  I .
 10201   AAATGCAGCA AGCAGTAATG CCATCGCAC CTCCAATGGA GGAGAAACTA TTGGATTTAT
         TTTACGTCGT TCGTCATTAC GGTAGACGTG GAGGTTACCT CCTCTTTGAT AACCTAAATA
         . N  Y  N    K  V  G   T  T  T    L  E  K    R  P  E   I  L  I  F .
 10261   AAATTATAAT AAAGTAGGTA CGACTACAAC ATTAGAAAAG AGGCCAGAAA TACTTATATT
         TTTAATATTA TTTCATCCAT GCTGATGTTG TAATCTTTTC TCCGGTCTTT ATGAATATAA
         . V  N  G    Y  P  I  K   F  L  L   D  T  G    A  D  I   T  I  L  N .
 10321   TGTAAATGGA TATCCTATAA AATTCTTATT AGATACAGGA GCAGATATAA CAATTTTAAA
         ACATTTACCT ATAGGATATT TTAAGAATAA TCTATGTCCT CGTCTATATT GTTAAAATTT
         . R  R  D    F  Q  V  K   N  S  I   E  N  G   R  Q  N  M    I  G  V .
 10381   TAGGAGAGAT TTTCAAGTAA AAAATTCTAT AGAAAATGGA AGGCAAAATA TGATTGGAGT
         ATCCTCTCTA AAAGTTCATT TTTTAAGATA TCTTTTACCT TCCGTTTTAT ACTAACCTCA
         . G  G  G   K  R  G  T    N  Y  I   N  V  H    L  E  I   R  D  E  N .
 10441   AGGAGGAGGA AAGAGAGGAA CAAATTATAT TAATGTACAT TTAGAGATTA GAGATGAAAA
         TCCTCCTCCT TTCTCTCCTT GTTTAATATA ATTACATGTA AATCTCTAAT CTCTACTTTT
         . Y  K  T    Q  C  I   F  G  N  V    C  V  L    E  D  N   S  L  I  Q .
 10501   TTATAAGACA CAATGTATAT TTGGTAATGT TTGTGTCTTA GAAGATAACT CATTAATACA
         AATATTCTGT GTTACATATA AACCATTACA AACACAGAAT CTTCTATTGA GTAATTATGT
         . P  L  L    G  R  D  N  M    I  K   F  N  I    R  L  V  M    * 
 10561   ACCATTATTG GGGAGAGATA ATATGATTAA ATTCAATATT AGGTTAGTAA TGTAAGTTTA
         TGGTAATAAC CCCTCTCTAT TATACTAATT TAAGTTATAA TCCAATCATT ACATTCAAAT
         SFV replicon 3'
 10621   AACTAATTAA TTGAATTACA TCCCTACGCA AACGTTTTAC GGCCGCCGGT GGCGCCCGCG
         TTGATTAATT AACTTAATGT AGGGATGCGT TTGCAAAATG CCGGCGGCCA CCGCGGGCGC
 10681   CCCGGCGGCC CGTCCTTGGC CGTTGCAGGC CACTCCGGTG GCTCCCGTCG TCCCGACTT
         GGGCCGCCGG GCAGGAACCG GCAACGTCCG GTGAGGCCAC CGAGGGCAGC AGGGGCTGAA
 10741   CCAGGCCCAG CAGATGCAGC AACTCATCAG CGCCGTAAAT GCGCTGACAA TGAGACAGAA
         GGTCCGGGTC GTCTACGTCG TTGAGTAGTC GCGGCATTTA CGCGACTGTT ACTCTGTCTT
 10801   CGCAATTGCT CCTGCTAGGC CTCCCAAACC AAAGAAGAAG AAGACAACCA AACCAAAGCC
         GCGTTAACGA GGACGATCCG GAGGGTTTGG TTTCTTCTTC TTCTGTTGGT TTGGTTTCGG
 10861   GAAAACGCAG CCCAAGAAGA TCAACGGAAA AGCCAGCAG CAAAAGAAGA AAGACAAGCA
         CTTTTGCGTC GGGTTCTTCT AGTTGCCTTT TCGGTCGTC GTTTTCTTCT TTCTGTTCGT
 10921   AGCCGACAAG AAGAAGAAGA AACCCGGAAA AAGAGAAAGA ATGTGCATGA AGATTGAAAA
         TCGGCTGTTC TTCTTCTTCT TTGGGCCTTT TTCTCTTTCT TACACGTACT TCTAACTTTT
 10981   TGACTGTATC TATGCGGCTA GCCACAGTAA CGTAGTGTTT CCAGACATGT CGGGCACCGC
```

FIG. 32J.

```
       ACTGACATAG ATACGCCGAT CGGTGTCATT GCATCACAAA GGTCTGTACA GCCCGTGGCG
11041  ACTATCATGG GTGCAGAAAA TCTCGGGTGG TCTGGGGGCC TTCGCAATCG GCGCTATCCT
       TGATAGTACC CACGTCTTTT AGAGCCCACC AGACCCCGG AAGCGTTAGC CGCGATAGGA
11101  GGTGCTGGTT GTGGTCACTT GCATTGGGCT CCGCAGATAA GTTAGGGTAG GCAATGGCAT
       CCACGACCAA CACCAGTGAA CGTAACCCGA GGCGTCTATT CAATCCCATC CGTTACCGTA
11161  TGATATAGCA AGAAAATTGA AAACAGAAAA AGTTAGGGTA AGCAATGGCA TATAACCATA
       ACTATATCGT TCTTTTAACT TTTGTCTTTT TCAATCCCAT TCGTTACCGT ATATTGGTAT
11221  ACTGTATAAC TTGTAACAAA GCGCAACAAG ACCTGCGCAA TTGGCCCCGT GGTCCGCCTC
       TGACATATTG AACATTGTTT CGCGTTGTTC TGGACGCGTT AACCGGGGCA CCAGGCGGAG
11281  ACGGAAACTC GGGGCAACTC ATATTGACAC ATTAATTGGC AATAATTGGA AGCTTACATA
       TGCCTTTGAG CCCCGTTGAG TATAACTGTG TAATTAACCG TTATTAACCT TCGAATGTAT
11341  AGCTTAATTC GACGAATAAT TGGATTTATA TTTTATTTTG CAATTGGTTT TTAATATTTC
       TCGAATTAAG CTGCTTATTA ACCTAAATAT AAAATAAAAC GTTAACCAAA AATTATAAAG
11401  CAAAAAAAAA AAAAAAAAAA AAAAAAAAAA AAAAAAAAAA AAAAAAAAAA AAAAAAACG
       GTTTTTTTTT TTTTTTTTTT TTTTTTTTTT TTTTTTTTTT TTTTTTTTTT TTTTTTTGC
       Ribozyme sequence
11461  GGTCGGCATG GCATCTCCAC CTCCTCGCGG TCCGACCTGG GCATCCGAAG GAGGACGCAC
       CCAGCCGTAC CGTAGAGGTG GAGGAGCGCC AGGCTGGACC CGTAGGCTTC CTCCTGCGTG
                                                              F8 right arm
11521  GTCCACTCGG ATGGCTAAGG GAGTTTTTCT ACTAGTTAAT CATAAGATAA ATAATATACA
       CAGGTGAGCC TACCGATTCC CTCAAAAAGA TGATCAATTA GTATTCTATT TATTATATGT
11581  GCATTGTAAC CATCGTCATC CGTTATACGG GGAATAATAT TACCATACAG TATTATTAAA
       CGTAACATTG GTAGCAGTAG GCAATATGCC CCTTATTATA ATGGTATGTC ATAATAATTT
11641  TTTTCTTACG AAGAATATAG ATCGGTATTT ATCGTTAGTT TATTTTACAT TTATTAATTA
       AAAAGAATGC TTCTTATATC TAGCCATAAA TAGCAATCAA ATAAAATGTA ATAATTAAT
11701  AACATGTCTA CTATTACCTG TTATGGAAAT GACAAATTTA GTTATATAAT TTATGATAAA
       TTGTACAGAT GATAATGGAC AATACCTTTA CTGTTTAAAT CAATATATTA AATACTATTT
11761  ATTAAGATAA TAATAATGAA ATCAAATAAT TATGTAAATG CTACTAGATT ATGTGAATTA
       TAATTCTATT ATTATTACTT TAGTTTATTA ATACATTTAC GATGATCTAA TACACTTAAT
11821  CGAGGAAGAA AGTTTACGAA CTGGAAAAAA TTAAGTGAAT CTAAAATATT AGTCGATAAT
       GCTCCTTCTT TCAAATGCTT GACCTTTTTT AATTCACTTA GATTTTATAA TCAGCTATTA
11881  GTAAAAAAAA TAAATGATAA AACTAACCAG TTAAAACGG ATATGATTAT ATACGTTAAG
       CATTTTTTTT ATTTACTATT TTGATTGGTC AATTTTTGCC TATACTAATA TATGCAATTC
11941  GATATTGATC ATAAAGGAAG AGATACTTGC GGTTACTATG TACACCAAGA TCTGGTATCT
       CTATAACTAG TATTTCCTTC TCTATGAACG CCAATGATAC ATGTGGTTCT AGACCATAGA
12001  TCTATATCAA ATTGGATATC TCCGTTATTC GCCGTTAAGG TAAATAAAAT TATTAACTAT
       AGATATAGTT TAACCTATAG AGGCAATAAG CGGCAATTCC ATTTATTTTA ATAATTGATA
12061  TATATATGTA ATGAATATGA TATACGACTT AGCGAAATGG AATCTGATAT GACAGAAGTA
       ATATATACAT TACTTATACT ATATGCTGAA TCGCTTTACC TTAGACTATA CTGTCTTCAT
12121  ATAGATGTAG TTGATAAATT AGTAGGAGGA TACAATGATG AAATAGCAGA ATAATATATAT
       TATCTACATC AACTATTTAA TCATCCTCCT ATGTTACTAC TTTATCGTCT TTATTATATA
12181  TTGTTTAATA AATTTATAGA AAAATATATT GCTAACATAT CGTTATCAAC TGAATTATCT
       AACAAATTAT TTAAATATCT TTTTATATAA CGATTGTATA GCAATAGTTG ACTTAATAGA
12241  AGTATATTAA ATAATTTTAT AAATTTTAAT AAAAAATACA ATAACGACAT AAAAGATATT
       TCATATAATT TATTAAAATA TTTAAAATTA TTTTTTATGT TATTGCTGTA TTTTCTATAA
12301  AAATCTTTAA TTCTTGATCT GAAAACACA TCTATAAAAC TAGATAAAAA GTTATTCGAT
       TTTAGAAATT AAGAACTAGA CTTTTTGTGT AGATATTTTG ATCTATTTTT CAATAAGCTA
12361  AAAGATAATA ATGAATCGAA CGATGAAAAA TTGGAAACAG AAGTTGATAA GCTAATTTTT
       TTTCTATTAT TACTTAGCTT GCTACTTTTT AACCTTTGTC TTCAACTATT CGATTAAAAA
12421  TTCATCTAAA TAGTATTATT TTATTGAAGT ACGAAGTTTT ACGTTAGATA AATAATAAAG
       AAGTAGATTT ATCATAATAA AATAACTTCA TGCTTCAAAA TGCAATCTAT TTATTATTTC
12481  GTCGATTTTT ATTTTGTTAA ATATCAAATA TGTCATTATC TGATAAAGAT ACAAAAACAC
       CAGCTAAAAA TAAAACAATT TATAGTTTAT ACAGTAATAG ACTATTTCTA TGTTTTTGTG
12541  ACGGTGATTA TCAACCATCT AACGAACAGA TATTACAAAA AATACGTCGG ACTATGGAAA
       TGCCACTAAT AGTTGGTAGA TTGCTTGTCT ATAATGTTTT TTATGCAGCC TGATACCTTT
12601  ACGAAGCTGA TAGCCTCAAT AGAAGAAGCA TTAAAGAAAT TGTTGTAGAT GTTATGAAGA
       TGCTTCGACT ATCGGAGTTA TCTTCTTCGT AATTTCTTTA ACAACATCTA CAATACTTCT
12661  ATTGGGATCA TCCTCTCAAC GAAGAAATAG ATAAAGTTCT AAACTGGAAA AATGATACAT
       TAACCCTAGT AGGAGAGTTG CTTCTTTATC TATTTCAAGA TTTGACCTTT TTACTATGTA
```

FIG. 32K.

```
12721   TAAACGATTT AGATCATCTA AATACAGATG ATAATATTAA GGAAATCATA CAATGTCTGA
        ATTTGCTAAA TCTAGTAGAT TTATGTCTAC TATTATAATT CCTTTAGTAT GTTACAGACT
12781   TTAGAGAATT TGCGTTTAAA AAGATCAATT CTATTATGTA TAGTTATGCT ATGGTAAAAC
        AATCTCTTAA ACGCAAATTT TTCTAGTTAA GATAATACAT ATCAATACGA TACCATTTTG
12841   TCAATTCAGA TAACGAAACA TTGAAAGATA AAATTAAGGA TTATTTTATA GAAACTATTC
        AGTTAAGTCT ATTGCTTTGT AACTTTCTAT TTTAATTCCT AATAAAATAT CTTTGATAAG
12901   TTAAAGACAA ACGTGGTTAT AAACAAAAGC CATTACCC
        AATTTCTGTT TGCACCAATA TTTGTTTTCG GTAATGGG
```

FIG. 33.

A schematic illustration of the generation of a fowlpox-SFV Arg650Asp+Ser259Pro chimera expressing FIV gag-pro (vFP2192)

Immunoblot analysis of FIV gag-pro protein expression
in C2C12 (mouse myoblast) cells 1. Mock infected cell lysate
2. ALVAC infected cell lysate
3. vCP2161 infected cell lysate
4. vCP2092 infected cell lysate
5. vCP2089 infected cell lysate
6. Fowlpox infected cell lysate
7. vFP2192 infected cell lysate
8. vFP2095 infected cell lysate Immunoblot analysis of cell culture media: secretion of the processed
FIV gag protein from infected C2C12 (mouse myoblast) cells 9. Mock infected cell lysate
10. ALVAC infected cell lysate
11. vCP2161 infected cell lysate
12. vCP2092 infected cell lysate
13. vCP2089 infected cell lysate
14. Fowlpox infected cell lysate
15. vFP2192 infected cell lysate
16. vFP2095 infected cell lysate Immunoblot analysis of FIV gag-pro protein expression in CRFK (Feline Kidney) cells 17. Mock infected cell lysate
18. Fowlpox infected cell lysate
19. vFP2192 infected cell lysate
20. vFP2095 infected cell lysate
21. ALVAC infected cell lysate
22. vCP2161 infected cell lysate
23. vCP2089 infected cell lysate
24. vCP2092 infected cell lysate

FIG. 36.

FIV gag-pro protein expression of chimeras in various mammalian cells

| | BHK | Vero | NIH3T3 | C2C12 | CRFK | MDBK | 293FT | SKMC |
|---|---|---|---|---|---|---|---|---|
| | Baby hamster kidney, fibroblast | Monkey kidney, fibroblast-like | Mouse Embryo fibroblast | Mouse muscle myoblast, fibroblast | Feline kidney, Epithelial-like | Bovine kidney, epithelial | Human embryo kidney, fibroblasttransformed with large T | Human primary skeletal muscle cell |
| vCP2092 | + | + | - | - | - | - | n.d | n.d. |
| vCP2161 | + | + | + | + | - | - | + | - |
| vFP2192 | n.d | n.d | + | + | + | + | n.d. | + |
| vCP2089 | + | + | + | + | + | + | + | n.d |
| vFP2095 | n.d. | n.d. | + | + | + | + | n.d. | n.d. |

CHIMERIC VECTORS

CROSS-REFERENCE TO RELATED APPLICATIONS

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

FIELD OF THE INVENTION

The present invention relates to chimeric vectors. More specifically, the invention relates to recombinant poxvirus vectors and viruses that are capable of expressing an alphaviral RNA replicon expressing a heterologous sequence of interest.

BACKGROUND OF THE INVENTION

Poxvirus is one of the most promising vaccine vectors to date. ALVAC, a canary poxvirus, is a member of the avipox virus genus in the Chordopoxvirus family, and has been developed as a vaccine vector for expressing foreign genes. Clear advantages of ALVAC as a vaccine vector include its wide tropism, capability for insertion of large DNA fragments and high immunogenicity, such as inducing a strong T-lymphocyte response. ALVAC-based recombinant vaccines have an excellent safety profile and their effectiveness against a variety of infectious agents has been demonstrated in both animals and humans. ALVAC undergoes abortive replication in mammalian cells. In ALVAC recombinants, the target genes are controlled by early promoters and are expressed before the block in replication. Inoculation of an ALVAC recombinant expressing rabies G glycoprotein into dogs was sufficient to protect against a lethal rabies virus challenge (Taylor, J. et al (1991) Vaccine 9: 190-93). Vaccination of cats with an ALVAC recombinant expressing feline leukemia virus (FeLV) A subtype Env and Gag protein protects against the development of persistent viremia after exposure to FeLV virus (Tartaglia, J. et al (1993) J. Virol. 67(4): 2370-5). ALVAC recombinants expressing HIV-1 Env and Gag-pol have been shown to induce HIV-1 specific antibodies and cytotoxic T-lymphocyte responses in humans (Evans, T. G. et al (1999(J. Infect. Dis. 180(2): 290-8; Girard, M. et al (1997) Virology 232(1): 98-104)). However, high doses of ALVAC are often required to achieve protective immunity. Therefore, there is a need to improve the immunogenicity of ALVAC-based recombinants. Similar to ALVAC, fowlpoxvirus, another member of the avipox virus genus in the Orthopoxvirus family, has also been developed as a vaccine vector. Fowlpoxvirus-based recombinant vaccines have demonstrated their efficacy against various infectious diseases in animals and particularly in poultry.

Semliki Forest virus (SFV), a positive sense single stranded RNA virus, is a member of the alphavirus genus in the Togaviridae family. The genomic RNA (49S) of SFV is 11,442 bp in length and contains a 5'-cap and a 3'-polyadenylated tail. Two-thirds of the genome at the 5'-end encodes nonstructural proteins (nsP) and the remaining one-third at the 3' end encodes structural proteins (sP). Upon infection of cells, the genomic RNA serves as mRNA to initiate the translation of a nonstructural polyprotein, which is subsequently cleaved into 4 nonstructural proteins termed "nsP1", "nsP2", "nsP3" and "nsP4". These proteins form replication complexes with host factors to initiate viral RNA replication and subgenomic RNA (26S) transcription. The subgenomic RNA, corresponding to the one-third of the genome at the 3'-end, is used as a template for translation of structural proteins, which are not required for viral RNA replication.

SFV has been recently engineered to produce a self-replicating RNA "replicon" by deletion of the structural protein genes (Liljestrom, P. and Garoff, H. (1991) Nat. Biotechnol. 9(12): 1356-61). This self-replicating RNA replicon can replicate in a variety of cell types ranging from insect to mammalian cells and expresses target genes at high levels. Recombinant vaccines based on the SFV replicon have been developed and have shown protective immunity against a variety of pathogens (Berglund, P. et al; Vaccine 17(5): 497-507; Berglund, P. et al (1997) AIDS Res. Hum. Retroviruses 13(17) 1487-95; Nilsson, C. et al (2001) Vaccine 19(25-26): 3526-36; Fleeton, M. N. et al (2001) J. Infect. Dis. 183(9): 1395-8). However, the SFV replicon expression system has limitations. For example, for efficient delivery of SFV replicons in vivo, it is necessary to package SFV replicons into virus particles. Packaging is achieved by co-transfection of cells with SFV and helper replicons, which express the viral capsid and envelope proteins using electroporation (Smerdou, C. and Liljestrom, P. (1999) J. Virol. 73(2): 1092-8). This packaging procedure not only requires the synthesis of RNAs in vitro, but also has not yet been developed for large-scale viral particle production. Furthermore, in most mammalian cells, host macromolecular synthesis is inhibited following the introduction of the alphavirus replicon, leading to cell death by an apoptotic mechanism. This limits the use of these replicons to express foreign proteins by transient expression. This also limits the use of this system for large-scale production of these vectors for therapeutic applications.

U.S. Pat. No. 6,015,686 describes a eukaryotic-layered vector system. In this system, a cDNA vector is used to launch an alphavirus replicon. While this system circumvents the requirement for isolating RNA, it still suffers from poor gene delivery efficiency common to all plasmid vectors. Therefore, it is essential to develop alternatives for efficient delivery of SFV replicons in vivo.

SUMMARY OF THE INVENTION

The present invention is concerned with recombinant poxvirus vectors and viruses that can express heterologous sequences of interest from a viral replicon capable of amplification as RNA. These recombinant poxvirus vectors and viruses can then be used to introduce and express a heterologous sequence of interest in an animal. These poxvirus vectors and viruses can be produced at large scale industrial levels.

In one aspect, the present invention provides a recombinant poxvirus vector, comprising a nucleic acid sequence operably linked to a poxviral promoter that directs transcription of the nucleic acid sequence to generate a transcribed viral replicon capable of amplification as RNA, wherein the transcribed viral replicon comprises at least one viral promoter operably linked to a heterologous sequence of interest, and a polymerase specific for replication of the viral replicon.

The poxvirus can be vaccinia virus, Modified Vaccinia Ankara, NYVAC, canarypox, ALVAC, fowlpox, or TROVAC, and the poxviral promoter is selected from the group consisting of H6 poxviral promoter, I3L poxviral promoter, 42K poxviral promoter, 7.5K poxviral promoter, thymidine kinase poxviral promoter, E3L poxviral promoter, K3L poxviral promoter, and a synthetic poxviral promoter. The invention also comprehends poxviral promoters that are mutated.

In one embodiment, the poxvirus vector comprises a C6 insertion locus and flanking sequences of the C6 insertion locus, wherein the flanking sequences promote homologous recombination of the nucleic acid sequence with the C6 insertion locus. The flanking sequences advantageously comprise the C6L and C6R sequences of canarypox, such as ALVAC. In another embodiment, the poxvirus vector comprises a F8 insertion locus and flanking sequences comprise the F8L and F8R sequences of fowlpox, such as TROVAC.

Another embodiment of the present invention describes a viral replicon derived from an alphavirus selected from the group consisting of Semliki Forest virus, Sindbis virus, Aura virus, VEE virus, WEE virus, EEE virus, Ross River virus, Mayaro virus, Chikungunya virus, Getah virus, Sagiyama virus, Mucambo virus, Pixuna virus, Middelburg virus, O'nyong-Nyong virus, Barmah forest virus, Bebaru virus, Una virus, Whataroa virus, Babanki virus, Kyzylagach virus, Highlands J virus, Fort Morgan virus and Ndumu virus.

In another embodiment of the invention, the viral replicon is derived from a positive-sense single-stranded RNA virus selected from the group consisting of poliovirus, rhinovirus, coxsackie virus, yellow fever virus, HCV, TGEV, IBV, MHV, BCV, astrovirus, tobamoviruses, potyviruses and bromoviruses.

Advantageously, the viral promoter is the 26S promoter and the polymerase is alphavirus nsP2. In particular embodiments, the alphavirus nsP2 is mutated at leucine 713 to produce a conditional mutant of nsP2. The mutation can also result in a non-temperature sensitive phenotype, rendering the replicon less cytopathic by, for example, altering the functions of nsP2.

Another embodiment of the present invention describes the heterologous sequence of interest, which can be an antigen, an antigenic fragment of a protein, a therapeutic agent, a cytokine, a toxin, an immunomodulator, an antisense RNA, a catalytic RNA, small interfering RNA, a protein, a peptide, an antibody, an antigen-binding fragment of an antibody, or an adjuvant.

Another aspect of the present invention provides a recombinant poxvirus comprising a nucleic acid sequence operably linked to a promoter that directs transcription of the nucleic acid sequence to generate a transcribed viral replicon capable of amplification as RNA, wherein the transcribed viral replicon comprises at least one viral promoter operably linked to a heterologous sequence of interest, and a polymerase specific for replication of the viral replicon.

In a further aspect, a method of producing a recombinant poxvirus vector is provided, comprising the steps of linearizing a donor plasmid with a restriction endonuclease, wherein the donor plasmid comprises restriction endonuclease cleavage sites or a multiple cloning site; and ligating at least one nucleic acid sequence comprising (i) a promoter operably linked to the nucleic acid molecule that directs transcription of the nucleic acid sequence to generate a transcribed viral replicon capable of amplification as RNA, wherein the transcribed viral replicon comprises at least one viral promoter operably linked to a heterologous sequence of interest and a polymerase specific for replication of the viral replicon; and (ii) a poxviral promoter sequence, and (iii) insertion sequences flanking (i) and (ii) that have complementary restriction endonuclease cleavage sites to the donor plasmid at the nucleic acid sequence, thereby producing the recombinant poxvirus vector.

Advantageously, the method further comprises the steps of introducing the vector into a cell permissive for replication of the vector; and isolating the vector from the cell.

An embodiment of the present invention further comprises a reporter gene, which is selected from the group consisting of neomycin resistance gene, ampicillin resistance gene, lacZ (β-galactosidase), luciferase, and green fluorescent protein (GFP).

In another embodiment, the cell permissive for growth of the vector is a chicken embryonic fibroblast.

Another aspect of the present invention provides a method for introducing and expressing a heterologous sequence of interest in an animal, comprising administering a poxvirus vector to the animal, wherein the poxvirus vector comprises a nucleic acid sequence operably linked to a poxviral promoter that directs transcription of the nucleic acid sequence to generate a transcribed viral replicon capable of amplification as RNA, and wherein the transcribed viral replicon comprises at least one viral promoter operably linked to the heterologous sequence of interest, and a polymerase specific for replication of the viral replicon, thereby expressing the heterologous sequence of interest in the animal.

In a further aspect, a method of introducing and expressing a heterologous sequence of interest in an animal is provided, comprising administering a poxvirus to the animal, wherein the poxvirus comprises a nucleic acid sequence operably linked to a poxviral promoter that directs transcription of the nucleic acid sequence to generate a transcribed viral replicon capable of amplification as RNA, and wherein the transcribed viral replicon comprises at least one viral promoter operably linked to the heterologous sequence of interest, and a polymerase specific for replication of the viral replicon, thereby expressing the heterologous sequence of interest in the animal.

Other features and advantages of the present invention will become apparent from the following detailed description.

BRIEF DESCRIPTION OF THE FIGURES

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting example and with reference to the accompanying drawings in which:

FIG. 1 shows a schematic illustration of the ALVAC-SFV chimeric virus.

FIG. 2 shows a schematic diagram illustrating the ALVAC genome and the C6 locus.

FIG. 3 shows an illustration of the SFV replicon.

FIG. 4 shows a schematic illustration of the generation of the ALVAC-SFV chimera.

FIGS. 5A and 5B show the construction scheme for SFV nsP2 Leu713 mutants by mutation of Leu 713. FIG. 5B discloses SEQ ID NOS: 15-24, respectively, in order of appearance.

FIG. 6 shows an immunoblot analysis of the protein expression from SFV replicon mutants in BHK-21 cells.

FIG. 7 shows an immunoblot demonstrating the temperature sensitivity of the SFV Leu713Ala replicon expressing GFP/Blasticidin.

FIGS. 8A and 8B show the construction scheme for an ALVAC C6 donor plasmid containing SFV-GFP/Bsd Leu713Ala.

FIG. 8C shows the oligonucleotide primers used to mutate the T5NT sequences in the SFV replicon. FIG. 8C discloses SEQ ID NOS: 25-33, respectively, in order of appearance.

FIG. 10A through I shows the nucleotide sequence and translation SEQ ID NOS: 6 and 7, respectively, in order of appearance of the C6 SFV-GFP/Bsd Leu713Ala insert from pJY505.1. This nucleotide sequence is also provided as SEQ ID No: 1.

FIG. 11 shows an illustration of the generation of an ALVAC-SFV chimera using a C6 donor plasmid containing SFV-GFP/Bsd Leu713Ala mutation.

FIG. 12 shows an immunoplaque assay of the ALVAC-SFV GFP/Bsd Leu713Ala chimera using anti-GFP antibody.

Figure 13:
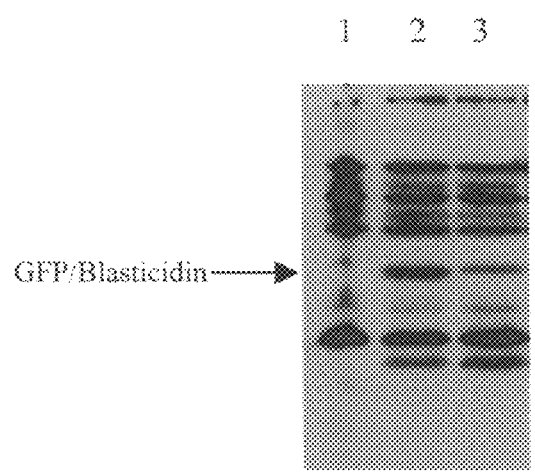

FIG. 13 shows an immunoblot analysis of the protein expression of ALVAC-SFV GFP/Bsd Leu713Ala chimera at 37 C and 38 C.

FIGS. 14A through D show the construction scheme for an ALVAC-SFV Leu713Ala C6 donor plasmid containing a multiple cloning site in panel A while FIG. 14B shows the construction scheme for an ALVAC-SFV Leu713Ala C6 donor plasmid containing two 26S promoters.

FIG. 15 shows the oligonucleotide primers SEQ ID NOS: 34-36, respectively, in order of appearance for construction of an ALVAC-SFV Leu713Ala C6 donor plasmid containing a multiple cloning site and/or two 26S promoters.

FIG. 16 shows illustration of the ALVAC-SFV Leu713Ala C6 donor plasmid containing a multiple cloning site, pJY C6 SFV L713A1.

FIGS. 17A through H show the nucleotide sequence and translation (SEQ ID NO: 8) of pJY C6 SFV L713A 1 from 17A through to 17H. The arrow indicates the insertion point of the $2^{nd}$ 26S promoter sequence to produce plasmid pJYC6SFVL713A2, while the sequence of the $1^{st}$ 26S promoter is underlined. This nucleotide sequence is also provided as SEQ ID No: 2.

FIG. 18 shows an illustration of the ALVAC-SFV Leu713Ala C6 donor plasmid containing two 26S promoters, pJY C6 SFV L713A2.

Figure 19A:
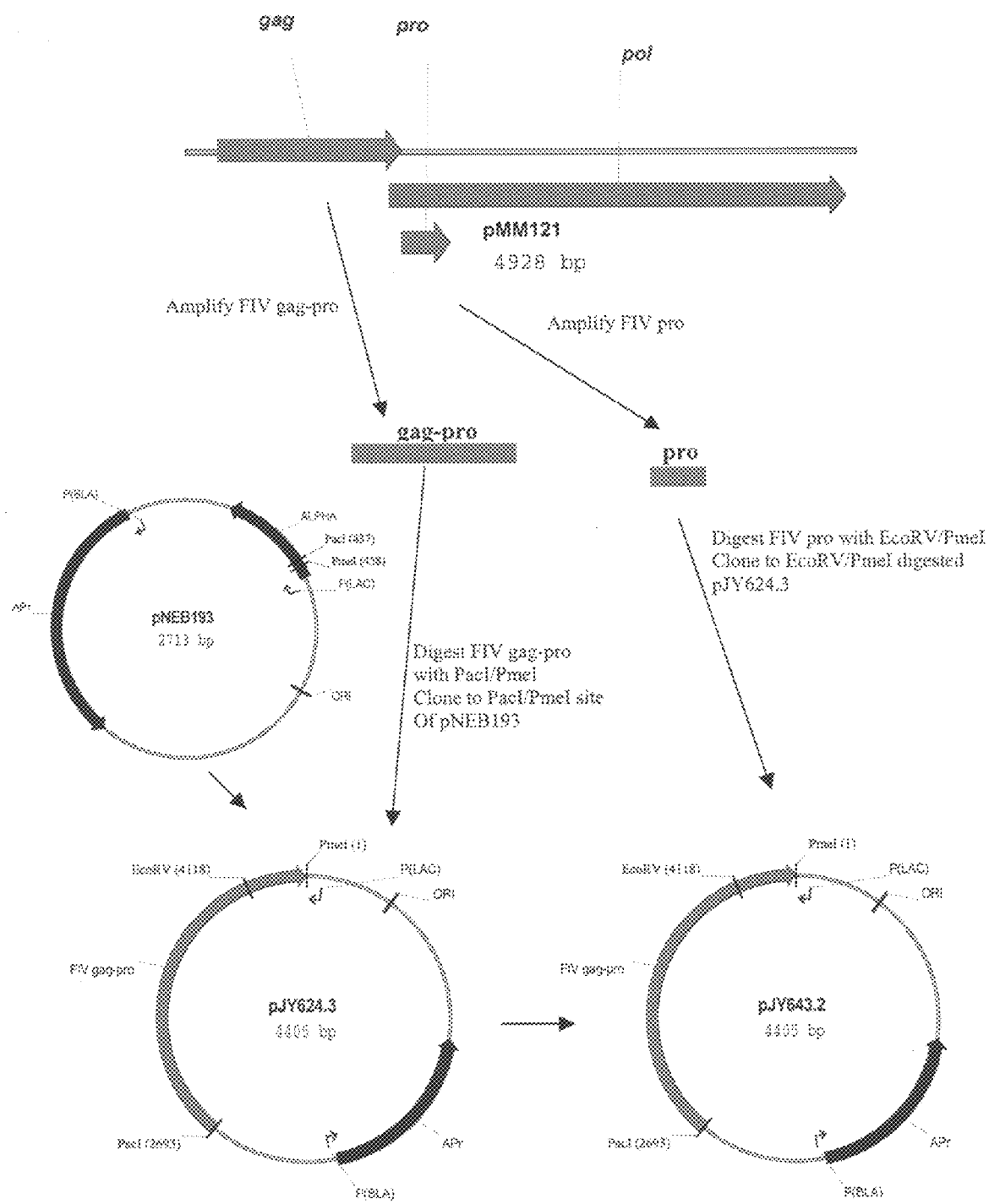

FIGS. 19A and 19B show the construction scheme for an ALVAC C6 donor plasmid containing SFV-Leu713Ala/FIV gag-pro. FIG. 19C shows the oligonucleotide primers used for the construction. FIG. 19C discloses SEQ ID NOS: 37-39, 60, 40-41, respectively, in order of appearance.

Figure 20:
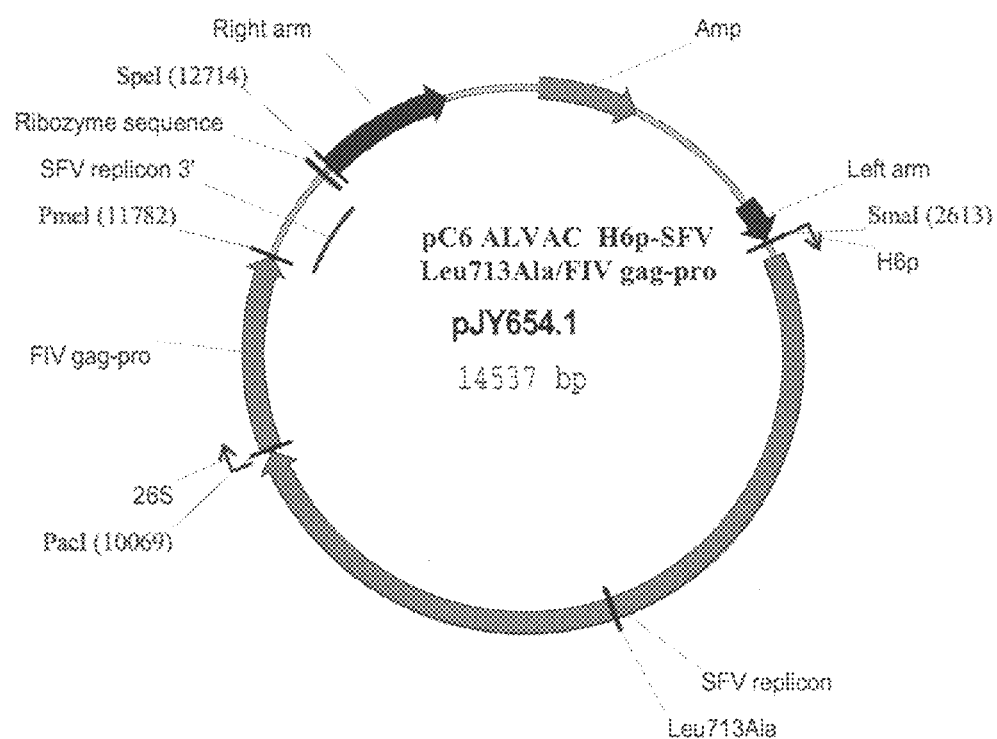

FIG. 20 shows a schematic illustration of the ALVAC C6 donor plasmid (pJY654.1) containing the SFV Leu713Ala/FIV gag-pro.

FIG. 21 shows an illustration of the generation of an ALVAC-SFV Leu713Ala chimera expressing FIV gag-pro.

Figure 22A:
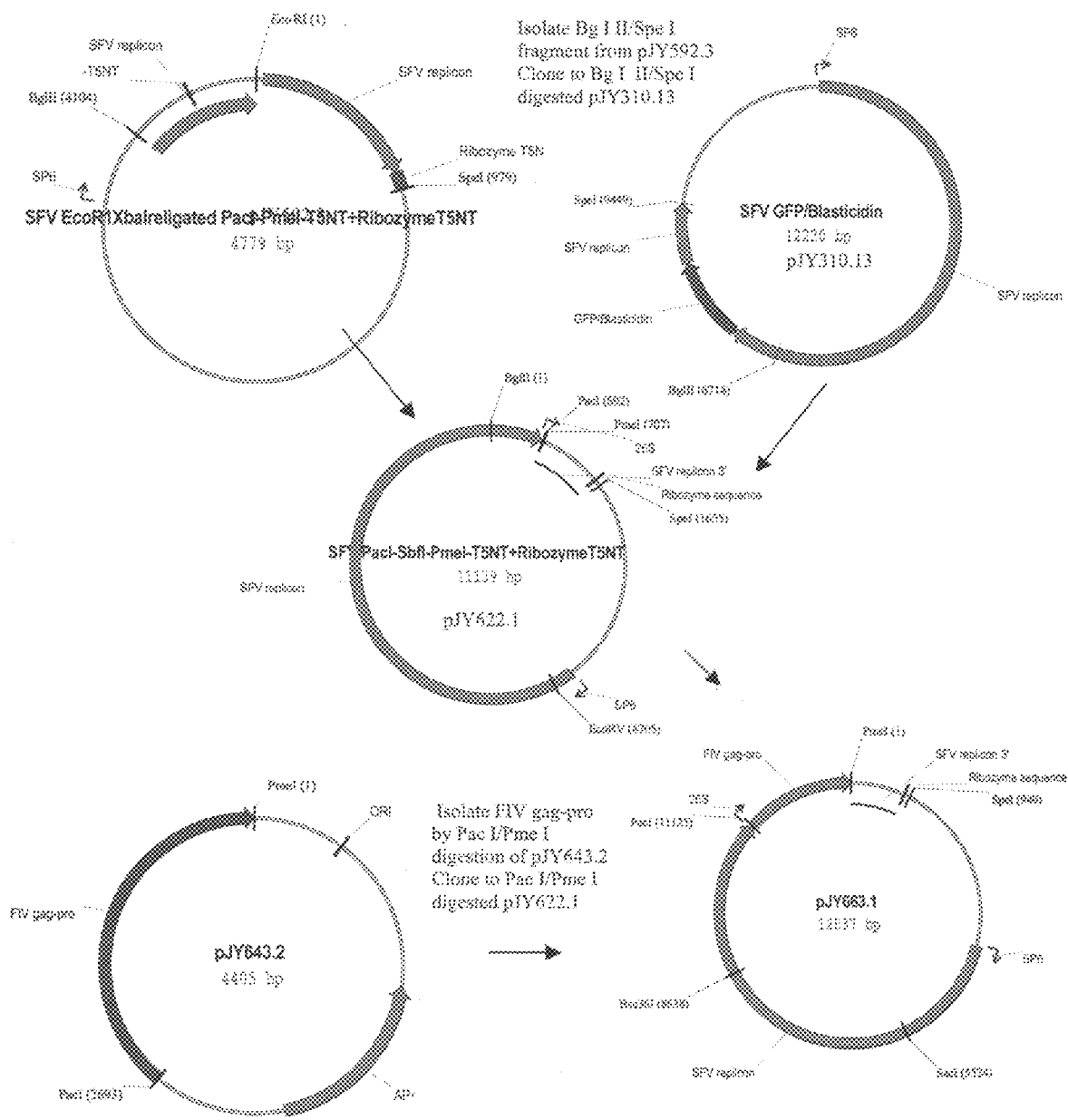

FIGS. 22A and 22B show the construction scheme for SFV nsP2 Arg650Asp mutant.

Figure 22C:
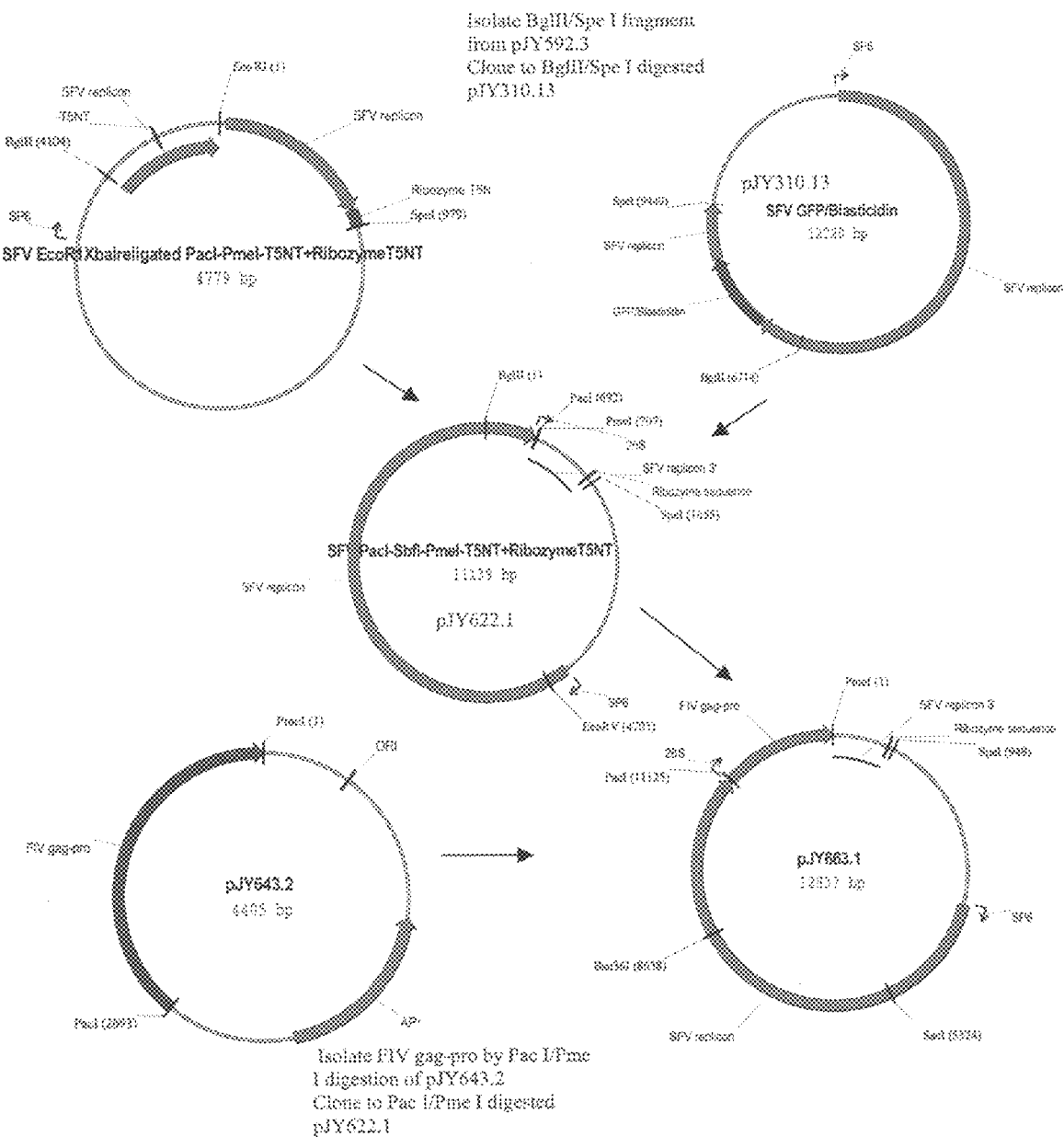
Figure 22D:
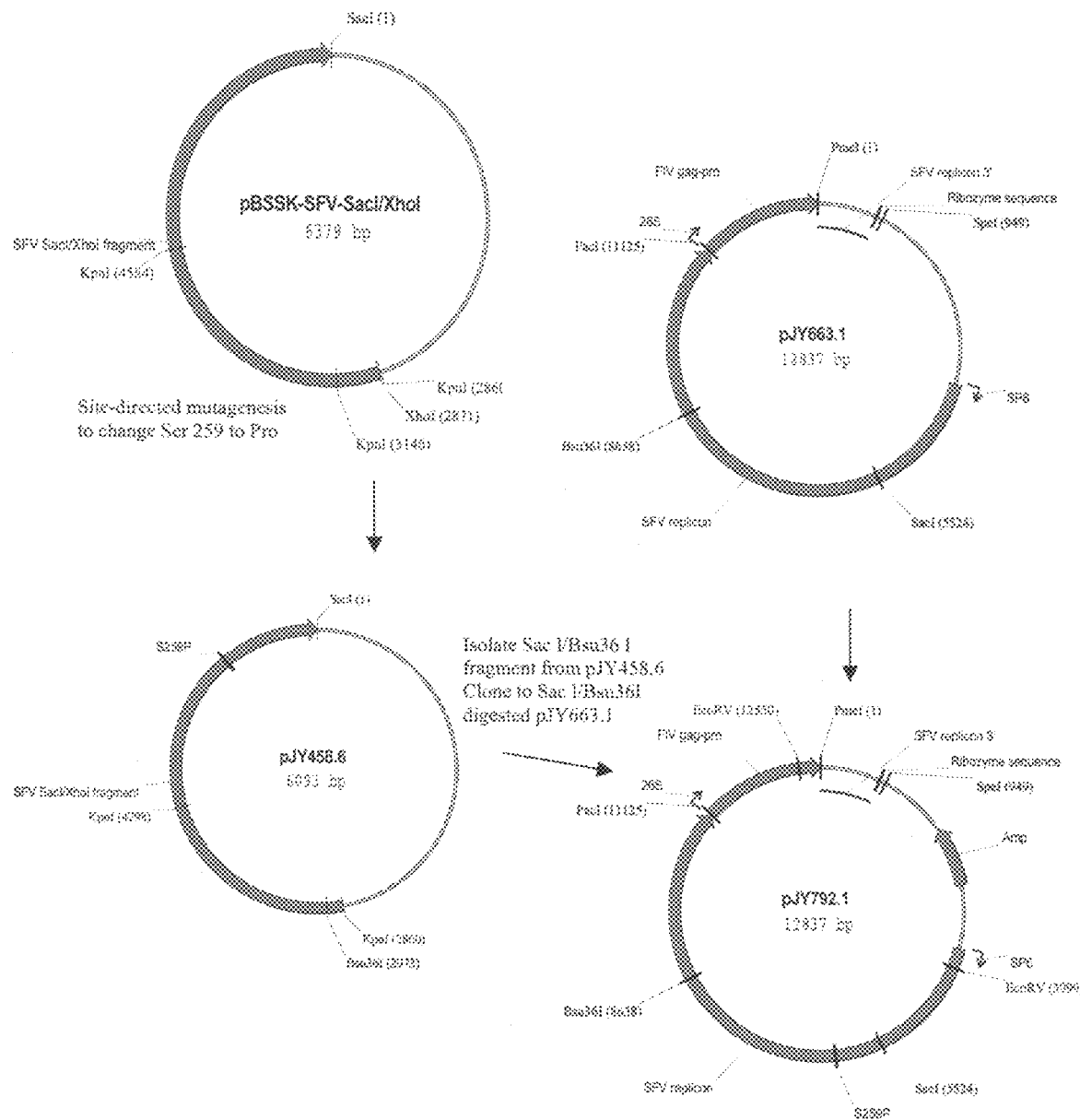

FIGS. 22C and 22D show the construction scheme for SFV nsP2 Ser259Pro mutant.

FIG. 22E shows the oligonucleotide primers used for the construction. FIG. 22E discloses SEQ ID NOS: 43, 42, 44, 46 and 45, respectively, in order of appearance.

FIG. 23 shows an immunoblot analysis of the protein expression from SFV Arg650Asp and Ser259Pro mutants in BHK-21 cells.

Figure 24C:
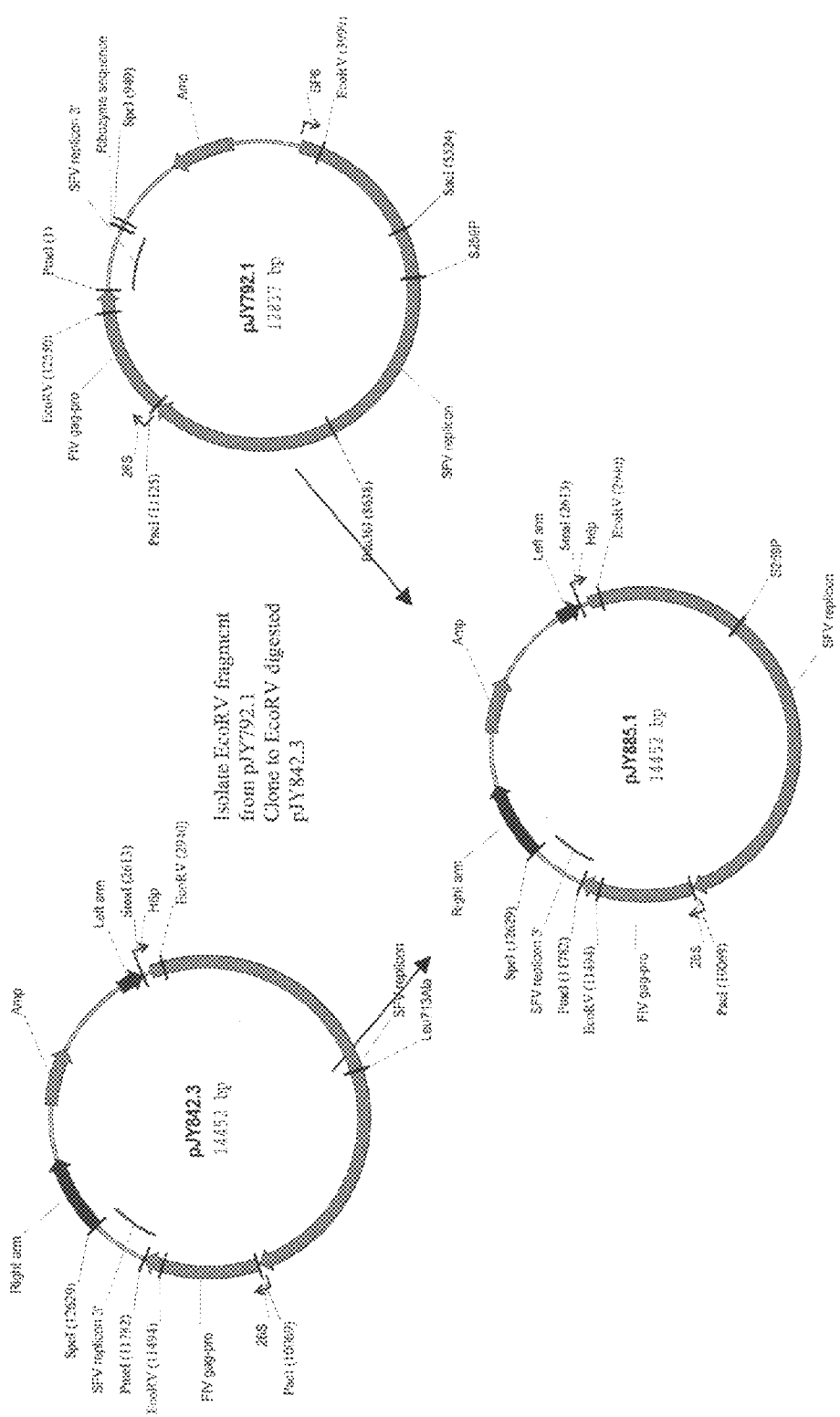

FIGS. 24A through 24C shows the construction scheme for an ALVAC C6 donor plasmid containing SFV Arg650Asp/FIV gag-pro or SFV Ser259Pro/FIV gag-pro under the control of H6 promoter.

FIG. 24D shows the oligonucleotide primers used for the construction. FIG. 24D discloses SEQ ID NOS: 48 and 49, respectively, in order of appearance.

Figure 25A:
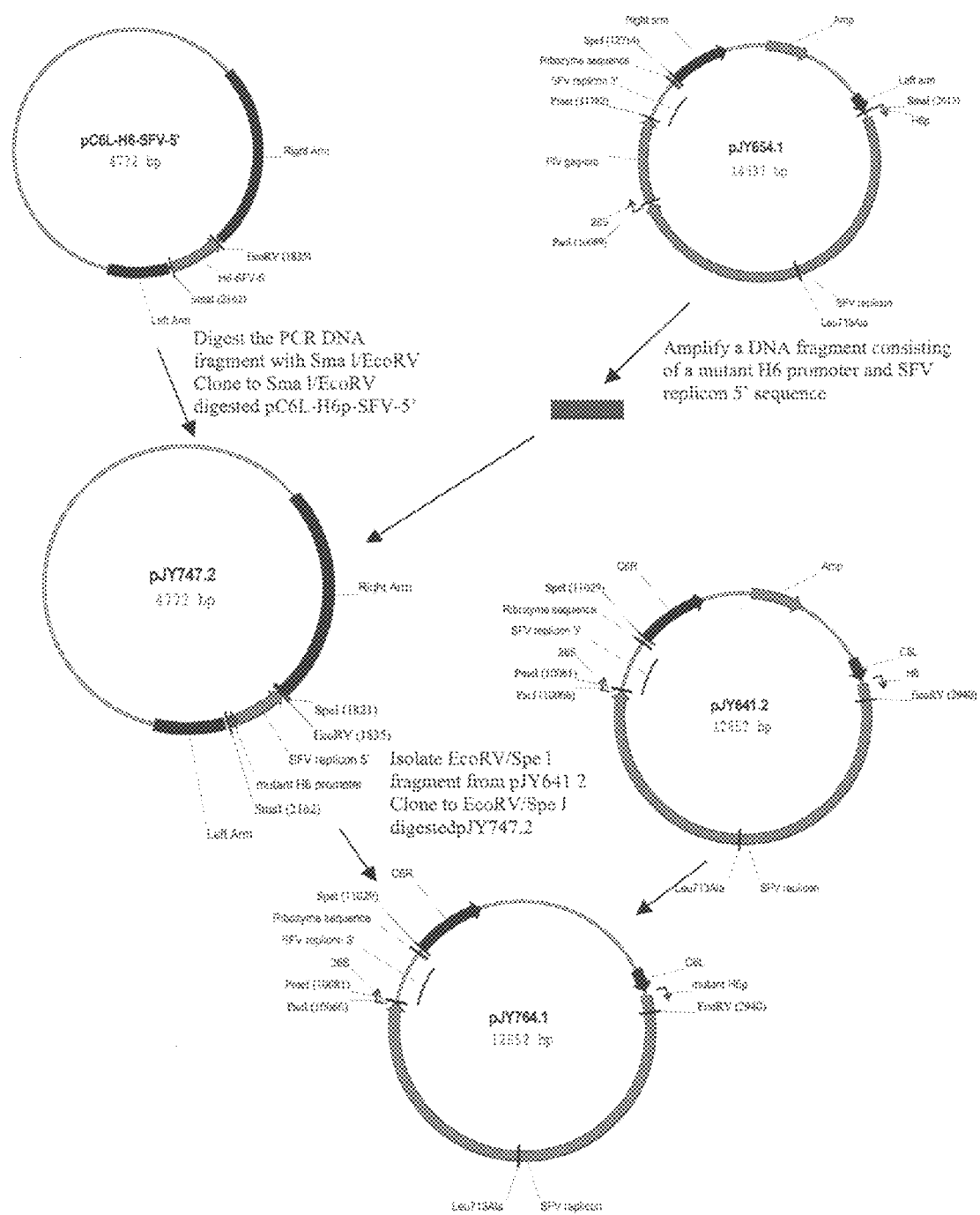

FIGS. 25A and 25B show the construction scheme for an ALVAC C6 donor plasmid containing SFV Arg650Asp/FIV gag-pro under the control of a mutant H6 promoter. FIG. 25C shows the oligonucleotide primers used for the construction. FIG. 25C discloses SEQ ID NOS: 50-53, respectively, in order of appearance.

Figure 26B:

FIGS. 26A and 26B shows the construction scheme for an ALVAC C6 donor plasmid containing SFV Arg650Asp+Ser259Pro/FIV gag-pro under the control of a mutated H6 promoter.

Figure 27:
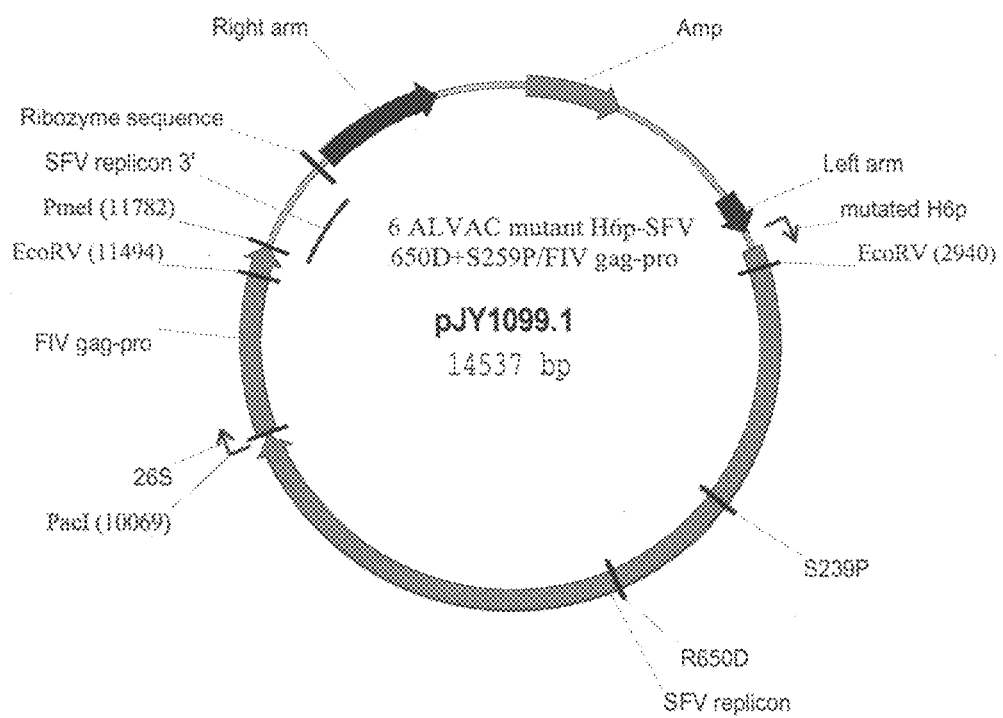

FIG. 27 shows a schematic illustration of the ALVAC C6 donor plasmid (pJY1099.1) containing SFV Arg650Asp+Ser259Pro/FIV gag-pro.

FIGS. 28A through 28J shows the nucleotide sequence SEQ ID NO: 4 and translation SEQ ID NOS: 9-11, respectively, in order of appearance of the ALVAC C6 donor plasmid containing SFV Arg650Asp+Ser259Pro/FIV gag-pro under the control of a mutant H6 promoter from pJY1099.1.

FIG. 29 shows an illustration of the generation of an ALVAC-SFV Arg650Asp+Ser259Pro chimera expressing FIV gag-pro.

FIG. 30 shows the construction scheme for a fowlpox F8 donor plasmid containing SFV Arg650Asp+Ser259Pro/FIV gag-pro under the control of a mutated H6 promoter.

FIG. 31 shows a schematic illustration of the fowlpox F8 donor plasmid containing SFV Arg650Asp+Ser259Pro/FIV gag-pro under the control of a mutant H6 promoter.

FIGS. 32A through 32K show the nucleotide sequence SEQ ID NO: 5 and translation SEQ ID NOS: 12-14, respectively, in order of appearance of the fowlpox F8 donor plasmid containing SFV Arg650Asp+Ser259Pro/FIV gag-pro under the control of a mutant H6 promoter from pJY1302.4.

FIG. 33 shows a schematic illustration of the generation of a fowlpox-SFV Arg650Asp+Ser259Pro chimera expressing FIV gag-pro.

Figure 34A:
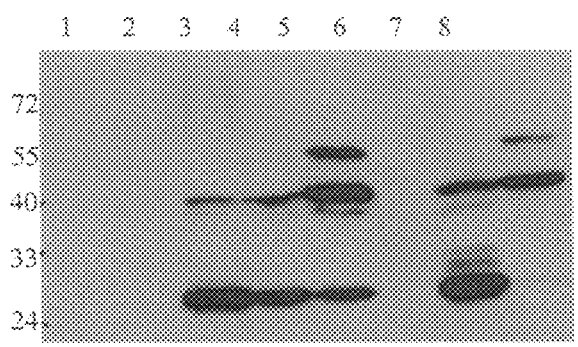

FIG. 34A shows an immunoblot analysis of FIV gag-pro protein expression in C2C12 murine myoblast cells.

Figure 34B:
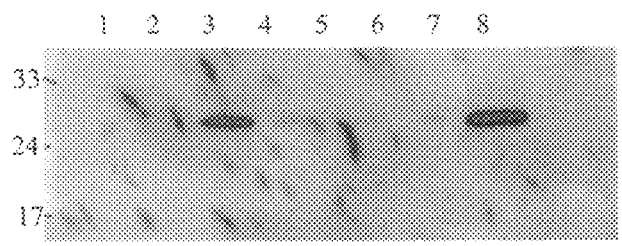

FIG. 34B shows an immunoblot analysis of cell culture media, detecting the secretion of processed FIV gag protein from infected C2C12 murine myoblast cells.

Figure 35:
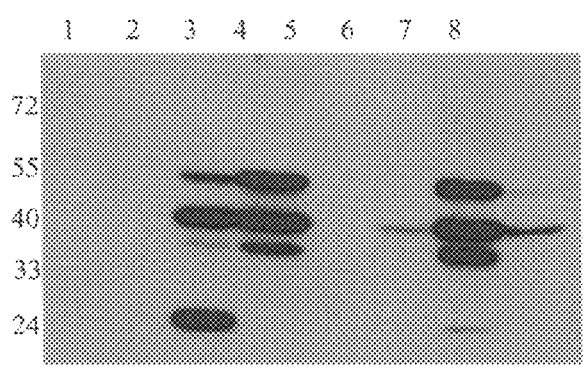

FIG. 35 shows an immunoblot analysis of FIV gag-pro protein expression in CRFK feline kidney cells.

FIG. 36 depicts FIV gag-pro protein expression of chimeras in various mammalian cells.

SEQ ID No: 1 is the nucleotide sequence and translation of the C6 SFV-GFP/Bsd Leu713Ala insert from pJY505.1. This sequence is also provided in FIGS. 10A through I.

SEQ ID No: 2 is the nucleotide sequence of pJY C6 SFV L713A 1 from 17A through to 17H. The arrow indicates the insertion point of the $2^{nd}$ 26S promoter sequence to produce plasmid pJYC6SFVL713A2, while the sequence of the $1^{st}$ 26S promoter is underlined. This sequence is also provided in FIGS. 17A through 17H.

SEQ ID No: 3 is the nucleotide sequence of the alphavirus 26S subgenomic promoter.

DETAILED DESCRIPTION

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the term "operably linked" means that the components described are in a relationship permitting them to function in their intended manner.

An "antigen" is a substance that is recognized by the immune system and induces an immune response. A similar term used in this context is "immunogen".

Figure 1:
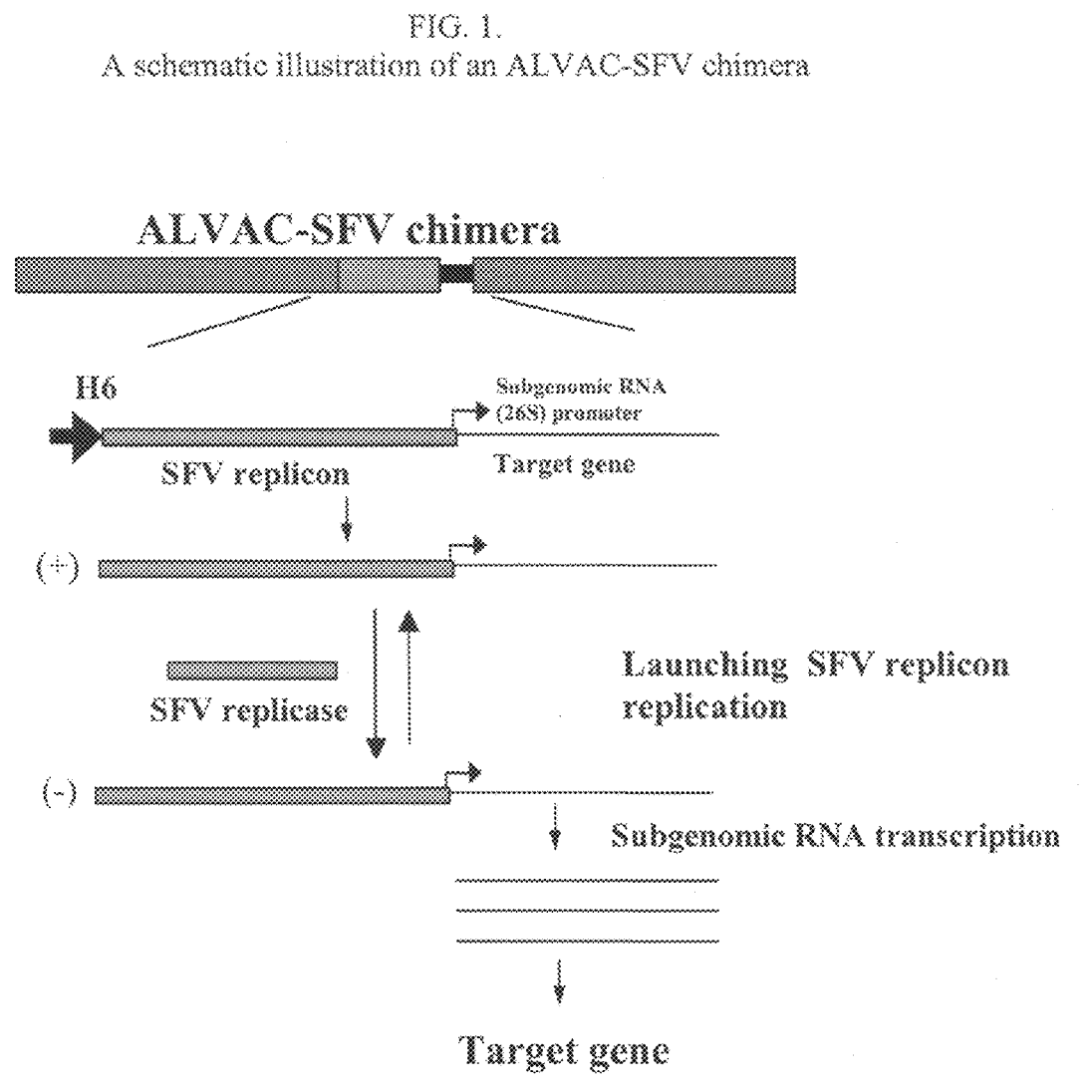

This invention, in narrow embodiments, describes the generation and use of an ALVAC-SFV chimera or a fowlpox-SFV chimera, wherein an SFV replicon cDNA is integrated into the genome of canarypox, ALVAC, fowlpox, or TROVAC under the control of a poxviral early promoter H6. This H6 promoter directs the transcription of SFV replicon RNA, such that the transcribed SFV replicon RNA is able to self-replicate and to express a heterologous sequence, which is driven by the SFV subgenomic 26S promoter. A schematic illustration of an ALVAC-SFV chimeric virus is shown in FIG. 1. However, the invention is not limited to the above embodiments.

The virus used according to the present invention is advantageously a poxvirus, such as vaccinia virus, Modified Vaccinia Ankara (MVA), and NYVAC, particularly an avipox virus, such as fowlpox virus or canarypox virus. Vaccinia virus has been used successfully to immunize against smallpox, culminating in the worldwide eradication of smallpox in 1980. With the eradication of smallpox, a new role for poxviruses became important, that of a genetically engineered vector for the expression of foreign genes (Panicali and Paoletti, 1982; Paoletti et al., 1984). Genes encoding heterologous antigens have been expressed in vaccinia, often resulting in protective immunity against challenge by the corresponding pathogen (reviewed in Tartaglia et al., 1990). A highly attenuated strain of vaccines, designated MVA, has also been used as a vector for poxvirus-based vaccines. Use of MVA is described in U.S. Pat. No. 5,185,146.

Other attenuated poxvirus vectors have been prepared by genetic modifications of wild type strains of virus. The NYVAC vector, derived by deletion of specific virulence and host-range genes from the Copenhagen strain of vaccinia (Tartaglia et al., 1992) has proven useful as a recombinant vector in eliciting a protective immune response against an expressed foreign antigen.

TROVAC refers to an attenuated fowlpox that was a plaque-cloned isolate derived from the FP-1 vaccine strain of fowlpoxvirus that is licensed for vaccination of 1-day-old chicks. ALVAC is an attenuated canarypox virus-based vector that was a plaque-cloned derivative of the licensed canarypox vaccine, Kanapox (Tartaglia et al., 1992). ALVAC-based recombinant viruses expressing extrinsic immunogens have also been demonstrated efficacious as vaccine vectors (Tartaglia et al., 1993 a,b). This avipox vector is restricted to avian species for productive replication. In human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to the extrinsic immunogen and provides protection against challenge with the cognate pathogen (Taylor et al., 1992; Taylor et al., 1991).

ALVAC and TROVAC have also been recognized as unique among avipoxviruses in that the National Institutes of Health ("NIH"; U.S. Public Health Service), Recombinant DNA Advisory Committee, which issues guidelines for the physical containment of genetic material such as viruses and vectors, i.e., guidelines for safety procedures for the use of such viruses and vectors, which are based upon the pathogenicity of the particular virus or vector, granted a reduction in physical containment level: from BSL2 to BSL1. No other avipoxvirus has a BSL1 physical containment level. Even the Copenhagen strain of vaccinia virus—the common smallpox vaccine—has a higher physical containment level; namely, BSL2. Accordingly, the art has recognized that ALVAC and TROVAC have a lower pathogenicity than other avipox viruses.

Advantageously, the poxvirus vector is an ALVAC or a canarypox virus (Rentschler vaccine strain), which was attenuated through 200 or more serial passages on chick embryo fibroblasts, after which a master seed therefrom was subjected to four successive plaque purifications under agar, from which a clone was amplified through five additional passages. The avipox virus vector can also be a fowlpox virus, or an attenuated fowlpox virus such as TROVAC.

Figure 2:
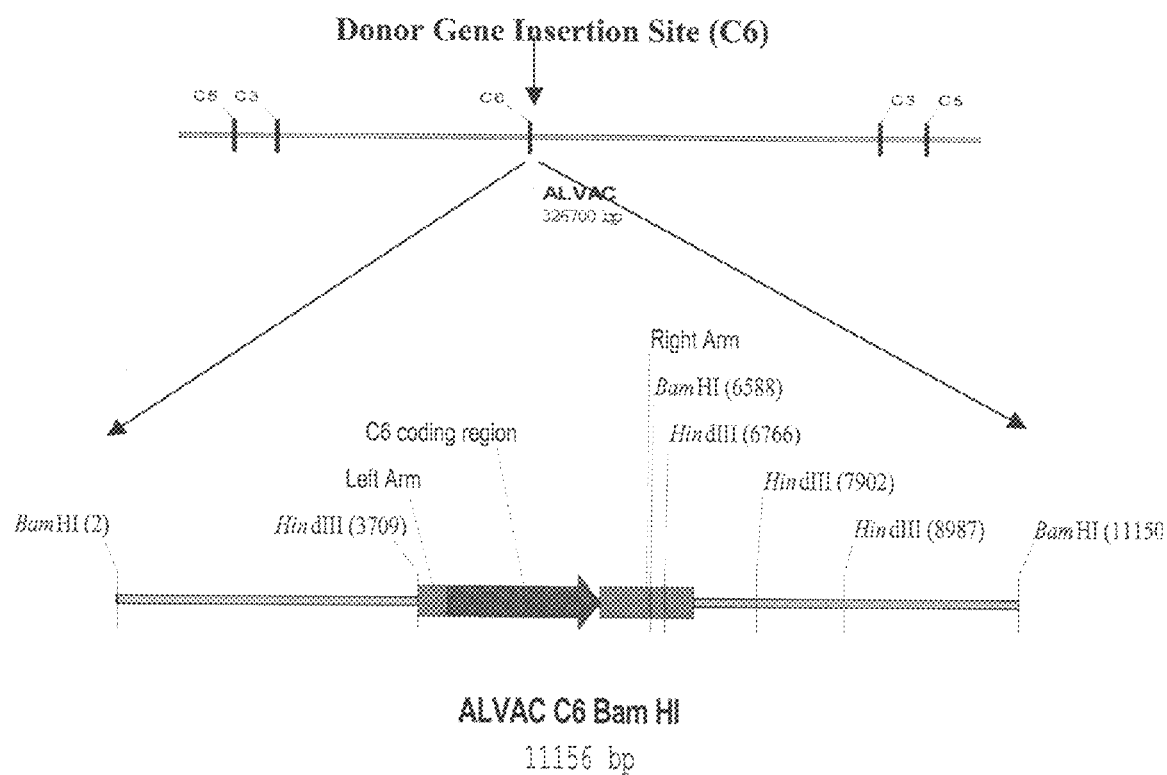
Figure 3:
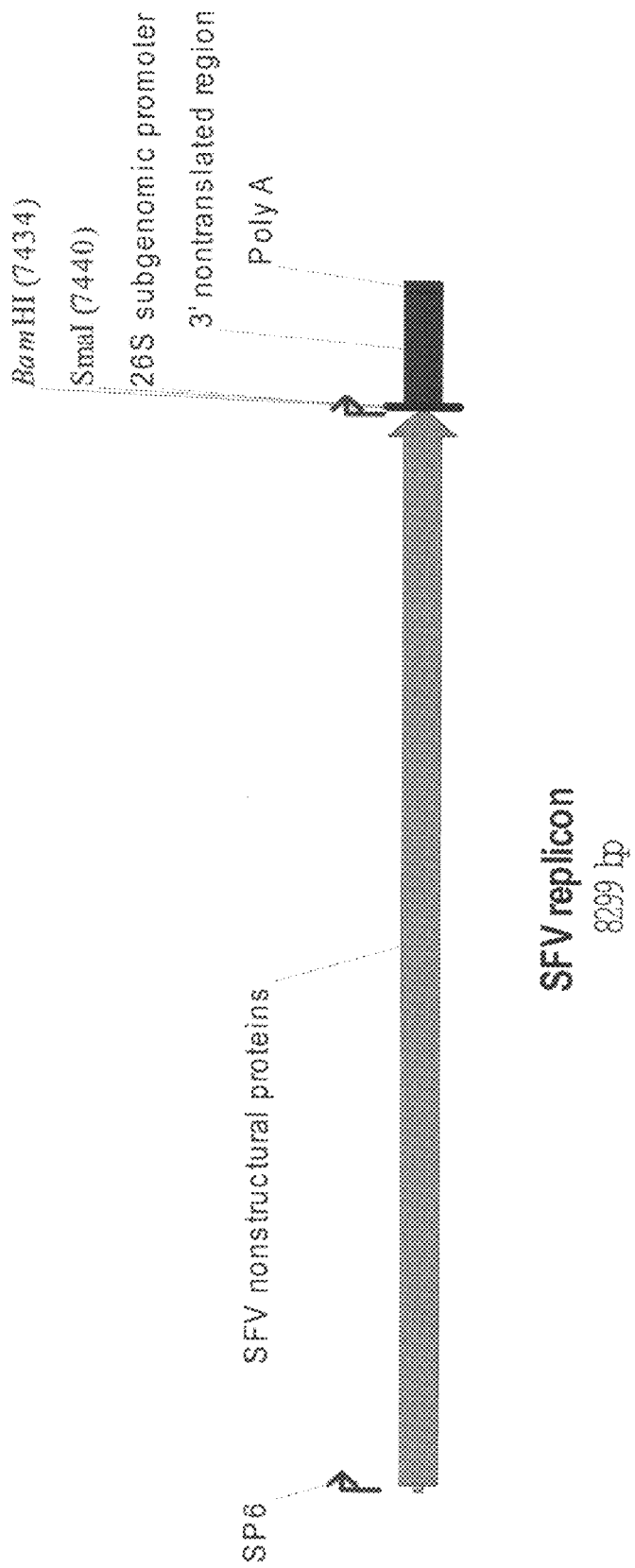

Three insertion sites and the corresponding insertion donor plasmids have been developed as described in U.S. Pat. No. 5,756,103 for ALVAC, designated as C3, C5 and C6. An illustration of the ALVAC genome and the C6 locus is shown in FIG. 2. Non-essential regions have been defined in the art (Johnson et al., (1993) Virology 196: 381-401) for vaccinia virus. These sites, also referred to herein as "insertion loci", are described in U.S. Pat. Nos. 6,340,462, and 5,756,103 for ALVAC, the contents of which are incorporated herein by reference, and include, but are not limited to, thymidine kinase (TK), hemagglutinin (HA), M2L, C6, and other loci. In a preferred embodiment, the insertion locus is C6. In another embodiment where fowlpox or TROVAC is used, the insertion locus is F8.

Insertion of nucleic acid sequences encoding heterologous sequences can be facilitated by homologous recombination, wherein the viral RNA replicon expressing the heterologous sequence of interest is flanked by sequences corresponding to poxvirus viral open reading frames immediately adjacent to the insertion locus (hereinafter referred to as "flanking sequences" or "insertion sequences"). Homologous recombination is facilitated by recognition of homologous flanking sequences, which promotes integration of the viral replicon into the insertion locus of interest. By way of example, insertion of heterologous sequences into the C6 locus requires the presence of the C6L and C6R sequences on either side of the nucleic acid sequence encoding the heterologous sequence of interest expressed from a viral replicon in the viral vector. Thus, advantageously the insertion loci is C6 and the flanking sequences comprise C6L and C6R. Where the F8 insertion locus is used, the flanking sequences comprise F8L and F8R.

The recombinant viral vectors of the invention expressing heterologous sequences expressed from a viral RNA replicon can be replicated or produced in cells or cell lines, or in vivo in a host or subject. One alternative embodiment consists of replicating the vector in cells permissive for replication of the vector.

It must be noted that certain poxviruses, such as MVA, NYVAC, and avipox, can only productively replicate in or be passaged through avian species or avian cell lines such as, for example, chicken embryonic fibroblasts. The recombinant poxviruses harvested from avian host cells, when inoculated into a non-avian vertebrate, such as a mammal, in a manner analogous to the inoculation of mammals by vaccinia virus, produce an inoculation lesion without productive replication of the avipox virus. Despite the failure of certain poxviruses, such as MVA, NYVAC, and avipox, to productively replicate in such an inoculated non-avian vertebrate, sufficient expression of the virus occurs so that the inoculated animal responds immunologically to the antigenic determinants of the recombinant poxvirus and also to the antigenic determinants encoded in exogenous genes therein. Thus, in one embodiment, when certain poxviruses or viral vectors (as disclosed above) are used, chicken embryonic fibroblasts are preferred as the cell permissive for viral vector replication.

The recombinant viral vectors and recombinant viruses can contain promoters that are operably linked to the viral RNA replicons of the present invention. The promoter is advantageously of poxviral origin, which may be, in particular, the promoter 7.5K of the vaccinia virus, I3L poxviral promoter, 42K poxviral promoter, H6 poxviral promoter, thymidine kinase poxviral promoter, E3L poxvirus promoter, K3L poxvirus promoter, or a synthetic poxviral promoter. The promoter can advantageously be an "early" promoter. An "early" promoter is known in the art and is defined as a promoter that drives expression of a gene that is rapidly and transiently expressed in the absence of de novo protein synthesis. The promoter can also be a "strong" or "weak" promoter. The terms "strong promoter" and "weak promoter" are known in the art and can be defined by the relative frequency of transcription initiation (times per minute) at the promoter. A "strong" or "weak" promoter can also be defined by its affinity to poxviral RNA polymerase.

The invention also provides for poxviral promoters that are mutated. Without being bound by theory, it is believed that high levels of expression of potentially toxic heterologous sequences expressed from viral RNA replicons, such as alphaviral replicons, can preclude formation of stable poxviral recombinants. Therefore, the present invention also comprehends the use of a mutated poxviral promoter, such as, for example, a mutated H6 promoter, such that the expression levels of the heterologous sequences expressed from viral RNA replicons are decreased compared with expression levels of the heterologous sequences under a wild type promoter. The mutated H6 promoter of the instant invention can be considered a weak promoter.

The mutated promoters can contain point mutations. The invention can also employ promoters other than H6, which contain point mutations that reduce their frequency of transcription initiation compared with the wild type promoter. In addition, other types of mutated promoters are suitable for use in the instant invention. For example, U.S. application Ser. No. 10/679,520, incorporated herein by reference, describes a truncated form of the H6 promoter (see also Davison, A. et al (1989) J. Mol. Biol. 210: 749-769; Taylor J. et al., Vaccine, 1988, 6, 504-508; Guo P. et al. J. Virol., 1989, 63, 4189-4198; Perkus M. et al., J. Virol., 1989, 63, 3829-3836).

The poxvirus vectors or viruses of the present invention can further comprise additional sequences to control transcription and translation of the heterologous sequences expressed from viral RNA replicons. For example, such sequences can comprise a T5NT termination recognition signal, which can be recognized by poxviral RNA polymerase for termination of early RNA transcription.

The present invention also relates to a method of producing a recombinant poxvirus vector comprising heterologous sequences expressed from viral RNA replicons, comprising the steps of linearizing a donor plasmid with a restriction endonuclease, wherein the donor plasmid comprises restriction endonuclease cleavage sites or a multiple cloning site, and ligating at least one nucleic acid sequence comprising (i) a nucleic acid sequence encoding a viral RNA replicon expressing one or more heterologous sequence(s) of interest, (ii) a viral promoter sequence, and (iii) insertion sequences flanking (i) and (ii) that have complementary restriction endonuclease cleavage sites to the donor plasmid at viral RNA replicon sequences, thereby producing the recombinant poxvirus vector. Advantageously, the method further comprises the steps of introducing the vector into a cell permissive for replication of the vector, and isolating the vector from the cell.

By definition, a donor plasmid expression vector (or donor plasmid) includes a DNA transcription unit comprising a polynucleotide sequence containing the cDNA to be expressed and the elements necessary for its expression in vivo. The circular, super-coiled or uncoiled plasmid form is preferred. The linear form also comes under the scope of this invention.

Methods for making and/or using vectors (or recombinants) for expression and uses of expression products and products therefrom (such as antibodies) can be by or analogous to the methods disclosed in herein cited documents and documents referenced or cited in herein cited documents. See, for example, Sambrook et al. *Molecular Cloning* (1999). The invention also includes the use of the poxvirus vectors expressing heterologous sequences expressed from viral RNA replicons in the research setting. The recombinant poxvirus vectors and recombinant poxviruses can be used to transfect or infect cells or cell lines of interest to study, for example, cellular responses to gene products expressed from the heterologous sequences of interest, or signal transduction pathways mediated by proteins encoded by the heterologous sequences of interest.

In the research setting, it is often advantageous to design recombinant vectors or viruses that comprise reporter genes that can be easily detected by laboratory assays and techniques. Reporter genes are well known in the art and can comprise resistance genes to antibiotics such as, but not limited to, ampicillin, neomycin, zeocin, kanamycin, bleomycin, hygromycin, chloramphenicol, among others. Reporter genes can also comprise green fluorescent protein, the lacZ gene (which encodes β-galactosidase), luciferase, and β-glucuronidase.

*Alphaviruses* are members of the Togaviridae family and are well known in the art. The virions are small, enveloped, 60-65 nm particles of positive-strand RNA. The genomic RNA (49S RNA) of alphaviruses is approximately 11-12 kb in length and contains a 5' cap and a 3' polyadenylated tail. Assembling viral nucleocapsid proteins onto genomic RNA in the cytoplasm produces infectious enveloped virus. Budding occurs through the host cell membrane, which has viral-encoded glycoproteins embedded within it. During viral replication, the genomic 49S RNA serves as template for the synthesis of a complementary negative strand. The negative strand in turn serves as template for full-length genomic RNA and for an internally initiated, positive-strand 26S subgenomic RNA. The nonstructural proteins are translated from the genomic RNA. Alphaviral structural proteins are translated from the subgenomic 26S RNA. All viral proteins are first synthesized as polyproteins and processed into individual proteins by post-translational proteolytic cleavage.

The terms "viral replicon" or "RNA replicon", as used in the context of the present invention, is used interchangeably to refer to RNA or DNA comprising portions of the 49S viral genomic RNA that are essential for transcription and for cytoplasmic amplification of the transported RNA and for subgenomic RNA expression of a heterologous nucleic acid sequence. Thus, the replicon encodes and expresses viral nonstructural proteins necessary for cytoplasmic amplification of the virus RNA and expression of the 26S subgenomic RNA. Advantageously, the viral replicon is not encapsidated to produce viral particles or virions. This can be achieved by replicons that lack one or more of the viral structural genes, and advantageously all of the structural genes. Advantageously, viral RNA replicons of the invention are capable of being transcribed and processed into RNA molecules with authentic viral-like 5' and 3' ends. Such replicons and expression vectors containing them are well known in the art, such as in U.S. Pat. Nos. 5,739,026; 5,766,602; 5,789,245; 5,814,482, and 5,843,723. It will be apparent to the skilled artisan that while many of the features of these replicons are useful for the present invention, not all are essential. As long as a portion of the viral replicon does not interfere with production of the primary RNA transcript, cytoplasmic amplification thereof and expression of the heterologous sequences, such portions can remain as part of the replicon. The skilled artisan can readily determine the nature of and remove any unnecessary or interfering sequences.

The viral RNA replicons can be incorporated as DNA or cDNA into viral genomes, such as poxvirus viral genomes using recombinant DNA techniques known in the art.

In accordance with the present invention, the viral RNA replicon comprises nucleic acid control sequences operably linked to a heterologous nucleic acid sequence to control expression thereof. These control sequences are sequence elements to control transcription and translation as needed. The sequence elements can include, but are not limited to, promoters, enhancers, transcription and translation termination signals, translation start sites, post-transcriptional regulatory sequences, and the like. Advantageously, the replicon also comprises a 3' hepatitis δ ribozyme sequence, which can self-cleave the transcribed RNA to produce the viral replicon RNA with a poly-A tract.

As used herein, the term "heterologous" refers to the relationship between the source of the viral replicon and the poxviral vector, and the source of the heterologous nucleic acid sequence of interest. Thus, the heterologous nucleic acid sequence does not encode a poxviral gene or a gene common to the virus from which the RNA replicon is derived, but rather encodes a gene that is either foreign or endogenous to host cells infected with the poxvirus vectors harboring viral replicons of the invention. As used herein, "foreign gene or nucleic acid sequence" can refer to a gene or a nucleic acid sequence encoding a protein or a fragment thereof, or antisense RNA, catalytic RNA, or small interfering RNA, which is foreign to the recipient animal, cell, or tissue, such as a vaccine antigen, an immunomodulator, or a therapeutic agent. An "endogenous gene or nucleic acid sequence" means a gene or nucleic sequence encoding a protein or part thereof, or antisense RNA, catalytic RNA, or small interfering RNA, which is naturally present in the recipient animal, cell, or tissue.

The heterologous sequence of interest can be constructed from naturally occurring gene sequences, or can be constructed from synthetically constructed gene sequences.

The use of viral replicons other than from Semliki Forest Virus is also comprehended by the present invention. It will be obvious to one skilled in the art that any viruses in the alphavirus genus of the Togaviridae family can be suitable as the source for replicon construction. Representatives include, but are not limited to, Sindbis virus, Aura virus, Venezuelan Equine Encephalitis virus (VEE) virus, Western Equine Encephalitis (WEE) virus, Eastern Equine Encephalitis (EEE) virus, Ross River virus, Mayaro virus, Chikungunya virus, Getah virus, Sagiyama virus, Mucambo virus, Pixuna virus, Middelburg virus, O'nyong-Nyong virus, Barmah forest virus, Bebaru virus, Una virus, Whataroa virus, Babanki virus, Kyzylagach virus, Highlands J virus, Fort Morgan virus and Ndumu virus. The replicon RNA can be also derived from a virus selected from the group consisting of a positive sense single stranded RNA virus, such as poliovirus, rhinovirus, coxsackievirus, yellow fever virus, hepatitis C (HCV), transmissible gastroenteritis virus (TGEV), infectious bronchitis virus (IBV), murine hepatitis virus (MHV), bovine coronavirus (BCV), astrovirus or a group consisting of tobamoviruses, potyviruses and bromoviruses.

To generate a poxvirus-RNA virus chimera, it is often necessary to allow the recombination between the poxviral genome and the donor plasmid containing the RNA replicon to occur and to isolate the chimera by screening of recombinant viral plaques. However, alphaviral replication, for example, is much faster than most poxviruses, such as vaccinia, MVA, NYVAC, ALVAC, canarypox, TROVAC, or fowlpox, and can be lytic to host cells. Replication of RNA viruses can affect poxviral replication and therefore inhibit recombinant generation. Previous attempts to isolate poxvirus-SFV chimeras were heretofore unsuccessful, and can be attributed to the cytopathic effect of the alphavirus replicon. To avoid the cytotoxicity of the RNA virus replication, it is particularly advantageous to generate a mutant viral RNA replicon with reduced cytotoxicity or to generate conditionally mutant viral RNA replicons, with, for example, temperature sensitivity. The mutant viral RNA replicon would be unable to replicate during the phase of recombinant generation at a non-permissive temperature, but would be able to launch replication under permissive conditions. An illustration of the generation of an ALVAC-SFV chimera using a temperature sensitive SFV replicon is shown in FIG. 4.

Expression of heterologous sequences of interest from viral RNA replicons, and self-replication of the replicon, requires the presence of an RNA virus polymerase. This polymerase can be contained on the same viral RNA replicon as the heterologous sequence(s) of interest, or supplied separately in situ in a separate donor plasmid. For example, the alphaviral RNA replicase is encoded by the nsP1, nsP2, nsP3, and nsP4 alphaviral genes, which interact with host factors to initiate alphaviral replication and 26S subgenomic RNA transcription. Mutations in these ns proteins can affect replication of the alphaviral replicon, thus making the ns proteins attractive targets for generating conditional replicon mutants, such as temperature-sensitive mutants. Other RNA virus polymerases can be used in the context of the present invention, when RNA viral replicons other than from alphaviruses are used. The skilled artisan can choose which polymerase is suitable for the particular RNA virus replicon desired, without undue experimentation.

In the context of SFV, the present inventors have demonstrated that mutation of leucine (hereinafter Leu) 713 in the nsP2 protein to alanine (Ala), threonine (Thr), arginine (Arg), glutamine (Gln) or phenylalanine (Phe), can generate conditional SFV mutant replicons (see Example 1). Mutation of the Leu713 in the nsP2 protein to proline was reported to affect SFV replication (Perri, S. et al (2000) J. Virol. 74(20): 9802-7). Several temperature-sensitive mutations exhibiting reduced DNA synthesis have been described for Sindbis virus (Boorsma, M. et al. (2000) Nat. Biotechnol. 18: 429-432) and all have been mapped to the nsP4 gene. Temperature-sensitive replicon-based DNA expression systems mapping to the nsP4 gene have also been described (Hahn, Y. et al (1989) J. Virol. 63: 1194-1202) in Sindbis virus. In this system, the replicase is active at a temperature less than 35° C. and inactive at 37° C. Of the SFV mutants described in the present invention, a mutant replicon containing the mutation of Leu713 to Ala (SFV Leu713Ala) was identified to be both less cytopathic to cells and temperature-sensitive. The SFV Leu713Ala replicon showed a reduced level of cytotoxicity at 37° C. and cannot replicate at 40° C. However, it still expresses the GFP/Blasticidin marker gene at 37° C., which is a physiologically relevant temperature for development of mammalian or avian vaccines. The inability of the mutant replicon SFV Leu713Ala to replicate at 40° C. allows for the generation of the ALVAC-SFV chimera at 40° C. Therefore, a preferred embodiment of the present invention describes a mutant alphaviral replicon comprising a temperature sensitive mutant of the alphaviral nsP2 protein. Advantageously, the mutation is at leucine 713 of the nsP2 alphaviral protein.

In addition to the SFV Leu713Ala mutant, other SFV nsP2 mutants could also be used for the chimera generation in the present invention. Example 7 describes the construction of additional SFV nsP2 mutants with reduced cytotoxicity. One mutant is based on an attenuated SFV strain (Rikkonen, M. (1996) Virology 218: 352-361) that has a point mutation changing Arg650 to Asp at the nuclear transport signal in the nsP2 protein. Another nsP2 mutant is derived from a single mutation of Ser 259 to Pro in the nsP2 protein, which has also been reported to render the SFV replicon less cytopathic (Lundstrom, K. et al (1999) Gene Ther. Mol. Biol. 4: 23-31). Example 10 describes ALVAC C6 donor plasmids containing a SFV double mutant Arg650Asp+Ser359Pro.

In the present invention, the heterologous sequences can also comprise an antigen, an antigenic fragment of a protein, a therapeutic agent, a cytokine, a toxin, an immunomodulator, an antisense RNA, a catalytic RNA, small interfering RNA, a protein, a peptide, an antibody, an antigen-binding fragment of an antibody, an adjuvant, or any other molecule encodable by DNA and desired for delivery to an animal or animal cell or tissue.

The heterologous sequence can be the sequence encoding a protein expressed in pathogens such as HW, HCV, HBV, HPV, EBV, HSV, CMV, HTLV, Hanta virus, Ebola virus, Lassa virus and influenza virus, among others. These constructs can be used advantageously as vaccines to protecting humans against disease caused by these viruses. The selected heterologous sequences also may be cancer antigens such as, but not limited to, prostate specific antigen, CEA, KSA, p53, gp100, Mart-1, Mage1/2, NY-ESO-1, BF44 and others.

The heterologous sequences can also be the HN and F genes of Newcastle Disease Virus, the polyprotein and VP2 genes from infectious Bursal Disease Virus, the S and N genes from Infectious Bronchitis Virus and the gB and gD genes from Mareks Disease Virus. These constructs can be used as vaccines for protecting poultry against disease caused by these viruses.

The heterologous sequences can also be selected from the gB, gC, gD and Immediate-Early genes from Bovine Herpesvirus type 1, the F and G genes from BRSV, the polyprotein, E1, E2 genes from BVDV, the HN and F genes from P13 virus or genes from Rotavirus. These constructs can be useful as vaccines for protecting cattle against disease caused by these viruses.

The heterologous sequences can also include the gB, gC, gD and Immediate-Early genes from PRV, the HA, NA, M and NP genes from Swine influenza virus, the polyprotein, E1, E2 from Hog Cholera Virus, the ORF1 and ORF2 genes from PCV2 virus, the ORF3, ORF4, ORF5, ORF6, or ORF7 from PRRSV virus or genes from *Mycoplasma hyopneumoniae*. These constructs can be useful as vaccines for protecting pigs against disease caused by these viruses.

The heterologous sequences can also include, the gB, gC, gD and Immediate-Early genes from Equine herpesvirus type 1, the gB, gC, gD and Immediate-Early genes from Equine herpesvirus type 4, the HA, NA, M and NP genes from Equine influenza virus, genes from Eastern Equine Encephalitis Virus, genes from Western Equine Encephalitis Virus, genes from Venezuelan Equine Encephalitis Virus, the prM-M-E genes from the West Nile Virus, and genes from Equine arteritis virus, but are not limited to these sequences. These constructs can be useful as vaccines for protecting horses against disease caused by these viruses.

The heterologous sequences can include the HA, F, NP genes from the Canine Distemper Virus, the capsid gene from the Canine Parvovirus, the spike, M, N genes from the Canine coronavirus, the HN and F genes from the canine parainfluenza 2, genes from leptospira, and the gB, gC and gD genes from the canine herpesvirus, among others. These constructs can be useful as vaccines for protecting dogs against disease caused by these viruses.

The heterologous sequences can also include the gB, gC and gD genes from the Feline Herpesvirus, the env and gag/pro genes from the FeLV, the env, gag/pol and the genes from the FIV virus, the capsid gene from the Feline calicivirus, the S modified gene, M, and N gene from the Feline Infectious Peritonitis Virus, and the VP2 gene from the Feline parvovirus. These constructs can be useful as vaccines for protecting cats against disease caused by these viruses.

The heterologous sequences can also be selected from bacterial antigens, for example, from any one of the following pathogenic bacteria: *Bordetella pertussis, Bordetella bronchiseptica, Streptococcus pneumoniae, Streptococcus equi, Chlamydia trachomatis, Chlamydia pneumoniae, Chlamydia psittaci, Mycobacterium tuberculosis, Mycobacterium pseudotuberulosis*, Group A *Streptococcus, Streptococcus agalactiae, Neisseria gonorrhoeae, Enterotoxigenic E. coli, Vibrio cholerae, Bacillus anthracis, Haemophilus influenzae, Haemophilus somnus, Salmonella* species, *Rickettsia* species, *Helicobacter pylori, Helicobacter felis, Shigella* species, *Listeria* species, *Legionella pneumoniae, Pseudomonas* species, *Borellia burgdorferi, Neisseria meningitides, Clostridium* species, among others.

The heterologous sequences can also be selected from parasitic antigens including, but are not limited to, *Plasmodium* species, *Trypanosome* species, *Giardia* species, *Boophilus* species, *Babesia* species, *Entamoeba* species, *Eimeria* species, *Leishmania* species, *Schistosome* species, *Brugia* species, *Fascida* species, *Dirofilaria* species, *Wuchereria* species, and *Onchocerea* species.

The heterologous sequences can also be antisense, catalytic, or small interfering RNA species, which can be targeted against any molecule present within the recipient cell or likely to be present within the recipient cell. These include, but are not limited to RNA species encoding cell regulatory molecules, such as interleukin-6, oncogenes such as Ras, causative agents of cancer such as human papillomavirus, enzymes, viral RNA and pathogen-derived RNA, such as HIV-1 RNA. The RNAs can also be targeted at non-transcribed DNA sequences, such as promoter or enhancer regions, or to any other molecule present in recipient cells, such as but not limited to, enzymes involved in DNA synthesis or tRNA molecules.

In addition cytokines and immunomodulators can be co-expressed with the vectors and viruses of the present invention. Examples include, but are not limited to, IL-2, IL-4, GM-CSF, IL-12, IGF-1, IFN-α, IFN-β, and IFN-γ.

The invention also relates to a method of eliciting an immune response against a heterologous antigen of interest in a subject comprising administering the recombinant poxvirus vectors or recombinant poxviruses according to the present invention to the subject. The subject can be any animal, in particular, bovine, ovine, porcine, or caprine species. Methods of administration and doses are defined herein.

The recombinant poxviruses expressing heterologous antigens of interest expressed from a viral RNA replicon, or an expression product thereof, immunological, antigenic or vaccine compositions or therapeutic compositions can be administered via a parenteral route (intradermal, intramuscular or subcutaneous). Such an administration enables a systemic immune response, or humoral or cell-mediated responses.

As used herein, the terms "immunogenic composition" and "immunological composition" and "immunogenic or immunological composition" cover any composition that elicits an immune response against the targeted antigens of interest expressed from viral RNA replicons; for instance, after administration of injection into the animal, elicits an immune response against the targeted antigen of interest. The terms "vaccinal composition" and "vaccine" and "vaccine composition" covers any composition that induces a protective immune response against the antigen(s) of interest, or which efficaciously protects against the antigen; for instance, after administration or injection into the animal, elicits an protective immune response against the targeted antigen or provides efficacious protection against the antigen expressed from viral RNA replicons. The term "pharmaceutical composition" means any composition comprising a vector expressing a therapeutic protein as, for example, erythropoietin (EPO).

More generally, the inventive recombinant poxviral vectors and recombinant poxviruses expressing antigen(s) expressed from viral RNA replicons, antigenic, immunogenic, immunological or vaccine poxvirus virus compositions or therapeutic compositions, can be prepared in accordance with standard techniques well known to those skilled in the pharmaceutical or veterinary arts. Such compositions can be administered in dosages and by techniques well known to those skilled in the medical or veterinary arts taking into consideration such factors as the age, sex, weight, species and condition of the particular patient, and the route of administration.

The compositions can be administered alone, or can be co-administered or sequentially administered with compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration. In this regard, reference is made to U.S. Pat. No. 5,843,456, incorporated herein by reference, and directed to rabies compositions and combination compositions and uses thereof.

Examples of compositions of the invention include liquid preparations for orifice, or mucosal, e.g., oral, nasal, anal, vaginal, peroral, intragastric, etc., administration such as suspensions, solutions, sprays, syrups or elixirs; and, preparations for parenteral, subcutaneous, intradermal, intramuscular or intravenous administration (e.g., injectable administration) such as sterile suspensions or emulsions. In such compositions, the recombinant poxvirus virus or recombinant poxvirus viral vectors may be in admixture with a suitable carrier, diluent, or excipient such as sterile water, physiological saline, glucose or the like. The compositions can also be lyophilized. The compositions can contain auxiliary substances, such as wetting or emulsifying agents, pH buffering agents, adjuvants, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions in forms for various administration routes are envisioned by the invention. And again, the effective dosage and route of administration are determined by known factors, such as age, sex, weight, condition and nature of the animal, as well as $LD_{50}$ and other screening procedures which are known and do not require undue experimentation. Dosages of each active agent can be as in herein cited documents (or documents referenced or cited in herein cited documents) and/or can range from one or a few to a few hundred or thousand micrograms, e.g., 1 μg to 1 mg, for an immunogenic, immunological or vaccine composition; and, $10^3$ to $10^{10}$ $TCID_{50}$ advantageously $10^6$ to $10^8$ $TCID_{50}$ for an immunogenic, immunological, pharmaceutical or vaccine composition.

Recombinants or vectors can be administered in a suitable amount to obtain in vivo expression corresponding to the dosages described herein and/or in herein cited documents. For instance, suitable ranges for viral suspensions can be determined empirically. The viral vector or recombinant in the invention can be administered to an animal or infected or transfected into cells in an amount of about at least $10^3$ pfu; more advantageously about $10^4$ pfu to about $10^{10}$ pfu, e.g., about $10^5$ pfu to about $10^9$ pfu, for instance about $10^6$ pfu to about $10^8$ pfu, with doses generally ranging from about $10^6$ to about $10^{10}$, advantageously about $10^{10}$ pfu/dose, and advantageously about $10^8$ pfu per dose of 2 ml. And, if more than one gene product is expressed by more than one recombinant, each recombinant can be administered in these amounts; or, each recombinant can be administered such that there is, in combination, a sum of recombinants comprising these amounts. In vector or plasmid compositions employed in the invention, dosages can be as described in documents cited herein or as described herein or as in documents referenced or cited in herein cited documents. Advantageously, the dosage should be a sufficient amount of plasmid to elicit a response analogous to compositions wherein the antigen(s) expressed from viral RNA replicons are directly present; or to have expression analogous to dosages in such compositions; or to have expression analogous to expression obtained in vivo by recombinant compositions. For instance, where DNA vaccines are administered, suitable quantities of each plasmid DNA in plasmid compositions can be 1 μg to 2 mg, advantageously 50 μg to 1 mg. Documents cited herein (or documents cited or referenced in herein cited documents) regarding DNA plasmid vectors can be consulted by the skilled artisan to ascertain other suitable dosages for DNA plasmid vector compositions of the invention, without undue experimentation.

However, the dosage of the composition(s), concentration of components therein and timing of administering the composition(s), which elicit a suitable immunological response, can be determined by methods such as by antibody titrations of sera, e.g., by ELISA and/or seroneutralization assay analysis. Such determinations do not require undue experimentation from the knowledge of the skilled artisan, this disclosure and the documents cited herein. And, the time for sequential administrations can be likewise ascertained with methods ascertainable from this disclosure, and the knowledge in the art, without undue experimentation.

The immunogenic or immunological compositions contemplated by the invention can also contain an adjuvant. Particularly suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one ore more non-methylated CpG units (Klinman D. M. et al., Proc. Natl. Acad. Sci., USA, 1996, 93, 2879-2883; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cationic lipids containing a quaternary ammonium salt, (5) cytokines, (6) aluminum hydroxide or aluminum phosphate or (7) other adjuvants discussed in any document cited and incorporated by reference into the instant application, or (8) any combinations or mixtures thereof. The DNA vaccines or immunogenic or immunological compositions encompassed by the invention can be formulated with a liposome, in the presence or absence of an adjuvant as described above.

Other suitable adjuvants include fMLP (N-formyl-methionyl-leucyl-phenylalanine; U.S. Pat. No. 6,017,537) and/or acrylic acid or methacrylic acid polymer and/or a copolymer of maleic anhydride and of alkenyl derivative. The acrylic acid or methacrylic acid polymers can be cross-linked, e.g., with polyalkenyl ethers of sugars or of polyalcohols. These compounds are known under the term "carbomer" (*Pharmeuropa*, Vol. 8, No. 2, June 1996). A person skilled in the art may also refer to U.S. Pat. No. 2,909,462 (incorporated by reference), which discusses such acrylic polymers cross-linked with a polyhydroxylated compound containing at least 3 hydroxyl groups: in one embodiment, a polyhydroxylated compound contains not more than 8 hydroxyl groups; in another embodiment, the hydrogen atoms of at least 3 hydroxyls are replaced with unsaturated aliphatic radicals containing at least 2 carbon atoms; in other embodiments, radicals contain from about 2 to about 4 carbon atoms, e.g., vinyls, allyls and other ethylenically unsaturated groups. The unsaturated radicals can themselves contain other substituents, such as methyl. The products sold under the name Carbopol® (Noveon Inc., Ohio, USA) are particularly suitable for use as an adjuvant. They are cross-linked with an allyl sucrose or with allylpentaerythritol, as to which, mention is made of the products Carbopol® 974P, 934P, and 971P.

As to the copolymers of maleic anhydride and of alkenyl derivative, mention is made of the EMA® products (Monsanto), which are copolymers of maleic anhydride and of ethylene, which may be linear or cross-linked, for example cross-linked with divinyl ether. Also, reference may be made to J. Fields et al., *Nature* 186:778-780, 1960 (incorporated by reference).

With regard to structure, the acrylic or methacrylic acid polymers and EMA are advantageously formed by basic units having the following formula:

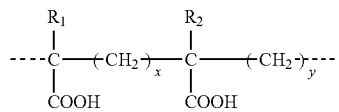

in which:
$R_1$ and $R_2$, which can be the same or different, represent H or $CH_3$
x=0 or 1, advantageously x=1
y=1 or 2, with x+y=2.
For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final vaccine composition can range between 0.01 and 1.5% w/v, advantageously 0.05 to 1% w/v and advantageously 0.1 to 0.4% w/v.

The cationic lipids containing a quaternary ammonium salt which are advantageously but not exclusively suitable for plasmids, are advantageously those having the following formula: in which $R_1$ is a saturated or unsaturated straight-chain aliphatic radical having 12 to 18 carbon

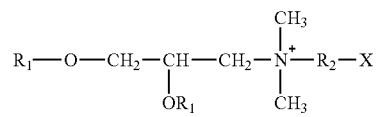

atoms, $R_2$ is another aliphatic radical containing 2 or 3 carbon atoms and X is an amine or hydroxyl group.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr J. P., 1994, Bioconjugate Chemistry, 5, 382-389), to form DMRIE-DOPE.

Advantageously, the plasmid mixture, or the recombinant vaccine mixture with the adjuvant is formed extemporaneously or contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95:about 5 to about 5:about 95, more advantageously about 1:about 1, e.g., 1:1.

The DMRIE or DMRIE-DOPE adjuvant:plasmid weight ratio can be between about 50:about 1 and about 1:about 10, such as about 10:about 1 and about 1:about 5, and advantageously about 1:about 1 and about 1:about 2, e.g., 1:1 and 1:2.

A recombinant vaccine or immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is available under the name Provax® (IDEC Pharmaceuticals, San Diego, Calif.).

The term "prime-boost" refers to the successive administrations of two different types of vaccine or immunogenic or immunological compositions having at least one antigen in common. The priming administration (priming) is the administration of a first vaccine or immunogenic or immunological composition type and may comprise one, two or more administrations. The boost administration is the administration of a second vaccine or immunogenic or immunological composition type and may comprise one, two or more administrations, and, for instance, may comprise or consist essentially of annual administrations.

Thus, the invention encompasses prime-boost immunization or vaccination method of an animal against at least one antigen expressed from viral RNA replicons, comprising administering to the animal a priming DNA vaccine or immunological or immunogenic composition comprising nucleic acid molecule(s) encoding and expressing in vivo an antigen(s) expressed from viral RNA replicons, and thereafter administering a boosting composition that comprises the antigen(s) expressed by the DNA vaccine or immunogenic or immunological composition, or a recombinant or modified vector, e.g., virus, such as a poxvirus (such as vaccinia, MVA, NYVAC, ALVAC, canarypox, TROVAC, or fowlpox virus) that contains and expresses in an animal host cell a nucleotide sequence encoding the antigen(s) expressed by the DNA vaccine or immunogenic or immunological composition. The boosting vaccine or immunogenic or immunological composition can be the same as or different than the DNA vaccine or immunogenic or immunological composition.

For instance, the boosting vaccine or immunogenic or immunological composition can be advantageously the antigen(s) expressed by the DNA vaccine (or immunogenic or immunological composition) and/or a recombinant or modified poxvirus vector, e.g., virus, vaccine or immunogenic or immunological composition. A recombinant or modified vector is advantageously an in vivo expression vector, such as a modified or recombinant bacteria, yeast, virus, e.g. poxvirus virus, comprising nucleic acid molecule(s) encoding and expressing in vivo antigen(s) expressed by the DNA vaccine or immunogenic or immunological composition. The boost is advantageously performed with an inactivated vaccine or immunogenic or immunological composition, or with a vaccine or immunogenic or immunological composition comprising a recombinant live viral vector, such as a recombinant poxvirus virus, that comprises nucleic acid molecule(s) encoding and expressing in vivo antigen(s) expressed by the DNA vaccine or immunogenic or immunological composition. Thus, it is advantageous that the boost either comprises the antigen expressed by the DNA vaccine or immunogenic or immunological composition or expresses in vivo antigen(s) expressed by the DNA vaccine or immunogenic or immunological composition. Advantageously, the boost comprises the recombinant poxvirus expressing antigens expressed from viral RNA replicons described herein.

Additionally or alternatively, immunogenic or immunological compositions of the invention can contain GM-CSF (granulocyte macrophage-colony stimulating factor; Clark S. C. et al. Science 1987. 230: 1229; Grant S. M. et al. Drugs 1992. 53: 516), or an expression vector that so expresses GM-CSF, with the "expression vector" including the viral replicon that expresses the antigen of interest. The expression vector that contains and expresses the GM-CSF can be a plasmid, or a recombinant or modified vector such as a recombinant or modified virus, bacteria, yeast, or can be contained on the viral RNA replicon expressing the antigen of interest. Thus, to the DNA vaccine or immunogenic or immunological composition is added GM-CSF or a vector that expresses GM-CSF, e.g. added to the non-adjuvanted or adjuvanted and/or liposome formulated vaccines or immunogenic or immunological compositions; or, the DNA plasmid that expresses antigens expressed from viral RNA replicons is constructed so that it also expresses GM-CSF. If an expression vector is providing the GM-CSF, a nucleic acid sequence encoding GM-CSF is in the expression vector under conditions allowing its expression in vivo (e.g., it is operably linked to s suitable promoter). Advantageously, the expression vector that expresses the GM-CSF is a plasmid, e.g. the plasmid containing the nucleotide sequence encoding the antigen(s) of interest or another plasmid.

In the vaccines or immunogenic or immunological compositions contemplated by the invention, e.g. in the non-adjuvanted or adjuvanted and/or liposome formulated vaccines or immunogenic or immunological compositions, containing or not GM-CSF or an expression vector expressing GM-CSF, the nucleotide sequence(s) encoding the expression products are in an optimized or modified form. Optimization is understood to mean any modification of the nucleotide sequence which manifests itself at least by a higher level of expression of this nucleotide sequence, and/or by an increase in the stability of the messenger RNA encoding this antigen, and/or by the triggered secretion of this antigen into the extracellular medium, and which may have as direct or indirect consequence an increase in the immune response induced.

Even further alternatively or additionally, in the immunogenic or immunological compositions encompassed by the present invention, the nucleotide sequence encoding the antigens expressed from viral RNA replicons can have deleted therefrom a portion encoding a transmembrane domain. Yet even further alternatively or additionally, the plasmid in the DNA vaccine or immunogenic composition can further contain and express in an animal host cell a nucleotide sequence encoding a heterologous tPA signal sequence such as human tPA and/or a stabilizing intron, such as intron II of the rabbit β-globin gene.

The DNA plasmid, or recombinant poxvirus vector or recombinant poxvirus expressing one or more nucleic acid sequences expressing a heterologous sequence of interest expressed from viral RNA replicons, e.g., virus and vector according to this disclosure, can be preserved and/or conserved and stored either in liquid form, at about 5° C., or in lyophilized or freeze-dried form, in the presence of a stabilizer. Freeze-drying can be according to well-known standard freeze-drying procedures. The pharmaceutically acceptable stabilizers may be SPGA (sucrose phosphate glutamate albumin; Bovarnik et al., *J. Bacteriology* 59:509, 1950), carbohydrates (e.g., sorbitol, mannitol, lactose, sucrose, glucose, dextran, trehalose), sodium glutamate (Tsvetkov T et al., *Cryobiology* 20(3): 318-23, 1983; Israeli E et al., *Cryobiology* 30(5): 519-23, 1993), proteins such as peptone, albumin or casein, protein containing agents such as skimmed milk (Mills C K et al., *Cryobiology* 25(2): 148-52, 1988; Wolff E et al., *Cryobiology* 27(5):569-75, 1990), and buffers (e.g., phosphate buffer, alkaline metal phosphate buffer). An adjuvant and/or a vehicle or excipient may be used to make soluble the freeze-dried preparations.

The invention further relates to the product of expression of the inventive recombinant poxvirus and uses thereof, such as to produce a protein in vitro, or to form antigenic, immunological or vaccine compositions for treatment, prevention, diagnosis or testing; and, to DNA from the recombinant poxvirus virus which are useful in constructing DNA probes and PCR primers.

In one aspect, the present invention relates to recombinant poxviruses containing at least one nucleic acid sequence expressing one or more heterologous sequences expressed from viral RNA replicons, advantageously in a non-essential region of the poxvirus genome. The poxvirus can be a vaccinia virus, especially an attenuated vaccinia virus such as MVA and NYVAC, or a fowlpox virus, especially an attenuated fowlpox virus such as TROVAC, or a canarypox virus, especially an attenuated canarypox virus, such as ALVAC.

According to the present invention, the recombinant poxvirus and poxviral vectors express at least one nucleic acid sequence encoding one or more products expressed from viral RNA replicons. In particular, any or all genes or open reading frames (ORFs) encoding the products can be isolated, characterized and inserted into poxvirus recombinants. The resulting recombinant poxvirus is used to infect an animal. Expression in the animal of the heterologous sequence can result in an immune response in the animal to the expression products of the heterologous sequence. Thus, the recombinant poxvirus of the present invention may be used in an immunological composition or vaccine to provide a means to induce an immune response, which may, but need not be, protective. The molecular biology techniques used are described by Sambrook et al. (1989). The invention also contemplates heterologous sequences expressed from viral RNA replicons that can be delivered as a naked DNA plasmid or vector, or DNA vaccine or immunological or immunogenic compositions comprising nucleic acid molecules encoding and expressing in vivo the expression product(s) of the heterologous sequence expressed in viral RNA replicons.

The invention will now be further described by way of the following non-limiting Examples, given by way of illustration. Methods of molecular genetics, protein biochemistry, and immunology used but not explicitly described in this disclosure and these Examples are amply reported in the scientific literature and are well within the ability of those skilled in the art.

EXAMPLES

Example 1

Construction and Characterization of SFV nsP2 Mutants

Figure 5A:
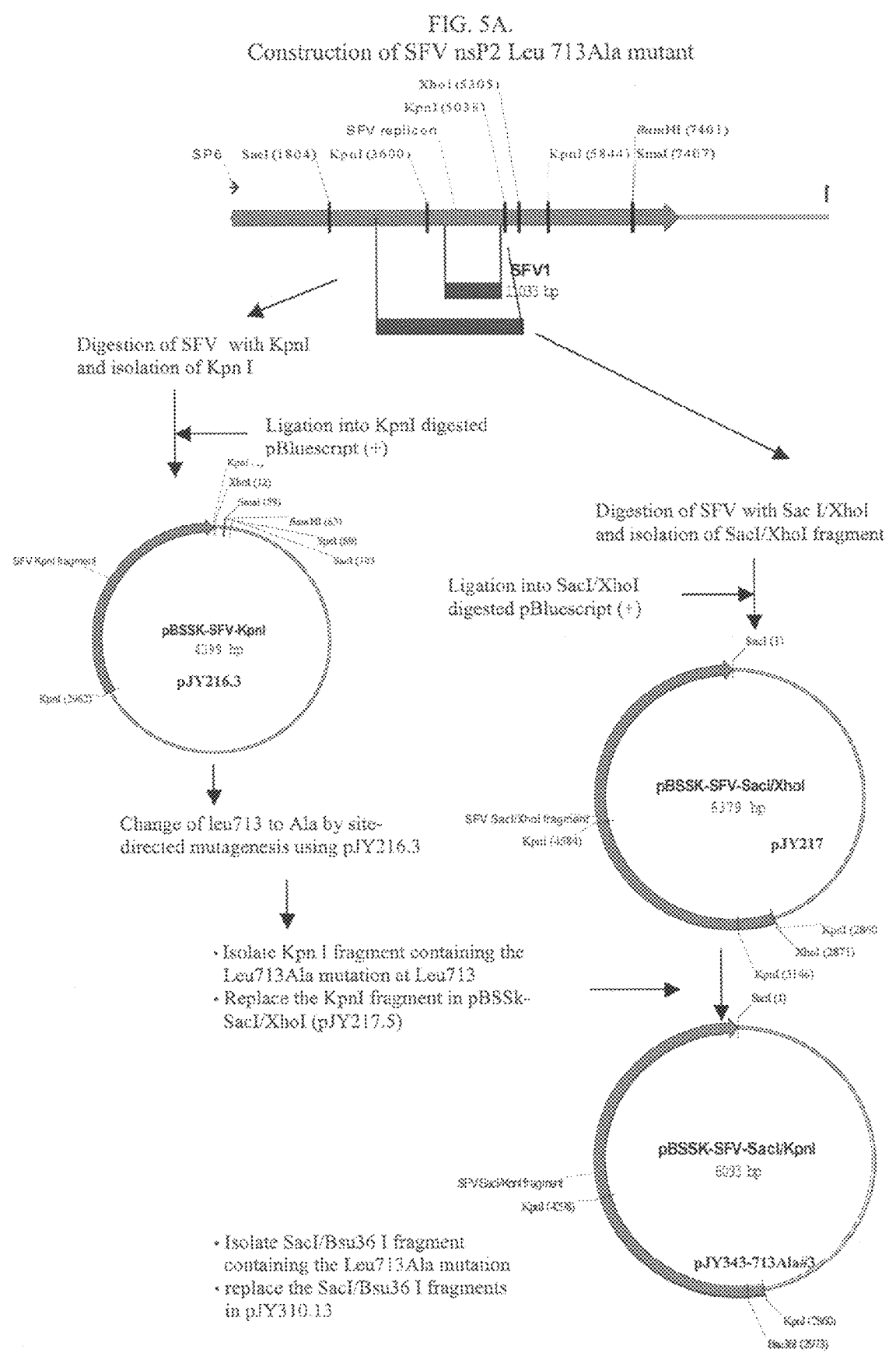
Figure 5B:
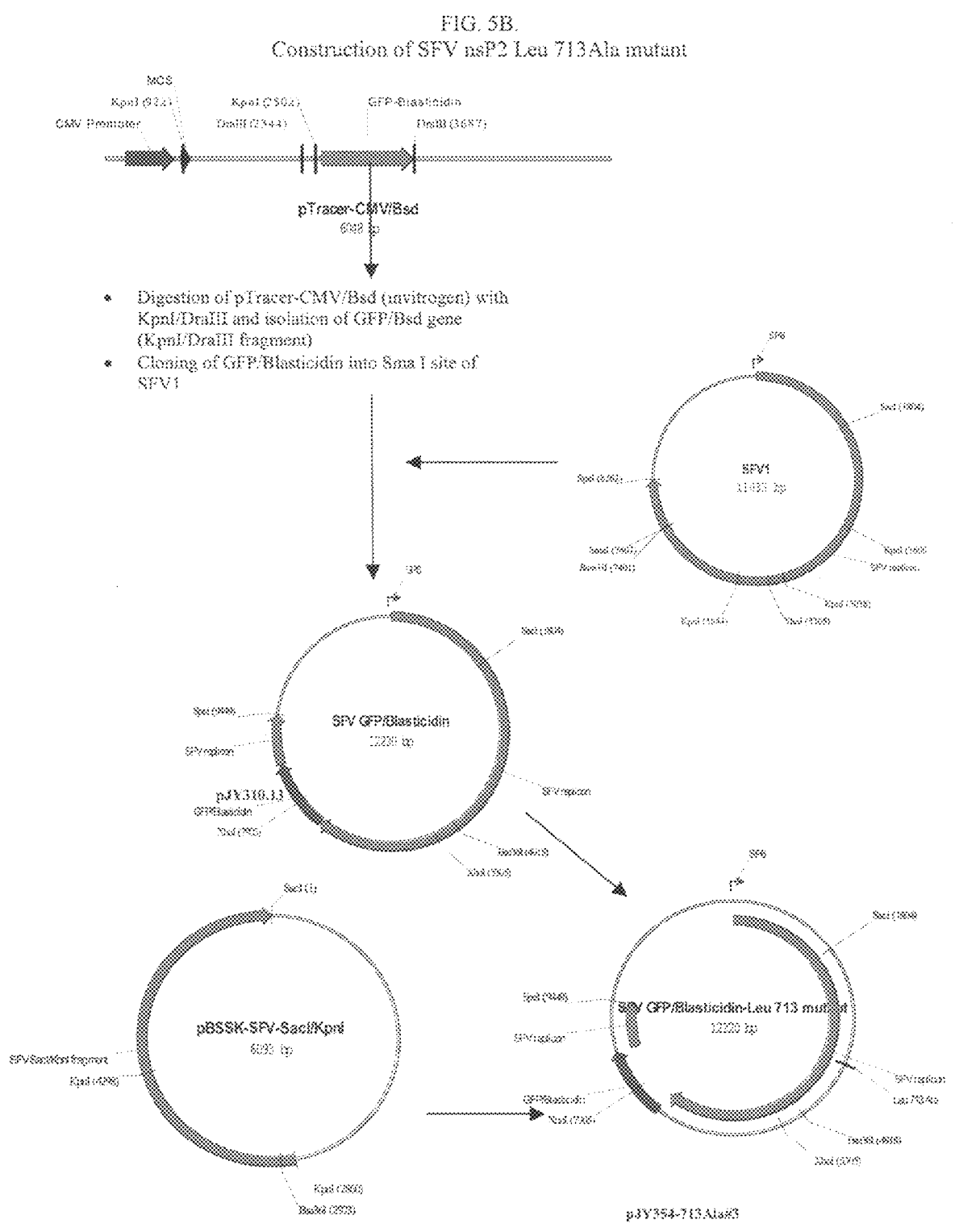

The construction of SFV nsP2 mutants by mutation of Leu 713 in the nsP2 protein is illustrated in FIGS. 5A and 5B. Plasmid SFV1 (GIBCO BRL) containing SFV replicon cDNA was used for the mutant construction. To facilitate the construction, plasmid SFV1 was digested with KpnI or SacI/XhoI, and the 1.4 kb KpnI fragment and 3.5 kb SacI/XhoI fragment were isolated. These two fragments were cloned into KpnI digested pBluescript (+) to create pBluescript-SFV-KpnI (pJY216.3) and into SacI/XhoI digested pBluescript (+) to create pBluescript-SFV-SacI/XhoI (pJY217.5). Mutagenesis was performed using a QuikChange site-directed mutagenesis kit (Stratagene) to change the nsP2 Leu 713 to Ala, Thr, Gln, Arg or Phe using pBluescript-SFV-KpnI (pJY216.3) as template and the primers shown below in Table 1.

TABLE 1

Mutagenesis Primers to Generate
a Temperature-Sensitive nsP2 SEQ ID NOS:
15-24, respectively, in order of appearance.

| Mutation | Primer Sequence |
| --- | --- |
| Leu713Ala8063JY | 5'-CAG ATG CTT GGG GGA GAT GCG GCA CGA CTG CTA AAA CCC GGC GGC-3' 5'-GCC GCC GGG TTT TAG CAG TCG TGC CGC ATC TCC CCC AAG CAT CTG-3' |
| Leu713Thr8067JY | 5'-CAG ATG CTT GGG GGA GAT GCG ACA CGA CTG CTA AAA CCC GGC GGC-3' 5'-GCC GCC GGG TTT TAG CAG TCG TGT CGC ATC TCC CCC AAG CAT CTG-3' |

TABLE 1-continued

Mutagenesis Primers to Generate
a Temperature-Sensitive nsP2 SEQ ID NOS:
15-24, respectively, in order of appearance.

| Mutation | Primer Sequence |
| --- | --- |
| Leu713Gln8069JY | 5'-CAG ATG CTT GGG GGA GAT GCG CAA CGA CTG CTA AAA CCC GGC GGC-3' 5'-GCC GCC GGG TTT TAG CAG TCG TTG CGC ATC TCC CCC AAG CAT CTG-3' |
| Leu713Phe8073JY | 5'-CAG ATG CTT GGG GGA GAT GCG TTT CGA CTG CTA AAA CCC GGC GGC-3' 5'-GCC GCC GGG TTT TAG CAG TCG AAA CGC ATC TCC CCC AAG CAT CTG-3' |
| Leu713Arg8075JY | 5'-CAG ATG CTT GGG GGA GAT GCG AGA CGA CTG CTA AAA CCC GGC GGC-3' 5'-GCC GCC GGG TTT TAG CAG TCG TCT CGC ATC TCC CCC AAG CAT CTG-3' |

The KpnI fragment containing each mutation was isolated and ligated to KpnI digested pBluescript-SFV-SacI/XhoI (pJY217.5) to create a series of pBluescript-SFV-SacI/KpnI plasmids containing Leu713Ala (pJY343-713Ala#3), Leu713Thr (pJY343-713Thr#1), Leu713Gln (pJY343-713Gln#4), Leu713Arg (pJY343-713Arg#1) or Leu713Phe (pJY343-713Phe#3). The mutations were confirmed by sequence analysis.

To examine the function of SFV nsP2 Leu 713 mutants, a marker gene, GFP/Blasticidin, was isolated from pTracer CMV/Blasticidin (Invitrogen) and cloned into the SmaI site of SFV1 to create SFV GFP/Blasticidin (pJY310.13). To construct SFV GFP/Blasticidin containing Leu713Ala, Leu713Thr, Leu713Gln, Leu713Arg, or Leu713Phe, the pBluescript-SFV-SacI/KpnI plasmids were digested with SacI/Bsu36I and the SacI/Bsu36I fragments containing each mutation were isolated. These fragments were then ligated to SacI/Bsu36I digested SFV GFP/Blasticidin (pJY310.13) to create a series of SFV GFP/Blasticidin plasmids containing Leu713Arg (pJY350-713Arg#1), Leu713Ala (pJY354-713Ala#3), Leu713Thr (pJY354-713Thr#2), Leu713Gln (pJY354-713Gln#1) or Leu713Phe (pJY354-713Phe#1).

To analyze the effect of each mutation on SFV replicon replication, immunoblot analysis was performed to examine the GFP/Blasticidin expression. Briefly, RNA was transcribed from each SFV GFP/Blasticidin Leu713 mutant and the transcribed RNAs were then electroporated into BHK-21 cells. The transfected cells were incubated at 37° C. in a 5% $CO_2$ incubator. After 48 h, cell lysates were prepared, separated on 10% SDS-PAGE gel and transferred onto nylon membranes. The blots were then probed with rabbit anti-GFP antiserum (Invitrogen) and visualized using a chemiluminescence reagent (NEN) after reacting with peroxidase-conjugated goat anti-rabbit antibodies. A considerable amount of GFP/Blasticidin expression was observed with mutants Leu713Ala and Leu713Thr at 37° C. (FIG. 6 lanes 2 and 5), whereas very low amounts of GFP/Blasticidin expression were observed with mutants Leu1713Gln, Leu713Phe and Leu713Arg (FIG. 6).

Figure 7:
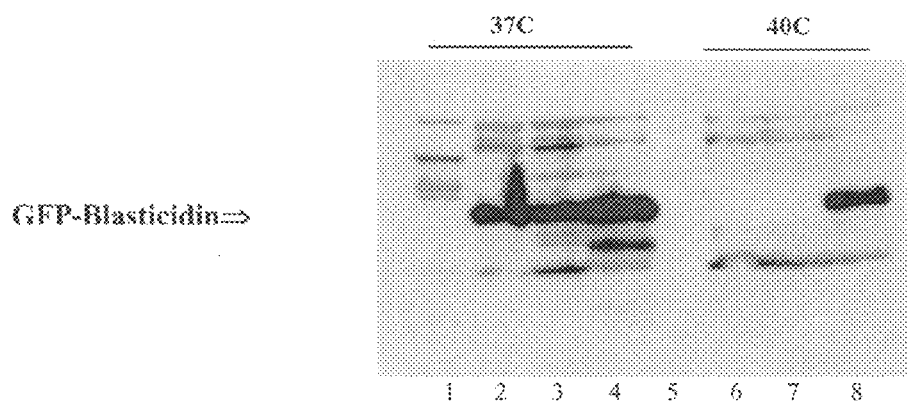

To assess the temperature sensitivity of the SFV GFP/Blasticidin Leu713Ala and SFV GFP/Blasticidin Leu713Thr mutants, the mutant RNAs were electroporated into BHK-21 cells and the transfected cells were incubated at 37° C. and 40° C. The expression of GFP/Blasticidin was then examined by immunoblot. It was found that the replication of the SFV GFP/Blasticidin Leu713Ala and SFV GFP/Blasticidin Leu713Thr mutant is temperature sensitive, since no protein expression was observed at 40° C. (FIG. 7, lanes 6 and 7).

The cytopathic effect (CPE) of each mutation on BHK cells was also investigated by qualitative analysis of CPE after transfection with the mutants. By microscopic examination, obvious CPE was seen for the BHK cells transfected with mutants Leu713Ala and Leu713Thr after 48 h. In contrast, the cells were completely lysed 48 h after transfection with the parental SFV replicon. These results demonstrated that the change of Leu713 to Ala or Thr renders the SFV replicon both temperature-sensitive and less cytopathic to cells while maintaining protein expression. The SFV GFP/Blasticidin Leu713Ala mutant (pJY354-713Ala#3) was chosen for the subsequent ALVAC-SFV C6 chimeric donor plasmid construction.

Example 2

Construction of a C6 Donor Plasmid Containing SFV-GFP/Bsd Leu713Ala

Figure 8B:
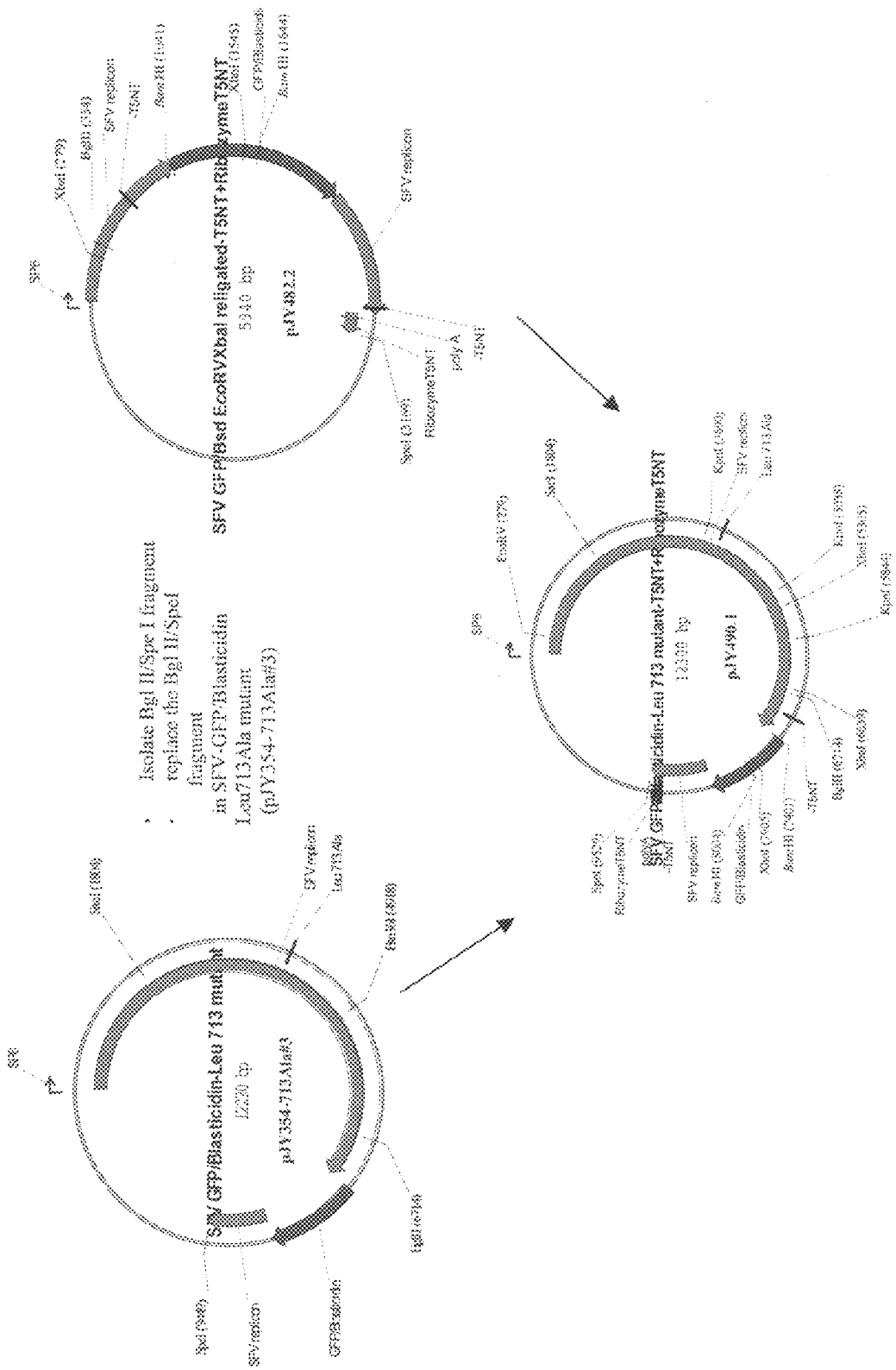

The construction scheme is illustrated in FIGS. 8A and 8B. Sequence analysis of SFV1 cDNA found that there are two T5NT sequences; TTTTTGT located at 7049-7055 by and TTTTTAT located at 8155-8161 bp. The T5NT sequence has been shown to result in premature termination of RNA transcription in poxviruses (Yuen, L. and Moss, B. (1987) Proc. Natl. Acad. Sci. USA 84: 6417-6421). These two T5NT sequences were removed by mutagenesis using a QuikChange site-directed mutagenesis kit (Stratagene) and the primers described in FIG. 8C.

To facilitate the mutations, the plasmid SFV-GFP/Bsd (pJY310.13) was digested with EcoRV/XbaI and religated to create a plasmid SFV GFP/Bsd EcoRV/XbaI-religated (pJY390.1). Mutation of TTTTTGT to TTTCTGT was accomplished using pJY390.1 as template and primers 8255JY and 8256JY to generate plasmid pJY415.1.

To mutate the TTTTTAT and introduce a sequence consisting of hepatitis δ ribozyme sequence followed by TTTTTCT at the end of the poly A tract of the SFV replicon, PCR amplification was performed to produce a DNA fragment comprising the sequences of SFV-3"-polyA-ribozyme followed by TTTTTCT-SpeI site using plasmid pMP76 (ATCC 203462) as template and primers 8257JY, 8258JY, 8259JY and 8284JY (FIG. 8B). pMP76 contains a full length SFV replicon cDNA followed by the hepatitis δ ribozyme sequence. The amplified DNA fragments were then digested with StuI/SpeI and ligated to StuI/SpeI digested pJY415.1 to create plasmid SFV GFP/Bsd EcoRV/XbaI-religated-T5NT+RibozymeT5NT (pJY482.2). Plasmid pJY482.2 was then digested with BglII/SpeI and the isolated BglII/SpeI fragment was ligated to BglII/SpeI digested SFV GFP/Bsd Leu713Ala (pJY354-713Ala#3) to create the full-length SFV GFP/Bsd Leu713Ala-T5NT+RibozymeT5NT plasmid (pJY490.1). The addition of the TTTTTCT sequence at the end of the poly A tract of the SFV replicon is for the termination of RNA transcription. The hepatitis δ ribozyme sequence is for the cleavage of the transcribed RNA in order to produce the SFV replicon RNA with a poly A tract.

Figure 9:
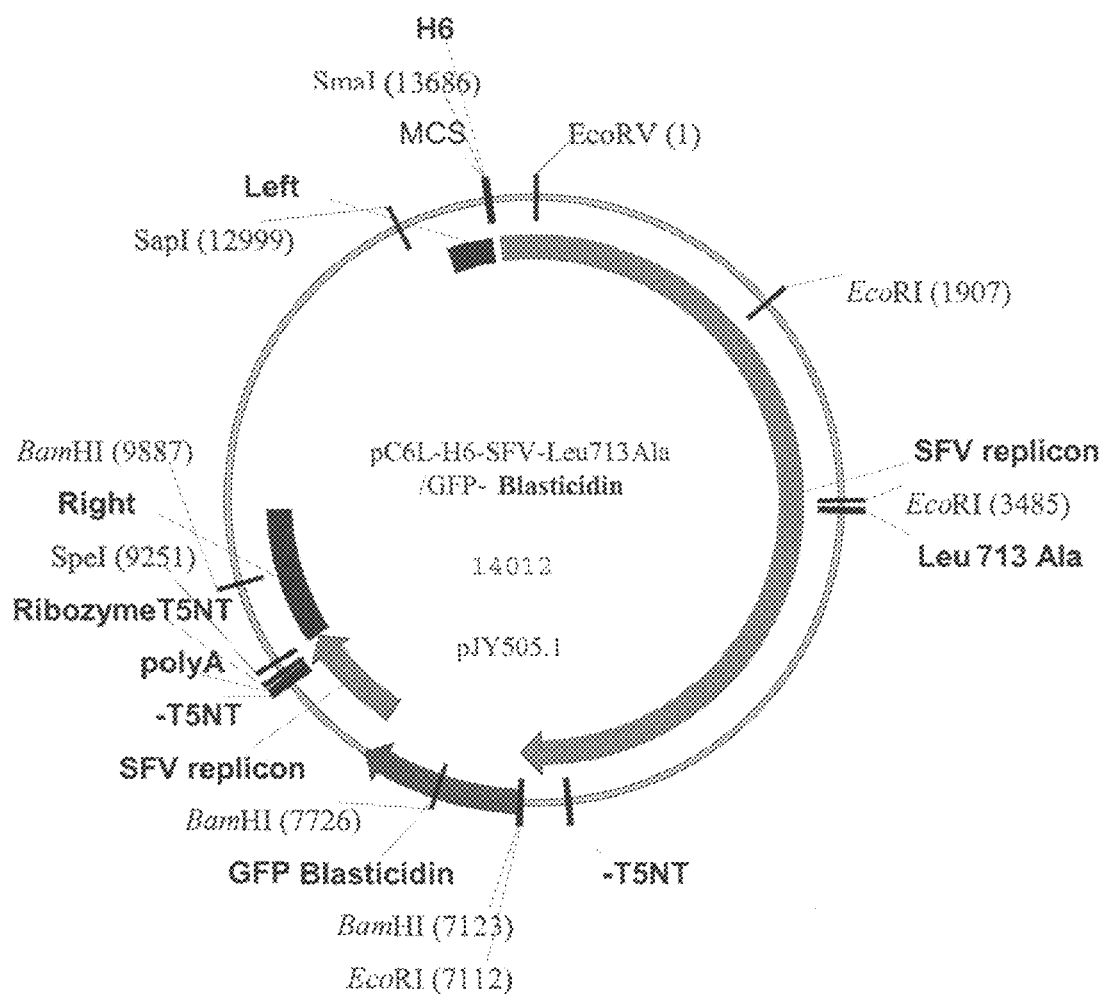
FIG. 9 shows a schematic illustration of the ALVAC C6 donor plasmid (pJY505.1) containing the SFV-GFP/Bsd Leu713Ala mutation.
Figure 10D:
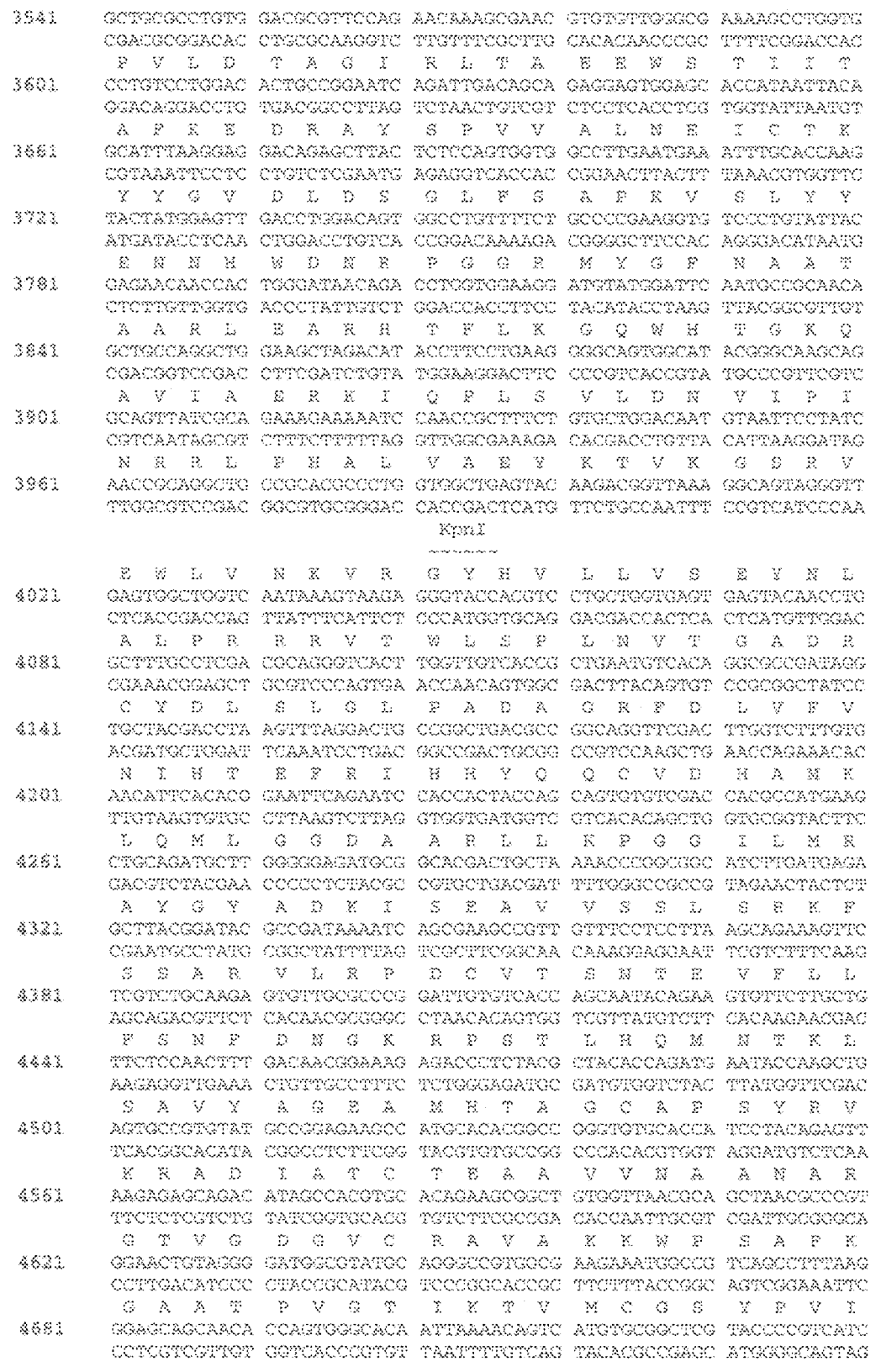
Figure 10G:
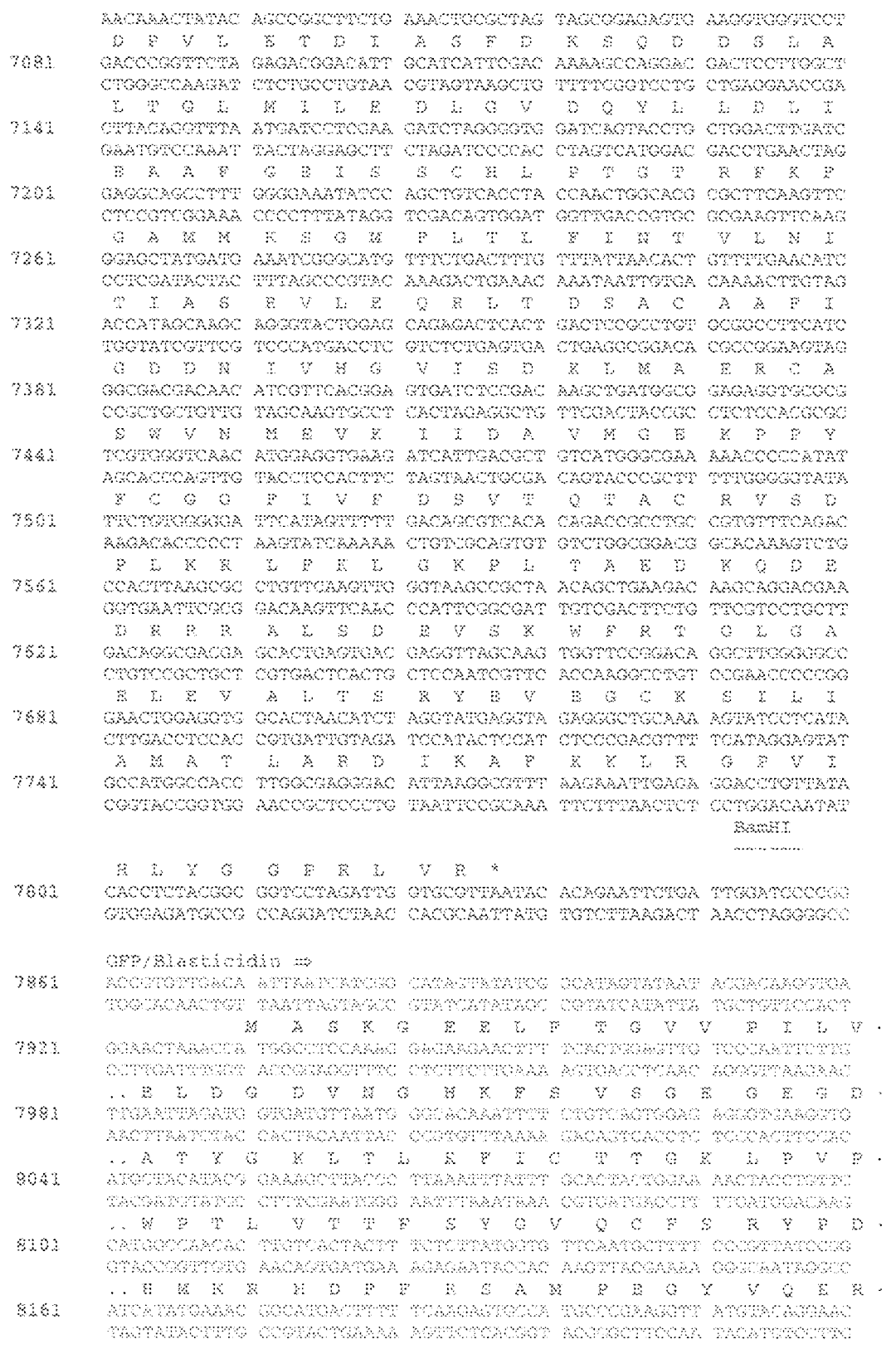

To facilitate the construction of the C6 donor plasmid containing the SFV-GFP/Bsd Leu713Ala, a DNA fragment consisting of the H6 promoter immediately upstream of the SFV-5' sequence was produced by PCR amplification using SFV GFP/Bsd plasmid as template and primers 8279JY and 8280JY as shown in FIG. 8C. The amplified DNA was digested with SmaI/SpeI and ligated to SmaI/SpeI digested pC6L donor plasmid to generate pC6L-H6-SFV-5' (pJY450.1). Plasmid pJY450.1 was then digested with EcoRV/SpeI and ligated with the EcoRV/SpeI fragment isolated from pJY490.1 to create the C6 donor plasmid containing the SFV GFP/Bsd Leu713Ala-T5NT+RibozymeT5NT (pJY505.1). Plasmid pJY505.1 was used for the generation of ALVAC-SFV chimera. An illustration of the pJY505.1 donor plasmid is shown in FIG. 9 and the sequence of pJY505.1 is shown in FIG. 10A through I (SEQ ID No: 1).

Example 3

Generation and Characterization of an ALVAC-SFV Leu713Ala Chimera Expressing GFP/Blasticidin An illustration of the ALVAC-SFV chimera generation using the C6 donor plasmid containing the SFV-GFP/Bsd Leu713Ala is shown in FIG. 11. To generate the ALVAC-SFV Leu713Ala chimera, an in vitro recombination (IVR) was performed by transfection of primary CEF cells with SapI-linearized C6 donor plasmid, containing the SFV GFP/Blasticidin Leu713Ala-T5NT+RibozymeT5NT (pJY505.1), using electroporation. The transfected cells were subsequently infected with ALVAC as rescue virus at MOI of 1.0 and incubated at 40° C. After 24 h, the transfected-infected cells were harvested, sonicated and used for recombinant virus screening.

Recombinant plaques were screened based on the plaque lift hybridization method using a SFV-specific probe, which was labeled with horseradish peroxidase according to the manufacturer's protocol (Amersham). After five sequential rounds of plaque purification at 40° C., the ALVAC-SFV GFP/Bsd Leu713Ala recombinant designated as vCP2064 was generated. Single plaques were selected from the fifth round of plaque purification, and expanded to obtain P1 (60 mm), P2 (T75 flask) and P3 (roller bottle) stocks of vCP2064.

To examine whether the chimeric virus plaque is able to express GFP/Blasticidin marker gene, plaque punches consisting of the chimeric virus and the parental ALVAC virus were taken during the process of plaque purification and were used to infect two sets of primary CEF cells. The infected cells were incubated at 40° C. for 4 days to allow the formation of individual plaques. One set of the infected CEF cells was transferred to 37° C. and further incubated for 1 day. An immunoplaque assay of the viral plaques at 37° C. and 40° C. was then performed. The results showed that the chimeric virus plaques expressed GFP/Blasticidin (indicated by the arrow) at 37° C. but not at 40° C. (FIG. 12).

To examine the protein expression of the ALVAC-SFV Leu713Ala chimera in mammalian cells, BHK-21 cells were infected with vCP2064 P3 stock at MOI of 10 and incubated for 24 hours at 37° C. and 38° C., respectively. The infected cells were harvested and suspended in a lysis buffer. The cell lysates were clarified and separated by 10% SDS-PAGE. The proteins were transferred onto nylon membranes and probed with rabbit anti-GFP antiserum as the primary antibody. After reaction with a peroxidase-conjugated goat anti-rabbit secondary antibody, the blot was visualized using the chemiluminescence reagent (NEN). As shown in FIG. 13, the ALVAC-SFV Leu713Ala chimera expressed GFP/Blasticidin (indicated by the arrow) at both 37° C. and 38° C., but the expression at 38° C. appears less than that at 37° C., confirming the temperature sensitivity of the ALVAC-SFV Leu713Ala chimera.

Example 4

Construction of an ALVAC-SFV Leu713Ala C6 Donor Plasmid Containing a Multiple Cloning Site or Two SFV 26S Promoters The construction of an ALVAC-SFV Leu713Ala C6 donor plasmid containing a multiple cloning site is illustrated in FIGS. 14A and 14B. The construction of an ALVAC-SFV Leu713Ala C6 donor plasmid containing two SFV 26S promoters is shown in FIGS. 14C and 14D. To construct the ALVAC-SFV Leu713Ala C6 donor plasmid containing a multiple cloning site, a PCR amplification was performed to produce a DNA fragment containing a cassette of the multiple cloning site PacI-SbfI-PmeI, using pJY505.1 as template and primers 8314JY and 8284JY as described in FIG. 15. The amplified DNA fragment containing the multiple cloning site PacI-SbfI-PmeI was then digested with EcoRI/SpeI and ligated to EcoRI/SpeI digested pJY482.2, to create pJY592.3. The BglII/SpeI fragment was isolated from plasmid pJY592.3 and ligated to BglII/SpeI digested SFV GFP/Bsd Leu713Ala (pJY354-713Ala#3) to create plasmid SFV Leu713Ala containing PacI-SbfI-PmeI cloning sites (pJY618.1). Plasmid pJY618.1 was digested with EcoRV/SpeI and the EcoRV/SpeI fragment was ligated to EcoRV/SpeI digested plasmid pJY450.1 to create the ALVAC-SFV C6 donor plasmid containing the multiple cloning sites designated as pJY C6 SFV L713A 1 (pJY641.2) (FIG. 16). The nucleotide sequence of pJY C6 SFV L713A 1 is shown in FIGS. 17A through H (SEQ ID No: 2).

Similarly, to construct the ALVAC-SFV Leu713Ala C6 donor plasmid containing two SFV 26S promoters, a PCR amplification was performed to produce a DNA fragment containing a sequence of 26S promoter-PacI-SbfI-26S promoter-PmeI, using pJY505.1 as template and primers 8315JY and 8284JY as shown in FIG. 15. The amplified DNA fragment containing the sequence of 26S promoter-PacI-SbfI-26S promoter-PmeI was digested with EcoRI/SpeI and ligated to EcoRI/SpeI digested pJY482.2, to create pJY591.6. Plasmid pJY591.6 was digested with BglII/SpeI and the isolated BglII/SpeI fragment was then ligated to BglII/SpeI digested SFV GFP/Bsd Leu713Ala (pJY354-713Ala#3), to create the plasmid SFV Leu713Ala, containing two SFV 26S promoters (pJY619.1). Finally, plasmid pJY619.1 was digested with EcoRV/SpeI and the EcoRV/SpeI fragment was ligated to EcoRV/SpeI digested pJY450.1, to create the ALVAC-SFV C6 donor plasmid containing two 26S promoters designated as pJY C6 SFV L713A 2 (pJY642.2) (FIG. 18). The nucleotide sequence of pJY C6 SFV L713A 2 is identical to that of pJY C6 SFV L713A1 (pJY641.2) as shown in FIGS. 17A through H with the addition of the $2^{nd}$ 26S promoter having the sequence 5'-ACC TCT ACG GCG GTC CTA GAT TGG TGC GTT AAT ACA CA-3' (SEQ ID No: 3) inserted just before the PmeI restriction site shown in FIGS. 17A through H. The point of insertion of the $2^{nd}$ 26S promoter sequence is indicated with an arrow on FIGS. 17A through H.

Example 5

Construction of an ALVAC C6 donor plasmid containing SFV Leu713Ala/FIV gag-pro gene under the control of the H6 promoter The construction scheme for an ALVAC C6 donor plasmid containing SFV Leu713Ala/FIV gag-pro gene under the control of the H6 promoter is shown in FIGS. 19A and 19B. To construct the ALVAC-SFV Leu713Ala/FIV gag-pro C6 donor plasmid, a PCR amplification was performed to produce a DNA fragment comprising PacI-FIV gag-pro-PmeI, using pMM121 as the template and a pair of primers; 8330JY 5'-GGT TAA TTA AAT GGG GAA TGG ACA GGG GCG A-3' (SEQ ID NO: 37) and 8331JY 5'-GGG TTT AAA CTT ACA TTA CTA ACC TAA TAT TGA A-3' (SEQ ID NO: 39; FIG. 19C). The amplified DNA fragment was digested with PacI/PmeI and ligated to PacI/PmeI digested pNEB193 (NEB) to create pJY624.3. Plasmid pMM121 contains a FIV gag-pol gene derived from FIV Villefranche strain. There is a TTTTTAT sequence located at 177-184 bp in the FIV protease protein. Therefore, site-directed mutagenesis to remove the T5NT was performed using pMM121 as the template and primer 8331JY (as shown above) and primer 8332JY 5'-AAT GGA TAT CCT ATA AAA TTC TTA TTA GAT ACA GGA GCA-3'. (SEQ ID NO: 41; FIG. 19C). This amplified DNA fragment was digested with EcoRV/PmeI and ligated to EcoRV/PmeI digested pJY624.3 to create pJY643.2. The FIV gag-pro fragment was then isolated from plasmid pJY643.2 by PacI/PmeI digestion and ligated to PacI/PmeI digested pJY641.2 (described in Example 4) to create the ALVAC C6 donor plasmid containing SFV Leu713Ala/FIV gag-pro (pC6 H6p-SFV L713A/FIV gag-pro, pJY654.1). An illustration of pJY654.1 donor plasmid is shown in FIG. 20.

Example 6

Generation and Characterization of an ALVAC-SFV Leu713Ala Chimera Expressing FIV Gag-Pro (vCP2092)

The generation of an ALVAC-SFV Leu713Ala chimera expressing FIV gag-pro is illustrated in FIG. 21. Briefly, an in vitro recombination (IVR) was performed by transfection of primary CEF cells with SapI-linearized C6 donor plasmid containing SFV Leu713Ala/FIV gag-pro (pJY654.1) using FuGENE 6 transfection reagents. The transfected cells were subsequently infected with ALVAC as rescue virus at MOI of 10. After 27 h, the transfected-infected cells were harvested, sonicated and used for recombinant virus screening.

Recombinant plaques were screened based on the plaque lift hybridization method using a SFV-specific probe which was labeled with horseradish peroxidase according to the manufacturer's protocol (Amersham). After four sequential rounds of plaque purification at 40° C., the ALVAC-SFV Leu713Ala/FIV gag-pro recombinant designated as vCP2092 was generated. Single plaques were selected from the fourth round of plaque purification, and expanded to obtain P1 (60 mm), P2 (T75 flask) and P3 (roller bottle) stocks of vCP2092. The P3 stocks of vCP2092 were confirmed by hybridization as 100% positive for the SFV specific probe and 100% negative for the C6 ORF. The chimeric viruses were characterized by restriction enzyme and Southern blot analyses. The C6-H6p-SFV Leu713Ala replicon-C6 locus was PCR-amplified and the complete sequence confirmed. Expression of the FIV gag-pro proteins was confirmed by immunoblot analyses.

Example 7

Construction and Characterization of Additional SFV nsP2 Mutants: SFV Arg650Asp Mutant and SFV Ser259Pro Mutant The construction of SFV nsP2 Arg650Asp mutant is illustrated in FIGS. 22A and 22B and the construction of SFV nsP2 Ser259Pro mutant is illustrated in FIGS. 22C and 22D.

To construct SFV Arg650Asp and SFV Ser259Pro mutants expressing FIV gag-pro, a SFV wild type replicon containing FIV gag-pro was first constructed. Briefly, a Bg/II-SpeI fragment was isolated from pJY 592.3 (described in Example 4) and ligated to Bg/II-SpeI digested SFV GFP/Bsd (pJY310.13, described in Example 1). The resulting plasmid pJY 622.1 was digested with PacI/PmeI and ligated to the FIV gag-pro fragment isolated from plasmid pJY643.2 (described in Example 5) to create the SFV wild type replicon containing FIV gag-pro (pJY663.1)

To mutate Arg 650 to Asp in the nsP2 protein, site-directed mutagenesis was performed using pBluescript-SFV-SacI/XhoI-pJY217.4 (identical to pJY217.5 as described in Example 1) as template and a pair of primers: 8267JY 5'-AGA GGG TAC CAC GTC CTG CTG GTG AGT GAG TAC AAC CTG GCT TTG CCT CGA CGC GAC GTC ACT TGG TTG TCA-3' (SEQ ID NO: 42) and 8286JY 5'-TCG TAA CGA CCG ATC TGA GTG GTC CGT CGT AGA TGC-3' (SEQ ID NO: 44; FIG. 22E). The amplified DNA fragment was digested with KpnI, and the KpnI fragment containing Arg650Asp mutation was ligated to KpnI digested pBluescript-SFV-SacI/XhoI (pJY217.5) to create a plasmid pBluescript-SFV-SacI/KpnI containing the mutation of Arg650Asp (pJY408.5). Because the KpnI fragment containing the mutation was in the wrong orientation in pJY408.5, a subsequent step to correct the orientation was performed. The resulting plasmid pJY456.6 was digested with SacI/Bsu36I, and the SacI/Bsu36I DNA fragment containing the Arg650Asp mutation was isolated and ligated to SacI/Bsu36I digested SFV wild type/FIV gag-pro (pJY663.1, as shown above) to create SFV Arg650Asp mutant containing FIV gag-pro (pJY793.1).

To mutate Ser 259 to Pro in the nsP2 protein, site-directed mutagenesis was performed using plasmid pJY217.5 (described in Example 1) as the template and a pair of primers: 8265JY 5'-GTG GAC GAG GCT TTC GCT TGC CAT CCC GGT ACT CTG CTG GCC CTA ATT GCT-3' (SEQ ID NO: 45) and 8266JY 5'-AGC AAT TAG GGC CAG CAG AGT ACC CCC ATG GCA AGC GAA AGC CTC GTC CAC-3' (SEQ ID NO: 47; FIG. 22E). The resulting plasmid pJY394.1 was confirmed to contain the Ser259Pro mutation except that an additional mutation by PCR error was found in the KpnI fragment. This KpnI fragment containing the PCR error was subsequently replaced with a correct one isolated from SFV-GFP/Bsd (pJY310.13 as described in Example 1), resulting in a new plasmid pJY458.6. A SacI/Bsu36I DNA fragment containing the Ser259Pro mutation was then isolated from pJY458.6 and ligated to SacI/Bsu36I digested SFV wildtype/FIV gag-pro (pJY663.1 as shown above) to create SFV Ser259Pro mutant containing FIV gag-pro (pJY792.1).

The effect of each mutation on SFV replicon replication was then examined by immunoblot analysis of FIV gag-pro protein expression. Briefly, RNA was transcribed from SFV Arg650Asp mutant or SFV Ser259Pro mutant and the transcribed RNAs were electroporated into BHK-21 cells. The transfected cells were incubated at 37° C. in a 5% $CO_2$ incubator. After 24 h, cell lysates were prepared, separated on 10% SDS-PAGE gel and transferred onto nylon membranes. The blots were then probed with an anti-FIV gag monoclonal antibody and visualized using a chemiluminescence reagent (NEN) after reacting with peroxidase-conjugated goat anti-mouse antibodies. FIV gag-pro was expressed in BHK-21 cells transfected with both SFV Arg650Asp and SFV Ser259Pro mutants and the protein expression level is comparable to that of wildtype SFV replicon (FIG. 23).

Example 8

Construction of an ALVAC C6 Donor Plasmid Containing SFV Arg650Asp/FIV Gag-Pro or SFV Ser259Pro/FIV Gag-Pro Under the Control of the H6 Promoter The construction of an ALVAC C6 donor plasmid containing SFV Arg650Asp/FIV gag-pro or SFV Ser259Pro/FIV gag-pro under the control of the H6 early promoter is illustrated in FIGS. 24A through C. In these two plasmids, the hepatitis δ ribozyme sequence (described in Example 2) was removed in order to examine if this sequence has an adverse effect on the generation of chimeras. To construct these two donor plasmids, a DNA fragment consisting of FIV gag-pro and SFV-3' sequence was amplified using pJY654.1 (described in Example 5) as the template and a pair of primers: 8281JY 5'-TAA TAC ACA GAA TTC TGA TTG-3' (SEQ ID NO: 48) and 8260JY 5'-CAG ACT AGT AGA AAA ATTTTTTTTTTTTTTTTTT-3' (SEQ ID NO: 49; FIG. 24D). The amplified DNA fragment was digested with PmeI/SpeI and ligated to PmeI/SpeI digested ALVAC-SFV Leu713Ala/FIV gag-pro C6 donor plasmid (pJY654.1, described in Example 5) to create ALVAC-SFV Leu713Ala/FIV gag-pro C6 donor plasmid (pJY842.3) without the hepatitis δ ribozyme sequence. An EcoRV-EcoRV DNA fragment comprising the FIV gag-pro sequence and SFV Arg650Asp replicon was isolated from plasmid SFV Arg650Asp/FIV gag-pro (pJY793.1, described in Example 7) and ligated to EcoRV digested pJY842.3 to create the ALVAC C6 donor plasmid containing SFV Arg650Asp/FIV gag-pro (pC6 H6p-SFV R650D/FIV gag-pro, pJY876.2). Similarly, an EcoRV-EcoRV DNA fragment was isolated from plasmid SFV Ser259Pro/FIV gag-pro (pJY792.1, described in Example 7) and ligated to EcoRV digested pJY842.3 to create the ALVAC C6 donor plasmid containing SFV Ser259Pro/FIV gag-pro (pC6 H6p SFV S259P/FIV gag-pro, pJY885.1).

Generation of an ALVAC-SFV Arg650Asp chimera or an ALVAC-SFV Ser259Pro chimera expressing FIV gag-pro under the control of the wild type H6 promoter has been attempted, however, no recombinants could be isolated. Removal of the hepatitis δ ribozyme sequence did not help the chimera generation.

Example 9

Construction of an ALVAC C6 Donor Plasmid Containing SFV Arg650Asp/FIV Gag-Pro Under the Control of a Mutant H6 Promoter The construction of an ALVAC C6 donor plasmid containing SFV Arg650Asp/FIV gag-pro under the control of a mutant H6 promoter is illustrated in FIG. 25A To mutate the H6 promoter, a DNA fragment comprising a mutated H6 promoter and SFV-5' sequence was amplified using pJY654.1 (described in Example 5) as the template and a pair of primers: 8424JY 5'-AA CCC GGG TTC TTT ATT CTA TAC TTA AAA AGT GCA AAT AAA TAC AAA GGT-3' (SEQ ID NO: 52) and 8280JY 5'-GCG TAC ACT AGT GCC GAT ATC AAA GAT GAG TGT GTC TTT GTC-3' (SEQ ID NO: 53). In primer 8424JY, a single nucleotide change (A to C) was introduced in the H6 promoter (FIG. 25C). The amplified DNA fragment was digested with SmaI/EcoRV and ligated to SmaI/EcoRV digested pC6L-H6-SFV-5' (pJY450.3 as described in Example 2) to create a C6 donor plasmid containing the sequences of a mutant H6 promoter and SFV-5' (pJY747.2). An ALVAC C6 donor plasmid containing SFV Leu713Ala under the control of the mutated H6 promoter (pJY764.1) was then constructed by ligation of EcoRV/SpeI digested pJY747.2 with an EcoRV/SpeI DNA fragment isolated from ALAVC C6 donor plasmid containing SFV Leu713Ala (pJY641.2, described in Example 4). A PacI-FIV gag-pro-PmeI DNA fragment isolated from pJY643.2 (described in Example 5) was then ligated to PacI/PmeI digested pJY764.1 to create an ALVAC C6 donor plasmid containing ALVAC-SFV Leu713Ala/FIV gag-pro under the control of the mutated H6 promoter (pJY778.1). Finally, an EcoRV-EcoRV DNA fragment containing the SFV Arg650Asp replicon and FIV gag-pro sequence was isolated from plasmid SFV Arg650Asp/FIV gag-pro (pJY793.1 described in Example 7) and ligated to EcoRV digested pJY778.1 to create an ALAVC C6 donor plasmid containing SFV Arg650Asp/FIV gag-pro under the control of the mutated H6 promoter (pC6 mutant H6p-SFV R650D/FIV gag-pro, pJY863.1).

Generation of an ALVAC-SFV Arg650Asp chimera expressing FIV gag-pro under the control of the mutated H6 promoter was successful, however, the recombinant was unstable and a pure population of recombinants could not be obtained.

Example 10

Construction of an ALVAC C6 Donor Plasmid Containing SFV Arg650Asp+Ser259Pro/FIV Gag-Pro Under the Control of a Mutant H6 Promoter The construction of an ALVAC C6 donor plasmid containing SFV Arg650Asp+Ser259Pro/FIV gag-pro under the control of a mutated H6 promoter is shown in FIGS. 26A and 26B. To construct this donor plasmid, a SFV replicon containing the double mutations of Arg650Asp and Ser259Pro was first constructed. Briefly, the KpnI DNA fragment containing the Arg650Asp mutation was isolated from pJY456.6 (as described in Example 7) and ligated to Kp 1 digested pJY458.6, which contains the Ser259Pro mutation (described in Example 7) to create plasmid pJY1092.1. A SacI/Bsu361 DNA fragment containing the double mutations was then isolated from pJY1092.1 and ligated to SacI/Bsu36I digested pJY663.1 (described in Example 7) to create SFV Arg650Asp+Ser259Pro/FIV gag-pro (pJY1095.8). Finally, an EcoRV-EcoRV DNA fragment comprising the FIV gag-pro sequence and the SFV replicon containing the Arg650Asp and Ser259Pro double mutations was isolated from pJY1095.8 and ligated to EcoRV digested pJY778.1 (described in Example 9) to create the ALVAC C6 donor plasmid containing SFV Arg650Asp+Ser259Pro/FIV gag-pro under the control of the mutated H6 promoter (pC6 mutant H6p-SFV R650D+S259P/FIV gag-pro, pJY1099.1). A schematic illustration of pC6 mutant H6p-SFV R650D+S259P/FIV gag-pro (pJY1099.1) is shown in FIG. 27. The nucleotide sequence of pC6 mutant H6p-SFV R650D+S259P/FIV gag-pro (pJY1099.1) is shown in FIGS. 28 through J (SEQ ID No: 4).

Example 11

Generation and Characterization of an ALVAC-SFV Arg650Asp+Ser259Pro Chimera Expressing FIV Gag-Pro Under the Control of a Mutant H6 Promoter (vCP2161)

The generation of an ALVAC-SFV Arg650Asp+Ser259Pro chimera expressing FIV gag-pro is illustrated in FIG. 29. Briefly, an in vitro recombination (IVR) was performed by transfection of primary CEF cells with SapI-linearized C6 donor plasmid containing SFV Arg650Asp+Ser259Pro/FIV gag-pro (pJY1099.1) using FuGENE 6 transfection reagents. The transfected cells were subsequently infected with ALVAC as rescue virus at MOI of 10. After 48 h of incubation at 37° C., the transfected-infected cells were harvested, sonicated and used for recombinant virus screening.

Recombinant plaques were screened based on the plaque lift hybridization method using a SFV-specific probe which was labeled with horseradish peroxidase according to the manufacturer's protocol (Amersham). After four sequential rounds of plaque purification at 37° C., the ALVAC-SFV Arg650Asp+Ser259Pro/FIV gag-pro recombinant designated as vCP2161 was generated. Single plaques were selected from the fourth round of plaque purification, and expanded to obtain P1 (60 mm), P2 (T75 flask) and P3 (roller bottle) stocks of vCP2161.

Example 12

Construction of a Fowlpox F8 Donor Plasmid Containing SFV Arg650Asp+Ser259Pro/FIV Gag-Pro Under the Control of a Mutant H6 Promoter The construction of a fowlpox F8 donor plasmid containing SFV Arg650Asp+Ser259Pro/FIV gag-pro under the control of a mutated H6 promoter is shown in FIG. 30. To construct this donor plasmid, a XmaI/SpeI DNA fragment comprising the expression cassette of mutant h6 promoter-SFV Arg650Asp+Ser259Pro/FIV gag-pro was isolated by XmaI/SpeI digestion of pJY1099.1 (described in Example 10) and ligated to XmaI/SpeI digested fowlpox donor plasmid pF8, to create the fowlpox F8 donor plasmid containing SFV Arg650Asp+Ser259Pro/FIV gag-pro under the control of a mutated H6 promoter (pF8 mutant H6p-SFV R650D+S259P/ FIV gag-pro, pJY1302.4). A schematic illustration of pF8 mutant H6p-SFV R650D+S259P/FIV gag-pro (pJY1302.4) is shown in FIG. 31. The nucleotide sequence of pF8 mutant H6p-SFV R650D+S259P/FIV gag-pro (pJY1302.4) is shown in FIG. 32A through K (SEQ ID No: 5).

Example 13

Generation and Characterization of a Fowlpox-SFV Arg650Asp+Ser259Pro Chimera Expressing FIV Gag-Pro Under the Control of a Mutant H6 Promoter (vFP2192)

The generation of a fowlpox-SFV Arg650Asp+Ser259Pro chimera expressing FIV gag-pro is illustrated in FIG. 33. To generate this recombinant, an in vitro recombination (IVR) was performed by transfection of primary CEF cells with SapI-linearized F8 donor plasmid containing SFV Arg650Asp+Ser259Pro/FIV gag-pro (pJY1302.4) using FuGENE 6 transfection reagents. The transfected cells were subsequently infected with fowlpox as rescue virus at MOI of 10. After 48 h of incubation at 37° C., the transfected-infected cells were harvested, sonicated and used for screening of recombinants.

Recombinant plaques were screened based on the plaque lift hybridization method using an SFV-specific probe, which was labeled with horseradish peroxidase according to the manufacturer's protocol (Amersham). After five sequential rounds of plaque purification at 37° C., the fowlpox-SFV Arg650Asp+Ser259Pro/FIV gag-pro recombinant designated as vFP2192 was generated. Single plaques were selected from the fifth round of plaque purification, and expanded to obtain P1 (60 mm), P2 (T75 flask) and P3 (roller bottle) stocks of vFP2192.

Example 14

Generation and Characterization of an ALVAC Recombinant Expressing FIV Gag-Pro (vCP2089) as a Control To generate an ALVAC-FIV gag-pro recombinant as a control, an ALVAC C6 donor plasmid containing FIV gag-pro was constructed. Briefly, a 292bp DNA fragment consisting of FIV protease was amplified using plasmid pMM121 (described in Example 5) as the template and a pair of primers: 8332JY: 5'-AAT GGA TAT CCT ATA AAA TTC TTA TTA GAT ACA GGA GCA-3' (SEQ ID NO: 41) and 8336CXL: 5'-TCC CCC GGG AGAAAAA TTA CAT TAC TAA CCT AAT-3'(SEQ ID NO: 54). The amplified DNA fragment was digested with EcoRV/XmaI and ligated to EcoRV/XmaI digested a C6 donor plasmid to make pCXL518.1. A DNA fragment comprising the sequences of EcoRV-H6 promoter and FIV gag-pro was amplified using pMM121 as the template and a pair of primers: 8334CXL 5'-GG GATATC CGT TAA GTT TGT ATC GTA ATG GGG AAT GGA CAG GGG CGA GAT TGG-3' (SEQ ID NO: 55) and 8335CXL 5'-TAG GATATC CAT TTA CAA ATA TAA GTA-3'(SEQ ID NO: 56). The amplified DNA was digested with EcoRV and ligated to EcoRV digested pCXL518.1 to create pC6 H6p-FIV gag-pro (pCXL520.1). Sequence analysis of this plasmid pC6 H6p-FIV gag-pro, however, found a nucleotide missing in the H6 promoter region, which was subsequently corrected. The resulting plasmid was designated as pCXL530.1.

An in vitro recombination (IVR) was performed by transfection of primary CEF cells with NotI-linearized C6 donor plasmid containing FIV gag-pro (pCXL530.1) using FuGENE 6 transfection reagents. The transfected cells were subsequently infected with ALVAC as rescue virus at MOI of 10. After 26 h of incubation at 37° C., the transfected-infected cells were harvested, sonicated and used for screening of recombinants. Recombinant plaques were screened based on the plaque lift hybridization method using a FIV gag-pro specific probe, which was labeled with horseradish peroxidase according to the manufacturer's protocol (Amersham). After four sequential rounds of plaque purification at 37° C., the recombinant expressing FIV gag-pro designated as vcP2089 was generated. Single plaques were selected from the fourth round of plaque purification, and expanded to obtain P1 (60 mm), P2 (T75 flask) and P3 (roller bottle) stocks of vCP2089. The P3 stocks of vCP2089 were confirmed by hybridization as 100% positive for the FIV specific probe and 100% negative for the C6 ORF. Recombinant viruses were characterized by restriction enzyme and Southern blot analyses. The C6-H6p-FIV gag-pro-C6 locus was PCR-amplified and the complete sequence confirmed. Expression of the FIV gag-pro proteins was confirmed by immunoblot analyses.

Example 15

Generation and Characterization of a Fowlpox Recombinant Expressing FIV Gag-Pro (vFP2095) as a Control To generate a fowlpox-FIV gag-pro recombinant as a control, a fowlpox F8 donor plasmid containing FIV gag-pro was constructed. Briefly, plasmid pMM121 (described in Example 5) was used as template for PCR amplification of the FIV gag-pro gene. Amplification with primers 8337.SL 5'-CGT CGC GAT ATC CGT TAA GTT TGT ATC GTA AAT GGG GAA TGG ACA GGG GCG AGA TTG GAA A-3' (SEQ ID NO: 57) and 8338.SL 5'-GCG GTC CAG AAA AAT TAC ATT ACT AAC CTA ATA TTG AAT TTA ATC AT-3' (SEQ ID NO: 58), resulted in a full-length fragment of FIV gag-pro which was cloned into pCR2.1, generating pSL5994.1.1. Sequence analysis revealed that this plasmid contained four PCR errors in the 3' 1.1 kb fragment. PCR amplification with primers 8338.SL (as shown above) and 8339.SL 5'-GAG GAA GGC CCT CCA CAG GCA TAT C-3'(SEQ ID NO: 59), yielded a 1.4 kb 3' FIV gag-pro fragment, which was cloned into pCR2.1, generating pSL6012.1.2. The insert sequence was correct. Fowlpox F8 donor plasmid was digested with NruI and BamHI and ligated with the 0.6 kb NruI-HindIII 5' FIV gag-pro fragment from pSL5994.1.1 and the HindIII-BamHI 1.1 kb 3' FIV gag-pro fragment from pSL6012.1.2, generating pF8 H6p-FIV gag-pro (pSL6032.1.6).

An in vitro recombination (IVR) was performed by transfection of primary CEF cells with NotI-linearized pF8 donor plasmid containing FIV gag-pro (pSL6032.1.6) using FuGENE 6 transfection reagents. The transfected cells were subsequently infected with fowlpox as rescue virus at MOI of 10. After 40 h of incubation at 37° C., the transfected-infected cells were harvested, sonicated and used for screening of recombinants. Recombinant plaques were screened based on the plaque lift hybridization method using a FIV gag-pro specific probe, which was labeled with horseradish peroxidase according to the manufacturer's protocol (Amersham). After three sequential rounds of plaque purification at 37° C., the recombinant expressing FIV gag-pro designated as vFP2095 was generated. Single plaques were selected from the third round of plaque purification, and expanded to obtain P1 (60 mm), P2 (T75 flask) and P3 and P4 (roller bottle) stocks of vFP2095. The P4 stocks of vFP2095 were confirmed by hybridization as 100% positive for the FIV specific probe and 100% negative for the F8 ORF. Recombinant viruses were characterized by restriction enzyme and Southern blot analyses. The F8-H6p-FIV gag-pro-F8 locus was PCR-amplified and the complete sequence confirmed. Expression of the FIV gag-pro proteins was confirmed by immunoblot analyses.

Expression of the FIV gag-pro proteins by the various chimeras in mammalian cells was analyzed by immunoblot using murine anti-FIV gag monoclonal antibodies (mAbs) and compared to that of ALVAC-FIV gag-pro or Fowlpox-FIV gag-pro recombinant. Mouse myoblast C2C12 cells or Feline Kidney CRFK cells were infected with chimeras vCP2092, vCP2161 and vFP2192 and ALVAC-FIV gag-pro recombinant vCP2089 and Fowlpox-FIV gag-pro recombinant vFP2095 at MOI of 10 at 37° C. After 24 h of infection, the cell lysates were prepared and culture media harvested for immunoblot analysis. Samples were electrophoresed on 10% SDS-PAGE gels, transferred to a nylon membrane and probed with murine anti FIV gag mAbs. Immunoblot analysis of the cell lysates from infected C2C12 cells demonstrated the expression of FIV gag-pro proteins from all of the chimeras vCP2092, vCP2092 and vFP2192 and the expression level is comparable to that of ALVAC based recombinant vCP2089 and Fowlpox based recombinant vFP2095 (FIG. 34A).

It is also notable that the processing of gag protein expressed by the chimeras vCP2092, vCP2161 and vFP2192 was much more efficient than that expressed by ALVAC recombinant vCP2089 or fowlpox recombinant vFP2095. Furthermore the processed FIV gag protein was efficiently secreted from C2C12 cells infected with chimeras vCP2161 and vFP2192 (FIG. 34B). In contrast, there is no secretion of gag protein in ALVAC recombinant vCP2089 or fowlpox recombinant vFP2095 infected cells (FIG. 34B). Immunoblot analysis of the cell lysates from infected CRFK cells, however, showed a different expression profile among the chimeras. Fowlpox based chimera vFP2192 expressed a considerable amount of gag-pro proteins, which is comparable to that of vCP2089 and vFP2095 (FIG. 35). On the other hand, there was much less expression of gag protein observed with ALVAC based chimeras vCP2092 and vCP2161 (FIG. 35), indicating that the level of protein expression among the chimeras is dependent on the cell types. The protein expression of chimeras in various mammalian cells is summarized in FIG. 36.

Although the foregoing invention has been described in some detail by way of illustration and example for purposes of clarity and understanding, it will be apparent to those skilled in the art that certain changes and modifications can be practiced. Therefore, the description and examples should not be construed as limiting the scope of the invention, which is delineated by the appended claims.

REFERENCES

1. Taylor, J. Trimarchi C, Weinberg R, Languet B, Uillemin F, Desmettre P and Paoletti E. Efficacy studies on a canarypox-rabies recombinant virus. Vaccine. 1991, 9:190-193.
2. Tartaglia J, Jarrett O, Neil J C, Desmettre P, and Paoletti E. Protection of cats against feline leukemia virus by vaccination with a canarypox virus recombinant, ALVAC-FL.J Virol. 1993; 67 (4): 2370-5.
3. Evans T G, Keefer M C, Weinhold K J, Wolff M, Montefiori D, Gorse G J, Graham B S, McElrath M J, Clements-Mann M L, Mulligan M J, Fast P, Walker M C, Excler J L, Duliege A M, and Tartaglia J. A canarypox vaccine expressing multiple human immunodeficiency virus type 1 genes given alone or with rgp12 elicits broad and durable CD8+ cytotoxic T lymphocyte responses in seronegative volunteers. J Infect Dis. 1999; 180(2): 290-8.
4. Girard M, van der Ryst E, Barre-Sinoussi F, Nara P, Tartaglia J, Paoletti E, Blondeau C, Jennings M, Verrier F, Meignier B, and Fultz P N. Challenge of chimpanzees immunized with a recombinant canarypox-HIV-1 virus. Virology 1997; 232(1): 98-104.
5. Liljestrom P and Garoff H. A new generation of animal cell expression vectors based on the Semliki Forest virus replicon. Nature Biotechnology (N Y). 1991. 9(12): 1356-61
6. Berglund P, Fleeton M N, Smerdou C, and Liljestrom P. Immunization with recombinant Semliki Forest virus induces protection against influenza challenge in mice. Vaccine. 1999. 17(5): 497-507.
7. Berglund P, Quesada-Rolander M, Putkonen P, Biberfeld G, Thorstensson R, and Liljestrom P. Outcome of immunization of cynomolgus monkeys with recombinant Semliki Forest virus encoding human immunodeficiency virus type 1 envelope protein and challenge with a high dose of SHIV-4 virus. AIDS Res Hum Retroviruses. 1997. 13(17): 1487-95.
8. Nilsson C, Makitalo B, Berglund P, Bex F, Liljestrom P, Sutter G, Erfle V, ten Haaft P, Heeney J, Biberfeld G, and Thorstensson R. Enhanced simian immunodeficiency virus-specific immune responses in macaques induced by priming with recombinant Semliki Forest virus and boosting with modified vaccinia virus Ankara. Vaccine. 2001. 19(25-26): 3526-36.
9. Fleeton M N, Chen M, Berglund P, Rhodes G, Parker S E, Murphy M, Atkins G J, and Liljestrom P. Self-replicative RNA vaccines elicit protection against influenza A virus, respiratory syncytial virus, and a tickborne encephalitis virus. J Infect Dis. 2001. 183(9): 1395-8.
10. Smerdou C, and Liljestrom P. Two-helper RNA system for production of recombinant Semliki forest virus particles. J Virol. 1999. 73(2): 1092-8.
11. Perri S, Driver D A, Gardner J P, Sherrill S, Belli B A, Dubensky T W Jr, and Polo J M. Replicon vectors derived from Sindbis virus and Semliki forest virus that establish persistent replication in host cells. J Virol. 2000. 74(20): 9802-7.
12. Yuen L and Moss B. Oligonucleotide sequence signaling transcriptional termination of vaccinia virus early genes. Proc Nat'l Acad Sci. USA 1987. 84:6417-6421.
13. Dryga S, Dryga O, and Schlesinger S. Identification of mutations in a Sindbis Virus variant able to establish persistent infection in BHK Cells: The Importance of a mutation in the nsP2 Gene. Virology 1997. 228: 74-83.
14. Boorsma M, Nieba L, Koller D, Bachmann M, Bailey J, and Renner W. A temperature-regulated repliconbased DNA expression system. Nature Biotechnology: 200. 18:429-432.
15. Hahn Y, Grakoui A, Rice C, Strauss E, and Strauss J. Mapping of RNA temperature-senstivie mutants of Sindbis virusComplementation group F mutants have lesions in nsP4. Journal of Virology 1989. 63:1194-1202.
16. Rikkonen, M. Functional significance of the nuclear-targeting and NTP-binding motifs in Semliki Forest virus nonstructural protein nsP2. Virology 1996. 218: 352-361.
17. Lundstrom K, Schweitzer C, Richards, J G, Ehrengruber M U, Jenck F, and Mulhard C. Semliki Forest virus vector for in vitro and in vivo applications. Gene Ther Mol Biol 1999. 4:23-31.

What is claimed is:

1. A recombinant poxvirus vector comprising a nucleic acid sequence operably linked to a poxviral promoter that directs transcription of the nucleic acid sequence to generate a transcribed viral replicon derived from a virus and capable of amplification as RNA,
   wherein the transcribed viral replicon comprises at least one viral promoter operably linked to a heterologous sequence of interest, and nucleic acid molecules encoding an nsP2 polymerase specific for replication of the viral replicon, wherein the nsP2 polymerase is mutated at leucine 713 and is changed to an amino acid selected from the group consisting of alanine, arginine, glutamine, threonine, and phenylalanine;

wherein the heterologous sequence of interest is downstream to the polymerase in the replicon, and wherein the viral replicon does not comprise nucleic acid molecules encoding a structural protein from the virus from which the replicon is derived.

2. The poxvirus vector of claim 1, wherein the poxvirus comprises vaccinia virus, Modified Vaccinia Ankara virus, NYVAC, canarypox, ALVAC, fowlpox, and TROVAC.

3. The poxvirus vector of claim 1, wherein the poxviral promoter is selected from the group consisting of H6 poxviral promoter, I3L poxviral promoter, 42K poxviral promoter, 7.5K poxviral promoter, thymidine kinase poxviral promoter, E3L poxviral promoter, K3L poxviral promoter, and a synthetic poxviral promoter.

4. The poxvirus vector of claim 3, wherein the poxviral promoter is mutated.

5. The poxvirus vector of claim 1, wherein the vector comprises a C6 insertion locus and wherein flanking sequences of the C6 insertion locus promote homologous recombination of the nucleic acid sequence with the C6 insertion locus of the poxvirus vector.

6. The poxvirus vector of claim 5, wherein the flanking sequences comprise C6L and C6R sequences of poxvirus.

7. The poxvirus vector of claim 1, wherein the vector comprises a F8 insertion locus and wherein flanking sequences of the F8 insertion locus promote homologous recombination of the nucleic acid sequence with the F8 insertion locus.

8. The poxvirus vector of claim 7, wherein the flanking sequences comprise F8L and F8R sequences of poxvirus.

9. The poxvirus vector of claim 1, wherein the viral replicon comprises nucleic acid sequences of portions of the genome of an alphavirus.

10. The poxvirus vector of claim 9, wherein the alphavirus is selected from the group consisting of Semliki Forest virus, Sindbis virus, Aura virus, VEE virus, WEE virus, EEE virus, Ross River virus, Mayaro virus, Chikungunya virus, Getah virus, Sagiyama virus, Mucambo virus, Pixuna virus, Middelburg virus, O'nyong-Nyong virus, Barmah forest virus, Bebaru virus, Una virus, Whataroa virus, Babanki virus, Kyzylagach virus, Highlands J virus, Fort Morgan virus and Ndumu virus.

11. The poxvirus vector of claim 1, wherein the viral replicon comprises nucleic acid sequences of portions of the genome of a positive-sense single-stranded RNA virus.

12. The poxvirus vector of claim 11, wherein the positive-sense single-stranded RNA virus is selected from the group consisting of poliovirus, rhinovirus, coxsackie virus, yellow fever virus, HCV, TGEV, IBV, MHV, BCV, astrovirus, tobamoviruses, potyviruses and bromoviruses.

13. The poxvirus vector of claim 1, wherein the viral promoter is the 26S promoter.

14. The poxvirus vector of claim 1, wherein the heterologous sequence of interest comprises an antigen, an antigenic fragment of a protein, a therapeutic agent, a cytokine, a toxin, an immunomodulator, an antisense RNA, a catalytic RNA, small interfering RNA, a protein, a peptide, an antibody, an antigen-binding fragment of an antibody, or an adjuvant.

15. A recombinant poxvirus comprising a nucleic acid sequence operably linked to a promoter that directs transcription of the nucleic acid sequence to generate a transcribed viral replicon derived from a virus and capable of amplification as RNA, wherein the transcribed viral replicon comprises at least one viral promoter operably linked to a heterologous sequence of interest, and nucleic acid molecules encoding an nsP2 polymerase specific for replication of the viral replicon, wherein the nsP2 polymerase is mutated at leucine 713 and is changed to an amino acid selected from the group consisting of alanine, arginine, glutamine, threonine, and phenylalanine;

wherein the heterologous sequence of interest is downstream to the polymerase in the replicon, and wherein the viral replicon does not comprise nucleic acid molecules encoding a structural protein from the virus from which the replicon is derived.

16. The poxvirus of claim 15, wherein the poxvirus comprises vaccinia virus, Modified Vaccinia Ankara virus, NYVAC, canarypox, ALVAC, fowlpox, and TROVAC.

17. The poxvirus of claim 15, wherein the promoter is selected from the group consisting of H6 poxviral promoter, I3L poxviral promoter, 42K poxviral promoter, 7.5K poxviral promoter, thymidine kinase poxviral promoter, E3L poxviral promoter, K3L poxviral promoter, and a synthetic poxviral promoter.

18. The poxvirus of claim 17, wherein the promoter is mutated.

19. The poxvirus of claim 15, wherein the virus comprises a C6 insertion locus and wherein flanking sequences of the C6 insertion locus promote homologous recombination of the nucleic acid sequence with the C6 insertion locus of the poxvirus.

20. The poxvirus of claim 19, wherein the flanking sequences comprise C6L and C6R sequences of poxvirus.

21. The poxvirus of claim 15, wherein the poxvirus comprises a F8 insertion locus and wherein flanking sequences of the F8 insertion locus promote homologous recombination of the nucleic acid sequence with the F8 insertion locus.

22. The poxvirus of claim 21, wherein the flanking sequences comprise F8L and F8R sequences of poxvirus.

23. The poxvirus of claim 15, wherein the viral replicon comprises nucleic acid sequences of portions of the genome of an alphavirus.

24. The poxvirus of claim 23, wherein the alphavirus is selected from the group consisting of Semliki Forest virus, Sindbis virus, Aura virus, VEE virus, WEE virus, EEE virus, Ross River virus, Mayaro virus, Chikungunya virus, Getah virus, Sagiyama virus, Mticambo virus, Pixuna virus, Middelburg virus, O'nyong-Nyong virus. Barmah forest virus, Bebaru virus, Una virus, Whataroa virus, Babanki virus, Kyzylagach virus, Highlands J virus, Fort Morgan virus and Ndumu virus.

25. The poxvirus of claim 15, wherein the viral replicon comprises nucleic acid sequences of portions of the genome of a positive-sense single-stranded RNA virus.

26. The poxvirus of claim 25, wherein the positive-sense single-stranded RNA virus is selected from the group consisting of poliovirus, rhinovirus, coxsackie virus, yellow fever virus, HCV, TGEV, IBV, MHV, BCV, astrovirus, tobamoviruses, potyviruses and bromoviruses.

27. The poxvirus of claim 15, wherein the viral promoter is the 26S promoter.

28. The poxvirus of claim 15, wherein the heterologous sequence of interest comprises an antigen, an antigenic fragment of a protein, a therapeutic agent, a cytokine, a toxin, an immunomodulator, an antisense RNA, a catalytic RNA, small interfering RNA, a protein, a peptide, an antibody, an antigen-binding fragment of an antibody, or an adjuvant.

* * * * *

SEQUENCE LISTING

```
<160> NUMBER OF SEQ ID NOS: 60

<210> SEQ ID NO 1
<211> LENGTH: 11150
<212> TYPE: DNA
<213> ORGANISM: Artificial Sequence
<220> FEATURE:
<223> OTHER INFORMATION: Description of Artificial Sequence: Synthetic
      pJY505.1 DNA sequence
<220> FEATURE:
<221> NAME/KEY: CDS
<222> LOCATION: (538)..(7830)
```

```
<220> FEATURE:
<221> NAME/KEY: CDS
<222> LOCATION: (7932)..(9032)

<400> SEQUENCE: 1
gcggccgcct atcaaaagtc ttaatgagtt aggtgtagat agtatagata ttactacaaa      60
ggtattcata tttcctatca attctaaagt agatgatatt ataactcaa agatgatgat     120 agtagataat agatacgctc atataatgac tgcaaatttg dacggttcac attttaatca    180
tcacgcgttc ataagtttca actgcataga tcaaaatctc actaaaaaga tagccgatgt    240
atttgagaga gattggacat ctaactacgc taaagaaatt acagttataa ataatacata    300
atggattttg ttatcatcag ttatatttaa cataagtaca ataaaaagta ttaaataaaa    360
atacttactt acgaaaaaat gactaattag ctataaaaac ccgggttctt tattctatac    420
ttaaaaagtg aaaataaata caaaggttct tgatggcgga tgtgtgacat acacgacgcc    480
aaaagatttt gttccagctc ctgccacctc cgctacgcga gagattaacc acccacg       537
```

| | | | | | | | | | | | | | | | | |
|---|---|---|---|---|---|---|---|---|---|---|---|---|---|---|---|---|
| atg | gcc | gcc | aaa | gtg | cat | gtt | gat | att | gag | gct | gac | agc | cca | ttc | atc | 585 |
| Met | Ala | Ala | Lys | Val | His | Val | Asp | Ile | Glu | Ala | Asp | Ser | Pro | Phe | Ile | |
| 1 | | | | 5 | | | | | 10 | | | | | 15 | | |

| aag | tct | ttg | cag | aag | gca | ttt | ccg | tcg | ttc | gag | gtg | gag | tca | ttg | cag | 633 |
|---|---|---|---|---|---|---|---|---|---|---|---|---|---|---|---|---|
| Lys | Ser | Leu | Gln | Lys | Ala | Phe | Pro | Ser | Phe | Glu | Val | Glu | Ser | Leu | Gln | |
| | | | 20 | | | | | 25 | | | | | 30 | | | |

| gtc | aca | cca | aat | gac | cat | gca | aat | gcc | aga | gca | ttt | tcg | cac | ctg | gct | 681 |
|---|---|---|---|---|---|---|---|---|---|---|---|---|---|---|---|---|
| Val | Thr | Pro | Asn | Asp | His | Ala | Asn | Ala | Arg | Ala | Phe | Ser | His | Leu | Ala | |
| | | 35 | | | | | 40 | | | | | 45 | | | | |

| acc | aaa | ttg | atc | gag | cag | gag | act | gac | aaa | gac | aca | ctc | atc | ttg | gat | 729 |
|---|---|---|---|---|---|---|---|---|---|---|---|---|---|---|---|---|
| Thr | Lys | Leu | Ile | Glu | Gln | Glu | Thr | Asp | Lys | Asp | Thr | Leu | Ile | Leu | Asp | |
| 50 | | | | | 55 | | | | | 60 | | | | | | |

| atc | ggc | agt | gcg | cct | tcc | agg | aga | atg | atg | tct | acg | cac | aaa | tac | cac | 777 |
|---|---|---|---|---|---|---|---|---|---|---|---|---|---|---|---|---|
| Ile | Gly | Ser | Ala | Pro | Ser | Arg | Arg | Met | Met | Ser | Thr | His | Lys | Tyr | His | |
| 65 | | | | | 70 | | | | | 75 | | | | | 80 | |

| tgc | gta | tgc | cct | atg | cgc | agc | gca | gaa | gac | ccc | gaa | agg | ctc | gat | agc | 825 |
|---|---|---|---|---|---|---|---|---|---|---|---|---|---|---|---|---|
| Cys | Val | Cys | Pro | Met | Arg | Ser | Ala | Glu | Asp | Pro | Glu | Arg | Leu | Asp | Ser | |
| | | | | 85 | | | | | 90 | | | | | 95 | | |

| tac | gca | aag | aaa | ctg | gca | gcg | gcc | tcc | ggg | aag | gtg | ctg | gat | aga | gag | 873 |
|---|---|---|---|---|---|---|---|---|---|---|---|---|---|---|---|---|
| Tyr | Ala | Lys | Lys | Leu | Ala | Ala | Ala | Ser | Gly | Lys | Val | Leu | Asp | Arg | Glu | |
| | | | 100 | | | | | 105 | | | | | 110 | | | |

| atc | gca | gga | aaa | atc | acc | gac | ctg | cag | acc | gtc | atg | gct | acg | cca | gac | 921 |
|---|---|---|---|---|---|---|---|---|---|---|---|---|---|---|---|---|
| Ile | Ala | Gly | Lys | Ile | Thr | Asp | Leu | Gln | Thr | Val | Met | Ala | Thr | Pro | Asp | |
| | | 115 | | | | | 120 | | | | | 125 | | | | |

| gct | gaa | tct | cct | acc | ttt | tgc | ctg | cat | aca | gac | gtc | acg | tgt | cgt | acg | 969 |
|---|---|---|---|---|---|---|---|---|---|---|---|---|---|---|---|---|
| Ala | Glu | Ser | Pro | Thr | Phe | Cys | Leu | His | Thr | Asp | Val | Thr | Cys | Arg | Thr | |
| 130 | | | | | 135 | | | | | 140 | | | | | | |

| gca | gcc | gaa | gtg | gcc | gta | tac | cag | gac | gtg | tat | gct | gta | cat | gca | cca | 1017 |
|---|---|---|---|---|---|---|---|---|---|---|---|---|---|---|---|---|
| Ala | Ala | Glu | Val | Ala | Val | Tyr | Gln | Asp | Val | Tyr | Ala | Val | His | Ala | Pro | |
| 145 | | | | | 150 | | | | | 155 | | | | | 160 | |

| aca | tcg | ctg | tac | cat | cag | gcg | atg | aaa | ggt | gtc | aga | acg | gcg | tat | tgg | 1065 |
|---|---|---|---|---|---|---|---|---|---|---|---|---|---|---|---|---|
| Thr | Ser | Leu | Tyr | His | Gln | Ala | Met | Lys | Gly | Val | Arg | Thr | Ala | Tyr | Trp | |
| | | | | 165 | | | | | 170 | | | | | 175 | | |

| att | ggg | ttt | gac | acc | acc | ccg | ttt | atg | ttt | gac | gcg | cta | gca | ggc | gcg | 1113 |
|---|---|---|---|---|---|---|---|---|---|---|---|---|---|---|---|---|
| Ile | Gly | Phe | Asp | Thr | Thr | Pro | Phe | Met | Phe | Asp | Ala | Leu | Ala | Gly | Ala | |
| | | | 180 | | | | | 185 | | | | | 190 | | | |

| tat | cca | acc | tac | gcc | aca | aac | tgg | gcc | gac | gag | cag | gtg | tta | cag | gcc | 1161 |
|---|---|---|---|---|---|---|---|---|---|---|---|---|---|---|---|---|
| Tyr | Pro | Thr | Tyr | Ala | Thr | Asn | Trp | Ala | Asp | Glu | Gln | Val | Leu | Gln | Ala | |
| | | 195 | | | | | 200 | | | | | 205 | | | | |

| agg | aac | ata | gga | ctg | tgt | gca | gca | tcc | ttg | act | gag | gga | aga | ctc | ggc | 1209 |
|---|---|---|---|---|---|---|---|---|---|---|---|---|---|---|---|---|
| Arg | Asn | Ile | Gly | Leu | Cys | Ala | Ala | Ser | Leu | Thr | Glu | Gly | Arg | Leu | Gly | |
| 210 | | | | | 215 | | | | | 220 | | | | | | |

```
aaa ctg tcc att ctc cgc aag aag caa ttg aaa cct tgc gac aca gtc      1257
Lys Leu Ser Ile Leu Arg Lys Lys Gln Leu Lys Pro Cys Asp Thr Val
225                 230                 235                 240 atg ttc tcg gta gga tct aca ttg tac act gag agc aga aag cta ctg      1305
Met Phe Ser Val Gly Ser Thr Leu Tyr Thr Glu Ser Arg Lys Leu Leu
                245                 250                 255 agg agc tgg cac tta ccc tcc gta ttc cac ctg aaa ggt aaa caa tcc      1353
Arg Ser Trp His Leu Pro Ser Val Phe His Leu Lys Gly Lys Gln Ser
            260                 265                 270 ttt acc tgt agg tgc gat acc atc gta tca tgt gaa ggg tac gta gtt      1401
Phe Thr Cys Arg Cys Asp Thr Ile Val Ser Cys Glu Gly Tyr Val Val
        275                 280                 285 aag aaa atc act atg tgc ccc ggc ctg tac ggt aaa acg gta ggg tac      1449
Lys Lys Ile Thr Met Cys Pro Gly Leu Tyr Gly Lys Thr Val Gly Tyr
    290                 295                 300 gcc gtg acg tat cac gcg gag gga ttc cta gtg tgc aag acc aca gac      1497
Ala Val Thr Tyr His Ala Glu Gly Phe Leu Val Cys Lys Thr Thr Asp
305                 310                 315                 320 act gtc aaa gga gaa aga gtc tca ttc cct gta tgc acc tac gtc ccc      1545
Thr Val Lys Gly Glu Arg Val Ser Phe Pro Val Cys Thr Tyr Val Pro
                325                 330                 335 tca acc atc tgt gat caa atg act ggc ata cta gcg acc gac gtc aca      1593
Ser Thr Ile Cys Asp Gln Met Thr Gly Ile Leu Ala Thr Asp Val Thr
            340                 345                 350 ccg gag gac gca cag aag ttg tta gtg gga ttg aat cag agg ata gtt      1641
Pro Glu Asp Ala Gln Lys Leu Leu Val Gly Leu Asn Gln Arg Ile Val
        355                 360                 365 gtg aac gga aga aca cag cga aac act aac acg atg aag aac tat ctg      1689
Val Asn Gly Arg Thr Gln Arg Asn Thr Asn Thr Met Lys Asn Tyr Leu
    370                 375                 380 ctt ccg att gtg gcc gtc gca ttt agc aag tgg gcg agg gaa tac aag      1737
Leu Pro Ile Val Ala Val Ala Phe Ser Lys Trp Ala Arg Glu Tyr Lys
385                 390                 395                 400 gca gac ctt gat gat gaa aaa cct ctg ggt gtc cga gag agg tca ctt      1785
Ala Asp Leu Asp Asp Glu Lys Pro Leu Gly Val Arg Glu Arg Ser Leu
                405                 410                 415 act tgc tgc tgc ttg tgg gca ttt aaa acg agg aag atg cac acc atg      1833
Thr Cys Cys Cys Leu Trp Ala Phe Lys Thr Arg Lys Met His Thr Met
            420                 425                 430 tac aag aaa cca gac acc cag aca ata gtg aag gtg cct tca gag ttt      1881
Tyr Lys Lys Pro Asp Thr Gln Thr Ile Val Lys Val Pro Ser Glu Phe
        435                 440                 445 aac tcg ttc gtc atc ccg agc cta tgg tct aca ggc ctc gca atc cca      1929
Asn Ser Phe Val Ile Pro Ser Leu Trp Ser Thr Gly Leu Ala Ile Pro
    450                 455                 460 gtc aga tca cgc att aag atg ctt ttg gcc aag aag acc aag cga gag      1977
Val Arg Ser Arg Ile Lys Met Leu Leu Ala Lys Lys Thr Lys Arg Glu
465                 470                 475                 480 tta ata cct gtt ctc gac gcg tcg tca gcc agg gat gct gaa caa gag      2025
Leu Ile Pro Val Leu Asp Ala Ser Ser Ala Arg Asp Ala Glu Gln Glu
                485                 490                 495 gag aag gag agg ttg gag gcc gag ctg act aga gaa gcc tta cca ccc      2073
Glu Lys Glu Arg Leu Glu Ala Glu Leu Thr Arg Glu Ala Leu Pro Pro
            500                 505                 510 ctc gtc ccc atc gcg ccg gcg gag acg gga gtc gtc gac gtc gac gtt      2121
Leu Val Pro Ile Ala Pro Ala Glu Thr Gly Val Val Asp Val Asp Val
        515                 520                 525 gaa gaa cta gag tat cac gca ggt gca ggg gtc gtg gaa aca cct cgc      2169
Glu Glu Leu Glu Tyr His Ala Gly Ala Gly Val Val Glu Thr Pro Arg
    530                 535                 540
```

```
agc gcg ttg aaa gtc acc gca cag ccg aac gac gta cta cta gga aat    2217
Ser Ala Leu Lys Val Thr Ala Gln Pro Asn Asp Val Leu Leu Gly Asn
545             550                 555                 560 tac gta gtt ctg tcc ccg cag acc gtg ctc aag agc tcc aag ttg gcc    2265
Tyr Val Val Leu Ser Pro Gln Thr Val Leu Lys Ser Ser Lys Leu Ala
                565                 570                 575 ccc gtg cac cct cta gca gag cag gtg aaa ata ata aca cat aac ggg    2313
Pro Val His Pro Leu Ala Glu Gln Val Lys Ile Ile Thr His Asn Gly
            580                 585                 590 agg gcc ggc ggt tac cag gtc gac gga tat gac gga agg gtc cta cta    2361
Arg Ala Gly Gly Tyr Gln Val Asp Gly Tyr Asp Gly Arg Val Leu Leu
        595                 600                 605 cca tgt gga tcg gcc att ccg gtc cct gag ttt caa gct ttg agc gag    2409
Pro Cys Gly Ser Ala Ile Pro Val Pro Glu Phe Gln Ala Leu Ser Glu
    610                 615                 620 agc gcc act atg gtg tac aac gaa agg gag ttc gtc aac agg aaa cta    2457
Ser Ala Thr Met Val Tyr Asn Glu Arg Glu Phe Val Asn Arg Lys Leu
625                 630                 635                 640 tac cat att gcc gtt cac gga ccg tcg ctg aac acc gac gag gag aac    2505
Tyr His Ile Ala Val His Gly Pro Ser Leu Asn Thr Asp Glu Glu Asn
                645                 650                 655 tac gag aaa gtc aga gct gaa aga act gac gcc gag tac gtg ttc gac    2553
Tyr Glu Lys Val Arg Ala Glu Arg Thr Asp Ala Glu Tyr Val Phe Asp
            660                 665                 670 gta gat aaa aaa tgc tgc gtc aag aga gag gaa gcg tcg ggt ttg gtg    2601
Val Asp Lys Lys Cys Cys Val Lys Arg Glu Glu Ala Ser Gly Leu Val
        675                 680                 685 ttg gtg gga gag cta acc aac ccc ccg ttc cat gaa ttc gcc tac gaa    2649
Leu Val Gly Glu Leu Thr Asn Pro Pro Phe His Glu Phe Ala Tyr Glu
    690                 695                 700 ggg ctg aag atc agg ccg tcg gca cca tat aag act aca gta gta gga    2697
Gly Leu Lys Ile Arg Pro Ser Ala Pro Tyr Lys Thr Thr Val Val Gly
705                 710                 715                 720 gtc ttt ggg gtt ccg gga tca ggc aag tct gct att att aag agc ctc    2745
Val Phe Gly Val Pro Gly Ser Gly Lys Ser Ala Ile Ile Lys Ser Leu
                725                 730                 735 gtg acc aaa cac gat ctg gtc acc agc ggc aag aag gag aac tgc cag    2793
Val Thr Lys His Asp Leu Val Thr Ser Gly Lys Lys Glu Asn Cys Gln
            740                 745                 750 gaa ata gtt aac gac gtg aag aag cac cgc ggg aag ggg aca agt agg    2841
Glu Ile Val Asn Asp Val Lys Lys His Arg Gly Lys Gly Thr Ser Arg
        755                 760                 765 gaa aac agt gac tcc atc ctg cta aac ggg tgt cgt cgt gcc gtg gac    2889
Glu Asn Ser Asp Ser Ile Leu Leu Asn Gly Cys Arg Arg Ala Val Asp
    770                 775                 780 atc cta tat gtg gac gag gct ttc gct tgc cat tcc ggt act ctg ctg    2937
Ile Leu Tyr Val Asp Glu Ala Phe Ala Cys His Ser Gly Thr Leu Leu
785                 790                 795                 800 gcc cta att gct ctt gtt aaa cct cgg agc aaa gtg gtg tta tgc gga    2985
Ala Leu Ile Ala Leu Val Lys Pro Arg Ser Lys Val Val Leu Cys Gly
                805                 810                 815 gac ccc aag caa tgc gga ttc ttc aat atg atg cag ctt aag gtg aac    3033
Asp Pro Lys Gln Cys Gly Phe Phe Asn Met Met Gln Leu Lys Val Asn
            820                 825                 830 ttc aac cac aac atc tgc act gaa gta tgt cat aaa agt ata tcc aga    3081
Phe Asn His Asn Ile Cys Thr Glu Val Cys His Lys Ser Ile Ser Arg
        835                 840                 845 cgt tgc acg cgt cca gtc acg gcc atc gtg tct acg ttg cac tac gga    3129
Arg Cys Thr Arg Pro Val Thr Ala Ile Val Ser Thr Leu His Tyr Gly
    850                 855                 860
```

| | |
|---|---|
| ggc aag atg cgc acg acc aac ccg tgc aac aaa ccc ata atc ata gac<br>Gly Lys Met Arg Thr Thr Asn Pro Cys Asn Lys Pro Ile Ile Ile Asp<br>865                    870                    875                    880 | 3177 |
| acc aca gga cag acc aag ccc aag cca gga gac atc gtg tta aca tgc<br>Thr Thr Gly Gln Thr Lys Pro Lys Pro Gly Asp Ile Val Leu Thr Cys<br>                    885                    890                    895 | 3225 |
| ttc cga ggc tgg gca aag cag ctg cag ttg gac tac cgt gga cac gaa<br>Phe Arg Gly Trp Ala Lys Gln Leu Gln Leu Asp Tyr Arg Gly His Glu<br>                900                    905                    910 | 3273 |
| gtc atg aca gca gca tct cag ggc ctc acc cgc aaa ggg gta tac<br>Val Met Thr Ala Ala Ser Gln Gly Leu Thr Arg Lys Gly Val Tyr<br>915                    920                    925 | 3321 |
| gcc gta agg cag aag gtg aat gaa aat ccc ttg tat gcc cct gcg tcg<br>Ala Val Arg Gln Lys Val Asn Glu Asn Pro Leu Tyr Ala Pro Ala Ser<br>930                    935                    940 | 3369 |
| gag cac gtg aat gta ctg ctg acg cgc act gag gat agg ctg gtg tgg<br>Glu His Val Asn Val Leu Leu Thr Arg Thr Glu Asp Arg Leu Val Trp<br>945                    950                    955                    960 | 3417 |
| aaa acg ctg gcc ggc gat ccc tgg att aag gtc cta tca aac att cca<br>Lys Thr Leu Ala Gly Asp Pro Trp Ile Lys Val Leu Ser Asn Ile Pro<br>                    965                    970                    975 | 3465 |
| cag ggt aac ttt acg gcc aca ttg gaa gaa tgg caa gaa gaa cac gac<br>Gln Gly Asn Phe Thr Ala Thr Leu Glu Glu Trp Gln Glu Glu His Asp<br>                980                    985                    990 | 3513 |
| aaa ata atg aag gtg att gaa gga ccg gct gcg cct gtg gac gcg ttc<br>Lys Ile Met Lys Val Ile Glu Gly Pro Ala Ala Pro Val Asp Ala Phe<br>                995                   1000                1005 | 3561 |
| cag aac aaa gcg aac gtg tgt tgg gcg aaa agc ctg gtg cct gtc ctg<br>Gln Asn Lys Ala Asn Val Cys Trp Ala Lys Ser Leu Val Pro Val Leu<br>1010                   1015                   1020 | 3609 |
| gac act gcc gga atc aga ttg aca gca gag gag tgg agc acc ata att<br>Asp Thr Ala Gly Ile Arg Leu Thr Ala Glu Glu Trp Ser Thr Ile Ile<br>1025                   1030                   1035                   1040 | 3657 |
| aca gca ttt aag gag gac aga gct tac tct cca gtg gtg gcc ttg aat<br>Thr Ala Phe Lys Glu Asp Arg Ala Tyr Ser Pro Val Val Ala Leu Asn<br>                    1045                   1050                   1055 | 3705 |
| gaa att tgc acc aag tac tat gga gtt gac ctg gac agt ggc ctg ttt<br>Glu Ile Cys Thr Lys Tyr Tyr Gly Val Asp Leu Asp Ser Gly Leu Phe<br>                    1060                   1065                   1070 | 3753 |
| tct gcc ccg aag gtg tcc ctg tat tac gag aac aac cac tgg gat aac<br>Ser Ala Pro Lys Val Ser Leu Tyr Tyr Glu Asn Asn His Trp Asp Asn<br>1075                   1080                   1085 | 3801 |
| aga cct ggt gga agg atg tat gga ttc aat gcc gca aca gct gcc agg<br>Arg Pro Gly Gly Arg Met Tyr Gly Phe Asn Ala Ala Thr Ala Ala Arg<br>1090                   1095                   1100 | 3849 |
| ctg gaa gct aga cat acc ttc ctg aag ggg cag tgg cat acg ggc aag<br>Leu Glu Ala Arg His Thr Phe Leu Lys Gly Gln Trp His Thr Gly Lys<br>1105                   1110                   1115                   1120 | 3897 |
| cag gca gtt atc gca gaa aga aaa atc caa ccg ctt tct gtg ctg gac<br>Gln Ala Val Ile Ala Glu Arg Lys Ile Gln Pro Leu Ser Val Leu Asp<br>                    1125                   1130                   1135 | 3945 |
| aat gta att cct atc aac cgc agg ctg ccg cac gcc ctg gtg gct gag<br>Asn Val Ile Pro Ile Asn Arg Arg Leu Pro His Ala Leu Val Ala Glu<br>                    1140                   1145                   1150 | 3993 |
| tac aag acg gtt aaa ggc agt agg gtt gag tgg ctg gtc aat aaa gta<br>Tyr Lys Thr Val Lys Gly Ser Arg Val Glu Trp Leu Val Asn Lys Val<br>                    1155                   1160                   1165 | 4041 |
| aga ggg tac cac gtc ctg ctg gtg agt gag tac aac ctg gct ttg cct<br>Arg Gly Tyr His Val Leu Leu Val Ser Glu Tyr Asn Leu Ala Leu Pro<br>1170                   1175                   1180 | 4089 |

| | |
|---|---|
| cga cgc agg gtc act tgg ttg tca ccg ctg aat gtc aca ggc gcc gat<br>Arg Arg Arg Val Thr Trp Leu Ser Pro Leu Asn Val Thr Gly Ala Asp<br>1185                1190                1195                1200 | 4137 |
| agg tgc tac gac cta agt tta gga ctg ccg gct gac gcc ggc agg ttc<br>Arg Cys Tyr Asp Leu Ser Leu Gly Leu Pro Ala Asp Ala Gly Arg Phe<br>                1205                1210                1215 | 4185 |
| gac ttg gtc ttt gtg aac att cac acg gaa ttc aga atc cac cac tac<br>Asp Leu Val Phe Val Asn Ile His Thr Glu Phe Arg Ile His His Tyr<br>1220                1225                1230 | 4233 |
| cag cag tgt gtc gac cac gcc atg aag ctg cag atg ctt ggg gga gat<br>Gln Gln Cys Val Asp His Ala Met Lys Leu Gln Met Leu Gly Gly Asp<br>        1235                1240                1245 | 4281 |
| gcg gca cga ctg cta aaa ccc ggc ggc atc ttg atg aga gct tac gga<br>Ala Ala Arg Leu Leu Lys Pro Gly Gly Ile Leu Met Arg Ala Tyr Gly<br>1250                1255                1260 | 4329 |
| tac gcc gat aaa atc agc gaa gcc gtt gtt tcc tcc tta agc aga aag<br>Tyr Ala Asp Lys Ile Ser Glu Ala Val Val Ser Ser Leu Ser Arg Lys<br>1265                1270                1275                1280 | 4377 |
| ttc tcg tct gca aga gtg ttg cgc ccg gat tgt gtc acc agc aat aca<br>Phe Ser Ser Ala Arg Val Leu Arg Pro Asp Cys Val Thr Ser Asn Thr<br>                1285                1290                1295 | 4425 |
| gaa gtg ttc ttg ctg ttc tcc aac ttt gac aac gga aag aga ccc tct<br>Glu Val Phe Leu Leu Phe Ser Asn Phe Asp Asn Gly Lys Arg Pro Ser<br>1300                1305                1310 | 4473 |
| acg cta cac cag atg aat acc aag ctg agt gcc gtg tat gcc gga gaa<br>Thr Leu His Gln Met Asn Thr Lys Leu Ser Ala Val Tyr Ala Gly Glu<br>        1315              1320                1325 | 4521 |
| gcc atg cac acg gcc ggg tgt gca cca tcc tac aga gtt aag aga gca<br>Ala Met His Thr Ala Gly Cys Ala Pro Ser Tyr Arg Val Lys Arg Ala<br>1330                1335                1340 | 4569 |
| gac ata gcc acg tgc aca gaa gcg gct gtg gtt aac gca gct aac gcc<br>Asp Ile Ala Thr Cys Thr Glu Ala Ala Val Val Asn Ala Ala Asn Ala<br>1345                1350                1355                1360 | 4617 |
| cgt gga act gta ggg gat ggc gta tgc agg gcc gtg gcg aag aaa tgg<br>Arg Gly Thr Val Gly Asp Gly Val Cys Arg Ala Val Ala Lys Lys Trp<br>                1365                1370                1375 | 4665 |
| ccg tca gcc ttt aag gga gca gca aca cca gtg ggc aca att aaa aca<br>Pro Ser Ala Phe Lys Gly Ala Ala Thr Pro Val Gly Thr Ile Lys Thr<br>1380                1385                1390 | 4713 |
| gtc atg tgc ggc tcg tac ccc gtc atc cac gct gta gcg cct aat ttc<br>Val Met Cys Gly Ser Tyr Pro Val Ile His Ala Val Ala Pro Asn Phe<br>        1395              1400                1405 | 4761 |
| tct gcc acg act gaa gcg gaa ggg gac cgc gaa ttg gcc gct gtc tac<br>Ser Ala Thr Thr Glu Ala Glu Gly Asp Arg Glu Leu Ala Ala Val Tyr<br>1410                1415                1420 | 4809 |
| cgg gca gtg gcc gcc gaa gta aac aga ctg tca ctg agc agc gta gcc<br>Arg Ala Val Ala Ala Glu Val Asn Arg Leu Ser Leu Ser Ser Val Ala<br>1425                1430                1435                1440 | 4857 |
| atc ccg ctg ctg tcc aca gga gtg ttc agc ggc gga aga gat agg ctg<br>Ile Pro Leu Leu Ser Thr Gly Val Phe Ser Gly Gly Arg Asp Arg Leu<br>                1445                1450                1455 | 4905 |
| cag caa tcc ctc aac cat cta ttc aca gca atg gac gcc acg gac gct<br>Gln Gln Ser Leu Asn His Leu Phe Thr Ala Met Asp Ala Thr Asp Ala<br>1460                1465                1470 | 4953 |
| gac gtg acc atc tac tgc aga gac aaa agt tgg gag aag aaa atc cag<br>Asp Val Thr Ile Tyr Cys Arg Asp Lys Ser Trp Glu Lys Lys Ile Gln<br>        1475              1480                1485 | 5001 |
| gaa gcc att gac atg agg acg gct gtg gag ttg ctc aat gat gac gtg<br>Glu Ala Ile Asp Met Arg Thr Ala Val Glu Leu Leu Asn Asp Asp Val<br>1490                1495                1500 | 5049 |

```
gag ctg acc aca gac ttg gtg aga gtg cac ccg gac agc agc ctg gtg      5097
Glu Leu Thr Thr Asp Leu Val Arg Val His Pro Asp Ser Ser Leu Val
1505                1510                1515                1520 ggt cgt aag ggc tac agt acc act gac ggg tcg ctg tac tcg tac ttt      5145
Gly Arg Lys Gly Tyr Ser Thr Thr Asp Gly Ser Leu Tyr Ser Tyr Phe
                1525                1530                1535 gaa ggt acg aaa ttc aac cag gct gct att gat atg gca gag ata ctg      5193
Glu Gly Thr Lys Phe Asn Gln Ala Ala Ile Asp Met Ala Glu Ile Leu
            1540                1545                1550 acg ttg tgg ccc aga ctg caa gag gca aac gaa cag ata tgc cta tac      5241
Thr Leu Trp Pro Arg Leu Gln Glu Ala Asn Glu Gln Ile Cys Leu Tyr
        1555                1560                1565 gcg ctg ggc gaa aca atg gac aac atc aga tcc aaa tgt ccg gtg aac      5289
Ala Leu Gly Glu Thr Met Asp Asn Ile Arg Ser Lys Cys Pro Val Asn
    1570                1575                1580 gat tcc gat tca tca aca cct ccc agg aca gtg ccc tgc ctg tgc cgc      5337
Asp Ser Asp Ser Ser Thr Pro Pro Arg Thr Val Pro Cys Leu Cys Arg
1585                1590                1595                1600 tac gca atg aca gca gaa cgg atc gcc cgc ctt agg tca cac caa gtt      5385
Tyr Ala Met Thr Ala Glu Arg Ile Ala Arg Leu Arg Ser His Gln Val
                1605                1610                1615 aaa agc atg gtg gtt tgc tca tct ttt ccc ctc ccg aaa tac cat gta      5433
Lys Ser Met Val Val Cys Ser Ser Phe Pro Leu Pro Lys Tyr His Val
            1620                1625                1630 gat ggg gtg cag aag gta aag tgc gag aag gtt ctc ctg ttc gac ccg      5481
Asp Gly Val Gln Lys Val Lys Cys Glu Lys Val Leu Leu Phe Asp Pro
        1635                1640                1645 acg gta cct tca gtg gtt agt ccg cgg aag tat gcc gca tct acg acg      5529
Thr Val Pro Ser Val Val Ser Pro Arg Lys Tyr Ala Ala Ser Thr Thr
    1650                1655                1660 gac cac tca gat cgg tcg tta cga ggg ttt gac ttg gac tgg acc acc      5577
Asp His Ser Asp Arg Ser Leu Arg Gly Phe Asp Leu Asp Trp Thr Thr
1665                1670                1675                1680 gac tcg tct tcc act gcc agc gat acc atg tcg cta ccc agt ttg cag      5625
Asp Ser Ser Ser Thr Ala Ser Asp Thr Met Ser Leu Pro Ser Leu Gln
                1685                1690                1695 tcg tgt gac atc gac tcg atc tac gag cca atg gct ccc ata gta gtg      5673
Ser Cys Asp Ile Asp Ser Ile Tyr Glu Pro Met Ala Pro Ile Val Val
            1700                1705                1710 acg gct gac gta cac cct gaa ccc gca ggc atc gcg gac ctg gcg gca      5721
Thr Ala Asp Val His Pro Glu Pro Ala Gly Ile Ala Asp Leu Ala Ala
        1715                1720                1725 gat gtg cac cct gaa ccc gca gac cat gtg gac ctc gag aac ccg att      5769
Asp Val His Pro Glu Pro Ala Asp His Val Asp Leu Glu Asn Pro Ile
    1730                1735                1740 cct cca ccg cgc ccg aag aga gct gca tac ctt gcc tcc cgc gcg gcg      5817
Pro Pro Pro Arg Pro Lys Arg Ala Ala Tyr Leu Ala Ser Arg Ala Ala
1745                1750                1755                1760 gag cga ccg gtg ccg gcg ccg aga aag ccg acg cct gcc cca agg act      5865
Glu Arg Pro Val Pro Ala Pro Arg Lys Pro Thr Pro Ala Pro Arg Thr
                1765                1770                1775 gcg ttt agg aac aag ctg cct ttg acg ttc ggc gac ttt gac gag cac      5913
Ala Phe Arg Asn Lys Leu Pro Leu Thr Phe Gly Asp Phe Asp Glu His
            1780                1785                1790 gag gtc gat gcg ttg gcc tcc ggg att act ttc gga gac ttc gac gac      5961
Glu Val Asp Ala Leu Ala Ser Gly Ile Thr Phe Gly Asp Phe Asp Asp
        1795                1800                1805 gtc ctg cga cta ggc cgc gcg ggt gca tat att ttc tcc tcg gac act      6009
Val Leu Arg Leu Gly Arg Ala Gly Ala Tyr Ile Phe Ser Ser Asp Thr
    1810                1815                1820
```

```
ggc agc gga cat tta caa caa aaa tcc gtt agg cag cac aat ctc cag      6057
Gly Ser Gly His Leu Gln Gln Lys Ser Val Arg Gln His Asn Leu Gln
        1825                1830                1835                1840 tgc gca caa ctg gat gcg gtc cag gag gag aaa atg tac ccg cca aaa      6105
Cys Ala Gln Leu Asp Ala Val Gln Glu Glu Lys Met Tyr Pro Pro Lys
            1845                1850                1855 ttg gat act gag agg gag aag ctg ttg ctg ctg aaa atg cag atg cac      6153
Leu Asp Thr Glu Arg Glu Lys Leu Leu Leu Leu Lys Met Gln Met His
        1860                1865                1870 cca tcg gag gct aat aag agt cga tac cag tct cgc aaa gtg gag aac      6201
Pro Ser Glu Ala Asn Lys Ser Arg Tyr Gln Ser Arg Lys Val Glu Asn
            1875                1880                1885 atg aaa gcc acg gtg gtg gac agg ctc aca tcg ggg gcc aga ttg tac      6249
Met Lys Ala Thr Val Val Asp Arg Leu Thr Ser Gly Ala Arg Leu Tyr
        1890                1895                1900 acg gga gcg gac gta ggc cgc ata cca aca tac gcg gtt cgg tac ccc      6297
Thr Gly Ala Asp Val Gly Arg Ile Pro Thr Tyr Ala Val Arg Tyr Pro
1905                1910                1915                1920 cgc ccc gtg tac tcc cct acc gtg atc gaa aga ttc tca agc ccc gat      6345
Arg Pro Val Tyr Ser Pro Thr Val Ile Glu Arg Phe Ser Ser Pro Asp
            1925                1930                1935 gta gca atc gca gcg tgc aac gaa tac cta tcc aga aat tac cca aca      6393
Val Ala Ile Ala Ala Cys Asn Glu Tyr Leu Ser Arg Asn Tyr Pro Thr
        1940                1945                1950 gtg gcg tcg tac cag ata aca gat gaa tac gac gca tac ttg gac atg      6441
Val Ala Ser Tyr Gln Ile Thr Asp Glu Tyr Asp Ala Tyr Leu Asp Met
            1955                1960                1965 gtt gac ggg tcg gat agt tgc ttg gac aga gcg aca ttc tgc ccg gcg      6489
Val Asp Gly Ser Asp Ser Cys Leu Asp Arg Ala Thr Phe Cys Pro Ala
        1970                1975                1980 aag ctc cgg tgc tac ccg aaa cat cat gcg tac cac cag ccg act gta      6537
Lys Leu Arg Cys Tyr Pro Lys His His Ala Tyr His Gln Pro Thr Val
1985                1990                1995                2000 cgc agt gcc gtc ccg tca ccc ttt cag aac aca cta cag aac gtg cta      6585
Arg Ser Ala Val Pro Ser Pro Phe Gln Asn Thr Leu Gln Asn Val Leu
            2005                2010                2015 gcg gcc gcc acc aag aga aac tgc aac gtc acg caa atg cga gaa cta      6633
Ala Ala Ala Thr Lys Arg Asn Cys Asn Val Thr Gln Met Arg Glu Leu
        2020                2025                2030 ccc acc atg gac tcg gca gtg ttc aac gtg gag tgc ttc aag cgc tat      6681
Pro Thr Met Asp Ser Ala Val Phe Asn Val Glu Cys Phe Lys Arg Tyr
            2035                2040                2045 gcc tgc tcc gga gaa tat tgg gaa gaa tat gct aaa caa cct atc cgg      6729
Ala Cys Ser Gly Glu Tyr Trp Glu Glu Tyr Ala Lys Gln Pro Ile Arg
        2050                2055                2060 ata acc act gag aac atc act acc tat gtg acc aaa ttg aaa ggc ccg      6777
Ile Thr Thr Glu Asn Ile Thr Thr Tyr Val Thr Lys Leu Lys Gly Pro
2065                2070                2075                2080 aaa gct gct gcc ttg ttc gct aag acc cac aac ttg gtt ccg ctg cag      6825
Lys Ala Ala Ala Leu Phe Ala Lys Thr His Asn Leu Val Pro Leu Gln
            2085                2090                2095 gag gtt ccc atg gac aga ttc acg gtc gac atg aaa cga gat gtc aaa      6873
Glu Val Pro Met Asp Arg Phe Thr Val Asp Met Lys Arg Asp Val Lys
        2100                2105                2110 gtc act cca ggg acg aaa cac aca gag gaa aga ccc aaa gtc cag gta      6921
Val Thr Pro Gly Thr Lys His Thr Glu Glu Arg Pro Lys Val Gln Val
            2115                2120                2125 att caa gca gcg gag cca ttg gcg acc gct tac ctg tgc ggc atc cac      6969
Ile Gln Ala Ala Glu Pro Leu Ala Thr Ala Tyr Leu Cys Gly Ile His
2130                2135                2140
```

| | |
|---|---|
| agg gaa tta gta agg aga cta aat gct gtg tta cgc cct aac gtg cac<br>Arg Glu Leu Val Arg Arg Leu Asn Ala Val Leu Arg Pro Asn Val His<br>2145                    2150                      2155                    2160 | 7017 |
| aca ttg ttt gat atg tcg gcc gaa gac ttt gac gca atc atc gcc tct<br>Thr Leu Phe Asp Met Ser Ala Glu Asp Phe Asp Ala Ile Ile Ala Ser<br>                2165                      2170                      2175 | 7065 |
| cac ttc cac cca gga gac ccg gtt cta gag acg gac att gca tca ttc<br>His Phe His Pro Gly Asp Pro Val Leu Glu Thr Asp Ile Ala Ser Phe<br>                    2180                      2185                    2190 | 7113 |
| gac aaa agc cag gac gac tcc ttg gct ctt aca ggt tta atg atc ctc<br>Asp Lys Ser Gln Asp Asp Ser Leu Ala Leu Thr Gly Leu Met Ile Leu<br>2195                    2200                      2205 | 7161 |
| gaa gat cta ggg gtg gat cag tac ctg ctg gac ttg atc gag gca gcc<br>Glu Asp Leu Gly Val Asp Gln Tyr Leu Leu Asp Leu Ile Glu Ala Ala<br>              2210                      2215                    2220 | 7209 |
| ttt ggg gaa ata tcc agc tgt cac cta cca act ggc acg cgc ttc aag<br>Phe Gly Glu Ile Ser Ser Cys His Leu Pro Thr Gly Thr Arg Phe Lys<br>2225                    2230                      2235                    2240 | 7257 |
| ttc gga gct atg atg aaa tcg ggc atg ttt ctg act ttg ttt att aac<br>Phe Gly Ala Met Met Lys Ser Gly Met Phe Leu Thr Leu Phe Ile Asn<br>                    2245                      2250                    2255 | 7305 |
| act gtt ttg aac atc acc ata gca agc agg gta ctg gag cag aga ctc<br>Thr Val Leu Asn Ile Thr Ile Ala Ser Arg Val Leu Glu Gln Arg Leu<br>              2260                      2265                    2270 | 7353 |
| act gac tcc gcc tgt gcg gcc ttc atc ggc gac gac aac atc gtt cac<br>Thr Asp Ser Ala Cys Ala Ala Phe Ile Gly Asp Asp Asn Ile Val His<br>              2275                      2280                    2285 | 7401 |
| gga gtg atc tcc gac aag ctg atg gcg gag agg tgc gcg tcg tgg gtc<br>Gly Val Ile Ser Asp Lys Leu Met Ala Glu Arg Cys Ala Ser Trp Val<br>            2290                      2295                    2300 | 7449 |
| aac atg gag gtg aag atc att gac gct gtc atg ggc gaa aaa ccc cca<br>Asn Met Glu Val Lys Ile Ile Asp Ala Val Met Gly Glu Lys Pro Pro<br>2305                    2310                      2315                    2320 | 7497 |
| tat ttc tgt ggg gga ttc ata gtt ttt gac agc gtc aca cag acc gcc<br>Tyr Phe Cys Gly Gly Phe Ile Val Phe Asp Ser Val Thr Gln Thr Ala<br>                    2325                      2330                    2335 | 7545 |
| tgc cgt gtt tca gac cca ctt aag cgc ctg ttc aag ttg ggt aag ccg<br>Cys Arg Val Ser Asp Pro Leu Lys Arg Leu Phe Lys Leu Gly Lys Pro<br>              2340                      2345                    2350 | 7593 |
| cta aca gct gaa gac aag cag gac gaa gac agg cga cga gca ctg agt<br>Leu Thr Ala Glu Asp Lys Gln Asp Glu Asp Arg Arg Arg Ala Leu Ser<br>            2355                      2360                    2365 | 7641 |
| gac gag gtt agc aag tgg ttc cgg aca ggc ttg ggg gcc gaa ctg gag<br>Asp Glu Val Ser Lys Trp Phe Arg Thr Gly Leu Gly Ala Glu Leu Glu<br>        2370                      2375                    2380 | 7689 |
| gtg gca cta aca tct agg tat gag gta gag ggc tgc aaa agt atc ctc<br>Val Ala Leu Thr Ser Arg Tyr Glu Val Glu Gly Cys Lys Ser Ile Leu<br>2385                    2390                      2395                    2400 | 7737 |
| ata gcc atg gcc acc ttg gcg agg gac att aag gcg ttt aag aaa ttg<br>Ile Ala Met Ala Thr Leu Ala Arg Asp Ile Lys Ala Phe Lys Lys Leu<br>                    2405                      2410                    2415 | 7785 |
| aga gga cct gtt ata cac ctc tac ggc ggt cct aga ttg gtg cgt<br>Arg Gly Pro Val Ile His Leu Tyr Gly Gly Pro Arg Leu Val Arg<br>              2420                      2425                    2430 | 7830 |
| taatacacag aattctgatt ggatccccgg accgtgttga caattaatca tcggcatagt | 7890 |
| atatcggcat agtataatac gacaaggtga ggaactaaac c atg gcc tcc aaa gga<br>                                                              Met Ala Ser Lys Gly<br>                                                                               2435 | 7946 |

```
gaa gaa ctt ttc act gga gtt gtc cca att ctt gtt gaa tta gat ggt     7994
Glu Glu Leu Phe Thr Gly Val Val Pro Ile Leu Val Glu Leu Asp Gly
        2440                2445                2450 gat gtt aat ggg cac aaa ttt tct gtc agt gga gag ggt gaa ggt gat     8042
Asp Val Asn Gly His Lys Phe Ser Val Ser Gly Glu Gly Glu Gly Asp
    2455                2460                2465 gct aca tac gga aag ctt acc ctt aaa ttt att tgc act act gga aaa     8090
Ala Thr Tyr Gly Lys Leu Thr Leu Lys Phe Ile Cys Thr Thr Gly Lys
2470                2475                2480 cta cct gtt cca tgg cca aca ctt gtc act act ttc tct tat ggt gtt     8138
Leu Pro Val Pro Trp Pro Thr Leu Val Thr Thr Phe Ser Tyr Gly Val
2485                2490                2495                2500 caa tgc ttt tcc cgt tat ccg gat cat atg aaa cgg cat gac ttt ttc     8186
Gln Cys Phe Ser Arg Tyr Pro Asp His Met Lys Arg His Asp Phe Phe
        2505                2510                2515 aag agt gcc atg ccc gaa ggt tat gta cag gaa cgc act ata tct ttc     8234
Lys Ser Ala Met Pro Glu Gly Tyr Val Gln Glu Arg Thr Ile Ser Phe
    2520                2525                2530 aaa gat gac ggg aac tac aag acg cgt gct gaa gtc aag ttt gaa ggt     8282
Lys Asp Asp Gly Asn Tyr Lys Thr Arg Ala Glu Val Lys Phe Glu Gly
        2535                2540                2545 gat acc ctt gtt aat cgt atc gag tta aaa ggt att gat ttt aaa gaa     8330
Asp Thr Leu Val Asn Arg Ile Glu Leu Lys Gly Ile Asp Phe Lys Glu
2550                2555                2560 gat gga aac att ctc gga cac aaa ctc gag tac aac tat aac tca cac     8378
Asp Gly Asn Ile Leu Gly His Lys Leu Glu Tyr Asn Tyr Asn Ser His
2565                2570                2575                2580 aat gta tac atc acg gca gac aaa caa aag aat gga atc aaa gct aac     8426
Asn Val Tyr Ile Thr Ala Asp Lys Gln Lys Asn Gly Ile Lys Ala Asn
        2585                2590                2595 ttc aaa att cgt cac aac att gaa gat gga tcc gtt caa cta gca gac     8474
Phe Lys Ile Arg His Asn Ile Glu Asp Gly Ser Val Gln Leu Ala Asp
            2600                2605                2610 cat tat caa caa aat act cca att ggc gat ggc cct gtc ctt tta cca     8522
His Tyr Gln Gln Asn Thr Pro Ile Gly Asp Gly Pro Val Leu Leu Pro
2615                2620                2625 gac aac cat tac ctg tcg aca caa tct gcc ctt tcg aaa gat ccc aac     8570
Asp Asn His Tyr Leu Ser Thr Gln Ser Ala Leu Ser Lys Asp Pro Asn
    2630                2635                2640 gaa aag cgt gac cac atg gtc ctt ctt gag ttt gta act gct gct ggg     8618
Glu Lys Arg Asp His Met Val Leu Leu Glu Phe Val Thr Ala Ala Gly
2645                2650                2655                2660 att aca cat ggc atg gat cag gcc aag cct ttg tct caa gaa gaa tcc     8666
Ile Thr His Gly Met Asp Gln Ala Lys Pro Leu Ser Gln Glu Glu Ser
        2665                2670                2675 acc ctc att gaa aga gca acg gct aca atc aac agc atc ccc atc tct     8714
Thr Leu Ile Glu Arg Ala Thr Ala Thr Ile Asn Ser Ile Pro Ile Ser
    2680                2685                2690 gaa gac tac agc gtc gcc agc gca gct ctc tct agc gac ggc cgc atc     8762
Glu Asp Tyr Ser Val Ala Ser Ala Ala Leu Ser Ser Asp Gly Arg Ile
        2695                2700                2705 ttc act ggt gtc aat gta tat cat ttt act ggg gga cct tgt gca gaa     8810
Phe Thr Gly Val Asn Val Tyr His Phe Thr Gly Gly Pro Cys Ala Glu
2710                2715                2720 ctc gtg gtg ctg ggc act gct gct gct gcg gca gct ggc aac ctg act     8858
Leu Val Val Leu Gly Thr Ala Ala Ala Ala Ala Ala Gly Asn Leu Thr
2725                2730                2735                2740 tgt atc gtc gcg atc gga aat gag aac agg ggc atc ttg agc ccc tgc     8906
Cys Ile Val Ala Ile Gly Asn Glu Asn Arg Gly Ile Leu Ser Pro Cys
        2745                2750                2755
```

```
gga cgg tgc cga cag gtg ctt ctc gat ctg cat cct ggg atc aaa gcc    8954
Gly Arg Cys Arg Gln Val Leu Leu Asp Leu His Pro Gly Ile Lys Ala
        2760                2765                2770 ata gtg aag gac agt gat gga cag ccg acg gca gtt ggg att cgt gaa    9002
Ile Val Lys Asp Ser Asp Gly Gln Pro Thr Ala Val Gly Ile Arg Glu
    2775                2780                2785 ttg ctg ccc tct ggt tat gtg tgg gag ggc taagcacttc gtgggtaatt      9052
Leu Leu Pro Ser Gly Tyr Val Trp Glu Gly
    2790                2795 aattgaatta catccctacg caaacgtttt acggccgccg gtggcgcccg cgccggcgg    9112
cccgtccttg gccgttgcag gccactccgg tggctcccgt cgtccccgac ttccaggccc    9172
agcagatgca gcaactcatc agcgccgtaa atgcgctgac aatgagacag aacgcaattg    9232
ctcctgctag gcctcccaaa ccaaagaaga agaagacaac caaaccaaag ccgaaaacgc    9292
agcccaagaa gatcaacgga aaaacgcagc agcaaaagaa gaaagacaag caagccgaca    9352
agaagaagaa gaaacccgga aaaagagaaa gaatgtgcat gaagattgaa aatgactgta    9412
tcttcgtatg cggctagcca cagtaacgta gtgtttccag acatgtcggg caccgcacta    9472
tcatgggtgc agaaaatctc gggtggtctg ggggccttcg caatcggcgc tatcctggtg    9532
ctggttgtgg tcacttgcat tgggctccgc agataagtta gggtaggcaa tggcattgat    9592
atagcaagaa aattgaaaac agaaaaagtt agggtaagca atggcatata accataactg    9652
tataacttgt aacaaagcgc aacaagacct gcgcaattgg ccccgtggtc cgcctcacgg    9712
aaactcgggg caactcatat tgacacatta attggcaata attggaagct tacataagct    9772
taattcgacg aataattgga tttatatttt attttgcaat tggttttaa tatttccaaa    9832
aaaaaaaaaa aaaaaaaaa aaaaaaaaa aaaaaaaaa aaaaaaaaa aaaacgggtc    9892
ggcatggcat ctccacctcc tcgcggtccg acctgggcat ccgaaggagg acgcacgtcc    9952
actcggatgg ctaagggagt ttttctacta gtcaaatgag tatatataat tgaaaaagta   10012
aaatataaat catataataa tgaaacgaaa tatcagtaat agacaggaac tggcagattc   10072
ttcttctaat gaagtaagta ctgctaaatc tccaaaatta gataaaaatg atacagcaaa   10132
tacagcttca ttcaacgaat tacctttaa tttttcaga cacaccttat tacaaactaa   10192
ctaagtcaga tgatgagaaa gtaaatataa atttaactta tgggtataat ataataaaga   10252
ttcatgatat taataattta cttaacgatg ttaatagact tattccatca acccttcaa    10312
accttctctgg atattataaa ataccagtta atgatattaa aatagattgt ttaagagatg   10372
taaataatta tttggaggta aaggatataa aattagtcta tctttcacat ggaaatgaat   10432
tacctaatat taataattat gataggaatt ttttaggatt tacagctgtt atatgtatca   10492
acaatacagg cagatctatg gttatggtaa aacactgtaa cgggaagcag cattctatgg   10552
taactggcct atgtttaata gccagatcat tttactctat aaacatttta ccacaaataa   10612
taggatcctc tagatattta atattatatc taacaacaac aaaaaaattt aacgatgtat   10672
ggccagaagt attttctact aataaagata agatagtct atcttatcta caagatatga   10732
aagaagataa tcatttagta gtagctacta atatggaaag aaatgtatac aaaaacgtgg   10792
aagctttat attaaatagc atattactag aagatttaaa atctagactt agtataacaa   10852
aacagttaaa tgccaatatc gattctatat ttcatcataa cagtagtaca ttaatcagtg   10912
atatactgaa acgatctaca gactcaacta tgcaaggaat aagcaatatg ccaattatgt   10972
ctaatatttt aactttagaa ctaaaacgtt ctaccaatac taaaaatagg atacgtgata   11032
```

```
ggctgttaaa agctgcaata aatagtaagg atgtagaaga atactttgt tctatacctt    11092 cggaggaaag aactttagaa caacttaagt ttaatcaaac ttgtatttat gaaggtac     11150

<210> SEQ ID NO 2
<211> LENGTH: 9981
<212> TYPE: DNA
<213> ORGANISM: Artificial Sequence
<220> FEATURE:
<223> OTHER INFORMATION: Description of Artificial Sequence: Synthetic
      pJYC6SFL713A1 DNA sequence
<220> FEATURE:
<221> NAME/KEY: CDS
<222> LOCATION: (530)..(7822)

<400> SEQUENCE: 2
ctatcaaaag tcttaatgag ttaggtgtag atagtataga tattactaca aaggtattca     60
tatttcctat caattctaaa gtagatgata ttaataactc aaagatgatg atagtagata    120
atagatacgc tcatataatg actgcaaatt tggacggttc acattttaat catcacgcgt    180
tcataagttt caactgcata gatcaaaatc tcactaaaaa gatagccgat gtatttgaga    240
gagattggac atctaactac gctaaagaaa ttacagttat aaataataca taatggattt    300
tgttatcatc agttatattt aacataagta caataaaaag tattaaataa aaatacttac    360
ttacgaaaaa atgactaatt agctataaaa acccgggttc tttattctat acttaaaaag    420
tgaaaataaa tacaaaggtt cttgatggcg gatgtgtgac atacacgacg ccaaaagatt    480
ttgttccagc tcctgccacc tccgctacgc gagagattaa ccacccacg atg gcc gcc    538
                                                       Met Ala Ala
                                                        1
```

| aaa gtg cat gtt gat att gag gct gac agc cca ttc atc aag tct ttg | 586 |
|---|---|
| Lys Val His Val Asp Ile Glu Ala Asp Ser Pro Phe Ile Lys Ser Leu | |
| 5              10              15 | |

| cag aag gca ttt ccg tcg ttc gag gtg gag tca ttg cag gtc aca cca | 634 |
|---|---|
| Gln Lys Ala Phe Pro Ser Phe Glu Val Glu Ser Leu Gln Val Thr Pro | |
| 20              25              30              35 | |

| aat gac cat gca aat gcc aga gca ttt tcg cac ctg gct acc aaa ttg | 682 |
|---|---|
| Asn Asp His Ala Asn Ala Arg Ala Phe Ser His Leu Ala Thr Lys Leu | |
| 40              45              50 | |

| atc gag cag gag act gac aaa gac aca ctc atc ttg gat atc ggc agt | 730 |
|---|---|
| Ile Glu Gln Glu Thr Asp Lys Asp Thr Leu Ile Leu Asp Ile Gly Ser | |
| 55              60              65 | |

| gcg cct tcc agg aga atg atg tct acg cac aaa tac cac tgc gta tgc | 778 |
|---|---|
| Ala Pro Ser Arg Arg Met Met Ser Thr His Lys Tyr His Cys Val Cys | |
| 70              75              80 | |

| cct atg cgc agc gca gaa gac ccc gaa agg ctc gat agc tac gca aag | 826 |
|---|---|
| Pro Met Arg Ser Ala Glu Asp Pro Glu Arg Leu Asp Ser Tyr Ala Lys | |
| 85              90              95 | |

| aaa ctg gca gcg gcc tcc ggg aag gtg ctg gat aga gag atc gca gga | 874 |
|---|---|
| Lys Leu Ala Ala Ala Ser Gly Lys Val Leu Asp Arg Glu Ile Ala Gly | |
| 100              105              110              115 | |

| aaa atc acc gac ctg cag acc gtc atg gct acg cca gac gct gaa tct | 922 |
|---|---|
| Lys Ile Thr Asp Leu Gln Thr Val Met Ala Thr Pro Asp Ala Glu Ser | |
| 120              125              130 | |

| cct acc ttt tgc ctg cat aca gac gtc acg tgt cgt acg gca gcc gaa | 970 |
|---|---|
| Pro Thr Phe Cys Leu His Thr Asp Val Thr Cys Arg Thr Ala Ala Glu | |
| 135              140              145 | |

| gtg gcc gta tac cag gac gtg tat gct gta cat gca cca aca tcg ctg | 1018 |
|---|---|
| Val Ala Val Tyr Gln Asp Val Tyr Ala Val His Ala Pro Thr Ser Leu | |
| 150              155              160 | |

```
tac cat cag gcg atg aaa ggt gtc aga acg gcg tat tgg att ggg ttt      1066
Tyr His Gln Ala Met Lys Gly Val Arg Thr Ala Tyr Trp Ile Gly Phe
    165                 170                 175 gac acc acc ccg ttt atg ttt gac gcg cta gca ggc gcg tat cca acc      1114
Asp Thr Thr Pro Phe Met Phe Asp Ala Leu Ala Gly Ala Tyr Pro Thr
180                 185                 190                 195 tac gcc aca aac tgg gcc gac gag cag gtg tta cag gcc agg aac ata      1162
Tyr Ala Thr Asn Trp Ala Asp Glu Gln Val Leu Gln Ala Arg Asn Ile
                200                 205                 210 gga ctg tgt gca gca tcc ttg act gag gga aga ctc ggc aaa ctg tcc      1210
Gly Leu Cys Ala Ala Ser Leu Thr Glu Gly Arg Leu Gly Lys Leu Ser
            215                 220                 225 att ctc cgc aag aag caa ttg aaa cct tgc gac aca gtc atg ttc tcg      1258
Ile Leu Arg Lys Lys Gln Leu Lys Pro Cys Asp Thr Val Met Phe Ser
        230                 235                 240 gta gga tct aca ttg tac act gag agc aga aag cta ctg agg agc tgg      1306
Val Gly Ser Thr Leu Tyr Thr Glu Ser Arg Lys Leu Leu Arg Ser Trp
    245                 250                 255 cac tta ccc tcc gta ttc cac ctg aaa ggt aaa caa tcc ttt acc tgt      1354
His Leu Pro Ser Val Phe His Leu Lys Gly Lys Gln Ser Phe Thr Cys
260                 265                 270                 275 agg tgc gat acc atc gta tca tgt gaa ggg tac gta gtt aag aaa atc      1402
Arg Cys Asp Thr Ile Val Ser Cys Glu Gly Tyr Val Val Lys Lys Ile
                280                 285                 290 act atg tgc ccc ggc ctg tac ggt aaa acg gta ggg tac gcc gtg acg      1450
Thr Met Cys Pro Gly Leu Tyr Gly Lys Thr Val Gly Tyr Ala Val Thr
            295                 300                 305 tat cac gcg gag gga ttc cta gtg tgc aag acc aca gac act gtc aaa      1498
Tyr His Ala Glu Gly Phe Leu Val Cys Lys Thr Thr Asp Thr Val Lys
        310                 315                 320 gga gaa aga gtc tca ttc cct gta tgc acc tac gtc ccc tca acc atc      1546
Gly Glu Arg Val Ser Phe Pro Val Cys Thr Tyr Val Pro Ser Thr Ile
    325                 330                 335 tgt gat caa atg act ggc ata cta gcg acc gac gtc aca ccg gag gac      1594
Cys Asp Gln Met Thr Gly Ile Leu Ala Thr Asp Val Thr Pro Glu Asp
340                 345                 350                 355 gca cag aag ttg tta gtg gga ttg aat cag agg ata gtt gtg aac gga      1642
Ala Gln Lys Leu Leu Val Gly Leu Asn Gln Arg Ile Val Val Asn Gly
                360                 365                 370 aga aca cag cga aac act aac acg atg aag aac tat ctg ctt ccg att      1690
Arg Thr Gln Arg Asn Thr Asn Thr Met Lys Asn Tyr Leu Leu Pro Ile
            375                 380                 385 gtg gcc gtc gca ttt agc aag tgg gcg agg gaa tac aag gca gac ctt      1738
Val Ala Val Ala Phe Ser Lys Trp Ala Arg Glu Tyr Lys Ala Asp Leu
        390                 395                 400 gat gat gaa aaa cct ctg ggt gtc cga gag agg tca ctt act tgc tgc      1786
Asp Asp Glu Lys Pro Leu Gly Val Arg Glu Arg Ser Leu Thr Cys Cys
    405                 410                 415 tgc ttg tgg gca ttt aaa acg agg aag atg cac acc atg tac aag aaa      1834
Cys Leu Trp Ala Phe Lys Thr Arg Lys Met His Thr Met Tyr Lys Lys
420                 425                 430                 435 cca gac acc cag aca ata gtg aag gtg cct tca gag ttt aac tcg ttc      1882
Pro Asp Thr Gln Thr Ile Val Lys Val Pro Ser Glu Phe Asn Ser Phe
                440                 445                 450 gtc atc ccg agc cta tgg tct aca ggc ctc gca atc cca gtc aga tca      1930
Val Ile Pro Ser Leu Trp Ser Thr Gly Leu Ala Ile Pro Val Arg Ser
            455                 460                 465 cgc att aag atg ctt ttg gcc aag aag acc aag cga gag tta ata cct      1978
Arg Ile Lys Met Leu Leu Ala Lys Lys Thr Lys Arg Glu Leu Ile Pro
        470                 475                 480
```

```
gtt ctc gac gcg tcg tca gcc agg gat gct gaa caa gag gag aag gag    2026
Val Leu Asp Ala Ser Ser Ala Arg Asp Ala Glu Gln Glu Glu Lys Glu
    485                 490                 495 agg ttg gag gcc gag ctg act aga gaa gcc tta cca ccc ctc gtc ccc    2074
Arg Leu Glu Ala Glu Leu Thr Arg Glu Ala Leu Pro Pro Leu Val Pro
500                 505                 510                 515 atc gcg ccg gcg gag acg gga gtc gtc gac gtc gac gtt gaa gaa cta    2122
Ile Ala Pro Ala Glu Thr Gly Val Val Asp Val Asp Val Glu Glu Leu
                520                 525                 530 gag tat cac gca ggt gca ggg gtc gtg gaa aca cct cgc agc gcg ttg    2170
Glu Tyr His Ala Gly Ala Gly Val Val Glu Thr Pro Arg Ser Ala Leu
            535                 540                 545 aaa gtc acc gca cag ccg aac gac gta cta cta gga aat tac gta gtt    2218
Lys Val Thr Ala Gln Pro Asn Asp Val Leu Leu Gly Asn Tyr Val Val
        550                 555                 560 ctg tcc ccg cag acc gtg ctc aag agc tcc aag ttg gcc ccc gtg cac    2266
Leu Ser Pro Gln Thr Val Leu Lys Ser Ser Lys Leu Ala Pro Val His
    565                 570                 575 cct cta gca gag cag gtg aaa ata ata aca cat aac ggg agg gcc ggc    2314
Pro Leu Ala Glu Gln Val Lys Ile Ile Thr His Asn Gly Arg Ala Gly
580                 585                 590                 595 ggt tac cag gtc gac gga tat gac ggc agg gtc cta cta cca tgt gga    2362
Gly Tyr Gln Val Asp Gly Tyr Asp Gly Arg Val Leu Leu Pro Cys Gly
                600                 605                 610 tcg gcc att ccg gtc cct gag ttt caa gct ttg agc gag agc gcc act    2410
Ser Ala Ile Pro Val Pro Glu Phe Gln Ala Leu Ser Glu Ser Ala Thr
            615                 620                 625 atg gtg tac aac gaa agg gag ttc gtc aac agg aaa cta tac cat att    2458
Met Val Tyr Asn Glu Arg Glu Phe Val Asn Arg Lys Leu Tyr His Ile
        630                 635                 640 gcc gtt cac gga ccg tcg ctg aac acc gac gag gag aac tac gag aaa    2506
Ala Val His Gly Pro Ser Leu Asn Thr Asp Glu Glu Asn Tyr Glu Lys
    645                 650                 655 gtc aga gct gaa aga act gac gcc gag tac gtg ttc gac gta gat aaa    2554
Val Arg Ala Glu Arg Thr Asp Ala Glu Tyr Val Phe Asp Val Asp Lys
660                 665                 670                 675 aaa tgc tgc gtc aag aga gag gaa gcg tcg ggt ttg gtg ttg gtg gga    2602
Lys Cys Cys Val Lys Arg Glu Glu Ala Ser Gly Leu Val Leu Val Gly
                680                 685                 690 gag cta acc aac ccc ccg ttc cat gaa ttc gcc tac gaa ggg ctg aag    2650
Glu Leu Thr Asn Pro Pro Phe His Glu Phe Ala Tyr Glu Gly Leu Lys
            695                 700                 705 atc agg ccg tcg gca cca tat aag act aca gta gta gga gtc ttt ggg    2698
Ile Arg Pro Ser Ala Pro Tyr Lys Thr Thr Val Val Gly Val Phe Gly
        710                 715                 720 gtt ccg gga tca ggc aag tct gct att att aag agc ctc gtg acc aaa    2746
Val Pro Gly Ser Gly Lys Ser Ala Ile Ile Lys Ser Leu Val Thr Lys
    725                 730                 735 cac gat ctg gtc acc agc ggc aag aag gag aac tgc cag gaa ata gtt    2794
His Asp Leu Val Thr Ser Gly Lys Lys Glu Asn Cys Gln Glu Ile Val
740                 745                 750                 755 aac gac gtg aag aag cac cgc ggg aag ggg aca agt agg gaa aac agt    2842
Asn Asp Val Lys Lys His Arg Gly Lys Gly Thr Ser Arg Glu Asn Ser
                760                 765                 770 gac tcc atc ctg cta aac ggg tgt cgt cgt gcc gtg gac atc cta tat    2890
Asp Ser Ile Leu Leu Asn Gly Cys Arg Arg Ala Val Asp Ile Leu Tyr
            775                 780                 785 gtg gac gag gct ttc gct tgc cat tcc ggt act ctg ctg gcc cta att    2938
Val Asp Glu Ala Phe Ala Cys His Ser Gly Thr Leu Leu Ala Leu Ile
        790                 795                 800
```

```
gct ctt gtt aaa cct cgg agc aaa gtg gtg tta tgc gga gac ccc aag    2986
Ala Leu Val Lys Pro Arg Ser Lys Val Val Leu Cys Gly Asp Pro Lys
805                 810                 815 caa tgc gga ttc ttc aat atg atg cag ctt aag gta aac ttc aac cac    3034
Gln Cys Gly Phe Phe Asn Met Met Gln Leu Lys Val Asn Phe Asn His
820                 825                 830                 835 aac atc tgc act gaa gta tgt cat aaa agt ata tcc aga cgt tgc acg    3082
Asn Ile Cys Thr Glu Val Cys His Lys Ser Ile Ser Arg Arg Cys Thr
                840                 845                 850 cgt cca gtc acg gcc atc gtg tct acg ttg cac tac gga ggc aag atg    3130
Arg Pro Val Thr Ala Ile Val Ser Thr Leu His Tyr Gly Gly Lys Met
855                 860                 865 cgc acg acc aac ccg tgc aac aaa ccc ata atc ata gac acc aca gga    3178
Arg Thr Thr Asn Pro Cys Asn Lys Pro Ile Ile Ile Asp Thr Thr Gly
870                 875                 880 cag acc aag ccc aag cca gga gac atc gtg tta aca tgc ttc cga ggc    3226
Gln Thr Lys Pro Lys Pro Gly Asp Ile Val Leu Thr Cys Phe Arg Gly
885                 890                 895 tgg gca aag cag ctg cag ttg gac tac cgt gga cac gaa gtc atg aca    3274
Trp Ala Lys Gln Leu Gln Leu Asp Tyr Arg Gly His Glu Val Met Thr
900                 905                 910                 915 gca gca gca tct cag ggc ctc acc cgc aaa ggg gta tac gcc gta agg    3322
Ala Ala Ala Ser Gln Gly Leu Thr Arg Lys Gly Val Tyr Ala Val Arg
                920                 925                 930 cag aag gtg aat gaa aat ccc ttg tat gcc cct gcg tcg gag cac gtg    3370
Gln Lys Val Asn Glu Asn Pro Leu Tyr Ala Pro Ala Ser Glu His Val
            935                 940                 945 aat gta ctg ctg acg cgc act gag gat agg ctg gtg tgg aaa acg ctg    3418
Asn Val Leu Leu Thr Arg Thr Glu Asp Arg Leu Val Trp Lys Thr Leu
        950                 955                 960 gcc ggc gat ccc tgg att aag gtc cta tca aac att cca cag ggt aac    3466
Ala Gly Asp Pro Trp Ile Lys Val Leu Ser Asn Ile Pro Gln Gly Asn
965                 970                 975 ttt acg gcc aca ttg gaa gaa tgg caa gaa gaa cac gac aaa ata atg    3514
Phe Thr Ala Thr Leu Glu Glu Trp Gln Glu Glu His Asp Lys Ile Met
980                 985                 990                 995 aag gtg att gaa gga ccg gct gcg cct gtg gac gcg ttc cag aac aaa    3562
Lys Val Ile Glu Gly Pro Ala Ala Pro Val Asp Ala Phe Gln Asn Lys
                1000                1005                1010 gcg aac gtg tgt tgg gcg aaa agc ctg gtg cct gtc ctg gac act gcc    3610
Ala Asn Val Cys Trp Ala Lys Ser Leu Val Pro Val Leu Asp Thr Ala
            1015                1020                1025 gga atc aga ttg aca gca gag gag tgg agc acc ata att aca gca ttt    3658
Gly Ile Arg Leu Thr Ala Glu Glu Trp Ser Thr Ile Ile Thr Ala Phe
        1030                1035                1040 aag gag gac aga gct tac tct cca gtg gtg gcc ttg aat gaa att tgc    3706
Lys Glu Asp Arg Ala Tyr Ser Pro Val Val Ala Leu Asn Glu Ile Cys
1045                1050                1055 acc aag tac tat gga gtt gac ctg gac agt ggc ctg ttt tct gcc ccg    3754
Thr Lys Tyr Tyr Gly Val Asp Leu Asp Ser Gly Leu Phe Ser Ala Pro
1060                1065                1070                1075 aag gtg tcc ctg tat tac gag aac aac cac tgg gat aac aga cct ggt    3802
Lys Val Ser Leu Tyr Tyr Glu Asn Asn His Trp Asp Asn Arg Pro Gly
                1080                1085                1090 gga agg atg tat gga ttc aat gcc gca aca gct gcc agg ctg gaa gct    3850
Gly Arg Met Tyr Gly Phe Asn Ala Ala Thr Ala Ala Arg Leu Glu Ala
            1095                1100                1105 aga cat acc ttc ctg aag ggg cag tgg cat acg ggc aag cag gca gtt    3898
Arg His Thr Phe Leu Lys Gly Gln Trp His Thr Gly Lys Gln Ala Val
        1110                1115                1120
```

```
atc gca gaa aga aaa atc caa ccg ctt tct gtg ctg gac aat gta att       3946
Ile Ala Glu Arg Lys Ile Gln Pro Leu Ser Val Leu Asp Asn Val Ile
   1125                1130                1135 cct atc aac cgc agg ctg ccg cac gcc ctg gtg gct gag tac aag acg       3994
Pro Ile Asn Arg Arg Leu Pro His Ala Leu Val Ala Glu Tyr Lys Thr
1140                1145                1150                1155 gtt aaa ggc agt agg gtt gag tgg ctg gtc aat aaa gta aga ggg tac       4042
Val Lys Gly Ser Arg Val Glu Trp Leu Val Asn Lys Val Arg Gly Tyr
            1160                1165                1170 cac gtc ctg ctg gtg agt gag tac aac ctg gct ttg cct cga cgc agg       4090
His Val Leu Leu Val Ser Glu Tyr Asn Leu Ala Leu Pro Arg Arg Arg
        1175                1180                1185 gtc act tgg ttg tca ccg ctg aat gtc aca ggc gcc gat agg tgc tac       4138
Val Thr Trp Leu Ser Pro Leu Asn Val Thr Gly Ala Asp Arg Cys Tyr
    1190                1195                1200 gac cta agt tta gga ctg ccg gct gac gcc ggc agg ttc gac ttg gtc       4186
Asp Leu Ser Leu Gly Leu Pro Ala Asp Ala Gly Arg Phe Asp Leu Val
   1205                1210                1215 ttt gtg aac att cac acg gaa ttc aga atc cac cac tac cag cag tgt       4234
Phe Val Asn Ile His Thr Glu Phe Arg Ile His His Tyr Gln Gln Cys
1220                1225                1230                1235 gtc gac cac gcc atg aag ctg cag atg ctt ggg gga gat gcg gca cga       4282
Val Asp His Ala Met Lys Leu Gln Met Leu Gly Gly Asp Ala Ala Arg
            1240                1245                1250 ctg cta aaa ccc ggc ggc atc ttg atg aga gct tac gga tac gcc gat       4330
Leu Leu Lys Pro Gly Gly Ile Leu Met Arg Ala Tyr Gly Tyr Ala Asp
        1255                1260                1265 aaa atc agc gaa gcc gtt gtt tcc tcc tta agc aga aag ttc tcg tct       4378
Lys Ile Ser Glu Ala Val Val Ser Ser Leu Ser Arg Lys Phe Ser Ser
    1270                1275                1280 gca aga gtg ttg cgc ccg gat tgt gtc acc agc aat aca gaa gtg ttc       4426
Ala Arg Val Leu Arg Pro Asp Cys Val Thr Ser Asn Thr Glu Val Phe
   1285                1290                1295 ttg ctg ttc tcc aac ttt gac aac gga aag aga ccc tct acg cta cac       4474
Leu Leu Phe Ser Asn Phe Asp Asn Gly Lys Arg Pro Ser Thr Leu His
1300                1305                1310                1315 cag atg aat acc aag ctg agt gcc gtg tat gcc gga gaa gcc atg cac       4522
Gln Met Asn Thr Lys Leu Ser Ala Val Tyr Ala Gly Glu Ala Met His
            1320                1325                1330 acg gcc ggg tgt gca cca tcc tac aga gtt aag aga gca gac ata gcc       4570
Thr Ala Gly Cys Ala Pro Ser Tyr Arg Val Lys Arg Ala Asp Ile Ala
        1335                1340                1345 acg tgc aca gaa gcg gct gtg gtt aac gca gct aac gcc cgt gga act       4618
Thr Cys Thr Glu Ala Ala Val Val Asn Ala Ala Asn Ala Arg Gly Thr
    1350                1355                1360 gta ggg gat ggc gta tgc agg gcc gtg gcg aag aaa tgg ccg tca gcc       4666
Val Gly Asp Gly Val Cys Arg Ala Val Ala Lys Lys Trp Pro Ser Ala
   1365                1370                1375 ttt aag gga gca gca aca cca gtg ggc aca att aaa aca gtc atg tgc       4714
Phe Lys Gly Ala Ala Thr Pro Val Gly Thr Ile Lys Thr Val Met Cys
1380                1385                1390                1395 ggc tcg tac ccc gtc atc cac gct gta gcg cct aat ttc tct gcc acg       4762
Gly Ser Tyr Pro Val Ile His Ala Val Ala Pro Asn Phe Ser Ala Thr
            1400                1405                1410 act gaa gcg gaa ggg gac cgc gaa ttg gcc gct gtc tac cgg gca gtg       4810
Thr Glu Ala Glu Gly Asp Arg Glu Leu Ala Ala Val Tyr Arg Ala Val
        1415                1420                1425 gcc gcc gaa gta aac aga ctg tca ctg agc agc gta gcc atc ccg ctg       4858
Ala Ala Glu Val Asn Arg Leu Ser Leu Ser Ser Val Ala Ile Pro Leu
    1430                1435                1440
```

```
ctg tcc aca gga gtg ttc agc ggc gga aga gat agg ctg cag caa tcc      4906
Leu Ser Thr Gly Val Phe Ser Gly Gly Arg Asp Arg Leu Gln Gln Ser
    1445                1450                1455 ctc aac cat cta ttc aca gca atg gac gcc acg gac gct gac gtg acc      4954
Leu Asn His Leu Phe Thr Ala Met Asp Ala Thr Asp Ala Asp Val Thr
1460                1465                1470                1475 atc tac tgc aga gac aaa agt tgg gag aag aaa atc cag gaa gcc att      5002
Ile Tyr Cys Arg Asp Lys Ser Trp Glu Lys Lys Ile Gln Glu Ala Ile
                1480                1485                1490 gac atg agg acg gct gtg gag ttg ctc aat gat gac gtg gag ctg acc      5050
Asp Met Arg Thr Ala Val Glu Leu Leu Asn Asp Asp Val Glu Leu Thr
            1495                1500                1505 aca gac ttg gtg aga gtg cac ccg gac agc agc ctg gtg ggt cgt aag      5098
Thr Asp Leu Val Arg Val His Pro Asp Ser Ser Leu Val Gly Arg Lys
        1510                1515                1520 ggc tac agt acc act gac ggg tcg ctg tac tcg tac ttt gaa ggt acg      5146
Gly Tyr Ser Thr Thr Asp Gly Ser Leu Tyr Ser Tyr Phe Glu Gly Thr
    1525                1530                1535 aaa ttc aac cag gct gct att gat atg gca gag ata ctg acg ttg tgg      5194
Lys Phe Asn Gln Ala Ala Ile Asp Met Ala Glu Ile Leu Thr Leu Trp
1540                1545                1550                1555 ccc aga ctg caa gag gca aac gaa cag ata tgc cta tac gcg ctg ggc      5242
Pro Arg Leu Gln Glu Ala Asn Glu Gln Ile Cys Leu Tyr Ala Leu Gly
                1560                1565                1570 gaa aca atg gac aac atc aga tcc aaa tgt ccg gtg aac gat tcc gat      5290
Glu Thr Met Asp Asn Ile Arg Ser Lys Cys Pro Val Asn Asp Ser Asp
            1575                1580                1585 tca tca aca cct ccc agg aca gtg ccc tgc ctg tgc cgc tac gca atg      5338
Ser Ser Thr Pro Pro Arg Thr Val Pro Cys Leu Cys Arg Tyr Ala Met
        1590                1595                1600 aca gca gaa cgg atc gcc cgc ctt agg tca cac caa gtt aaa agc atg      5386
Thr Ala Glu Arg Ile Ala Arg Leu Arg Ser His Gln Val Lys Ser Met
    1605                1610                1615 gtg gtt tgc tca tct ttt ccc ctc ccg aaa tac cat gta gat ggg gtg      5434
Val Val Cys Ser Ser Phe Pro Leu Pro Lys Tyr His Val Asp Gly Val
1620                1625                1630                1635 cag aag gta aag tgc gag aag gtt ctc ctg ttc gac ccg acg gta cct      5482
Gln Lys Val Lys Cys Glu Lys Val Leu Leu Phe Asp Pro Thr Val Pro
                1640                1645                1650 tca gtg gtt agt ccg cgg aag tat gcc gca tct acg acg gac cac tca      5530
Ser Val Val Ser Pro Arg Lys Tyr Ala Ala Ser Thr Thr Asp His Ser
            1655                1660                1665 gat cgg tcg tta cga ggg ttt gac ttg gac tgg acc acc gac tcg tct      5578
Asp Arg Ser Leu Arg Gly Phe Asp Leu Asp Trp Thr Thr Asp Ser Ser
        1670                1675                1680 tcc act gcc agc gat acc atg tcg cta ccc agt ttg cag tcg tgt gac      5626
Ser Thr Ala Ser Asp Thr Met Ser Leu Pro Ser Leu Gln Ser Cys Asp
    1685                1690                1695 atc gac tcg atc tac gag cca atg gct ccc ata gta gtg acg gct gac      5674
Ile Asp Ser Ile Tyr Glu Pro Met Ala Pro Ile Val Val Thr Ala Asp
1700                1705                1710                1715 gta cac cct gaa ccc gca ggc atc gcg gac ctg gcg gca gat gtg cac      5722
Val His Pro Glu Pro Ala Gly Ile Ala Asp Leu Ala Ala Asp Val His
                1720                1725                1730 cct gaa ccc gca gac cat gtg gac ctc gag aac ccg att cct cca ccg      5770
Pro Glu Pro Ala Asp His Val Asp Leu Glu Asn Pro Ile Pro Pro Pro
            1735                1740                1745 cgc ccg aag aga gct gca tac ctt gcc tcc cgc gcg gcg gag cga ccg      5818
Arg Pro Lys Arg Ala Ala Tyr Leu Ala Ser Arg Ala Ala Glu Arg Pro
        1750                1755                1760
```

```
gtg ccg gcg ccg aga aag ccg acg cct gcc cca agg act gcg ttt agg    5866
Val Pro Ala Pro Arg Lys Pro Thr Pro Ala Pro Arg Thr Ala Phe Arg
   1765               1770                1775 aac aag ctg cct ttg acg ttc ggc gac ttt gac gag cac gag gtc gat    5914
Asn Lys Leu Pro Leu Thr Phe Gly Asp Phe Asp Glu His Glu Val Asp
1780                1785                1790                1795 gcg ttg gcc tcc ggg att act ttc gga gac ttc gac gac gtc ctg cga    5962
Ala Leu Ala Ser Gly Ile Thr Phe Gly Asp Phe Asp Asp Val Leu Arg
            1800                1805                1810 cta ggc cgc gcg ggt gca tat att ttc tcc tcg gac act ggc agc gga    6010
Leu Gly Arg Ala Gly Ala Tyr Ile Phe Ser Ser Asp Thr Gly Ser Gly
        1815                1820                1825 cat tta caa caa aaa tcc gtt agg cag cac aat ctc cag tgc gca caa    6058
His Leu Gln Gln Lys Ser Val Arg Gln His Asn Leu Gln Cys Ala Gln
    1830                1835                1840 ctg gat gcg gtc cag gag gag aaa atg tac ccg cca aaa ttg gat act    6106
Leu Asp Ala Val Gln Glu Glu Lys Met Tyr Pro Pro Lys Leu Asp Thr
1845                1850                1855 gag agg gag aag ctg ttg ctg ctg aaa atg cag atg cac cca tcg gag    6154
Glu Arg Glu Lys Leu Leu Leu Leu Lys Met Gln Met His Pro Ser Glu
1860                1865                1870                1875 gct aat aag agt cga tac cag tct cgc aaa gtg gag aac atg aaa gcc    6202
Ala Asn Lys Ser Arg Tyr Gln Ser Arg Lys Val Glu Asn Met Lys Ala
            1880                1885                1890 acg gtg gtg gac agg ctc aca tcg ggg gcc aga ttg tac acg gga gcg    6250
Thr Val Val Asp Arg Leu Thr Ser Gly Ala Arg Leu Tyr Thr Gly Ala
        1895                1900                1905 gac gta ggc cgc ata cca aca tac gcg gtt cgg tac ccc cgc ccc gtg    6298
Asp Val Gly Arg Ile Pro Thr Tyr Ala Val Arg Tyr Pro Arg Pro Val
    1910                1915                1920 tac tcc cct acc gtg atc gaa aga ttc tca agc ccc gat gta gca atc    6346
Tyr Ser Pro Thr Val Ile Glu Arg Phe Ser Ser Pro Asp Val Ala Ile
1925                1930                1935 gca gcg tgc aac gaa tac cta tcc aga aat tac cca aca gtg gcg tcg    6394
Ala Ala Cys Asn Glu Tyr Leu Ser Arg Asn Tyr Pro Thr Val Ala Ser
1940                1945                1950                1955 tac cag ata aca gat gaa tac gac gca tac ttg gac atg gtt gac ggg    6442
Tyr Gln Ile Thr Asp Glu Tyr Asp Ala Tyr Leu Asp Met Val Asp Gly
            1960                1965                1970 tcg gat agt tgc ttg gac aga gcg aca ttc tgc ccg gcg aag ctc cgg    6490
Ser Asp Ser Cys Leu Asp Arg Ala Thr Phe Cys Pro Ala Lys Leu Arg
        1975                1980                1985 tgc tac ccg aaa cat cat gcg tac cac cag ccg act gta cgc agt gcc    6538
Cys Tyr Pro Lys His His Ala Tyr His Gln Pro Thr Val Arg Ser Ala
    1990                1995                2000 gtc ccg tca ccc ttt cag aac aca cta cag aac gtg cta gcg gcc gcc    6586
Val Pro Ser Pro Phe Gln Asn Thr Leu Gln Asn Val Leu Ala Ala Ala
2005                2010                2015 acc aag aga aac tgc aac gtc acg caa atg cga gaa cta ccc acc atg    6634
Thr Lys Arg Asn Cys Asn Val Thr Gln Met Arg Glu Leu Pro Thr Met
2020                2025                2030                2035 gac tcg gca gtg ttc aac gtg gag tgc ttc aag cgc tat gcc tgc tcc    6682
Asp Ser Ala Val Phe Asn Val Glu Cys Phe Lys Arg Tyr Ala Cys Ser
            2040                2045                2050 gga gaa tat tgg gaa gaa tat gct aaa caa cct atc cgg ata acc act    6730
Gly Glu Tyr Trp Glu Glu Tyr Ala Lys Gln Pro Ile Arg Ile Thr Thr
        2055                2060                2065 gag aac atc act acc tat gtg acc aaa ttg aaa ggc ccg aaa gct gct    6778
Glu Asn Ile Thr Thr Tyr Val Thr Lys Leu Lys Gly Pro Lys Ala Ala
    2070                2075                2080
```

| | | |
|---|---|---|
| gcc ttg ttc gct aag acc cac aac ttg gtt ccg ctg cag gag gtt ccc<br>Ala Leu Phe Ala Lys Thr His Asn Leu Val Pro Leu Gln Glu Val Pro<br>        2085                      2090                     2095 | | 6826 |
| atg gac aga ttc acg gtc gac atg aaa cga gat gtc aaa gtc act cca<br>Met Asp Arg Phe Thr Val Asp Met Lys Arg Asp Val Lys Val Thr Pro<br>2100                   2105                   2110                 2115 | | 6874 |
| ggg acg aaa cac aca gag gaa aga ccc aaa gtc cag gta att caa gca<br>Gly Thr Lys His Thr Glu Glu Arg Pro Lys Val Gln Val Ile Gln Ala<br>        2120                     2125                 2130 | | 6922 |
| gcg gag cca ttg gcg acc gct tac ctg tgc ggc atc cac agg gaa tta<br>Ala Glu Pro Leu Ala Thr Ala Tyr Leu Cys Gly Ile His Arg Glu Leu<br>2135                   2140                   2145 | | 6970 |
| gta agg aga cta aat gct gtg tta cgc cct aac gtg cac aca ttg ttt<br>Val Arg Arg Leu Asn Ala Val Leu Arg Pro Asn Val His Thr Leu Phe<br>        2150                     2155                 2160 | | 7018 |
| gat atg tcg gcc gaa gac ttt gac gcg atc atc gcc tct cac ttc cac<br>Asp Met Ser Ala Glu Asp Phe Asp Ala Ile Ile Ala Ser His Phe His<br>2165                   2170                   2175 | | 7066 |
| cca gga gac ccg gtt cta gag acg gac att gca tca ttc gac aaa agc<br>Pro Gly Asp Pro Val Leu Glu Thr Asp Ile Ala Ser Phe Asp Lys Ser<br>2180                   2185                   2190                 2195 | | 7114 |
| cag gac gac tcc ttg gct ctt aca ggt tta atg atc ctc gaa gat cta<br>Gln Asp Asp Ser Leu Ala Leu Thr Gly Leu Met Ile Leu Glu Asp Leu<br>        2200                     2205                 2210 | | 7162 |
| ggg gtg gat cag tac ctg ctg gac ttg atc gag gca gcc ttt ggg gaa<br>Gly Val Asp Gln Tyr Leu Leu Asp Leu Ile Glu Ala Ala Phe Gly Glu<br>2215                   2220                   2225 | | 7210 |
| ata tcc agc tgt cac cta cca act ggc acg cgc ttc aag ttc gga gct<br>Ile Ser Ser Cys His Leu Pro Thr Gly Thr Arg Phe Lys Phe Gly Ala<br>        2230                     2235                 2240 | | 7258 |
| atg atg aaa tcg ggc atg ttt ctg act ttg ttt att aac act gtt ttg<br>Met Met Lys Ser Gly Met Phe Leu Thr Leu Phe Ile Asn Thr Val Leu<br>2245                   2250                   2255 | | 7306 |
| aac atc acc ata gca agc agg gta ctg gag cag aga ctc act gac tcc<br>Asn Ile Thr Ile Ala Ser Arg Val Leu Glu Gln Arg Leu Thr Asp Ser<br>2260                   2265                   2270                 2275 | | 7354 |
| gcc tgt gcg gcc ttc atc ggc gac gac aac atc gtt cac gga gtg atc<br>Ala Cys Ala Ala Phe Ile Gly Asp Asp Asn Ile Val His Gly Val Ile<br>        2280                     2285                   2290 | | 7402 |
| tcc gac aag ctg atg gcg gag agg tgc gcg tcg tgg gtc aac atg gag<br>Ser Asp Lys Leu Met Ala Glu Arg Cys Ala Ser Trp Val Asn Met Glu<br>2295                   2300                   2305 | | 7450 |
| gtg aag atc att gac gct gtc atg ggc gaa aaa ccc cca tat ttc tgt<br>Val Lys Ile Ile Asp Ala Val Met Gly Glu Lys Pro Pro Tyr Phe Cys<br>        2310                     2315                   2320 | | 7498 |
| ggg gga ttc ata gtt ttt gac agc gtc aca cag acc gcc tgc cgt gtt<br>Gly Gly Phe Ile Val Phe Asp Ser Val Thr Gln Thr Ala Cys Arg Val<br>2325                   2330                   2335 | | 7546 |
| tca gac cca ctt aag cgc ctg ttc aag ttg ggt aag ccg cta aca gct<br>Ser Asp Pro Leu Lys Arg Leu Phe Lys Leu Gly Lys Pro Leu Thr Ala<br>2340                   2345                   2350                 2355 | | 7594 |
| gaa gac aag cag gac gaa gac agg cga cga gca ctg agt gac gag gtt<br>Glu Asp Lys Gln Asp Glu Asp Arg Arg Arg Ala Leu Ser Asp Glu Val<br>        2360                     2365                 2370 | | 7642 |
| agc aag tgg ttc cgg aca ggc ttg ggg gcc gaa ctg gag gtg gca cta<br>Ser Lys Trp Phe Arg Thr Gly Leu Gly Ala Glu Leu Glu Val Ala Leu<br>2375                   2380                   2385 | | 7690 |
| aca tct agg tat gag gta gag ggc tgc aaa agt atc ctc ata gcc atg<br>Thr Ser Arg Tyr Glu Val Glu Gly Cys Lys Ser Ile Leu Ile Ala Met<br>        2390                     2395                 2400 | | 7738 |

```
gcc acc ttg gcg agg gac att aag gcg ttt aag aaa ttg aga gga cct       7786
Ala Thr Leu Ala Arg Asp Ile Lys Ala Phe Lys Lys Leu Arg Gly Pro
  2405                2410                2415 gtt ata cac ctc tac ggc ggt cct aga ttg gtg cgt taatacacag            7832
Val Ile His Leu Tyr Gly Gly Pro Arg Leu Val Arg
2420                2425                2430 aattctgatt ttaattaacc tgcagggttt aaactaatta attgaattac atccctacgc     7892
aaacgtttta cggccgccgg tggcgcccgc gccggcggc ccgtccttgg ccgttgcagg      7952
ccactccggt ggctcccgtc gtccccgact ccaggccca gcagatgcag caactcatca     8012
gcgccgtaaa tgcgctgaca atgagacaga acgcaattgc tcctgctagg cctcccaaac   8072
caaagaagaa gaagacaacc aaaccaaagc cgaaaacgca gcccaagaag atcaacggaa   8132
aaacgcagca gcaaaagaag aaagacaagc aagccgacaa gaagaagaag aaacccggaa   8192
aaagagaaag aatgtgcatg aagattgaaa atgactgtat cttcgtatgc ggctagccac   8252
agtaacgtag tgtttccaga catgtcgggc accgcactat catgggtgca gaaaatctcg   8312
ggtggtctgg gggccttcgc aatcggcgct atcctggtgc tggttgtggt cacttgcatt   8372
gggctccgca gataagttag ggtaggcaat ggcattgata tagcaagaaa attgaaaaca   8432
gaaaagttta gggtaagcaa tggcatataa ccataactgt ataacttgta acaaagcgca   8492
acaagacctg cgcaattggc cccgtggtcc gcctcacgga aactcggggc aactcatatt   8552
gacacattaa ttggcaataa ttggaagctt acataagctt aattcgacga ataattggat   8612
ttatatttta ttttgcaatt ggttttaat atttccaaaa aaaaaaaaa aaaaaaaaa       8672
aaaaaaaaaa aaaaaaaaaa aaaaaaaaaa aaaaaaaaaa aaaacgggt cggcatggca    8732
tctccacctc ctcgcggtcc gacctgggca tccgaaggag gacgcacgtc cactcggatg    8792
gctaagggag ttttctact agtcaaatga gtatatataa ttgaaaaagt aaaatataaa     8852
tcatataata atgaaacgaa atatcagtaa tagacaggaa ctggcagatt cttcttctaa   8912
tgaagtaagt actgctaaat ctccaaaatt agataaaaat gatacagcaa atacagcttc   8972
attcaacgaa ttaccttta atttttcag acacaccta ttacaaacta actaagtcag       9032
atgatgagaa agtaaatata aatttaactt atgggtataa tataataaag attcatgata   9092
ttaataattt acttaacgat gttaatagac ttattccatc aaccccttca aacctttctg   9152
gatattataa aataccagtt aatgatatta aaatagattg tttaagagat gtaaataatt   9212
atttggaggt aaaggatata aaattagtct atctttcaca tggaaatgaa ttacctaata   9272
ttaataatta tgataggaat ttttaggat ttacagctgt tatatgtatc aacaatacag    9332
gcagatctat ggttatggta aaacactgta acgggaagca gcattctatg gtaactggcc   9392
tatgtttaat agccagatca ttttactcta taaacatttt accacaaata ataggatcct   9452
ctagatattt aatattatat ctaacaacaa caaaaaaatt taacgatgta tggccagaag   9512
tattttctac taataaagat aaagatagtc tatcttatct acaagatatg aaagaagata   9572
atcatttagt agtagctact aatatggaaa gaaatgtata caaaaacgtg gaagcttta     9632
tattaaatag catattacta gaagatttaa aatctagact tagtataaca aaacagttaa   9692
atgccaatat cgattctata tttcatcata acagtagtac attaatcagt gatatactga   9752
aacgatctac agactcaact atgcaaggaa taagcaatat gccaattatg tctaatattt   9812
taactttaga actaaaacgt tctaccaata ctaaaaatag gatacgtgat aggctgttaa   9872
aagctgcaat aaatagtaag gatgtagaag aaatactttg ttctataccct tcggaggaaa   9932
gaactttaga acaacttaag tttaatcaaa cttgtattta tgaaggtac                9981
```

-continued

```
<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: Synthetic
      promoter sequence

<400> SEQUENCE: 3
acctctacgg cggtcctaga ttggtgcgtt aatacaca                          38

<210> SEQ ID NO 4
<211> LENGTH: 11661
<212> TYPE: DNA
<213> ORGANISM: Artificial Sequence
<220> FEATURE:
<223> OTHER INFORMATION: Description of Artificial Sequence: Synthetic
      pJY1099.1 DNA sequence
<220> FEATURE:
<221> NAME/KEY: CDS
<222> LOCATION: (530)..(7825)
<220> FEATURE:
<221> NAME/KEY: CDS
<222> LOCATION: (7854)..(9203)

<400> SEQUENCE: 4
ctatcaaaag tcttaatgag ttaggtgtag atagtataga tattactaca aaggtattca    60
tatttcctat caattctaaa gtagatgata ttaataactc aaagatgatg atagtagata   120
atagatacgc tcatataatg actgcaaatt tggacggttc acattttaat catcacgcgt   180
tcataagttt caactgcata gatcaaaatc tcactaaaaa gatagccgat gtatttgaga   240
gagattggac atctaactac gctaaagaaa ttacagttat aaataataca taatggattt   300
tgttatcatc agttatattt aacataagta caataaaaag tattaaataa aaatacttac   360
ttacgaaaaa atgactaatt agctataaaa acccgggttc tttattctat acttaaaaag   420
tgcaaataaa tacaaaggtt cttgatggcg gatgtgtgac atacacgacg ccaaaagatt   480
ttgttccagc tcctgccacc tccgctacgc gagagattaa ccacccacg atg gcc gcc   538
                                                        Met Ala Ala
                                                          1 aaa gtg cat gtt gat att gag gct gac agc cca ttc atc aag tct ttg      586
Lys Val His Val Asp Ile Glu Ala Asp Ser Pro Phe Ile Lys Ser Leu
       5                  10                  15 cag aag gca ttt ccg tcg ttc gag gtg gag tca ttg cag gtc aca cca      634
Gln Lys Ala Phe Pro Ser Phe Glu Val Glu Ser Leu Gln Val Thr Pro
 20                  25                  30                  35 aat gac cat gca aat gcc aga gca ttt tcg cac ctg gct acc aaa ttg      682
Asn Asp His Ala Asn Ala Arg Ala Phe Ser His Leu Ala Thr Lys Leu
                 40                  45                  50 atc gag cag gag act gac aaa gac aca ctc atc ttg gat atc ggc agt      730
Ile Glu Gln Glu Thr Asp Lys Asp Thr Leu Ile Leu Asp Ile Gly Ser
             55                  60                  65 gcg cct tcc agg aga atg atg tct acg cac aaa tac cac tgc gta tgc      778
Ala Pro Ser Arg Arg Met Met Ser Thr His Lys Tyr His Cys Val Cys
         70                  75                  80 cct atg cgc agc gca gaa gac ccc gaa agg ctc gta tgc tac gca aag      826
Pro Met Arg Ser Ala Glu Asp Pro Glu Arg Leu Val Cys Tyr Ala Lys
     85                  90                  95 aaa ctg gca gcg gcc tcc ggg aag gtg ctg gat aga gag atc gca gga      874
Lys Leu Ala Ala Ala Ser Gly Lys Val Leu Asp Arg Glu Ile Ala Gly
100                 105                 110                 115 aaa atc acc gac ctg cag acc gtc atg gct acg cca gac gct gaa tct      922
Lys Ile Thr Asp Leu Gln Thr Val Met Ala Thr Pro Asp Ala Glu Ser
                120                 125                 130
```

```
cct acc ttt tgc ctg cat aca gac gtc acg tgt cgt acg gca gcc gaa    970
Pro Thr Phe Cys Leu His Thr Asp Val Thr Cys Arg Thr Ala Ala Glu
            135                 140                 145 gtg gcc gta tac cag gac gtg tat gct gta cat gca cca aca tcg ctg   1018
Val Ala Val Tyr Gln Asp Val Tyr Ala Val His Ala Pro Thr Ser Leu
        150                 155                 160 tac cat cag gcg atg aaa ggt gtc aga acg gcg tat tgg att ggg ttt   1066
Tyr His Gln Ala Met Lys Gly Val Arg Thr Ala Tyr Trp Ile Gly Phe
    165                 170                 175 gac acc acc ccg ttt atg ttt gac gcg cta gca ggc gcg tat cca acc   1114
Asp Thr Thr Pro Phe Met Phe Asp Ala Leu Ala Gly Ala Tyr Pro Thr
180                 185                 190                 195 tac gcc aca aac tgg gcc gac gag cag gtg tta cag gcc agg aac ata   1162
Tyr Ala Thr Asn Trp Ala Asp Glu Gln Val Leu Gln Ala Arg Asn Ile
                200                 205                 210 gga ctg tgt gca gca tcc ttg act gag gga aga ctc ggc aaa ctg tcc   1210
Gly Leu Cys Ala Ala Ser Leu Thr Glu Gly Arg Leu Gly Lys Leu Ser
            215                 220                 225 att ctc cgc aag aag caa ttg aaa cct tgc gac aca gtc atg ttc tcg   1258
Ile Leu Arg Lys Lys Gln Leu Lys Pro Cys Asp Thr Val Met Phe Ser
        230                 235                 240 gta gga tct aca ttg tac act gag agc aga aag cta ctg agg agc tgg   1306
Val Gly Ser Thr Leu Tyr Thr Glu Ser Arg Lys Leu Leu Arg Ser Trp
    245                 250                 255 cac tta ccc tcc gta ttc cac ctg aaa ggt aaa caa tcc ttt acc tgt   1354
His Leu Pro Ser Val Phe His Leu Lys Gly Lys Gln Ser Phe Thr Cys
260                 265                 270                 275 agg tgc gat acc atc gta tca tgt gaa ggg tac gta gtt aag aaa atc   1402
Arg Cys Asp Thr Ile Val Ser Cys Glu Gly Tyr Val Val Lys Lys Ile
                280                 285                 290 act atg tgc ccc ggc ctg tac ggt aaa acg gta ggg tac gcc gtg acg   1450
Thr Met Cys Pro Gly Leu Tyr Gly Lys Thr Val Gly Tyr Ala Val Thr
            295                 300                 305 tat cac gcg gag gga ttc cta gtg tgc aag acc aca gac act gtc aaa   1498
Tyr His Ala Glu Gly Phe Leu Val Cys Lys Thr Thr Asp Thr Val Lys
        310                 315                 320 gga gaa aga gtc tca ttc cct gta tgc acc tac gtc ccc tca acc atc   1546
Gly Glu Arg Val Ser Phe Pro Val Cys Thr Tyr Val Pro Ser Thr Ile
    325                 330                 335 tgt gat caa atg act ggc ata cta gcg acc gac gtc aca ccg gag gac   1594
Cys Asp Gln Met Thr Gly Ile Leu Ala Thr Asp Val Thr Pro Glu Asp
340                 345                 350                 355 gca cag aag ttg tta gtg gga ttg aat cag agg ata gtt gtg aac gga   1642
Ala Gln Lys Leu Leu Val Gly Leu Asn Gln Arg Ile Val Val Asn Gly
                360                 365                 370 aga aca cag cga aac act aac acg atg aag aac tat ctg ctt ccg att   1690
Arg Thr Gln Arg Asn Thr Asn Thr Met Lys Asn Tyr Leu Leu Pro Ile
            375                 380                 385 gtg gcc gtc gca ttt agc aag tgg gcg agg gaa tac aag gca gac ctt   1738
Val Ala Val Ala Phe Ser Lys Trp Ala Arg Glu Tyr Lys Ala Asp Leu
        390                 395                 400 gat gat gaa aaa cct ctg ggt gtc cga gag agg tca ctt act tgc tgc   1786
Asp Asp Glu Lys Pro Leu Gly Val Arg Glu Arg Ser Leu Thr Cys Cys
    405                 410                 415 tgc ttg tgg gca ttt aaa acg agg aag atg cac acc atg tac aag aaa   1834
Cys Leu Trp Ala Phe Lys Thr Arg Lys Met His Thr Met Tyr Lys Lys
420                 425                 430                 435 cca gac acc cag aca ata gtg aag gtg cct tca gag ttt aac tcg ttc   1882
Pro Asp Thr Gln Thr Ile Val Lys Val Pro Ser Glu Phe Asn Ser Phe
                440                 445                 450
```

| | | | | | | | | | | | | | | | | |
|---|---|---|---|---|---|---|---|---|---|---|---|---|---|---|---|---|
| gtc | atc | ccg | agc | cta | tgg | tct | aca | ggc | ctc | gca | atc | cca | gtc | aga | tca | 1930 |
| Val | Ile | Pro | Ser | Leu | Trp | Ser | Thr | Gly | Leu | Ala | Ile | Pro | Val | Arg | Ser | |
| | | | 455 | | | | | 460 | | | | | 465 | | | |
| cgc | att | aag | atg | ctt | ttg | gcc | aag | aag | acc | aag | cga | gag | tta | ata | cct | 1978 |
| Arg | Ile | Lys | Met | Leu | Leu | Ala | Lys | Lys | Thr | Lys | Arg | Glu | Leu | Ile | Pro | |
| | 470 | | | | | 475 | | | | | 480 | | | | | |
| gtt | ctc | gac | gcg | tcg | tca | gcc | agg | gat | gct | gaa | caa | gag | gag | aag | gag | 2026 |
| Val | Leu | Asp | Ala | Ser | Ser | Ala | Arg | Asp | Ala | Glu | Gln | Glu | Glu | Lys | Glu | |
| | 485 | | | | | 490 | | | | | 495 | | | | | |
| agg | ttg | gag | gcc | gag | ctg | act | aga | gaa | gcc | tta | cca | ccc | ctc | gtc | ccc | 2074 |
| Arg | Leu | Glu | Ala | Glu | Leu | Thr | Arg | Glu | Ala | Leu | Pro | Pro | Leu | Val | Pro | |
| 500 | | | | | 505 | | | | | 510 | | | | | 515 | |
| atc | gcg | ccg | gcg | gag | acg | gga | gtc | gtc | gac | gtc | gac | gtt | gaa | gaa | cta | 2122 |
| Ile | Ala | Pro | Ala | Glu | Thr | Gly | Val | Val | Asp | Val | Asp | Val | Glu | Glu | Leu | |
| | | | | 520 | | | | | 525 | | | | | 530 | | |
| gag | tat | cac | gca | ggt | gca | ggg | gtc | gtg | gaa | aca | cct | cgc | agc | gcg | ttg | 2170 |
| Glu | Tyr | His | Ala | Gly | Ala | Gly | Val | Val | Glu | Thr | Pro | Arg | Ser | Ala | Leu | |
| | | | 535 | | | | | 540 | | | | | 545 | | | |
| aaa | gtc | acc | gca | cag | ccg | aac | gac | gta | cta | cta | gga | aat | tac | gta | gtt | 2218 |
| Lys | Val | Thr | Ala | Gln | Pro | Asn | Asp | Val | Leu | Leu | Gly | Asn | Tyr | Val | Val | |
| | | 550 | | | | | 555 | | | | | 560 | | | | |
| ctg | tcc | ccg | cag | acc | gtg | ctc | aag | agc | tcc | aag | ttg | gcc | ccc | gtg | cac | 2266 |
| Leu | Ser | Pro | Gln | Thr | Val | Leu | Lys | Ser | Ser | Lys | Leu | Ala | Pro | Val | His | |
| | 565 | | | | | 570 | | | | | 575 | | | | | |
| cct | cta | gca | gag | cag | gtg | aaa | ata | ata | aca | cat | aac | ggg | agg | gcc | ggc | 2314 |
| Pro | Leu | Ala | Glu | Gln | Val | Lys | Ile | Ile | Thr | His | Asn | Gly | Arg | Ala | Gly | |
| 580 | | | | | 585 | | | | | 590 | | | | | 595 | |
| cgt | tac | cag | gtc | gac | gga | tat | gac | ggc | agg | gtc | cta | cta | cca | tgt | gga | 2362 |
| Arg | Tyr | Gln | Val | Asp | Gly | Tyr | Asp | Gly | Arg | Val | Leu | Leu | Pro | Cys | Gly | |
| | | | | 600 | | | | | 605 | | | | | 610 | | |
| tcg | gcc | att | ccg | gtc | cct | gag | ttt | caa | gct | ttg | agc | gag | agc | gcc | act | 2410 |
| Ser | Ala | Ile | Pro | Val | Pro | Glu | Phe | Gln | Ala | Leu | Ser | Glu | Ser | Ala | Thr | |
| | | | 615 | | | | | 620 | | | | | 625 | | | |
| atg | gtg | tac | aac | gaa | agg | gag | ttc | gtc | aac | agg | aaa | cta | tac | cat | att | 2458 |
| Met | Val | Tyr | Asn | Glu | Arg | Glu | Phe | Val | Asn | Arg | Lys | Leu | Tyr | His | Ile | |
| | | | 630 | | | | | 635 | | | | | 640 | | | |
| gcc | gtt | cac | gga | ccg | tcg | ctg | aac | acc | gac | gag | gag | aac | tac | gag | aaa | 2506 |
| Ala | Val | His | Gly | Pro | Ser | Leu | Asn | Thr | Asp | Glu | Glu | Asn | Tyr | Glu | Lys | |
| | 645 | | | | | 650 | | | | | 655 | | | | | |
| gtc | aga | gct | gaa | aga | act | gac | gcc | gag | tac | gtg | ttc | gac | gta | gat | aaa | 2554 |
| Val | Arg | Ala | Glu | Arg | Thr | Asp | Ala | Glu | Tyr | Val | Phe | Asp | Val | Asp | Lys | |
| 660 | | | | | 665 | | | | | 670 | | | | | 675 | |
| aaa | tgc | tgc | gtc | aag | aga | gag | gaa | gcg | tcg | ggt | ttg | gtg | ttg | gtg | gga | 2602 |
| Lys | Cys | Cys | Val | Lys | Arg | Glu | Glu | Ala | Ser | Gly | Leu | Val | Leu | Val | Gly | |
| | | | | 680 | | | | | 685 | | | | | 690 | | |
| gag | cta | acc | aac | ccc | ccg | ttc | cat | gaa | ttc | gcc | tac | gaa | ggg | ctg | aag | 2650 |
| Glu | Leu | Thr | Asn | Pro | Pro | Phe | His | Glu | Phe | Ala | Tyr | Glu | Gly | Leu | Lys | |
| | | | | 695 | | | | | 700 | | | | | 705 | | |
| atc | agg | ccg | tcg | gca | cca | tat | aag | act | aca | gta | gta | gga | gtc | ttt | ggg | 2698 |
| Ile | Arg | Pro | Ser | Ala | Pro | Tyr | Lys | Thr | Thr | Val | Val | Gly | Val | Phe | Gly | |
| | | 710 | | | | | 715 | | | | | 720 | | | | |
| gtt | ccg | gga | tca | ggc | aag | tct | gct | att | att | aag | agc | ctc | gtg | acc | aaa | 2746 |
| Val | Pro | Gly | Ser | Gly | Lys | Ser | Ala | Ile | Ile | Lys | Ser | Leu | Val | Thr | Lys | |
| | 725 | | | | | 730 | | | | | 735 | | | | | |
| cac | gat | ctg | gtc | acc | agc | ggc | aag | aag | gag | aac | tgc | cag | gaa | ata | gtc | 2794 |
| His | Asp | Leu | Val | Thr | Ser | Gly | Lys | Lys | Glu | Asn | Cys | Gln | Glu | Ile | Val | |
| 740 | | | | | 745 | | | | | 750 | | | | | 755 | |
| aac | gac | gtg | aag | aag | cac | cgc | gga | ctg | gac | atc | cag | gca | aaa | aca | gtg | 2842 |
| Asn | Asp | Val | Lys | Lys | His | Arg | Gly | Leu | Asp | Ile | Gln | Ala | Lys | Thr | Val | |
| | | | | 760 | | | | | 765 | | | | | 770 | | |

```
gac tcc atc ctg cta aac ggg tgt cgt cgt gcc gtg gac atc cta tat      2890
Asp Ser Ile Leu Leu Asn Gly Cys Arg Arg Ala Val Asp Ile Leu Tyr
            775                 780                 785 gtg gac gag gct ttc gct tgc cat ccc ggt act ctg gcc cta att          2938
Val Asp Glu Ala Phe Ala Cys His Pro Gly Thr Leu Ala Leu Ile
        790                 795                 800 gct ctt gtt aaa cct cgg agc aaa gtg gtg tta tgc gga gac ccc aag      2986
Ala Leu Val Lys Pro Arg Ser Lys Val Val Leu Cys Gly Asp Pro Lys
805                 810                 815 caa tgc gga ttc ttc aat atg atg cag ctt aag gtg aac ttc aac cac      3034
Gln Cys Gly Phe Phe Asn Met Met Gln Leu Lys Val Asn Phe Asn His
820                 825                 830                 835 aac atc tgc act gaa gta tgt cat aaa agt ata tcc aga cgt tgc acg      3082
Asn Ile Cys Thr Glu Val Cys His Lys Ser Ile Ser Arg Arg Cys Thr
            840                 845                 850 cgt cca gtc acg gcc atc gtg tct acg ttg cac tac gga ggc aag atg      3130
Arg Pro Val Thr Ala Ile Val Ser Thr Leu His Tyr Gly Gly Lys Met
        855                 860                 865 cgc acg acc aac ccg tgc aac aaa ccc ata atc ata gac acc aca gga      3178
Arg Thr Thr Asn Pro Cys Asn Lys Pro Ile Ile Ile Asp Thr Thr Gly
    870                 875                 880 cag acc aag ccc aag cca gga gac atc gtg tta aca tgc ttc cga ggc      3226
Gln Thr Lys Pro Lys Pro Gly Asp Ile Val Leu Thr Cys Phe Arg Gly
885                 890                 895 tgg gta aag cag ctg cag ttg gac tac cgt gga cac gaa gtc atg aca      3274
Trp Val Lys Gln Leu Gln Leu Asp Tyr Arg Gly His Glu Val Met Thr
900                 905                 910                 915 gca gca gca tct cag ggc ctc acc cgc aaa ggg gta tac gcc gta agg      3322
Ala Ala Ala Ser Gln Gly Leu Thr Arg Lys Gly Val Tyr Ala Val Arg
            920                 925                 930 cag aag gtg aat gaa aat ccc ttg tat gcc cct gcg tcg gag cac gtg      3370
Gln Lys Val Asn Glu Asn Pro Leu Tyr Ala Pro Ala Ser Glu His Val
        935                 940                 945 aat gta ctg ctg acg cgc act gag gat agg ctg gtg tgg aaa acg ctg      3418
Asn Val Leu Leu Thr Arg Thr Glu Asp Arg Leu Val Trp Lys Thr Leu
    950                 955                 960 gcc ggc gat ccc tgg att aag gtc cta tca aac att cca cag ggt aac      3466
Ala Gly Asp Pro Trp Ile Lys Val Leu Ser Asn Ile Pro Gln Gly Asn
965                 970                 975 ttt acg gcc aca ttg gaa gaa tgg caa gaa gaa cac gac aaa ata atg      3514
Phe Thr Ala Thr Leu Glu Glu Trp Gln Glu Glu His Asp Lys Ile Met
980                 985                 990                 995 aag gtg att gaa gga ccg gct gcg cct gtg gac gcg ttc cag aac aaa      3562
Lys Val Ile Glu Gly Pro Ala Ala Pro Val Asp Ala Phe Gln Asn Lys
            1000                1005                1010 gcg aac gtg tgt tgg gcg aaa agc ctg gtg cct gtc ctg gac act gcc      3610
Ala Asn Val Cys Trp Ala Lys Ser Leu Val Pro Val Leu Asp Thr Ala
        1015                1020                1025 gga atc aga ttg aca gca gag gag tgg agc acc ata att aca gca ttt      3658
Gly Ile Arg Leu Thr Ala Glu Glu Trp Ser Thr Ile Ile Thr Ala Phe
    1030                1035                1040 aag gag gac aga gct tac tct cca gtg gtg gcc ttg aat gaa att tgc      3706
Lys Glu Asp Arg Ala Tyr Ser Pro Val Val Ala Leu Asn Glu Ile Cys
1045                1050                1055 acc aag tac tat gga gtt gac ctg gac agt ggc ctg ttt tct gcc ccg      3754
Thr Lys Tyr Tyr Gly Val Asp Leu Asp Ser Gly Leu Phe Ser Ala Pro
1060                1065                1070                1075 aag gtg tcc ctg tat tac gag aac aac cac tgg gat aac aga cct ggt      3802
Lys Val Ser Leu Tyr Tyr Glu Asn Asn His Trp Asp Asn Arg Pro Gly
            1080                1085                1090
```

```
gga agg atg tat gga ttc aat gcc gca aca gct gcc agg ctg gaa gct    3850
Gly Arg Met Tyr Gly Phe Asn Ala Ala Thr Ala Ala Arg Leu Glu Ala
            1095                1100                1105 aga cat acc ttc ctg aag ggg cag tgg cat acg ggc aag cag gca gtt    3898
Arg His Thr Phe Leu Lys Gly Gln Trp His Thr Gly Lys Gln Ala Val
        1110                1115                1120 atc gca gaa aga aaa atc caa ccg ctt tct gtg ctg gac aat gta att    3946
Ile Ala Glu Arg Lys Ile Gln Pro Leu Ser Val Leu Asp Asn Val Ile
    1125                1130                1135 cct atc aac cgc agg ctg ccg cac gcc ctg gtg gct gag tac aag acg    3994
Pro Ile Asn Arg Arg Leu Pro His Ala Leu Val Ala Glu Tyr Lys Thr
1140                1145                1150                1155 gtt aaa ggc agt agg gtt gag tgg ctg gtc aat aaa gta aga ggg tac    4042
Val Lys Gly Ser Arg Val Glu Trp Leu Val Asn Lys Val Arg Gly Tyr
            1160                1165                1170 cac gtc ctg ctg gtg agt gag tac aac ctg gct ttg cct cga cgc gac    4090
His Val Leu Leu Val Ser Glu Tyr Asn Leu Ala Leu Pro Arg Arg Asp
        1175                1180                1185 gtc act tgg ttg tca ccg ctg aat gtc aca ggc gcc gat agg tgc tac    4138
Val Thr Trp Leu Ser Pro Leu Asn Val Thr Gly Ala Asp Arg Cys Tyr
    1190                1195                1200 gac cta agt tta gga ctg ccg gct gac gcc ggc agg ttc gac ttg gtc    4186
Asp Leu Ser Leu Gly Leu Pro Ala Asp Ala Gly Arg Phe Asp Leu Val
1205                1210                1215 ttt gtg aac att cac acg gaa ttc aga atc cac cac tac cag cag tgt    4234
Phe Val Asn Ile His Thr Glu Phe Arg Ile His His Tyr Gln Gln Cys
1220                1225                1230                1235 gtc gac cac gcc atg aag ctg cag atg ctt ggg gga gat gcg cta cga    4282
Val Asp His Ala Met Lys Leu Gln Met Leu Gly Gly Asp Ala Leu Arg
            1240                1245                1250 ctg cta aaa ccc ggc ggc agc ctc ttg atg aga gct tac gga tac gcc    4330
Leu Leu Lys Pro Gly Gly Ser Leu Leu Met Arg Ala Tyr Gly Tyr Ala
        1255                1260                1265 gat aaa atc agc gaa gcc gtt gtt tcc tcc tta agc aga aag ttc tcg    4378
Asp Lys Ile Ser Glu Ala Val Val Ser Ser Leu Ser Arg Lys Phe Ser
    1270                1275                1280 tct gca aga gtg ttg cgc ccg gat tgt gtc acc agc aat aca gaa gtg    4426
Ser Ala Arg Val Leu Arg Pro Asp Cys Val Thr Ser Asn Thr Glu Val
1285                1290                1295 ttc ttg ctg ttc tcc aac ttt gac aac gga aag aga ccc tct acg cta    4474
Phe Leu Leu Phe Ser Asn Phe Asp Asn Gly Lys Arg Pro Ser Thr Leu
1300                1305                1310                1315 cac cag atg aat acc aag ctg agt gcc gtg tat gcc gga gaa gcc atg    4522
His Gln Met Asn Thr Lys Leu Ser Ala Val Tyr Ala Gly Glu Ala Met
            1320                1325                1330 cac acg gcc ggg tgt gca cca tcc tac aga gtt aag aga gca gac ata    4570
His Thr Ala Gly Cys Ala Pro Ser Tyr Arg Val Lys Arg Ala Asp Ile
        1335                1340                1345 gcc acg tgc aca gaa gcg gct gtg gtt aac gca gct aac gcc cgt gga    4618
Ala Thr Cys Thr Glu Ala Ala Val Val Asn Ala Ala Asn Ala Arg Gly
    1350                1355                1360 act gta ggg gat ggc gta tgc agg gcc gtg gcg aag aaa tgg ccg tca    4666
Thr Val Gly Asp Gly Val Cys Arg Ala Val Ala Lys Lys Trp Pro Ser
1365                1370                1375 gcc ttt aag gga gaa gca aca cca gtg ggc aca att aaa aca gtc atg    4714
Ala Phe Lys Gly Glu Ala Thr Pro Val Gly Thr Ile Lys Thr Val Met
1380                1385                1390                1395 tgc ggc tcg tac ccc gtc atc cac gct gta gcg cct aat ttc tct gcc    4762
Cys Gly Ser Tyr Pro Val Ile His Ala Val Ala Pro Asn Phe Ser Ala
            1400                1405                1410
```

| | | |
|---|---|---|
| acg act gaa gcg gaa ggg gac cgc gaa ttg gcc gct gtc tac cgg gca<br>Thr Thr Glu Ala Glu Gly Asp Arg Glu Leu Ala Ala Val Tyr Arg Ala<br>              1415                            1420                        1425 | 4810 |
| gtg gcc gcc gaa gta aac aga ctg tca ctg agc agc gta gcc atc ccg<br>Val Ala Ala Glu Val Asn Arg Leu Ser Leu Ser Ser Val Ala Ile Pro<br>1430                        1435                        1440 | 4858 |
| ctg ctg tcc aca gga gtg ttc agc ggc gga aga gat agg ctg cag caa<br>Leu Leu Ser Thr Gly Val Phe Ser Gly Gly Arg Asp Arg Leu Gln Gln<br>      1445                        1450                        1455 | 4906 |
| tcc ctc aac cat cta ttc aca gca atg gac gcc acg gac gct gac gtg<br>Ser Leu Asn His Leu Phe Thr Ala Met Asp Ala Thr Asp Ala Asp Val<br>1460                        1465                        1470                        1475 | 4954 |
| acc atc tac tgc aga gac aaa agt tgg gag aag aaa atc cag gaa gcc<br>Thr Ile Tyr Cys Arg Asp Lys Ser Trp Glu Lys Lys Ile Gln Glu Ala<br>              1480                          1485                        1490 | 5002 |
| ata gac atg agg acg gct gtg gag ttg ctc aat gat gac gtg gag ctg<br>Ile Asp Met Arg Thr Ala Val Glu Leu Leu Asn Asp Asp Val Glu Leu<br>                  1495                        1500                        1505 | 5050 |
| acc aca gac ttg gtg aga gtg cac ccg gac agc agc ctg gtg ggt cgt<br>Thr Thr Asp Leu Val Arg Val His Pro Asp Ser Ser Leu Val Gly Arg<br>          1510                        1515                        1520 | 5098 |
| aag ggc tac agt acc act gac ggg tcg ctg tac tcg tac ttt gaa ggt<br>Lys Gly Tyr Ser Thr Thr Asp Gly Ser Leu Tyr Ser Tyr Phe Glu Gly<br>              1525                          1530                        1535 | 5146 |
| acg aaa ttc aac cag gct gct att gat atg gca gag ata ctg acg ttg<br>Thr Lys Phe Asn Gln Ala Ala Ile Asp Met Ala Glu Ile Leu Thr Leu<br>1540                        1545                        1550                        1555 | 5194 |
| tgg ccc aga ctg caa gag gca aac gaa cag ata tgc cta tac gcg ctg<br>Trp Pro Arg Leu Gln Glu Ala Asn Glu Gln Ile Cys Leu Tyr Ala Leu<br>                  1560                        1565                        1570 | 5242 |
| ggc gaa aca atg gac aac atc aga tcc aaa tgt ccg gtg aac gat tcc<br>Gly Glu Thr Met Asp Asn Ile Arg Ser Lys Cys Pro Val Asn Asp Ser<br>            1575                        1580                        1585 | 5290 |
| gat tca tca aca cct ccc agg aca gtg ccc tgc ctg tgc cgc tac gca<br>Asp Ser Ser Thr Pro Pro Arg Thr Val Pro Cys Leu Cys Arg Tyr Ala<br>        1590                        1595                        1600 | 5338 |
| atg aca gca gaa cgg atc gcc cgc ctt agg tca cac caa gtt aaa agc<br>Met Thr Ala Glu Arg Ile Ala Arg Leu Arg Ser His Gln Val Lys Ser<br>1605                        1610                        1615 | 5386 |
| atg gtg gtt tgc tca tct ttt ccc ctc ccg aaa tac cat gta gat ggg<br>Met Val Val Cys Ser Ser Phe Pro Leu Pro Lys Tyr His Val Asp Gly<br>1620                        1625                        1630                        1635 | 5434 |
| gtg cag aag gta aag tgc gag aag gtt ctc ctg ttc gac ccg acg gta<br>Val Gln Lys Val Lys Cys Glu Lys Val Leu Leu Phe Asp Pro Thr Val<br>                  1640                        1645                        1650 | 5482 |
| cct tca gtg gtt agt ccg cgg aag tat gcc gca tct acg acg gac cac<br>Pro Ser Val Val Ser Pro Arg Lys Tyr Ala Ala Ser Thr Thr Asp His<br>              1655                          1660                        1665 | 5530 |
| tca gat cgg tcg tta cga ggg ttt gac ttg gac tgg acc acc gac tcg<br>Ser Asp Arg Ser Leu Arg Gly Phe Asp Leu Asp Trp Thr Thr Asp Ser<br>            1670                        1675                        1680 | 5578 |
| tct tcc act gcc agc gat acc atg tcg cta ccc agt ttg cag tcg tgt<br>Ser Ser Thr Ala Ser Asp Thr Met Ser Leu Pro Ser Leu Gln Ser Cys<br>        1685                        1690                        1695 | 5626 |
| gac atc gac tcg atc tac gag cca atg gct ccc ata gta gtg acg gct<br>Asp Ile Asp Ser Ile Tyr Glu Pro Met Ala Pro Ile Val Val Thr Ala<br>1700                        1705                        1710                        1715 | 5674 |
| gac gta cac cct gaa ccc gca ggc atc gcg gac ctg gcg gca gat gtg<br>Asp Val His Pro Glu Pro Ala Gly Ile Ala Asp Leu Ala Ala Asp Val<br>                  1720                        1725                        1730 | 5722 |

```
cat cct gaa ccc gca gac cat gtg gac ctc gag aac ccg att cct cca      5770
His Pro Glu Pro Ala Asp His Val Asp Leu Glu Asn Pro Ile Pro Pro
        1735                1740                1745 ccg cgc ccg aag aga gct gca tac ctt gcc tcc cgc gcg gcg gag cga      5818
Pro Arg Pro Lys Arg Ala Ala Tyr Leu Ala Ser Arg Ala Ala Glu Arg
    1750                1755                1760 ccg gtg ccg gcg ccg aga aag ccg acg cct gcc cca agg act gcg ttt      5866
Pro Val Pro Ala Pro Arg Lys Pro Thr Pro Ala Pro Arg Thr Ala Phe
1765                1770                1775 agg aac aag ctg cct ttg acg ttc ggc gac ttt gac gag cac gag gtc      5914
Arg Asn Lys Leu Pro Leu Thr Phe Gly Asp Phe Asp Glu His Glu Val
            1780                1785                1790                1795 gat gcg ttg gcc tcc ggg att act ttc gga gac ttc gac gac gtc ctg      5962
Asp Ala Leu Ala Ser Gly Ile Thr Phe Gly Asp Phe Asp Asp Val Leu
                    1800                1805                1810 cga cta ggc cgc gcg ggt gca tat att ttc tcc tcg gac act ggc agc      6010
Arg Leu Gly Arg Ala Gly Ala Tyr Ile Phe Ser Ser Asp Thr Gly Ser
    1815                1820                1825 gga cat tta caa caa aaa tcc gtt agg cag cac aat ctc cag tgc gca      6058
Gly His Leu Gln Gln Lys Ser Val Arg Gln His Asn Leu Gln Cys Ala
        1830                1835                1840 caa ctg gat gcg gtc gag gag gag aaa atg tac ccg cca aaa ttg gat      6106
Gln Leu Asp Ala Val Glu Glu Glu Lys Met Tyr Pro Pro Lys Leu Asp
    1845                1850                1855 act gag agg gag aag ctg ttg ctg ctg aaa atg cag atg cac cca tcg      6154
Thr Glu Arg Glu Lys Leu Leu Leu Leu Lys Met Gln Met His Pro Ser
1860                1865                1870                1875 gag gct aat aag agt cga tac cag tct cgc aaa gtg gag aac atg aaa      6202
Glu Ala Asn Lys Ser Arg Tyr Gln Ser Arg Lys Val Glu Asn Met Lys
            1880                1885                1890 gcc acg gtg gtg gac agg ctc aca tcg ggg gcc aga ttg tac acg gga      6250
Ala Thr Val Val Asp Arg Leu Thr Ser Gly Ala Arg Leu Tyr Thr Gly
                1895                1900                1905 gcg gac gta ggc cgc ata cca aca tac gcg gtt cgg tac ccc cgc ccc      6298
Ala Asp Val Gly Arg Ile Pro Thr Tyr Ala Val Arg Tyr Pro Arg Pro
    1910                1915                1920 gtg tac tcc cct acc gtg atc gaa aga ttc tca agc ccc gat gta gca      6346
Val Tyr Ser Pro Thr Val Ile Glu Arg Phe Ser Ser Pro Asp Val Ala
    1925                1930                1935 atc gca gcg tgc aac gaa tac cta tcc aga aat tac cca aca gtg gcg      6394
Ile Ala Ala Cys Asn Glu Tyr Leu Ser Arg Asn Tyr Pro Thr Val Ala
1940                1945                1950                1955 tcg tac cag ata aca gat gaa tac gac gca tac ttg gac atg gtt gac      6442
Ser Tyr Gln Ile Thr Asp Glu Tyr Asp Ala Tyr Leu Asp Met Val Asp
            1960                1965                1970 ggg tcg gat agt tgc ttg gac aga gcg aca ttc tgc ccg gcg aag ctc      6490
Gly Ser Asp Ser Cys Leu Asp Arg Ala Thr Phe Cys Pro Ala Lys Leu
                1975                1980                1985 cgg tgc tac ccg aaa cat cat gcg tac cac cag ccg act gta cgc agt      6538
Arg Cys Tyr Pro Lys His His Ala Tyr His Gln Pro Thr Val Arg Ser
    1990                1995                2000 gcc gtc ccg tca ccc ttt cag aac aca cta cag aac gtg cta gcg gcc      6586
Ala Val Pro Ser Pro Phe Gln Asn Thr Leu Gln Asn Val Leu Ala Ala
    2005                2010                2015 gcc acc aag aga aac tgc aac gtc acg caa atg cga gaa cta ccc acc      6634
Ala Thr Lys Arg Asn Cys Asn Val Thr Gln Met Arg Glu Leu Pro Thr
2020                2025                2030                2035 atg gac tcg gca gtg ttc aac gtg gag tgc ttc aag cgc tat gcc tgc      6682
Met Asp Ser Ala Val Phe Asn Val Glu Cys Phe Lys Arg Tyr Ala Cys
            2040                2045                2050
```

```
tcc gga gaa tat tgg gaa gaa tat gct aaa caa cct atc cgg ata acc      6730
Ser Gly Glu Tyr Trp Glu Glu Tyr Ala Lys Gln Pro Ile Arg Ile Thr
        2055                2060                2065 act gag aac atc act acc tat gtg acc aaa ttg aaa ggc ccg aaa gct      6778
Thr Glu Asn Ile Thr Thr Tyr Val Thr Lys Leu Lys Gly Pro Lys Ala
2070                2075                2080 gct gcc ttg ttc gct aag acc cac aac ttg gtt ccg ctg cag gag gtt      6826
Ala Ala Leu Phe Ala Lys Thr His Asn Leu Val Pro Leu Gln Glu Val
            2085                2090                2095 ccc atg gac aga ttc acg gtc gac atg aaa cga gat gtc aaa gtc act      6874
Pro Met Asp Arg Phe Thr Val Asp Met Lys Arg Asp Val Lys Val Thr
2100                2105                2110                2115 cca ggg acg aaa cac aca gag gaa aga ccc aaa gtc cag gta att caa      6922
Pro Gly Thr Lys His Thr Glu Glu Arg Pro Lys Val Gln Val Ile Gln
            2120                2125                2130 gca gcg gag cca ttg gcg acc gct tac ctg tgc ggc atc cac agg gaa      6970
Ala Ala Glu Pro Leu Ala Thr Ala Tyr Leu Cys Gly Ile His Arg Glu
        2135                2140                2145 tta gta agg aga cta aat gct gtg tta cgc cct aac gtg cac aca ttg      7018
Leu Val Arg Arg Leu Asn Ala Val Leu Arg Pro Asn Val His Thr Leu
            2150                2155                2160 ttt gat atg tcg gcc gaa gac ttt gac gcg atc atc gcc tct cac ttc      7066
Phe Asp Met Ser Ala Glu Asp Phe Asp Ala Ile Ile Ala Ser His Phe
    2165                2170                2175 cac cca gga gac ccg gtt cta gag acg gac att gca tca ttc gac aaa      7114
His Pro Gly Asp Pro Val Leu Glu Thr Asp Ile Ala Ser Phe Asp Lys
2180                2185                2190                2195 agc cag gac gac tcc ttg gct ctt aca ggt tta atg atc ctc gaa gat      7162
Ser Gln Asp Asp Ser Leu Ala Leu Thr Gly Leu Met Ile Leu Glu Asp
            2200                2205                2210 cta ggg gtg gat cag tac ctg ctg gac ttg atc gag gca gcc ttt ggg      7210
Leu Gly Val Asp Gln Tyr Leu Leu Asp Leu Ile Glu Ala Ala Phe Gly
        2215                2220                2225 gaa ata tcc agc tgt cac cta cca act ggc acg cgc ttc aag ttc gga      7258
Glu Ile Ser Ser Cys His Leu Pro Thr Gly Thr Arg Phe Lys Phe Gly
            2230                2235                2240 gct atg atg aaa tcg ggc atg ttt ctg act ttg ttt att aac act gtt      7306
Ala Met Met Lys Ser Gly Met Phe Leu Thr Leu Phe Ile Asn Thr Val
    2245                2250                2255 ttg aac atc acc ata gca agc agg gta ctg gag cag aga ctc act gac      7354
Leu Asn Ile Thr Ile Ala Ser Arg Val Leu Glu Gln Arg Leu Thr Asp
2260                2265                2270                2275 tcc gcc tgt gcg gcc ttc atc ggc gac gac aac atc gtt cac gga gtg      7402
Ser Ala Cys Ala Ala Phe Ile Gly Asp Asp Asn Ile Val His Gly Val
            2280                2285                2290 atc tcc gac aag ctg atg gcg gag agg tgc gcg tcg tgg gtc aac atg      7450
Ile Ser Asp Lys Leu Met Ala Glu Arg Cys Ala Ser Trp Val Asn Met
        2295                2300                2305 gag gtg aag atc att gac gct gtc atg ggc gaa aaa ccc cca tat ttc      7498
Glu Val Lys Ile Ile Asp Ala Val Met Gly Glu Lys Pro Pro Tyr Phe
            2310                2315                2320 tgt ggg gga ttc ata gtt ttt gac agc gtc aca cag acc gcc tgc cgt      7546
Cys Gly Gly Phe Ile Val Phe Asp Ser Val Thr Gln Thr Ala Cys Arg
    2325                2330                2335 gtt tca gac cca ctt aag cgc ctg ttc aag ttg ggt aag ccg cta aca      7594
Val Ser Asp Pro Leu Lys Arg Leu Phe Lys Leu Gly Lys Pro Leu Thr
2340                2345                2350                2355 gct gaa gac aag cag gac gaa gac agg cga cga gca ctg agt gac gag      7642
Ala Glu Asp Lys Gln Asp Glu Asp Arg Arg Arg Ala Leu Ser Asp Glu
            2360                2365                2370
```

| | |
|---|---|
| gtt agc aag tgg ttc cgg aca ggc ttg ggg gcc gaa ctg gag gtg gca<br>Val Ser Lys Trp Phe Arg Thr Gly Leu Gly Ala Glu Leu Glu Val Ala<br>      2375                 2380                 2385 | 7690 |
| cta aca tct agg tat gag gta gag ggc tgc aaa agt atc ctc ata gcc<br>Leu Thr Ser Arg Tyr Glu Val Glu Gly Cys Lys Ser Ile Leu Ile Ala<br>     2390                2395                 2400 | 7738 |
| atg gcc acc ttg gcg agg gac att aag gcg ttt aag aaa ttg aga gga<br>Met Ala Thr Leu Ala Arg Asp Ile Lys Ala Phe Lys Lys Leu Arg Gly<br>2405                2410                 2415 | 7786 |
| cct gtt ata cac ctc tac ggc ggt cct aga ttg gtg cgt taatacacag<br>Pro Val Ile His Leu Tyr Gly Gly Pro Arg Leu Val Arg<br>2420                2425                 2430 | 7835 |
| aattctgatt ttaattaa atg ggg aat gga cag ggg cga gat tgg aaa atg<br>                          Met Gly Asn Gly Gln Gly Arg Asp Trp Lys Met<br>                                      2435                 2440 | 7886 |
| gcc att aag aga tgt agt aat gtt gct gta gga gta ggg ggg aag agt<br>Ala Ile Lys Arg Cys Ser Asn Val Ala Val Gly Val Gly Gly Lys Ser<br>     2445                2450                 2455 | 7934 |
| aaa aaa ttt gga gaa ggg aat ttc aga tgg gcc att aga atg gct aat<br>Lys Lys Phe Gly Glu Gly Asn Phe Arg Trp Ala Ile Arg Met Ala Asn<br>2460                2465                2470                2475 | 7982 |
| gta tct aca gga cga gaa cct ggt gat ata cca gag act tta gat caa<br>Val Ser Thr Gly Arg Glu Pro Gly Asp Ile Pro Glu Thr Leu Asp Gln<br>                 2480                2485                2490 | 8030 |
| cta agg ttg gtt att tgc gat tta caa gaa aga aga gaa aaa ttt gga<br>Leu Arg Leu Val Ile Cys Asp Leu Gln Glu Arg Arg Glu Lys Phe Gly<br>     2495                2500                2505 | 8078 |
| tct agc aaa gaa att gat atg gca att gtg aca tta aaa gtc ttt gcg<br>Ser Ser Lys Glu Ile Asp Met Ala Ile Val Thr Leu Lys Val Phe Ala<br>                 2510                2515                2520 | 8126 |
| gta gca gga ctt ttg aat atg acg gtg tct act gct gct gca gct gaa<br>Val Ala Gly Leu Leu Asn Met Thr Val Ser Thr Ala Ala Ala Ala Glu<br>2525                2530                2535 | 8174 |
| aat atg tat tct caa atg gga tta gac act agg cca tct atg aaa gaa<br>Asn Met Tyr Ser Gln Met Gly Leu Asp Thr Arg Pro Ser Met Lys Glu<br>2540                2545                2550                2555 | 8222 |
| gca ggt gga aaa gag gaa ggc cct cca cag gca tat cct att caa aca<br>Ala Gly Gly Lys Glu Glu Gly Pro Pro Gln Ala Tyr Pro Ile Gln Thr<br>                 2560                2565                2570 | 8270 |
| gta aat gga gta cca caa tat gta gca ctt gac cca aaa atg gtg tcc<br>Val Asn Gly Val Pro Gln Tyr Val Ala Leu Asp Pro Lys Met Val Ser<br>     2575                2580                2585 | 8318 |
| att ttc atg gaa aag gca aga gaa gga cta gga ggg gag gaa gtt caa<br>Ile Phe Met Glu Lys Ala Arg Glu Gly Leu Gly Gly Glu Glu Val Gln<br>2590                2595                2600 | 8366 |
| cta tgg ttt act gcc ttc tct gca aat tta aca cct act gac atg gcc<br>Leu Trp Phe Thr Ala Phe Ser Ala Asn Leu Thr Pro Thr Asp Met Ala<br>     2605                2610                2615 | 8414 |
| aca tta ata atg gcc gca cca ggg tgc gct gca gat aaa gaa ata ttg<br>Thr Leu Ile Met Ala Ala Pro Gly Cys Ala Ala Asp Lys Glu Ile Leu<br>2620                2625                2630                2635 | 8462 |
| gat gaa agc tta aag caa ctg aca gca gaa tat gat cgc aca cat ccc<br>Asp Glu Ser Leu Lys Gln Leu Thr Ala Glu Tyr Asp Arg Thr His Pro<br>                 2640                2645                2650 | 8510 |
| cct gat gct ccc aga cca tta ccc tat ttt act gca gca gaa att atg<br>Pro Asp Ala Pro Arg Pro Leu Pro Tyr Phe Thr Ala Ala Glu Ile Met<br>     2655                2660                2665 | 8558 |
| ggt ata gga tta act caa gaa caa caa gca gaa gca aga ttt gca cca<br>Gly Ile Gly Leu Thr Gln Glu Gln Gln Ala Glu Ala Arg Phe Ala Pro<br>2670                2675                2680 | 8606 |

```
gct agg atg cag tgt aga gca tgg tat ctc gag gca tta gga aaa ttg      8654
Ala Arg Met Gln Cys Arg Ala Trp Tyr Leu Glu Ala Leu Gly Lys Leu
    2685                2690                2695 gct gcc ata aaa gct aag tct cct cga gct gtg cag tta aga caa gga      8702
Ala Ala Ile Lys Ala Lys Ser Pro Arg Ala Val Gln Leu Arg Gln Gly
2700                2705                2710                2715 gct aag gaa gat tat tca tcc ttt ata gac aga ttg ttt gcc caa ata      8750
Ala Lys Glu Asp Tyr Ser Ser Phe Ile Asp Arg Leu Phe Ala Gln Ile
            2720                2725                2730 gat caa gaa caa aat aca gct gaa gtt aag tta tat tta aaa cag tca      8798
Asp Gln Glu Gln Asn Thr Ala Glu Val Lys Leu Tyr Leu Lys Gln Ser
                2735                2740                2745 tta agc ata gct aat gct aat gca gac tgt aaa aag gca atg agc cac      8846
Leu Ser Ile Ala Asn Ala Asn Ala Asp Cys Lys Lys Ala Met Ser His
        2750                2755                2760 ctt aag cca gaa agt acc cta gaa gaa aag ttg aga gct tgt caa gaa      8894
Leu Lys Pro Glu Ser Thr Leu Glu Glu Lys Leu Arg Ala Cys Gln Glu
    2765                2770                2775 ata ggc tca cca gga tat aaa atg caa ctc ttg gca gaa gct ctt aca      8942
Ile Gly Ser Pro Gly Tyr Lys Met Gln Leu Leu Ala Glu Ala Leu Thr
2780                2785                2790                2795 aaa gtt caa gta gtg caa tca aaa gga tca gga cca gtg tgt ttt aat      8990
Lys Val Gln Val Val Gln Ser Lys Gly Ser Gly Pro Val Cys Phe Asn
            2800                2805                2810 tgt aaa aaa cca gga cat cta gca aga caa tgt aga gaa gtg aaa aaa      9038
Cys Lys Lys Pro Gly His Leu Ala Arg Gln Cys Arg Glu Val Lys Lys
                2815                2820                2825 tgt aat aaa tgt gga aaa cct ggt cat cta gct gcc aaa tgt tgg caa      9086
Cys Asn Lys Cys Gly Lys Pro Gly His Leu Ala Ala Lys Cys Trp Gln
        2830                2835                2840 gga aat aga aag aat tcg gga aac tgg aag gcg ggg cga gct gca gcc      9134
Gly Asn Arg Lys Asn Ser Gly Asn Trp Lys Ala Gly Arg Ala Ala Ala
    2845                2850                2855 cca gtg aat caa atg cag caa gca gta atg cca tct gca cct cca atg      9182
Pro Val Asn Gln Met Gln Gln Ala Val Met Pro Ser Ala Pro Pro Met
2860                2865                2870                2875 gag gag aaa cta ttg gat tta taaattataa taaagtaggt acgactacaa         9233
Glu Glu Lys Leu Leu Asp Leu
            2880 cattagaaaa gaggccagaa atacttatat ttgtaaatgg atatcctata aaattcttat    9293 tagatacagg agcagatata acaattttaa ataggagaga ttttcaagta aaaaattcta   9353 tagaaaatgg aaggcaaaat atgattggag taggaggagg aaagagagga acaaattata   9413 ttaatgtaca tttagagatt agagatgaaa attataagac acaatgtata tttggtaatg   9473 tttgtgtctt agaagataac tcattaatac aaccattatt ggggagagat aatatgatta   9533 aattcaatat taggttagta atgtaagttt aaactaatta attgaattac atccctacgc   9593 aaacgtttta cggccgccgg tggcgcccgc gcccggcggc ccgtccttgg ccgttgcagg   9653 ccactccggt ggctcccgtc gtccccgact tccaggccca gcagatgcag caactcatca   9713 gcgccgtaaa tgcgctgaca atgagacaga acgcaattgc tcctgctagg cctcccaaac   9773 caaagaagaa gaagacaacc aaaccaaagc cgaaaacgca gcccaagaag atcaacggaa   9833 aaacgcagca gcaaaagaag aaagacaagc aagccgacaa gaagaagaag aaacccggaa   9893 aaagagaaag aatgtgcatg aagattgaaa atgactgtat ctatgcggct agccacagta   9953 acgtagtgtt tccagacatg tcgggcaccg cactatcatg ggtgcagaaa atctcgggtg   10013 gtctgggggc cttcgcaatc ggcgctatcc tggtgctggt tgtggtcact tgcattgggc   10073
```

```
tccgcagata agttagggta ggcaatggca ttgatatagc aagaaaattg aaaacagaaa    10133
aagttagggt aagcaatggc atataaccat aactgtataa cttgtaacaa agcgcaacaa    10193
gacctgcgca attggccccg tggtccgcct cacggaaact cggggcaact catattgaca    10253
cattaattgg caataattgg aagcttacat aagcttaatt cgacgaataa ttggatttat    10313
attttatttt gcaattggtt tttaatattt ccaaaaaaaa aaaaaaaaa aaaaaaaaaa     10373 aaaaaaaaaa aaaaaaaaaa aaaaaaaac gggtcggcat ggcatctcca cctcctcgcg     10433
gtccgacctg ggcatccgaa ggaggacgca cgtccactcg gatggctaag ggagttttc    10493 tactagtcaa atgagtatat ataattgaaa agtaaaata taaatcatat aataatgaaa    10553
cgaaatatca gtaatagaca ggaactggca gattcttctt ctaatgaagt aagtactgct    10613
aaatctccaa aattagataa aaatgataca gcaaatacag cttcattcaa cgaattacct    10673
tttaattttt tcagacacac cttattacaa actaactaag tcagatgatg agaaagtaaa    10733
tataaattta acttatgggt ataatataat aaagattcat gatattaata atttacttaa    10793
cgatgttaat agacttattc catcaacccc ttcaaacctt tctggatatt ataaaatacc    10853
agttaatgat attaaaatag attgtttaag agatgtaaat aattatttgg aggtaaagga    10913
tataaaatta gtctatcttt cacatggaaa tgaattacct aatattaata attatgatag    10973
gaatttttta ggatttacag ctgttatatg tatcaacaat acaggcagat ctatggttat    11033
ggtaaaacac tgtaacggga agcagcattc tatggtaact ggcctatgtt taatagccag    11093
atcattttac tctataaaca ttttaccaca aataatagga tcctctagat atttaatatt    11153
atatctaaca acaacaaaaa aatttaacga tgtatggcca gaagtatttt ctactaataa    11213
agataaagat agtctatctt atctacaaga tatgaaagaa gataatcatt tagtagtagc    11273
tactaatatg gaagaaatg tatacaaaaa cgtggaagct tttatattaa atagcatatt    11333
actagaagat ttaaaatcta gacttagtat aacaaaacag ttaaatgcca atatcgattc    11393
tatatttcat cataacagta gtacattaat cagtgatata ctgaaacgat ctacagactc    11453
aactatgcaa ggaataagca atatgccaat tatgtctaat attttaactt tagaactaaa    11513
acgttctacc aatactaaaa ataggatacg tgataggctg ttaaaagctg caataaatag    11573
taaggatgta gaagaaatac tttgttctat accttcggag gaaagaactt tagaacaact    11633
taagtttaat caaacttgta tttatgaa                                       11661
```

<210> SEQ ID NO 5
<211> LENGTH: 12945
<212> TYPE: DNA
<213> ORGANISM: Artificial Sequence
<220> FEATURE:
<223> OTHER INFORMATION: Description of Artificial Sequence: Synthetic
      pJY1302.4 DNA sequence
<220> FEATURE:
<221> NAME/KEY: CDS
<222> LOCATION: (1586)..(8881)
<220> FEATURE:
<221> NAME/KEY: CDS
<222> LOCATION: (8910)..(10259)

<400> SEQUENCE: 5

```
gacccttttac aagaataaaa gaagaaacaa ctgtgaaata gtttataaat gtaattcgta    60
tgcagaaaac gataatatat tttggtatga gaaatctaaa ggagacatag tttgtataga   120
catgcgctct tccgatgaga tattcgatgc ttttctaatg tatcatatag ctacaagata   180
tgcctatcat gatgatgata tatatctaca aatagtgtta tattattcta ataatcaaaa   240
tgttatatct tatattacga aaaataaata cgttaagtat ataagaaata aaactagaga   300
```

```
cgatattcat aaagtaaaaa tattagctct agaagacttt acaacggaag aaatatattg    360
ttggattagt aatatataac agcgtagctg cacggttttg atcattttcc aacaatataa    420
accaatgaag gaggacgact catcaaacat aaataacatt cacggaaaat attcagtatc    480
agatttatca caagatgatt atgttattga atgtatagac ggatcttttg attcgatcaa    540
gtatagagat ataaaggtta taataatgaa gaataacggt tacgttaatt gtagtaaatt    600
atgtaaaatg cggaataaat acttttctag atggttgcgt ctttctactt ctaaagcatt    660
attagacatt tacaataata agtcagtaga taatgctatt gttaaagtct atggtaaagg    720
taagaaactt attataacag gattttatct caaacaaaat atgatacgtt atgttattga    780
gtggataggg gatgatttta caaacgatat atacaaaatg attaatttct ataatgcgtt    840
attcggtaac gatgaattaa aaatagtatc ctgtgaaaac actctatgcc cgtttataga    900
acttggtaga tgctattatg gtaaaaaatg taagtatata cacggagatc aatgtgatat    960
ctgtggtcta tatatactac accctaccga tattaaccaa cgagtttctc acaagaaaac   1020
ttgtttagta gatagagatt ctttgattgt gtttaaaaga agtaccagta aaaagtgtgg   1080
catatgcata gaagaaataa acaaaaaaca tatttccgaa cagtattttg gaattctccc   1140
aagttgtaaa catatttttt gcctatcatg tataagacgt tgggcagata ctaccagaaa   1200
tacagatact gaaaatacgt gtcctgaatg tagaatagtt tttcctttca taatacccag   1260
taggtattgg atagataata aatatgaaaa aaaaatatta tataatagat ataagaaaat   1320
gatttttaca aaaataccta taagaacaat aaaaatataa ttacatttac ggaaaatagc   1380 tggtttttagt ttaccaactt agagtaatta tcatattgaa tctatattgc taattagcta   1440
ataaaaaccc gggttctttta ttctatactt aaaaagtgca aataaataca aaggttcttg   1500
atggcggatg tgtgacatac acgacgccaa aagattttgt tccagctcct gccacctccg   1560
ctacgcgaga gattaaccac ccacg atg gcc gcc aaa gtg cat gtt gat att       1612
                             Met Ala Ala Lys Val His Val Asp Ile
                              1               5 gag gct gac agc cca ttc atc aag tct ttg cag aag gca ttt ccg tcg       1660
Glu Ala Asp Ser Pro Phe Ile Lys Ser Leu Gln Lys Ala Phe Pro Ser
 10              15                  20                  25 ttc gag gtg gag tca ttg cag gtc aca cca aat gac cat gca aat gcc       1708
Phe Glu Val Glu Ser Leu Gln Val Thr Pro Asn Asp His Ala Asn Ala
         30                  35                  40 aga gca ttt tcg cac ctg gct acc aaa ttg atc gag cag gag act gac       1756
Arg Ala Phe Ser His Leu Ala Thr Lys Leu Ile Glu Gln Glu Thr Asp
     45                  50                  55 aaa gac aca ctc atc ttg gat atc ggc agt gcg cct tcc agg aga atg       1804
Lys Asp Thr Leu Ile Leu Asp Ile Gly Ser Ala Pro Ser Arg Arg Met
 60                  65                  70 atg tct acg cac aaa tac cac tgc gta tgc cct atg cgc agc gca gaa       1852
Met Ser Thr His Lys Tyr His Cys Val Cys Pro Met Arg Ser Ala Glu
 75                  80                  85 gac ccc gaa agg ctc gta tgc tac gca aag aaa ctg gca gcg gcc tcc       1900
Asp Pro Glu Arg Leu Val Cys Tyr Ala Lys Lys Leu Ala Ala Ala Ser
 90                  95                 100                 105 ggg aag gtg ctg gat aga gag atc gca gga aaa atc acc gac ctg cag       1948
Gly Lys Val Leu Asp Arg Glu Ile Ala Gly Lys Ile Thr Asp Leu Gln
                110                 115                 120 acc gtc atg gct acg cca gac gct gaa tct cct acc ttt tgc ctg cat       1996
Thr Val Met Ala Thr Pro Asp Ala Glu Ser Pro Thr Phe Cys Leu His
                125                 130                 135
```

| | | | | | | | | | | | | | | | | |
|---|---|---|---|---|---|---|---|---|---|---|---|---|---|---|---|---|
| aca | gac | gtc | acg | tgt | cgt | acg | gca | gcc | gaa | gtg | gcc | gta | tac | cag | gac | 2044 |
| Thr | Asp | Val | Thr | Cys | Arg | Thr | Ala | Ala | Glu | Val | Ala | Val | Tyr | Gln | Asp | |
| | | 140 | | | | 145 | | | | 150 | | | | | | |
| gtg | tat | gct | gta | cat | gca | cca | aca | tcg | ctg | tac | cat | cag | gcg | atg | aaa | 2092 |
| Val | Tyr | Ala | Val | His | Ala | Pro | Thr | Ser | Leu | Tyr | His | Gln | Ala | Met | Lys | |
| 155 | | | | | 160 | | | | | 165 | | | | | | |
| ggt | gtc | aga | acg | gcg | tat | tgg | att | ggg | ttt | gac | acc | acc | ccg | ttt | atg | 2140 |
| Gly | Val | Arg | Thr | Ala | Tyr | Trp | Ile | Gly | Phe | Asp | Thr | Thr | Pro | Phe | Met | |
| 170 | | | | | 175 | | | | | 180 | | | | | 185 | |
| ttt | gac | gcg | cta | gca | ggc | gcg | tat | cca | acc | tac | gcc | aca | aac | tgg | gcc | 2188 |
| Phe | Asp | Ala | Leu | Ala | Gly | Ala | Tyr | Pro | Thr | Tyr | Ala | Thr | Asn | Trp | Ala | |
| | | | 190 | | | | | 195 | | | | | 200 | | | |
| gac | gag | cag | gtg | tta | cag | gcc | agg | aac | ata | gga | ctg | tgt | gca | gca | tcc | 2236 |
| Asp | Glu | Gln | Val | Leu | Gln | Ala | Arg | Asn | Ile | Gly | Leu | Cys | Ala | Ala | Ser | |
| | | | 205 | | | | | 210 | | | | | 215 | | | |
| ttg | act | gag | gga | aga | ctc | ggc | aaa | ctg | tcc | att | ctc | cgc | aag | aag | caa | 2284 |
| Leu | Thr | Glu | Gly | Arg | Leu | Gly | Lys | Leu | Ser | Ile | Leu | Arg | Lys | Lys | Gln | |
| | | 220 | | | | | 225 | | | | | 230 | | | | |
| ttg | aaa | cct | tgc | gac | aca | gtc | atg | ttc | tcg | gta | gga | tct | aca | ttg | tac | 2332 |
| Leu | Lys | Pro | Cys | Asp | Thr | Val | Met | Phe | Ser | Val | Gly | Ser | Thr | Leu | Tyr | |
| | 235 | | | | | 240 | | | | | 245 | | | | | |
| act | gag | agc | aga | aag | cta | ctg | agg | agc | tgg | cac | tta | ccc | tcc | gta | ttc | 2380 |
| Thr | Glu | Ser | Arg | Lys | Leu | Leu | Arg | Ser | Trp | His | Leu | Pro | Ser | Val | Phe | |
| 250 | | | | | 255 | | | | | 260 | | | | | 265 | |
| cac | ctg | aaa | ggt | aaa | caa | tcc | ttt | acc | tgt | agg | tgc | gat | acc | atc | gta | 2428 |
| His | Leu | Lys | Gly | Lys | Gln | Ser | Phe | Thr | Cys | Arg | Cys | Asp | Thr | Ile | Val | |
| | | | 270 | | | | | 275 | | | | | 280 | | | |
| tca | tgt | gaa | ggg | tac | gta | gtt | aag | aaa | atc | act | atg | tgc | ccc | ggc | ctg | 2476 |
| Ser | Cys | Glu | Gly | Tyr | Val | Val | Lys | Lys | Ile | Thr | Met | Cys | Pro | Gly | Leu | |
| | | | 285 | | | | | 290 | | | | | 295 | | | |
| tac | ggt | aaa | acg | gta | ggg | tac | gcc | gtg | acg | tat | cac | gcg | gag | gga | ttc | 2524 |
| Tyr | Gly | Lys | Thr | Val | Gly | Tyr | Ala | Val | Thr | Tyr | His | Ala | Glu | Gly | Phe | |
| | | 300 | | | | | 305 | | | | | 310 | | | | |
| cta | gtg | tgc | aag | acc | aca | gac | act | gtc | aaa | gga | gaa | aga | gtc | tca | ttc | 2572 |
| Leu | Val | Cys | Lys | Thr | Thr | Asp | Thr | Val | Lys | Gly | Glu | Arg | Val | Ser | Phe | |
| 315 | | | | | 320 | | | | | 325 | | | | | | |
| cct | gta | tgc | acc | tac | gtc | ccc | tca | acc | atc | tgt | gat | caa | atg | act | ggc | 2620 |
| Pro | Val | Cys | Thr | Tyr | Val | Pro | Ser | Thr | Ile | Cys | Asp | Gln | Met | Thr | Gly | |
| 330 | | | | | 335 | | | | | 340 | | | | | 345 | |
| ata | cta | gcg | acc | gac | gtc | aca | ccg | gag | gac | gca | cag | aag | ttg | tta | gtg | 2668 |
| Ile | Leu | Ala | Thr | Asp | Val | Thr | Pro | Glu | Asp | Ala | Gln | Lys | Leu | Leu | Val | |
| | | | 350 | | | | | 355 | | | | | 360 | | | |
| gga | ttg | aat | cag | agg | ata | gtt | gtg | aac | gga | aga | aca | cag | cga | aac | act | 2716 |
| Gly | Leu | Asn | Gln | Arg | Ile | Val | Val | Asn | Gly | Arg | Thr | Gln | Arg | Asn | Thr | |
| | | | 365 | | | | | 370 | | | | | 375 | | | |
| aac | acg | atg | aag | aac | tat | ctg | ctt | ccg | att | gtg | gcc | gtc | gca | ttt | agc | 2764 |
| Asn | Thr | Met | Lys | Asn | Tyr | Leu | Leu | Pro | Ile | Val | Ala | Val | Ala | Phe | Ser | |
| | | 380 | | | | | 385 | | | | | 390 | | | | |
| aag | tgg | gcg | agg | gaa | tac | aag | gca | gac | ctt | gat | gat | gaa | aaa | cct | ctg | 2812 |
| Lys | Trp | Ala | Arg | Glu | Tyr | Lys | Ala | Asp | Leu | Asp | Asp | Glu | Lys | Pro | Leu | |
| 395 | | | | | 400 | | | | | 405 | | | | | | |
| ggt | gtc | cga | gag | agg | tca | ctt | act | tgc | tgc | tgc | ttg | tgg | gca | ttt | aaa | 2860 |
| Gly | Val | Arg | Glu | Arg | Ser | Leu | Thr | Cys | Cys | Cys | Leu | Trp | Ala | Phe | Lys | |
| 410 | | | | | 415 | | | | | 420 | | | | | 425 | |
| acg | agg | aag | atg | cac | acc | atg | tac | aag | aaa | cca | gac | acc | cag | aca | ata | 2908 |
| Thr | Arg | Lys | Met | His | Thr | Met | Tyr | Lys | Lys | Pro | Asp | Thr | Gln | Thr | Ile | |
| | | | 430 | | | | | 435 | | | | | 440 | | | |
| gtg | aag | gtg | cct | tca | gag | ttt | aac | tcg | ttc | gtc | atc | ccg | agc | cta | tgg | 2956 |
| Val | Lys | Val | Pro | Ser | Glu | Phe | Asn | Ser | Phe | Val | Ile | Pro | Ser | Leu | Trp | |
| | | | 445 | | | | | 450 | | | | | 455 | | | |

```
tct aca ggc ctc gca atc cca gtc aga tca cgc att aag atg ctt ttg      3004
Ser Thr Gly Leu Ala Ile Pro Val Arg Ser Arg Ile Lys Met Leu Leu
        460                 465                 470 gcc aag aag acc aag cga gag tta ata cct gtt ctc gac gcg tcg tca      3052
Ala Lys Lys Thr Lys Arg Glu Leu Ile Pro Val Leu Asp Ala Ser Ser
    475                 480                 485 gcc agg gat gct gaa caa gag gag aag gag agg ttg gag gcc gag ctg      3100
Ala Arg Asp Ala Glu Gln Glu Glu Lys Glu Arg Leu Glu Ala Glu Leu
490                 495                 500                 505 act aga gaa gcc tta cca ccc ctc gtc ccc atc gcg ccg gcg gag acg      3148
Thr Arg Glu Ala Leu Pro Pro Leu Val Pro Ile Ala Pro Ala Glu Thr
                510                 515                 520 gga gtc gtc gac gtc gac gtt gaa gaa cta gag tat cac gca ggt gca      3196
Gly Val Val Asp Val Asp Val Glu Glu Leu Glu Tyr His Ala Gly Ala
            525                 530                 535 ggg gtc gtg gaa aca cct cgc agc gcg ttg aaa gtc acc gca cag ccg      3244
Gly Val Val Glu Thr Pro Arg Ser Ala Leu Lys Val Thr Ala Gln Pro
        540                 545                 550 aac gac gta cta cta gga aat tac gta gtt ctg tcc ccg cag acc gtg      3292
Asn Asp Val Leu Leu Gly Asn Tyr Val Val Leu Ser Pro Gln Thr Val
    555                 560                 565 ctc aag agc tcc aag ttg gcc ccc gtg cac cct cta gca gag cag gtg      3340
Leu Lys Ser Ser Lys Leu Ala Pro Val His Pro Leu Ala Glu Gln Val
570                 575                 580                 585 aaa ata ata aca cat aac ggg agg gcc ggc cgt tac cag gtc gac gga      3388
Lys Ile Ile Thr His Asn Gly Arg Ala Gly Arg Tyr Gln Val Asp Gly
                590                 595                 600 tat gac ggc agg gtc cta cta cca tgt gga tcg gcc att ccg gtc cct      3436
Tyr Asp Gly Arg Val Leu Leu Pro Cys Gly Ser Ala Ile Pro Val Pro
            605                 610                 615 gag ttt caa gct ttg agc gag agc gcc act atg gtg tac aac gaa agg      3484
Glu Phe Gln Ala Leu Ser Glu Ser Ala Thr Met Val Tyr Asn Glu Arg
        620                 625                 630 gag ttc gtc aac agg aaa cta tac cat att gcc gtt cac gga ccg tcg      3532
Glu Phe Val Asn Arg Lys Leu Tyr His Ile Ala Val His Gly Pro Ser
    635                 640                 645 ctg aac acc gac gag gag aac tac gag aaa gtc aga gct gaa aga act      3580
Leu Asn Thr Asp Glu Glu Asn Tyr Glu Lys Val Arg Ala Glu Arg Thr
650                 655                 660                 665 gac gcc gag tac gtg ttc gac gta gat aaa aaa tgc tgc gtc aag aga      3628
Asp Ala Glu Tyr Val Phe Asp Val Asp Lys Lys Cys Cys Val Lys Arg
                670                 675                 680 gag gaa gcg tcg ggt ttg gtg ttg gtg gga gag cta acc aac ccc ccg      3676
Glu Glu Ala Ser Gly Leu Val Leu Val Gly Glu Leu Thr Asn Pro Pro
            685                 690                 695 ttc cat gaa ttc gcc tac gaa ggg ctg aag atc agg ccg tcg gca cca      3724
Phe His Glu Phe Ala Tyr Glu Gly Leu Lys Ile Arg Pro Ser Ala Pro
        700                 705                 710 tat aag act aca gta gta gga gtc ttt ggg gtt ccg gga tca ggc aag      3772
Tyr Lys Thr Thr Val Val Gly Val Phe Gly Val Pro Gly Ser Gly Lys
    715                 720                 725 tct gct att att aag agc ctc gtg acc aaa cac gat ctg gtc acc agc      3820
Ser Ala Ile Ile Lys Ser Leu Val Thr Lys His Asp Leu Val Thr Ser
730                 735                 740                 745 ggc aag aag gag aac tgc cag gaa ata gtc aac gac gtg aag aag cac      3868
Gly Lys Lys Glu Asn Cys Gln Glu Ile Val Asn Asp Val Lys Lys His
                750                 755                 760 cgc gga ctg gac atc cag gca aaa aca gtg gac tcc atc ctg cta aac      3916
Arg Gly Leu Asp Ile Gln Ala Lys Thr Val Asp Ser Ile Leu Leu Asn
            765                 770                 775
```

-continued

```
ggg tgt cgt cgt gcc gtg gac atc cta tat gtg gac gag gct ttc gct     3964
Gly Cys Arg Arg Ala Val Asp Ile Leu Tyr Val Asp Glu Ala Phe Ala
        780                 785                 790 tgc cat ccc ggt act ctg cta gcc cta att gct ctt gtt aaa cct cgg     4012
Cys His Pro Gly Thr Leu Leu Ala Leu Ile Ala Leu Val Lys Pro Arg
    795                 800                 805 agc aaa gtg gtg tta tgc gga gac ccc aag caa tgc gga ttc ttc aat     4060
Ser Lys Val Val Leu Cys Gly Asp Pro Lys Gln Cys Gly Phe Phe Asn
810                 815                 820                 825 atg atg cag ctt aag gtg aac ttc aac cac aac atc tgc act gaa gta     4108
Met Met Gln Leu Lys Val Asn Phe Asn His Asn Ile Cys Thr Glu Val
                830                 835                 840 tgt cat aaa agt ata tcc aga cgt tgc acg cgt cca gtc acg gcc atc     4156
Cys His Lys Ser Ile Ser Arg Arg Cys Thr Arg Pro Val Thr Ala Ile
    845                 850                 855 gtg tct acg ttg cac tac gga ggc aag atg cgc acg acc aac ccg tgc     4204
Val Ser Thr Leu His Tyr Gly Gly Lys Met Arg Thr Thr Asn Pro Cys
            860                 865                 870 aac aaa ccc ata atc ata gac acc aca gga cag acc aag ccc aag cca     4252
Asn Lys Pro Ile Ile Ile Asp Thr Thr Gly Gln Thr Lys Pro Lys Pro
875                 880                 885 gga gac atc gtg tta aca tgc ttc cga ggc tgg gta aag cag ctg cag     4300
Gly Asp Ile Val Leu Thr Cys Phe Arg Gly Trp Val Lys Gln Leu Gln
890                 895                 900                 905 ttg gac tac cgt gga cac gaa gtc atg aca gca gca gca tct cag ggc     4348
Leu Asp Tyr Arg Gly His Glu Val Met Thr Ala Ala Ala Ser Gln Gly
                910                 915                 920 ctc acc cgc aaa ggg gta tac gcc gta agg cag aag gtg aat gaa aat     4396
Leu Thr Arg Lys Gly Val Tyr Ala Val Arg Gln Lys Val Asn Glu Asn
            925                 930                 935 ccc ttg tat gcc cct gcg tcg gag cac gtg aat gta ctg ctg acg cgc     4444
Pro Leu Tyr Ala Pro Ala Ser Glu His Val Asn Val Leu Leu Thr Arg
        940                 945                 950 act gag gat agg ctg gtg tgg aaa acg ctg gcc ggc gat ccc tgg att     4492
Thr Glu Asp Arg Leu Val Trp Lys Thr Leu Ala Gly Asp Pro Trp Ile
955                 960                 965 aag gtc cta tca aac att cca cag ggt aac ttt acg gcc aca ttg gaa     4540
Lys Val Leu Ser Asn Ile Pro Gln Gly Asn Phe Thr Ala Thr Leu Glu
970                 975                 980                 985 gaa tgg caa gaa gaa cac gac aaa ata atg aag gtg att gaa gga ccg     4588
Glu Trp Gln Glu Glu His Asp Lys Ile Met Lys Val Ile Glu Gly Pro
                990                 995                 1000 gct gcg cct gtg gac gcg ttc cag aac aaa gcg aac gtg tgt tgg gcg     4636
Ala Ala Pro Val Asp Ala Phe Gln Asn Lys Ala Asn Val Cys Trp Ala
            1005                1010                1015 aaa agc ctg gtg cct gtc ctg gac act gcc gga atc aga ttg aca gca     4684
Lys Ser Leu Val Pro Val Leu Asp Thr Ala Gly Ile Arg Leu Thr Ala
        1020                1025                1030 gag gag tgg agc acc ata att aca gca ttt aag gag gac aga gct tac     4732
Glu Glu Trp Ser Thr Ile Ile Thr Ala Phe Lys Glu Asp Arg Ala Tyr
    1035                1040                1045 tct cca gtg gtg gcc ttg aat gaa att tgc acc aag tac tat gga gtt     4780
Ser Pro Val Val Ala Leu Asn Glu Ile Cys Thr Lys Tyr Tyr Gly Val
1050                1055                1060                1065 gac ctg gac agt ggc ctg ttt tct gcc ccg aag gtg tcc ctg tat tac     4828
Asp Leu Asp Ser Gly Leu Phe Ser Ala Pro Lys Val Ser Leu Tyr Tyr
                1070                1075                1080 gag aac aac cac tgg gat aac aga cct ggt gga agg atg tat gga ttc     4876
Glu Asn Asn His Trp Asp Asn Arg Pro Gly Gly Arg Met Tyr Gly Phe
            1085                1090                1095
```

-continued

| | |
|---|---|
| aat gcc gca aca gct gcc agg ctg gaa gct aga cat acc ttc ctg aag<br>Asn Ala Ala Thr Ala Ala Arg Leu Glu Ala Arg His Thr Phe Leu Lys<br>    1100                        1105                      1110 | 4924 |
| ggg cag tgg cat acg ggc aag cag gca gtt atc gca gaa aga aaa atc<br>Gly Gln Trp His Thr Gly Lys Gln Ala Val Ile Ala Glu Arg Lys Ile<br>    1115                        1120                      1125 | 4972 |
| caa ccg ctt tct gtg ctg gac aat gta att cct atc aac cgc agg ctg<br>Gln Pro Leu Ser Val Leu Asp Asn Val Ile Pro Ile Asn Arg Arg Leu<br>1130                        1135                      1140                      1145 | 5020 |
| ccg cac gcc ctg gtg gct gag tac aag acg gtt aaa ggc agt agg gtt<br>Pro His Ala Leu Val Ala Glu Tyr Lys Thr Val Lys Gly Ser Arg Val<br>                  1150                      1155                      1160 | 5068 |
| gag tgg ctg gtc aat aaa gta aga ggg tac cac gtc ctg ctg gtg agt<br>Glu Trp Leu Val Asn Lys Val Arg Gly Tyr His Val Leu Leu Val Ser<br>                  1165                      1170                      1175 | 5116 |
| gag tac aac ctg gct ttg cct cga cgc gac gtc act tgg ttg tca ccg<br>Glu Tyr Asn Leu Ala Leu Pro Arg Arg Asp Val Thr Trp Leu Ser Pro<br>                  1180                      1185                      1190 | 5164 |
| ctg aat gtc aca ggc gcc gat agg tgc tac gac cta agt tta gga ctg<br>Leu Asn Val Thr Gly Ala Asp Arg Cys Tyr Asp Leu Ser Leu Gly Leu<br>    1195                        1200                      1205 | 5212 |
| ccg gct gac gcc ggc agg ttc gac ttg gtc ttt gtg aac att cac acg<br>Pro Ala Asp Ala Gly Arg Phe Asp Leu Val Phe Val Asn Ile His Thr<br>1210                        1215                      1220                      1225 | 5260 |
| gaa ttc aga atc cac cac tac cag cag tgt gtc gac cac gcc atg aag<br>Glu Phe Arg Ile His His Tyr Gln Gln Cys Val Asp His Ala Met Lys<br>                  1230                      1235                      1240 | 5308 |
| ctg cag atg ctt ggg gga gat gcg cta cga ctg cta aaa ccc ggc ggc<br>Leu Gln Met Leu Gly Gly Asp Ala Leu Arg Leu Leu Lys Pro Gly Gly<br>    1245                        1250                      1255 | 5356 |
| agc ctc ttg atg aga gct tac gga tac gcc gat aaa atc agc gaa gcc<br>Ser Leu Leu Met Arg Ala Tyr Gly Tyr Ala Asp Lys Ile Ser Glu Ala<br>                  1260                      1265                      1270 | 5404 |
| gtt gtt tcc tcc tta agc aga aag ttc tcg tct gca aga gtg ttg cgc<br>Val Val Ser Ser Leu Ser Arg Lys Phe Ser Ser Ala Arg Val Leu Arg<br>    1275                        1280                      1285 | 5452 |
| ccg gat tgt gtc acc agc aat aca gaa gtg ttc ttg ctg ttc tcc aac<br>Pro Asp Cys Val Thr Ser Asn Thr Glu Val Phe Leu Leu Phe Ser Asn<br>1290                        1295                      1300                      1305 | 5500 |
| ttt gac aac gga aag aga ccc tct acg cta cac cag atg aat acc aag<br>Phe Asp Asn Gly Lys Arg Pro Ser Thr Leu His Gln Met Asn Thr Lys<br>                  1310                      1315                      1320 | 5548 |
| ctg agt gcc gtg tat gcc gga gaa gcc atg cac acg gcc ggg tgt gca<br>Leu Ser Ala Val Tyr Ala Gly Glu Ala Met His Thr Ala Gly Cys Ala<br>    1325                        1330                      1335 | 5596 |
| cca tcc tac aga gtt aag aga gca gac ata gcc acg tgc aca gaa gcg<br>Pro Ser Tyr Arg Val Lys Arg Ala Asp Ile Ala Thr Cys Thr Glu Ala<br>                  1340                      1345                      1350 | 5644 |
| gct gtg gtt aac gca gct aac gcc cgt gga act gta ggg gat ggc gta<br>Ala Val Val Asn Ala Ala Asn Ala Arg Gly Thr Val Gly Asp Gly Val<br>    1355                        1360                      1365 | 5692 |
| tgc agg gcc gtg gcg aag aaa tgg ccg tca gcc ttt aag gga gaa gca<br>Cys Arg Ala Val Ala Lys Lys Trp Pro Ser Ala Phe Lys Gly Glu Ala<br>1370                        1375                      1380                      1385 | 5740 |
| aca cca gtg ggc aca att aaa aca gtc atg tgc ggc tcg tac ccc gtc<br>Thr Pro Val Gly Thr Ile Lys Thr Val Met Cys Gly Ser Tyr Pro Val<br>                  1390                      1395                      1400 | 5788 |
| atc cac gct gta gcg cct aat ttc tct gcc acg act gaa gcg gaa ggg<br>Ile His Ala Val Ala Pro Asn Phe Ser Ala Thr Thr Glu Ala Glu Gly<br>                  1405                      1410                      1415 | 5836 |

```
gac cgc gaa ttg gcc gct gtc tac cgg gca gtg gcc gcc gaa gta aac      5884
Asp Arg Glu Leu Ala Ala Val Tyr Arg Ala Val Ala Ala Glu Val Asn
        1420            1425            1430 aga ctg tca ctg agc agc gta gcc atc ccg ctg ctg tcc aca gga gtg      5932
Arg Leu Ser Leu Ser Ser Val Ala Ile Pro Leu Leu Ser Thr Gly Val
        1435            1440            1445 ttc agc ggc gga aga gat agg ctg cag caa tcc ctc aac cat cta ttc      5980
Phe Ser Gly Gly Arg Asp Arg Leu Gln Gln Ser Leu Asn His Leu Phe
1450            1455            1460            1465 aca gca atg gac gcc acg gac gct gac gtg acc atc tac tgc aga gac      6028
Thr Ala Met Asp Ala Thr Asp Ala Asp Val Thr Ile Tyr Cys Arg Asp
        1470            1475            1480 aaa agt tgg gag aag aaa atc cag gaa gcc ata gac atg agg acg gct      6076
Lys Ser Trp Glu Lys Lys Ile Gln Glu Ala Ile Asp Met Arg Thr Ala
        1485            1490            1495 gtg gag ttg ctc aat gat gac gtg gag ctg acc aca gac ttg gtg aga      6124
Val Glu Leu Leu Asn Asp Asp Val Glu Leu Thr Thr Asp Leu Val Arg
        1500            1505            1510 gtg cac ccg gac agc agc ctg gtg ggt cgt aag ggc tac agt acc act      6172
Val His Pro Asp Ser Ser Leu Val Gly Arg Lys Gly Tyr Ser Thr Thr
    1515            1520            1525 gac ggg tcg ctg tac tcg tac ttt gaa ggt acg aaa ttc aac cag gct      6220
Asp Gly Ser Leu Tyr Ser Tyr Phe Glu Gly Thr Lys Phe Asn Gln Ala
1530            1535            1540            1545 gct att gat atg gca gag ata ctg acg ttg tgg ccc aga ctg caa gag      6268
Ala Ile Asp Met Ala Glu Ile Leu Thr Leu Trp Pro Arg Leu Gln Glu
        1550            1555            1560 gca aac gaa cag ata tgc cta tac gcg ctg ggc gaa aca atg gac aac      6316
Ala Asn Glu Gln Ile Cys Leu Tyr Ala Leu Gly Glu Thr Met Asp Asn
        1565            1570            1575 atc aga tcc aaa tgt ccg gtg aac gat tcc gat tca tca aca cct ccc      6364
Ile Arg Ser Lys Cys Pro Val Asn Asp Ser Asp Ser Ser Thr Pro Pro
        1580            1585            1590 agg aca gtg ccc tgc ctg tgc cgc tac gca atg aca gca gaa cgg atc      6412
Arg Thr Val Pro Cys Leu Cys Arg Tyr Ala Met Thr Ala Glu Arg Ile
    1595            1600            1605 gcc cgc ctt agg tca cac caa gtt aaa agc atg gtg gtt tgc tca tct      6460
Ala Arg Leu Arg Ser His Gln Val Lys Ser Met Val Val Cys Ser Ser
1610            1615            1620            1625 ttt ccc ctc ccg aaa tac cat gta gat ggg gtg cag aag gta aag tgc      6508
Phe Pro Leu Pro Lys Tyr His Val Asp Gly Val Gln Lys Val Lys Cys
            1630            1635            1640 gag aag gtt ctc ctg ttc gac ccg acg gta cct tca gtg gtt agt ccg      6556
Glu Lys Val Leu Leu Phe Asp Pro Thr Val Pro Ser Val Val Ser Pro
        1645            1650            1655 cgg aag tat gcc gca tct acg acg gac cac tca gat cgg tcg tta cga      6604
Arg Lys Tyr Ala Ala Ser Thr Thr Asp His Ser Asp Arg Ser Leu Arg
        1660            1665            1670 ggg ttt gac ttg gac tgg acc acc gac tcg tct tcc act gcc agc gat      6652
Gly Phe Asp Leu Asp Trp Thr Thr Asp Ser Ser Ser Thr Ala Ser Asp
1675            1680            1685 acc atg tcg cta ccc agt ttg cag tcg tgt gac atc gac tcg atc tac      6700
Thr Met Ser Leu Pro Ser Leu Gln Ser Cys Asp Ile Asp Ser Ile Tyr
1690            1695            1700            1705 gag cca atg gct ccc ata gta gtg acg gct gac gta cac cct gaa ccc      6748
Glu Pro Met Ala Pro Ile Val Val Thr Ala Asp Val His Pro Glu Pro
        1710            1715            1720 gca ggc atc gcg gac ctg gcg gca gat gtg cat cct gaa ccc gca gac      6796
Ala Gly Ile Ala Asp Leu Ala Ala Asp Val His Pro Glu Pro Ala Asp
        1725            1730            1735
```

```
cat gtg gac ctc gag aac ccg att cct cca ccg cgc ccg aag aga gct    6844
His Val Asp Leu Glu Asn Pro Ile Pro Pro Pro Arg Pro Lys Arg Ala
        1740                1745                1750 gca tac ctt gcc tcc cgc gcg gcg gag cga ccg gtg ccg gcg ccg aga    6892
Ala Tyr Leu Ala Ser Arg Ala Ala Glu Arg Pro Val Pro Ala Pro Arg
    1755                1760                1765 aag ccg acg cct gcc cca agg act gcg ttt agg aac aag ctg cct ttg    6940
Lys Pro Thr Pro Ala Pro Arg Thr Ala Phe Arg Asn Lys Leu Pro Leu
1770                1775                1780                1785 acg ttc ggc gac ttt gac gag cac gag gtc gat gcg ttg gcc tcc ggg    6988
Thr Phe Gly Asp Phe Asp Glu His Glu Val Asp Ala Leu Ala Ser Gly
                1790                1795                1800 att act ttc gga gac ttc gac gac gtc ctg cga cta ggc cgc gcg ggt    7036
Ile Thr Phe Gly Asp Phe Asp Asp Val Leu Arg Leu Gly Arg Ala Gly
            1805                1810                1815 gca tat att ttc tcc tcg gac act ggc agc gga cat tta caa caa aaa    7084
Ala Tyr Ile Phe Ser Ser Asp Thr Gly Ser Gly His Leu Gln Gln Lys
        1820                1825                1830 tcc gtt agg cag cac aat ctc cag tgc gca caa ctg gat gcg gtc gag    7132
Ser Val Arg Gln His Asn Leu Gln Cys Ala Gln Leu Asp Ala Val Glu
    1835                1840                1845 gag gag aaa atg tac ccg cca aaa ttg gat act gag agg gag aag ctg    7180
Glu Glu Lys Met Tyr Pro Pro Lys Leu Asp Thr Glu Arg Glu Lys Leu
1850                1855                1860                1865 ttg ctg ctg aaa atg cag atg cac cca tcg gag gct aat aag agt cga    7228
Leu Leu Leu Lys Met Gln Met His Pro Ser Glu Ala Asn Lys Ser Arg
                1870                1875                1880 tac cag tct cgc aaa gtg gag aac atg aaa gcc acg gtg gtg gac agg    7276
Tyr Gln Ser Arg Lys Val Glu Asn Met Lys Ala Thr Val Val Asp Arg
            1885                1890                1895 ctc aca tcg ggg gcc aga ttg tac acg gga gcg gac gta ggc cgc ata    7324
Leu Thr Ser Gly Ala Arg Leu Tyr Thr Gly Ala Asp Val Gly Arg Ile
        1900                1905                1910 cca aca tac gcg gtt cgg tac ccc cgc ccc gtg tac tcc cct acc gtg    7372
Pro Thr Tyr Ala Val Arg Tyr Pro Arg Pro Val Tyr Ser Pro Thr Val
    1915                1920                1925 atc gaa aga ttc tca agc ccc gat gta gca atc gca gcg tgc aac gaa    7420
Ile Glu Arg Phe Ser Ser Pro Asp Val Ala Ile Ala Ala Cys Asn Glu
1930                1935                1940                1945 tac cta tcc aga aat tac cca aca gtg gcg tcg tac cag ata aca gat    7468
Tyr Leu Ser Arg Asn Tyr Pro Thr Val Ala Ser Tyr Gln Ile Thr Asp
                1950                1955                1960 gaa tac gac gca tac ttg gac atg gtt gac ggg tcg gat agt tgc ttg    7516
Glu Tyr Asp Ala Tyr Leu Asp Met Val Asp Gly Ser Asp Ser Cys Leu
            1965                1970                1975 gac aga gcg aca ttc tgc ccg gcg aag ctc cgg tgc tac ccg aaa cat    7564
Asp Arg Ala Thr Phe Cys Pro Ala Lys Leu Arg Cys Tyr Pro Lys His
        1980                1985                1990 cat gcg tac cac cag ccg act gta cgc agt gcc gtc ccg tca ccc ttt    7612
His Ala Tyr His Gln Pro Thr Val Arg Ser Ala Val Pro Ser Pro Phe
    1995                2000                2005 cag aac aca cta cag aac gtg cta gcg gcc gcc acc aag aga aac tgc    7660
Gln Asn Thr Leu Gln Asn Val Leu Ala Ala Ala Thr Lys Arg Asn Cys
2010                2015                2020                2025 aac gtc acg caa atg cga gaa cta ccc acc atg gac tcg gca gtg ttc    7708
Asn Val Thr Gln Met Arg Glu Leu Pro Thr Met Asp Ser Ala Val Phe
                2030                2035                2040 aac gtg gag tgc ttc aag cgc tat gcc tgc tcc gga gaa tat tgg gaa    7756
Asn Val Glu Cys Phe Lys Arg Tyr Ala Cys Ser Gly Glu Tyr Trp Glu
            2045                2050                2055
```

```
gaa tat gct aaa caa cct atc cgg ata acc act gag aac atc act acc    7804
Glu Tyr Ala Lys Gln Pro Ile Arg Ile Thr Thr Glu Asn Ile Thr Thr
        2060            2065            2070 tat gtg acc aaa ttg aaa ggc ccg aaa gct gct gcc ttg ttc gct aag    7852
Tyr Val Thr Lys Leu Lys Gly Pro Lys Ala Ala Ala Leu Phe Ala Lys
    2075            2080            2085 acc cac aac ttg gtt ccg ctg cag gag gtt ccc atg gac aga ttc acg    7900
Thr His Asn Leu Val Pro Leu Gln Glu Val Pro Met Asp Arg Phe Thr
2090            2095            2100            2105 gtc gac atg aaa cga gat gtc aaa gtc act cca ggg acg aaa cac aca    7948
Val Asp Met Lys Arg Asp Val Lys Val Thr Pro Gly Thr Lys His Thr
            2110            2115            2120 gag gaa aga ccc aaa gtc cag gta att caa gca gcg gag cca ttg gcg    7996
Glu Glu Arg Pro Lys Val Gln Val Ile Gln Ala Ala Glu Pro Leu Ala
        2125            2130            2135 acc gct tac ctg tgc ggc atc cac agg gaa tta gta agg aga cta aat    8044
Thr Ala Tyr Leu Cys Gly Ile His Arg Glu Leu Val Arg Arg Leu Asn
    2140            2145            2150 gct gtg tta cgc cct aac gtg cac aca ttg ttt gat atg tcg gcc gaa    8092
Ala Val Leu Arg Pro Asn Val His Thr Leu Phe Asp Met Ser Ala Glu
2155            2160            2165 gac ttt gac gcg atc atc gcc tct cac ttc cac cca gga gac ccg gtt    8140
Asp Phe Asp Ala Ile Ile Ala Ser His Phe His Pro Gly Asp Pro Val
2170            2175            2180            2185 cta gag acg gac att gca tca ttc gac aaa agc cag gac gac tcc ttg    8188
Leu Glu Thr Asp Ile Ala Ser Phe Asp Lys Ser Gln Asp Asp Ser Leu
        2190            2195            2200 gct ctt aca ggt tta atg atc ctc gaa gat cta ggg gtg gat cag tac    8236
Ala Leu Thr Gly Leu Met Ile Leu Glu Asp Leu Gly Val Asp Gln Tyr
    2205            2210            2215 ctg ctg gac ttg atc gag gca gcc ttt ggg gaa ata tcc agc tgt cac    8284
Leu Leu Asp Leu Ile Glu Ala Ala Phe Gly Glu Ile Ser Ser Cys His
2220            2225            2230 cta cca act ggc acg cgc ttc aag ttc gga gct atg atg aaa tcg ggc    8332
Leu Pro Thr Gly Thr Arg Phe Lys Phe Gly Ala Met Met Lys Ser Gly
        2235            2240            2245 atg ttt ctg act ttg ttt att aac act gtt ttg aac atc acc ata gca    8380
Met Phe Leu Thr Leu Phe Ile Asn Thr Val Leu Asn Ile Thr Ile Ala
2250            2255            2260            2265 agc agg gta ctg gag cag aga ctc act gac tcc gcc tgt gcg gcc ttc    8428
Ser Arg Val Leu Glu Gln Arg Leu Thr Asp Ser Ala Cys Ala Ala Phe
        2270            2275            2280 atc ggc gac gac aac atc gtt cac gga gtg atc tcc gac aag ctg atg    8476
Ile Gly Asp Asp Asn Ile Val His Gly Val Ile Ser Asp Lys Leu Met
    2285            2290            2295 gcg gag agg tgc gcg tcg tgg gtc aac atg gag gtg aag atc att gac    8524
Ala Glu Arg Cys Ala Ser Trp Val Asn Met Glu Val Lys Ile Ile Asp
2300            2305            2310 gct gtc atg ggc gaa aaa ccc cca tat ttc tgt ggg gga ttc ata gtt    8572
Ala Val Met Gly Glu Lys Pro Pro Tyr Phe Cys Gly Gly Phe Ile Val
        2315            2320            2325 ttt gac agc gtc aca cag acc gcc tgc cgt gtt tca gac cca ctt aag    8620
Phe Asp Ser Val Thr Gln Thr Ala Cys Arg Val Ser Asp Pro Leu Lys
2330            2335            2340            2345 cgc ctg ttc aag ttg ggt aag ccg cta aca gct gaa gac aag cag gac    8668
Arg Leu Phe Lys Leu Gly Lys Pro Leu Thr Ala Glu Asp Lys Gln Asp
        2350            2355            2360 gaa gac agg cga cga gca ctg agt gac gag gtt agc aag tgg ttc cgg    8716
Glu Asp Arg Arg Arg Ala Leu Ser Asp Glu Val Ser Lys Trp Phe Arg
    2365            2370            2375
```

```
aca ggc ttg ggg gcc gaa ctg gag gtg gca cta aca tct agg tat gag    8764
Thr Gly Leu Gly Ala Glu Leu Glu Val Ala Leu Thr Ser Arg Tyr Glu
    2380                2385                2390 gta gag ggc tgc aaa agt atc ctc ata gcc atg gcc acc ttg gcg agg    8812
Val Glu Gly Cys Lys Ser Ile Leu Ile Ala Met Ala Thr Leu Ala Arg
2395                2400                2405 gac att aag gcg ttt aag aaa ttg aga gga cct gtt ata cac ctc tac    8860
Asp Ile Lys Ala Phe Lys Lys Leu Arg Gly Pro Val Ile His Leu Tyr
2410                2415                2420                2425 ggc ggt cct aga ttg gtg cgt taatacacag aattctgatt ttaattaa atg     8912
Gly Gly Pro Arg Leu Val Arg                                 Met
            2430 ggg aat gga cag ggg cga gat tgg aaa atg gcc att aag aga tgt agt    8960
Gly Asn Gly Gln Gly Arg Asp Trp Lys Met Ala Ile Lys Arg Cys Ser
    2435                2440                2445 aat gtt gct gta gga gta ggg ggg aag agt aaa aaa ttt gga gaa ggg    9008
Asn Val Ala Val Gly Val Gly Gly Lys Ser Lys Lys Phe Gly Glu Gly
2450                2455                2460                2465 aat ttc aga tgg gcc att aga atg gct aat gta tct aca gga cga gaa    9056
Asn Phe Arg Trp Ala Ile Arg Met Ala Asn Val Ser Thr Gly Arg Glu
    2470                2475                2480 cct ggt gat ata cca gag act tta gat caa cta agg ttg gtt att tgc    9104
Pro Gly Asp Ile Pro Glu Thr Leu Asp Gln Leu Arg Leu Val Ile Cys
        2485                2490                2495 gat tta caa gaa aga aga gaa aaa ttt gga tct agc aaa gaa att gat    9152
Asp Leu Gln Glu Arg Arg Glu Lys Phe Gly Ser Ser Lys Glu Ile Asp
    2500                2505                2510 atg gca att gtg aca tta aaa gtc ttt gcg gta gca gga ctt ttg aat    9200
Met Ala Ile Val Thr Leu Lys Val Phe Ala Val Ala Gly Leu Leu Asn
2515                2520                2525 atg acg gtg tct act gct gct gca gct gaa aat atg tat tct caa atg    9248
Met Thr Val Ser Thr Ala Ala Ala Ala Glu Asn Met Tyr Ser Gln Met
2530                2535                2540                2545 gga tta gac act agg cca tct atg aaa gaa gca ggt gga aaa gag gaa    9296
Gly Leu Asp Thr Arg Pro Ser Met Lys Glu Ala Gly Gly Lys Glu Glu
    2550                2555                2560 ggc cct cca cag gca tat cct att caa aca gta aat gga gta cca caa    9344
Gly Pro Pro Gln Ala Tyr Pro Ile Gln Thr Val Asn Gly Val Pro Gln
        2565                2570                2575 tat gta gca ctt gac cca aaa atg gtg tcc att ttc atg gaa aag gca    9392
Tyr Val Ala Leu Asp Pro Lys Met Val Ser Ile Phe Met Glu Lys Ala
    2580                2585                2590 aga gaa gga cta gga ggg gag gaa gtt caa cta tgg ttt act gcc ttc    9440
Arg Glu Gly Leu Gly Gly Glu Glu Val Gln Leu Trp Phe Thr Ala Phe
2595                2600                2605 tct gca aat tta aca cct act gac atg gcc aca tta ata atg gcc gca    9488
Ser Ala Asn Leu Thr Pro Thr Asp Met Ala Thr Leu Ile Met Ala Ala
2610                2615                2620                2625 cca ggg tgc gct gca gat aaa gaa ata ttg gat gaa agc tta aag caa    9536
Pro Gly Cys Ala Ala Asp Lys Glu Ile Leu Asp Glu Ser Leu Lys Gln
    2630                2635                2640 ctg aca gca gaa tat gat cgc aca cat ccc cct gat gct ccc aga cca    9584
Leu Thr Ala Glu Tyr Asp Arg Thr His Pro Pro Asp Ala Pro Arg Pro
        2645                2650                2655 tta ccc tat ttt act gca gca gaa att atg ggt ata gga tta act caa    9632
Leu Pro Tyr Phe Thr Ala Ala Glu Ile Met Gly Ile Gly Leu Thr Gln
    2660                2665                2670 gaa caa caa gca gaa gca aga ttt gca cca gct agg atg cag tgt aga    9680
Glu Gln Gln Ala Glu Ala Arg Phe Ala Pro Ala Arg Met Gln Cys Arg
2675                2680                2685
```

| | |
|---|---|
| gca tgg tat ctc gag gca tta gga aaa ttg gct gcc ata aaa gct aag<br>Ala Trp Tyr Leu Glu Ala Leu Gly Lys Leu Ala Ala Ile Lys Ala Lys<br>2690                       2695                   2700                    2705 | 9728 |
| tct cct cga gct gtg cag tta aga caa gga gct aag gaa gat tat tca<br>Ser Pro Arg Ala Val Gln Leu Arg Gln Gly Ala Lys Glu Asp Tyr Ser<br>         2710                   2715                    2720 | 9776 |
| tcc ttt ata gac aga ttg ttt gcc caa ata gat caa gaa caa aat aca<br>Ser Phe Ile Asp Arg Leu Phe Ala Gln Ile Asp Gln Glu Gln Asn Thr<br>2725                       2730                   2735 | 9824 |
| gct gaa gtt aag tta tat tta aaa cag tca tta agc ata gct aat gct<br>Ala Glu Val Lys Leu Tyr Leu Lys Gln Ser Leu Ser Ile Ala Asn Ala<br>         2740                   2745                    2750 | 9872 |
| aat gca gac tgt aaa aag gca atg agc cac ctt aag cca gaa agt acc<br>Asn Ala Asp Cys Lys Lys Ala Met Ser His Leu Lys Pro Glu Ser Thr<br>2755                       2760                   2765 | 9920 |
| cta gaa gaa aag ttg aga gct tgt caa gaa ata ggc tca cca gga tat<br>Leu Glu Glu Lys Leu Arg Ala Cys Gln Glu Ile Gly Ser Pro Gly Tyr<br>2770                       2775                   2780                    2785 | 9968 |
| aaa atg caa ctc ttg gca gaa gct ctt aca aaa gtt caa gta gtg caa<br>Lys Met Gln Leu Leu Ala Glu Ala Leu Thr Lys Val Gln Val Val Gln<br>         2790                   2795                    2800 | 10016 |
| tca aaa gga tca gga cca gtg tgt ttt aat tgt aaa aaa cca gga cat<br>Ser Lys Gly Ser Gly Pro Val Cys Phe Asn Cys Lys Lys Pro Gly His<br>2805                       2810                   2815 | 10064 |
| cta gca aga caa tgt aga gaa gtg aaa aaa tgt aat aaa tgt gga aaa<br>Leu Ala Arg Gln Cys Arg Glu Val Lys Lys Cys Asn Lys Cys Gly Lys<br>         2820                   2825                    2830 | 10112 |
| cct ggt cat cta gct gcc aaa tgt tgg caa gga aat aga aag aat tcg<br>Pro Gly His Leu Ala Ala Lys Cys Trp Gln Gly Asn Arg Lys Asn Ser<br>2835                       2840                   2845 | 10160 |
| gga aac tgg aag gcg ggg cga gct gca gcc cca gtg aat caa atg cag<br>Gly Asn Trp Lys Ala Gly Arg Ala Ala Ala Pro Val Asn Gln Met Gln<br>2850                       2855                   2860                    2865 | 10208 |
| caa gca gta atg cca tct gca cct cca atg gag gag aaa cta ttg gat<br>Gln Ala Val Met Pro Ser Ala Pro Pro Met Glu Glu Lys Leu Leu Asp<br>         2870                   2875                    2880 | 10256 |
| tta taaattataa taaagtaggt acgactacaa cattagaaaa gaggccagaa<br>Leu | 10309 |
| atacttatat ttgtaaatgg atatcctata aaattcttat tagatacagg agcagatata | 10369 |
| acaatttaa ataggagaga ttttcaagta aaaaattcta tagaaatgg aaggcaaaat | 10429 |
| atgattggag taggaggagg aaagagagga acaaattata ttaatgtaca tttagagatt | 10489 |
| agagatgaaa attataagac acaatgtata tttggtaatg tttgtgtctt agaagataac | 10549 |
| tcattaatac aaccattatt ggggagagat aatatgatta aattcaatat taggttagta | 10609 |
| atgtaagttt aaactaatta attgaattac atccctacgc aaacgtttta cggccgccgg | 10669 |
| tggcgcccgc gcccggcggc ccgtccttgg ccgttgcagg ccactccggt ggctcccgtc | 10729 |
| gtccccgact tccaggccca gcagatgcag caactcatca gcgccgtaaa tgcgctgaca | 10789 |
| atgagacaga acgcaattgc tcctgctagg cctcccaaac caagaagaa gaagacaacc | 10849 |
| aaaccaaagc cgaaacgca gcccaagaag atcaacggaa aaacgcagca gcaaaagaag | 10909 |
| aaagacaagc aagccgacaa gaagaagaag aaacccggaa aaagagaaag aatgtgcatg | 10969 |
| aagattgaaa atgactgtat ctatgcggct agccacagta acgtagtgtt tccagacatg | 11029 |
| tcgggcaccg cactatcatg ggtgcagaaa atctcgggtg gtctggggc cttcgcaatc | 11089 |
| ggcgctatcc tggtgctggt tgtggtcact tgcattgggc tccgcagata agttaggta | 11149 |
| ggcaatggca ttgatatagc aagaaaattg aaaacagaaa aagttagggt aagcaatggc | 11209 |

-continued

```
atataaccat aactgtataa cttgtaacaa agcgcaacaa gacctgcgca attggccccg    11269
tggtccgcct cacggaaact cggggcaact catattgaca cattaattgg caataattgg    11329
aagcttacat aagcttaatt cgacgaataa ttggatttat atttattttt gcaattggtt    11389
tttaatatttt ccaaaaaaaa aaaaaaaaaa aaaaaaaaaa aaaaaaaaaa aaaaaaaaaa    11449
aaaaaaaaac gggtcggcat ggcatctcca cctcctcgcg gtccgacctg ggcatccgaa    11509
ggaggacgca crghtarmgt ccactcggat ggctaaggga gtttttctac tagttaatca    11569
taagataaat aatatacagc attgtaacca tcgtcatccg ttatacgggg aataatatta    11629
ccatacagta ttattaaatt ttcttacgaa gaatatagat cggtatttat cgttagttta    11689
ttttacatttt attaattaaa catgtctact attacctgtt atggaaatga caaatttagt    11749
tatataattt atgataaaat taagataata ataatgaaat caaataatta tgtaaatgct    11809
actagattat gtgaattacg aggaagaaag tttacgaact ggaaaaaatt aagtgaatct    11869
aaaatattag tcgataatgt aaaaaaaata aatgataaaa ctaaccagtt aaaaacggat    11929
atgattatat acgttaagga tattgatcat aaaggaagag atacttgcgg ttactatgta    11989
caccaagatc tggtatcttc tatatcaaat tggatatctc cgttattcgc cgttaaggta    12049
aataaaatta ttaactatta tatatgtaat gaatatgata tacgacttag cgaaatggaa    12109
tctgatatga cagaagtaat agatgtagtt gataaattag taggaggata caatgatgaa    12169
atagcagaaa taatatattt gtttaataaa tttatagaaa aatatattgc taacatatcg    12229
ttatcaactg aattatctag tatattaaat aattttataa attttaataa aaaatacaat    12289
aacgacataa aagatattaa atctttaatt cttgatctga aaaacacatc tataaaacta    12349
gataaaaagt tattcgataa agataataat gaatcgaacg atgaaaaatt ggaaacagaa    12409
gttgataagc taatttttttt catctaaata gtattatttt attgaagtac gaagttttac    12469
gttagataaa taataaaggt cgattttttat tttgttaaat atcaaatatg tcattatctg    12529
ataaagatac aaaaacacac ggtgattatc aaccatctaa cgaacagata ttacaaaaaa    12589
tacgtcggac tatggaaaac gaagctgata gcctcaatag aagaagcatt aagaaaattg    12649
ttgtagatgt tatgaagaat tgggatcatc ctctcaacga agaaatagat aaagttctaa    12709
actggaaaaa tgatacatta aacgatttag atcatctaaa tacagatgat aatattaagg    12769
aaatcataca atgtctgatt agagaatttg cgtttaaaaa gatcaattct attatgtata    12829
gttatgctat ggtaaaactc aattcagata acgaaacatt gaaagataaa attaaggatt    12889
attttataga aactattctt aaagacaaac gtggttataa acaaaagcca ttaccc       12945
```

<210> SEQ ID NO 6
<211> LENGTH: 2431
<212> TYPE: PRT
<213> ORGANISM: Artificial Sequence
<220> FEATURE:
<223> OTHER INFORMATION: Description of Artificial Sequence: Synthetic pJY505.1 amino acid sequence

<400> SEQUENCE: 6

Met Ala Ala Lys Val His Val Asp Ile Glu Ala Asp Ser Pro Phe Ile
1               5                   10                  15

Lys Ser Leu Gln Lys Ala Phe Pro Ser Phe Glu Val Glu Ser Leu Gln
            20                  25                  30

Val Thr Pro Asn Asp His Ala Asn Ala Arg Ala Phe Ser His Leu Ala
        35                  40                  45

Thr Lys Leu Ile Glu Gln Glu Thr Asp Lys Asp Thr Leu Ile Leu Asp
    50                  55                  60

-continued

Ile Gly Ser Ala Pro Ser Arg Arg Met Met Ser Thr His Lys Tyr His
65                  70                  75                  80

Cys Val Cys Pro Met Arg Ser Ala Glu Asp Pro Glu Arg Leu Asp Ser
            85                  90                  95

Tyr Ala Lys Lys Leu Ala Ala Ala Ser Gly Lys Val Leu Asp Arg Glu
        100                 105                 110

Ile Ala Gly Lys Ile Thr Asp Leu Gln Thr Val Met Ala Thr Pro Asp
        115                 120                 125

Ala Glu Ser Pro Thr Phe Cys Leu His Thr Asp Val Thr Cys Arg Thr
    130                 135                 140

Ala Ala Glu Val Ala Val Tyr Gln Asp Val Tyr Ala Val His Ala Pro
145                 150                 155                 160

Thr Ser Leu Tyr His Gln Ala Met Lys Gly Val Arg Thr Ala Tyr Trp
                165                 170                 175

Ile Gly Phe Asp Thr Thr Pro Phe Met Phe Asp Ala Leu Ala Gly Ala
            180                 185                 190

Tyr Pro Thr Tyr Ala Thr Asn Trp Ala Asp Glu Gln Val Leu Gln Ala
        195                 200                 205

Arg Asn Ile Gly Leu Cys Ala Ala Ser Leu Thr Glu Gly Arg Leu Gly
210                 215                 220

Lys Leu Ser Ile Leu Arg Lys Lys Gln Leu Lys Pro Cys Asp Thr Val
225                 230                 235                 240

Met Phe Ser Val Gly Ser Thr Leu Tyr Thr Glu Ser Arg Lys Leu Leu
                245                 250                 255

Arg Ser Trp His Leu Pro Ser Val Phe His Leu Lys Gly Lys Gln Ser
            260                 265                 270

Phe Thr Cys Arg Cys Asp Thr Ile Val Ser Cys Glu Gly Tyr Val Val
        275                 280                 285

Lys Lys Ile Thr Met Cys Pro Gly Leu Tyr Gly Lys Thr Val Gly Tyr
        290                 295                 300

Ala Val Thr Tyr His Ala Glu Gly Phe Leu Val Cys Lys Thr Thr Asp
305                 310                 315                 320

Thr Val Lys Gly Glu Arg Val Ser Phe Pro Val Cys Thr Tyr Val Pro
                325                 330                 335

Ser Thr Ile Cys Asp Gln Met Thr Gly Ile Leu Ala Thr Asp Val Thr
            340                 345                 350

Pro Glu Asp Ala Gln Lys Leu Leu Val Gly Leu Asn Gln Arg Ile Val
        355                 360                 365

Val Asn Gly Arg Thr Gln Arg Asn Thr Asn Thr Met Lys Asn Tyr Leu
        370                 375                 380

Leu Pro Ile Val Ala Val Ala Phe Ser Lys Trp Ala Arg Glu Tyr Lys
385                 390                 395                 400

Ala Asp Leu Asp Asp Glu Lys Pro Leu Gly Val Arg Glu Arg Ser Leu
                405                 410                 415

Thr Cys Cys Cys Leu Trp Ala Phe Lys Thr Arg Lys Met His Thr Met
            420                 425                 430

Tyr Lys Lys Pro Asp Thr Gln Thr Ile Val Lys Val Pro Ser Glu Phe
        435                 440                 445

Asn Ser Phe Val Ile Pro Ser Leu Trp Ser Thr Gly Leu Ala Ile Pro
450                 455                 460

Val Arg Ser Arg Ile Lys Met Leu Leu Ala Lys Lys Thr Lys Arg Glu
465                 470                 475                 480

Leu Ile Pro Val Leu Asp Ala Ser Ser Ala Arg Asp Ala Glu Gln Glu
                485                 490                 495

-continued

```
Glu Lys Glu Arg Leu Glu Ala Glu Leu Thr Arg Glu Ala Leu Pro Pro
            500                 505                 510
Leu Val Pro Ile Ala Pro Ala Glu Thr Gly Val Val Asp Val Asp Val
            515                 520                 525
Glu Glu Leu Glu Tyr His Ala Gly Ala Gly Val Val Glu Thr Pro Arg
            530                 535                 540
Ser Ala Leu Lys Val Thr Ala Gln Pro Asn Asp Val Leu Leu Gly Asn
545                 550                 555                 560
Tyr Val Val Leu Ser Pro Gln Thr Val Leu Lys Ser Ser Lys Leu Ala
                565                 570                 575
Pro Val His Pro Leu Ala Glu Gln Val Lys Ile Ile Thr His Asn Gly
            580                 585                 590
Arg Ala Gly Gly Tyr Gln Val Asp Gly Tyr Asp Gly Arg Val Leu Leu
            595                 600                 605
Pro Cys Gly Ser Ala Ile Pro Val Pro Glu Phe Gln Ala Leu Ser Glu
            610                 615                 620
Ser Ala Thr Met Val Tyr Asn Glu Arg Glu Phe Val Asn Arg Lys Leu
625                 630                 635                 640
Tyr His Ile Ala Val His Gly Pro Ser Leu Asn Thr Asp Glu Glu Asn
                645                 650                 655
Tyr Glu Lys Val Arg Ala Glu Arg Thr Asp Ala Glu Tyr Val Phe Asp
            660                 665                 670
Val Asp Lys Lys Cys Cys Val Lys Arg Glu Glu Ala Ser Gly Leu Val
            675                 680                 685
Leu Val Gly Glu Leu Thr Asn Pro Pro Phe His Glu Phe Ala Tyr Glu
            690                 695                 700
Gly Leu Lys Ile Arg Pro Ser Ala Pro Tyr Lys Thr Thr Val Val Gly
705                 710                 715                 720
Val Phe Gly Val Pro Gly Ser Gly Lys Ser Ala Ile Ile Lys Ser Leu
                725                 730                 735
Val Thr Lys His Asp Leu Val Thr Ser Gly Lys Lys Glu Asn Cys Gln
            740                 745                 750
Glu Ile Val Asn Asp Val Lys Lys His Arg Gly Lys Gly Thr Ser Arg
            755                 760                 765
Glu Asn Ser Asp Ser Ile Leu Leu Asn Gly Cys Arg Arg Ala Val Asp
            770                 775                 780
Ile Leu Tyr Val Asp Glu Ala Phe Ala Cys His Ser Gly Thr Leu Leu
785                 790                 795                 800
Ala Leu Ile Ala Leu Val Lys Pro Arg Ser Lys Val Val Leu Cys Gly
                805                 810                 815
Asp Pro Lys Gln Cys Gly Phe Phe Asn Met Met Gln Leu Lys Val Asn
            820                 825                 830
Phe Asn His Asn Ile Cys Thr Glu Val Cys His Lys Ser Ile Ser Arg
            835                 840                 845
Arg Cys Thr Arg Pro Val Thr Ala Ile Val Ser Thr Leu His Tyr Gly
            850                 855                 860
Gly Lys Met Arg Thr Thr Asn Pro Cys Asn Lys Pro Ile Ile Ile Asp
865                 870                 875                 880
Thr Thr Gly Gln Thr Lys Pro Lys Pro Gly Asp Ile Val Leu Thr Cys
                885                 890                 895
Phe Arg Gly Trp Ala Lys Gln Leu Gln Leu Asp Tyr Arg Gly His Glu
            900                 905                 910
Val Met Thr Ala Ala Ala Ser Gln Gly Leu Thr Arg Lys Gly Val Tyr
            915                 920                 925
```

```
Ala Val Arg Gln Lys Val Asn Glu Asn Pro Leu Tyr Ala Pro Ala Ser
    930                 935                 940

Glu His Val Asn Val Leu Leu Thr Arg Thr Glu Asp Arg Leu Val Trp
945                 950                 955                 960

Lys Thr Leu Ala Gly Asp Pro Trp Ile Lys Val Leu Ser Asn Ile Pro
                965                 970                 975

Gln Gly Asn Phe Thr Ala Thr Leu Glu Glu Trp Gln Glu Glu His Asp
                980                 985                 990

Lys Ile Met Lys Val Ile Glu Gly Pro Ala Ala Pro Val Asp Ala Phe
            995                1000                1005

Gln Asn Lys Ala Asn Val Cys Trp Ala Lys Ser Leu Val Pro Val Leu
   1010                1015                1020

Asp Thr Ala Gly Ile Arg Leu Thr Ala Glu Glu Trp Ser Thr Ile Ile
1025                1030                1035                1040

Thr Ala Phe Lys Glu Asp Arg Ala Tyr Ser Pro Val Val Ala Leu Asn
                1045                1050                1055

Glu Ile Cys Thr Lys Tyr Tyr Gly Val Asp Leu Asp Ser Gly Leu Phe
                1060                1065                1070

Ser Ala Pro Lys Val Ser Leu Tyr Tyr Glu Asn Asn His Trp Asp Asn
            1075                1080                1085

Arg Pro Gly Gly Arg Met Tyr Gly Phe Asn Ala Ala Thr Ala Ala Arg
   1090                1095                1100

Leu Glu Ala Arg His Thr Phe Leu Lys Gly Gln Trp His Thr Gly Lys
1105                1110                1115                1120

Gln Ala Val Ile Ala Glu Arg Lys Ile Gln Pro Leu Ser Val Leu Asp
                1125                1130                1135

Asn Val Ile Pro Ile Asn Arg Arg Leu Pro His Ala Leu Val Ala Glu
            1140                1145                1150

Tyr Lys Thr Val Lys Gly Ser Arg Val Glu Trp Leu Val Asn Lys Val
            1155                1160                1165

Arg Gly Tyr His Val Leu Leu Val Ser Glu Tyr Asn Leu Ala Leu Pro
   1170                1175                1180

Arg Arg Arg Val Thr Trp Leu Ser Pro Leu Asn Val Thr Gly Ala Asp
1185                1190                1195                1200

Arg Cys Tyr Asp Leu Ser Leu Gly Leu Pro Ala Asp Ala Gly Arg Phe
                1205                1210                1215

Asp Leu Val Phe Val Asn Ile His Thr Glu Phe Arg Ile His His Tyr
            1220                1225                1230

Gln Gln Cys Val Asp His Ala Met Lys Leu Gln Met Leu Gly Gly Asp
   1235                1240                1245

Ala Ala Arg Leu Leu Lys Pro Gly Gly Ile Leu Met Arg Ala Tyr Gly
   1250                1255                1260

Tyr Ala Asp Lys Ile Ser Glu Ala Val Val Ser Ser Leu Ser Arg Lys
1265                1270                1275                1280

Phe Ser Ser Ala Arg Val Leu Arg Pro Asp Cys Val Thr Ser Asn Thr
                1285                1290                1295

Glu Val Phe Leu Leu Phe Ser Asn Phe Asp Asn Gly Lys Arg Pro Ser
            1300                1305                1310

Thr Leu His Gln Met Asn Thr Lys Leu Ser Ala Val Tyr Ala Gly Glu
            1315                1320                1325

Ala Met His Thr Ala Gly Cys Ala Pro Ser Tyr Arg Val Lys Arg Ala
   1330                1335                1340

Asp Ile Ala Thr Cys Thr Glu Ala Ala Val Val Asn Ala Ala Asn Ala
1345                1350                1355                1360
```

```
Arg Gly Thr Val Gly Asp Gly Val Cys Arg Ala Val Ala Lys Lys Trp
                1365                1370                1375

Pro Ser Ala Phe Lys Gly Ala Ala Thr Pro Val Gly Thr Ile Lys Thr
                1380                1385                1390

Val Met Cys Gly Ser Tyr Pro Val Ile His Ala Val Ala Pro Asn Phe
                1395                1400            1405

Ser Ala Thr Thr Glu Ala Glu Gly Asp Arg Glu Leu Ala Ala Val Tyr
    1410                1415                1420

Arg Ala Val Ala Ala Glu Val Asn Arg Leu Ser Leu Ser Ser Val Ala
1425                1430                1435                1440

Ile Pro Leu Leu Ser Thr Gly Val Phe Ser Gly Gly Arg Asp Arg Leu
                1445                1450                1455

Gln Gln Ser Leu Asn His Leu Phe Thr Ala Met Asp Ala Thr Asp Ala
            1460                1465                1470

Asp Val Thr Ile Tyr Cys Arg Asp Lys Ser Trp Glu Lys Lys Ile Gln
                1475                1480                1485

Glu Ala Ile Asp Met Arg Thr Ala Val Glu Leu Leu Asn Asp Asp Val
    1490                1495                1500

Glu Leu Thr Thr Asp Leu Val Arg Val His Pro Asp Ser Ser Leu Val
1505                1510                1515                1520

Gly Arg Lys Gly Tyr Ser Thr Thr Asp Gly Ser Leu Tyr Ser Tyr Phe
                1525                1530                1535

Glu Gly Thr Lys Phe Asn Gln Ala Ala Ile Asp Met Ala Glu Ile Leu
            1540                1545                1550

Thr Leu Trp Pro Arg Leu Gln Glu Ala Asn Gln Ile Cys Leu Tyr
                1555                1560                1565

Ala Leu Gly Glu Thr Met Asp Asn Ile Arg Ser Lys Cys Pro Val Asn
    1570                1575                1580

Asp Ser Asp Ser Ser Thr Pro Pro Arg Thr Val Pro Cys Leu Cys Arg
1585                1590                1595                1600

Tyr Ala Met Thr Ala Glu Arg Ile Ala Arg Leu Arg Ser His Gln Val
                1605                1610                1615

Lys Ser Met Val Val Cys Ser Ser Phe Pro Leu Pro Lys Tyr His Val
            1620                1625                1630

Asp Gly Val Gln Lys Val Lys Cys Glu Lys Val Leu Leu Phe Asp Pro
                1635                1640                1645

Thr Val Pro Ser Val Val Ser Pro Arg Lys Tyr Ala Ala Ser Thr Thr
    1650                1655                1660

Asp His Ser Asp Arg Ser Leu Arg Gly Phe Asp Leu Asp Trp Thr Thr
1665                1670                1675                1680

Asp Ser Ser Ser Thr Ala Ser Asp Thr Met Ser Leu Pro Ser Leu Gln
                1685                1690                1695

Ser Cys Asp Ile Asp Ser Ile Tyr Glu Pro Met Ala Pro Ile Val Val
            1700                1705                1710

Thr Ala Asp Val His Pro Glu Pro Ala Gly Ile Ala Asp Leu Ala Ala
                1715                1720                1725

Asp Val His Pro Glu Pro Ala Asp His Val Asp Leu Glu Asn Pro Ile
    1730                1735                1740

Pro Pro Pro Arg Pro Lys Arg Ala Ala Tyr Leu Ala Ser Arg Ala Ala
1745                1750                1755                1760

Glu Arg Pro Val Pro Ala Pro Arg Lys Pro Thr Pro Ala Pro Arg Thr
                1765                1770                1775

Ala Phe Arg Asn Lys Leu Pro Leu Thr Phe Gly Asp Phe Asp Glu His
            1780                1785                1790
```

-continued

Glu Val Asp Ala Leu Ala Ser Gly Ile Thr Phe Gly Asp Phe Asp Asp
    1795                1800                1805

Val Leu Arg Leu Gly Arg Ala Gly Ala Tyr Ile Phe Ser Ser Asp Thr
    1810                1815                1820

Gly Ser Gly His Leu Gln Gln Lys Ser Val Arg Gln His Asn Leu Gln
1825                1830                1835                1840

Cys Ala Gln Leu Asp Ala Val Gln Glu Glu Lys Met Tyr Pro Pro Lys
            1845                1850                1855

Leu Asp Thr Glu Arg Glu Lys Leu Leu Leu Lys Met Gln Met His
        1860                1865                1870

Pro Ser Glu Ala Asn Lys Ser Arg Tyr Gln Ser Arg Lys Val Glu Asn
    1875                1880                1885

Met Lys Ala Thr Val Val Asp Arg Leu Thr Ser Gly Ala Arg Leu Tyr
    1890                1895                1900

Thr Gly Ala Asp Val Gly Arg Ile Pro Thr Tyr Ala Val Arg Tyr Pro
1905                1910                1915                1920

Arg Pro Val Tyr Ser Pro Thr Val Ile Glu Arg Phe Ser Ser Pro Asp
            1925                1930                1935

Val Ala Ile Ala Ala Cys Asn Glu Tyr Leu Ser Arg Asn Tyr Pro Thr
        1940                1945                1950

Val Ala Ser Tyr Gln Ile Thr Asp Glu Tyr Asp Ala Tyr Leu Asp Met
        1955                1960                1965

Val Asp Gly Ser Asp Ser Cys Leu Asp Arg Ala Thr Phe Cys Pro Ala
    1970                1975                1980

Lys Leu Arg Cys Tyr Pro Lys His His Ala Tyr His Gln Pro Thr Val
1985                1990                1995                2000

Arg Ser Ala Val Pro Ser Pro Phe Gln Asn Thr Leu Gln Asn Val Leu
            2005                2010                2015

Ala Ala Ala Thr Lys Arg Asn Cys Asn Val Thr Gln Met Arg Glu Leu
        2020                2025                2030

Pro Thr Met Asp Ser Ala Val Phe Asn Val Glu Cys Phe Lys Arg Tyr
    2035                2040                2045

Ala Cys Ser Gly Glu Tyr Trp Glu Glu Tyr Ala Lys Gln Pro Ile Arg
    2050                2055                2060

Ile Thr Thr Glu Asn Ile Thr Thr Tyr Val Thr Lys Leu Lys Gly Pro
2065                2070                2075                2080

Lys Ala Ala Ala Leu Phe Ala Lys Thr His Asn Leu Val Pro Leu Gln
            2085                2090                2095

Glu Val Pro Met Asp Arg Phe Thr Val Asp Met Lys Arg Asp Val Lys
        2100                2105                2110

Val Thr Pro Gly Thr Lys His Thr Glu Glu Arg Pro Lys Val Gln Val
        2115                2120                2125

Ile Gln Ala Ala Glu Pro Leu Ala Thr Ala Tyr Leu Cys Gly Ile His
    2130                2135                2140

Arg Glu Leu Val Arg Arg Leu Asn Ala Val Leu Arg Pro Asn Val His
2145                2150                2155                2160

Thr Leu Phe Asp Met Ser Ala Glu Asp Phe Asp Ala Ile Ile Ala Ser
            2165                2170                2175

His Phe His Pro Gly Asp Pro Val Leu Glu Thr Asp Ile Ala Ser Phe
        2180                2185                2190

Asp Lys Ser Gln Asp Asp Ser Leu Ala Leu Thr Gly Leu Met Ile Leu
    2195                2200                2205

Glu Asp Leu Gly Val Asp Gln Tyr Leu Leu Asp Leu Ile Glu Ala Ala
    2210                2215                2220

Phe Gly Glu Ile Ser Ser Cys His Leu Pro Thr Gly Thr Arg Phe Lys
2225                2230                2235                2240

Phe Gly Ala Met Met Lys Ser Gly Met Phe Leu Thr Leu Phe Ile Asn
            2245                2250                2255

Thr Val Leu Asn Ile Thr Ile Ala Ser Arg Val Leu Glu Gln Arg Leu
        2260                2265                2270

Thr Asp Ser Ala Cys Ala Ala Phe Ile Gly Asp Asp Asn Ile Val His
    2275                2280                2285

Gly Val Ile Ser Asp Lys Leu Met Ala Glu Arg Cys Ala Ser Trp Val
2290                2295                2300

Asn Met Glu Val Lys Ile Ile Asp Ala Val Met Gly Glu Lys Pro Pro
2305                2310                2315                2320

Tyr Phe Cys Gly Gly Phe Ile Val Phe Asp Ser Val Thr Gln Thr Ala
            2325                2330                2335

Cys Arg Val Ser Asp Pro Leu Lys Arg Leu Phe Lys Leu Gly Lys Pro
        2340                2345                2350

Leu Thr Ala Glu Asp Lys Gln Asp Glu Asp Arg Arg Arg Ala Leu Ser
    2355                2360                2365

Asp Glu Val Ser Lys Trp Phe Arg Thr Gly Leu Gly Ala Glu Leu Glu
    2370                2375                2380

Val Ala Leu Thr Ser Arg Tyr Glu Val Glu Gly Cys Lys Ser Ile Leu
2385                2390                2395                2400

Ile Ala Met Ala Thr Leu Ala Arg Asp Ile Lys Ala Phe Lys Lys Leu
            2405                2410                2415

Arg Gly Pro Val Ile His Leu Tyr Gly Gly Pro Arg Leu Val Arg
        2420                2425                2430

<210> SEQ ID NO 7
<211> LENGTH: 367
<212> TYPE: PRT
<213> ORGANISM: Artificial Sequence
<220> FEATURE:
<223> OTHER INFORMATION: Description of Artificial Sequence: Synthetic
      pJY505.1 amino acid sequence

<400> SEQUENCE: 7

Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

```
Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Gln Ala Lys Pro Leu
225                 230                 235                 240

Ser Gln Glu Glu Ser Thr Leu Ile Glu Arg Ala Thr Ala Thr Ile Asn
                245                 250                 255

Ser Ile Pro Ile Ser Glu Asp Tyr Ser Val Ala Ser Ala Ala Leu Ser
                260                 265                 270

Ser Asp Gly Arg Ile Phe Thr Gly Val Asn Val Tyr His Phe Thr Gly
            275                 280                 285

Gly Pro Cys Ala Glu Leu Val Val Leu Gly Thr Ala Ala Ala Ala Ala
        290                 295                 300

Ala Gly Asn Leu Thr Cys Ile Val Ala Ile Gly Asn Glu Asn Arg Gly
305                 310                 315                 320

Ile Leu Ser Pro Cys Gly Arg Cys Arg Gln Val Leu Leu Asp Leu His
                325                 330                 335

Pro Gly Ile Lys Ala Ile Val Lys Asp Ser Asp Gly Gln Pro Thr Ala
                340                 345                 350

Val Gly Ile Arg Glu Leu Leu Pro Ser Gly Tyr Val Trp Glu Gly
            355                 360                 365

<210> SEQ ID NO 8
<211> LENGTH: 2431
<212> TYPE: PRT
<213> ORGANISM: Artificial Sequence
<220> FEATURE:
<223> OTHER INFORMATION: Description of Artificial Sequence: Synthetic
      pJYC6SFL713A1 amino acid sequence

<400> SEQUENCE: 8

Met Ala Ala Lys Val His Val Asp Ile Glu Ala Asp Ser Pro Phe Ile
1               5                   10                  15

Lys Ser Leu Gln Lys Ala Phe Pro Ser Phe Glu Val Glu Ser Leu Gln
            20                  25                  30

Val Thr Pro Asn Asp His Ala Asn Ala Arg Ala Phe Ser His Leu Ala
        35                  40                  45

Thr Lys Leu Ile Glu Gln Glu Thr Asp Lys Asp Thr Leu Ile Leu Asp
    50                  55                  60

Ile Gly Ser Ala Pro Ser Arg Arg Met Met Ser Thr His Lys Tyr His
65                  70                  75                  80

Cys Val Cys Pro Met Arg Ser Ala Glu Asp Pro Glu Arg Leu Asp Ser
                85                  90                  95

Tyr Ala Lys Lys Leu Ala Ala Ala Ser Gly Lys Val Leu Asp Arg Glu
            100                 105                 110

Ile Ala Gly Lys Ile Thr Asp Leu Gln Thr Val Met Ala Thr Pro Asp
        115                 120                 125

Ala Glu Ser Pro Thr Phe Cys Leu His Thr Asp Val Thr Cys Arg Thr
    130                 135                 140

Ala Ala Glu Val Ala Val Tyr Gln Asp Val Tyr Ala Val His Ala Pro
145                 150                 155                 160
```

-continued

```
Thr Ser Leu Tyr His Gln Ala Met Lys Gly Val Arg Thr Ala Tyr Trp
                165                 170                 175
Ile Gly Phe Asp Thr Thr Pro Phe Met Phe Asp Ala Leu Ala Gly Ala
            180                 185                 190
Tyr Pro Thr Tyr Ala Thr Asn Trp Ala Asp Glu Gln Val Leu Gln Ala
        195                 200                 205
Arg Asn Ile Gly Leu Cys Ala Ala Ser Leu Thr Glu Gly Arg Leu Gly
    210                 215                 220
Lys Leu Ser Ile Leu Arg Lys Lys Gln Leu Lys Pro Cys Asp Thr Val
225                 230                 235                 240
Met Phe Ser Val Gly Ser Thr Leu Tyr Thr Glu Ser Arg Lys Leu Leu
                245                 250                 255
Arg Ser Trp His Leu Pro Ser Val Phe His Leu Lys Gly Lys Gln Ser
            260                 265                 270
Phe Thr Cys Arg Cys Asp Thr Ile Val Ser Cys Glu Gly Tyr Val Val
        275                 280                 285
Lys Lys Ile Thr Met Cys Pro Gly Leu Tyr Gly Lys Thr Val Gly Tyr
    290                 295                 300
Ala Val Thr Tyr His Ala Glu Gly Phe Leu Val Cys Lys Thr Thr Asp
305                 310                 315                 320
Thr Val Lys Gly Glu Arg Val Ser Phe Pro Val Cys Thr Tyr Val Pro
                325                 330                 335
Ser Thr Ile Cys Asp Gln Met Thr Gly Ile Leu Ala Thr Asp Val Thr
            340                 345                 350
Pro Glu Asp Ala Gln Lys Leu Leu Val Gly Leu Asn Gln Arg Ile Val
        355                 360                 365
Val Asn Gly Arg Thr Gln Arg Asn Thr Asn Thr Met Lys Asn Tyr Leu
    370                 375                 380
Leu Pro Ile Val Ala Val Ala Phe Ser Lys Trp Ala Arg Glu Tyr Lys
385                 390                 395                 400
Ala Asp Leu Asp Asp Glu Lys Pro Leu Gly Val Arg Glu Arg Ser Leu
                405                 410                 415
Thr Cys Cys Cys Leu Trp Ala Phe Lys Thr Arg Lys Met His Thr Met
            420                 425                 430
Tyr Lys Lys Pro Asp Thr Gln Thr Ile Val Lys Val Pro Ser Glu Phe
        435                 440                 445
Asn Ser Phe Val Ile Pro Ser Leu Trp Ser Thr Gly Leu Ala Ile Pro
    450                 455                 460
Val Arg Ser Arg Ile Lys Met Leu Leu Ala Lys Lys Thr Lys Arg Glu
465                 470                 475                 480
Leu Ile Pro Val Leu Asp Ala Ser Ser Ala Arg Asp Ala Glu Gln Glu
                485                 490                 495
Glu Lys Glu Arg Leu Glu Ala Glu Leu Thr Arg Glu Ala Leu Pro Pro
            500                 505                 510
Leu Val Pro Ile Ala Pro Ala Glu Thr Gly Val Val Asp Val Asp Val
        515                 520                 525
Glu Glu Leu Glu Tyr His Ala Gly Ala Gly Val Val Glu Thr Pro Arg
    530                 535                 540
Ser Ala Leu Lys Val Thr Ala Gln Pro Asn Asp Val Leu Leu Gly Asn
545                 550                 555                 560
Tyr Val Val Leu Ser Pro Gln Thr Val Leu Lys Ser Ser Lys Leu Ala
                565                 570                 575
Pro Val His Pro Leu Ala Glu Gln Val Lys Ile Ile Thr His Asn Gly
            580                 585                 590
```

-continued

Arg Ala Gly Gly Tyr Gln Val Asp Gly Tyr Asp Gly Arg Val Leu Leu
            595                 600                 605
Pro Cys Gly Ser Ala Ile Pro Val Pro Glu Phe Gln Ala Leu Ser Glu
610                 615                 620
Ser Ala Thr Met Val Tyr Asn Glu Arg Glu Phe Val Asn Arg Lys Leu
625                 630                 635                 640
Tyr His Ile Ala Val His Gly Pro Ser Leu Asn Thr Asp Glu Glu Asn
            645                 650                 655
Tyr Glu Lys Val Arg Ala Glu Arg Thr Asp Ala Glu Tyr Val Phe Asp
            660                 665                 670
Val Asp Lys Lys Cys Cys Val Lys Arg Glu Ala Ser Gly Leu Val
            675                 680                 685
Leu Val Gly Glu Leu Thr Asn Pro Pro Phe His Glu Phe Ala Tyr Glu
    690                 695                 700
Gly Leu Lys Ile Arg Pro Ser Ala Pro Tyr Lys Thr Thr Val Gly
705                 710                 715                 720
Val Phe Gly Val Pro Gly Ser Gly Lys Ser Ala Ile Ile Lys Ser Leu
                    725                 730                 735
Val Thr Lys His Asp Leu Val Thr Ser Gly Lys Glu Asn Cys Gln
            740                 745                 750
Glu Ile Val Asn Asp Val Lys Lys His Arg Gly Lys Gly Thr Ser Arg
    755                 760                 765
Glu Asn Ser Asp Ser Ile Leu Leu Asn Gly Cys Arg Arg Ala Val Asp
    770                 775                 780
Ile Leu Tyr Val Asp Glu Ala Phe Ala Cys His Ser Gly Thr Leu Leu
785                 790                 795                 800
Ala Leu Ile Ala Leu Val Lys Pro Arg Ser Lys Val Val Leu Cys Gly
                    805                 810                 815
Asp Pro Lys Gln Cys Gly Phe Phe Asn Met Met Gln Leu Lys Val Asn
                    820                 825                 830
Phe Asn His Asn Ile Cys Thr Glu Val Cys His Lys Ser Ile Ser Arg
            835                 840                 845
Arg Cys Thr Arg Pro Val Thr Ala Ile Val Ser Thr Leu His Tyr Gly
    850                 855                 860
Gly Lys Met Arg Thr Thr Asn Pro Cys Asn Lys Pro Ile Ile Ile Asp
865                 870                 875                 880
Thr Thr Gly Gln Thr Lys Pro Lys Pro Gly Asp Ile Val Leu Thr Cys
                885                 890                 895
Phe Arg Gly Trp Ala Lys Gln Leu Gln Leu Asp Tyr Arg Gly His Glu
            900                 905                 910
Val Met Thr Ala Ala Ala Ser Gln Gly Leu Thr Arg Lys Gly Val Tyr
            915                 920                 925
Ala Val Arg Gln Lys Val Asn Glu Asn Pro Leu Tyr Ala Pro Ala Ser
    930                 935                 940
Glu His Val Asn Val Leu Leu Thr Arg Thr Glu Asp Arg Leu Val Trp
945                 950                 955                 960
Lys Thr Leu Ala Gly Asp Pro Trp Ile Lys Val Leu Ser Asn Ile Pro
                965                 970                 975
Gln Gly Asn Phe Thr Ala Thr Leu Glu Glu Trp Gln Glu Glu His Asp
            980                 985                 990
Lys Ile Met Lys Val Ile Glu Gly Pro Ala Ala Pro Val Asp Ala Phe
    995                 1000                1005
Gln Asn Lys Ala Asn Val Cys Trp Ala Lys Ser Leu Val Pro Val Leu
    1010                1015                1020

-continued

Asp Thr Ala Gly Ile Arg Leu Thr Ala Glu Glu Trp Ser Thr Ile Ile
1025                1030                1035                1040

Thr Ala Phe Lys Glu Asp Arg Ala Tyr Ser Pro Val Ala Leu Asn
        1045                1050                1055

Glu Ile Cys Thr Lys Tyr Tyr Gly Val Asp Leu Asp Ser Gly Leu Phe
            1060                1065                1070

Ser Ala Pro Lys Val Ser Leu Tyr Tyr Glu Asn Asn His Trp Asp Asn
    1075                1080                1085

Arg Pro Gly Gly Arg Met Tyr Gly Phe Asn Ala Ala Thr Ala Ala Arg
1090                1095                1100

Leu Glu Ala Arg His Thr Phe Leu Lys Gly Gln Trp His Thr Gly Lys
1105                1110                1115                1120

Gln Ala Val Ile Ala Glu Arg Lys Ile Gln Pro Leu Ser Val Leu Asp
            1125                1130                1135

Asn Val Ile Pro Ile Asn Arg Arg Leu Pro His Ala Leu Val Ala Glu
                1140                1145                1150

Tyr Lys Thr Val Lys Gly Ser Arg Val Glu Trp Leu Val Asn Lys Val
        1155                1160                1165

Arg Gly Tyr His Val Leu Leu Val Ser Glu Tyr Asn Leu Ala Leu Pro
    1170                1175                1180

Arg Arg Arg Val Thr Trp Leu Ser Pro Leu Asn Val Thr Gly Ala Asp
1185                1190                1195                1200

Arg Cys Tyr Asp Leu Ser Leu Gly Leu Pro Ala Asp Ala Gly Arg Phe
            1205                1210                1215

Asp Leu Val Phe Val Asn Ile His Thr Glu Phe Arg Ile His His Tyr
                1220                1225                1230

Gln Gln Cys Val Asp His Ala Met Lys Leu Gln Met Leu Gly Gly Asp
        1235                1240                1245

Ala Ala Arg Leu Leu Lys Pro Gly Gly Ile Leu Met Arg Ala Tyr Gly
    1250                1255                1260

Tyr Ala Asp Lys Ile Ser Glu Ala Val Val Ser Ser Leu Ser Arg Lys
1265                1270                1275                1280

Phe Ser Ser Ala Arg Val Leu Arg Pro Asp Cys Val Thr Ser Asn Thr
            1285                1290                1295

Glu Val Phe Leu Leu Phe Ser Asn Phe Asp Asn Gly Lys Arg Pro Ser
                1300                1305                1310

Thr Leu His Gln Met Asn Thr Lys Leu Ser Ala Val Tyr Ala Gly Glu
        1315                1320                1325

Ala Met His Thr Ala Gly Cys Ala Pro Ser Tyr Arg Val Lys Arg Ala
    1330                1335                1340

Asp Ile Ala Thr Cys Thr Glu Ala Ala Val Val Asn Ala Ala Asn Ala
1345                1350                1355                1360

Arg Gly Thr Val Gly Asp Gly Val Cys Arg Ala Val Ala Lys Lys Trp
            1365                1370                1375

Pro Ser Ala Phe Lys Gly Ala Ala Thr Pro Val Gly Thr Ile Lys Thr
                1380                1385                1390

Val Met Cys Gly Ser Tyr Pro Val Ile His Ala Val Ala Pro Asn Phe
        1395                1400                1405

Ser Ala Thr Thr Glu Ala Glu Gly Asp Arg Glu Leu Ala Ala Val Tyr
    1410                1415                1420

Arg Ala Val Ala Ala Glu Val Asn Arg Leu Ser Leu Ser Ser Val Ala
1425                1430                1435                1440

Ile Pro Leu Leu Ser Thr Gly Val Phe Ser Gly Gly Arg Asp Arg Leu
            1445                1450                1455

```
Gln Gln Ser Leu Asn His Leu Phe Thr Ala Met Asp Ala Thr Asp Ala
        1460                1465                1470

Asp Val Thr Ile Tyr Cys Arg Asp Lys Ser Trp Glu Lys Lys Ile Gln
1475                1480                1485

Glu Ala Ile Asp Met Arg Thr Ala Val Glu Leu Leu Asn Asp Asp Val
    1490                1495                1500

Glu Leu Thr Thr Asp Leu Val Arg Val His Pro Asp Ser Ser Leu Val
1505                1510                1515                1520

Gly Arg Lys Gly Tyr Ser Thr Thr Asp Gly Ser Leu Tyr Ser Tyr Phe
            1525                1530                1535

Glu Gly Thr Lys Phe Asn Gln Ala Ala Ile Asp Met Ala Glu Ile Leu
        1540                1545                1550

Thr Leu Trp Pro Arg Leu Gln Glu Ala Asn Glu Gln Ile Cys Leu Tyr
    1555                1560                1565

Ala Leu Gly Glu Thr Met Asp Asn Ile Arg Ser Lys Cys Pro Val Asn
    1570                1575                1580

Asp Ser Asp Ser Ser Thr Pro Pro Arg Thr Val Pro Cys Leu Cys Arg
1585                1590                1595                1600

Tyr Ala Met Thr Ala Glu Arg Ile Ala Arg Leu Arg Ser His Gln Val
            1605                1610                1615

Lys Ser Met Val Val Cys Ser Ser Phe Pro Leu Pro Lys Tyr His Val
        1620                1625                1630

Asp Gly Val Gln Lys Val Lys Cys Glu Lys Val Leu Leu Phe Asp Pro
    1635                1640                1645

Thr Val Pro Ser Val Val Ser Pro Arg Lys Tyr Ala Ala Ser Thr Thr
    1650                1655                1660

Asp His Ser Asp Arg Ser Leu Arg Gly Phe Asp Leu Asp Trp Thr Thr
1665                1670                1675                1680

Asp Ser Ser Ser Thr Ala Ser Asp Thr Met Ser Leu Pro Ser Leu Gln
            1685                1690                1695

Ser Cys Asp Ile Asp Ser Ile Tyr Glu Pro Met Ala Pro Ile Val Val
        1700                1705                1710

Thr Ala Asp Val His Pro Glu Pro Ala Gly Ile Ala Asp Leu Ala Ala
    1715                1720                1725

Asp Val His Pro Glu Pro Ala Asp His Val Asp Leu Glu Asn Pro Ile
1730                1735                1740

Pro Pro Pro Arg Pro Lys Arg Ala Ala Tyr Leu Ala Ser Arg Ala Ala
1745                1750                1755                1760

Glu Arg Pro Val Pro Ala Pro Arg Lys Pro Thr Pro Ala Pro Arg Thr
            1765                1770                1775

Ala Phe Arg Asn Lys Leu Pro Leu Thr Phe Gly Asp Phe Asp Glu His
        1780                1785                1790

Glu Val Asp Ala Leu Ala Ser Gly Ile Thr Phe Gly Asp Phe Asp Asp
    1795                1800                1805

Val Leu Arg Leu Gly Arg Ala Gly Ala Tyr Ile Phe Ser Ser Asp Thr
    1810                1815                1820

Gly Ser Gly His Leu Gln Gln Lys Ser Val Arg Gln His Asn Leu Gln
1825                1830                1835                1840

Cys Ala Gln Leu Asp Ala Val Gln Glu Glu Lys Met Tyr Pro Pro Lys
            1845                1850                1855

Leu Asp Thr Glu Arg Glu Lys Leu Leu Leu Leu Lys Met Gln Met His
        1860                1865                1870

Pro Ser Glu Ala Asn Lys Ser Arg Tyr Gln Ser Arg Lys Val Glu Asn
    1875                1880                1885
```

```
Met Lys Ala Thr Val Val Asp Arg Leu Thr Ser Gly Ala Arg Leu Tyr
    1890                1895                1900

Thr Gly Ala Asp Val Gly Arg Ile Pro Thr Tyr Ala Val Arg Tyr Pro
1905                1910                1915                1920

Arg Pro Val Tyr Ser Pro Thr Val Ile Glu Arg Phe Ser Ser Pro Asp
            1925                1930                1935

Val Ala Ile Ala Ala Cys Asn Glu Tyr Leu Ser Arg Asn Tyr Pro Thr
        1940                1945                1950

Val Ala Ser Tyr Gln Ile Thr Asp Glu Tyr Asp Ala Tyr Leu Asp Met
    1955                1960                1965

Val Asp Gly Ser Asp Ser Cys Leu Asp Arg Ala Thr Phe Cys Pro Ala
    1970                1975                1980

Lys Leu Arg Cys Tyr Pro Lys His His Ala Tyr His Gln Pro Thr Val
1985                1990                1995                2000

Arg Ser Ala Val Pro Ser Pro Phe Gln Asn Thr Leu Gln Asn Val Leu
            2005                2010                2015

Ala Ala Ala Thr Lys Arg Asn Cys Asn Val Thr Gln Met Arg Glu Leu
        2020                2025                2030

Pro Thr Met Asp Ser Ala Val Phe Asn Val Glu Cys Phe Lys Arg Tyr
    2035                2040                2045

Ala Cys Ser Gly Glu Tyr Trp Glu Tyr Ala Lys Gln Pro Ile Arg
    2050                2055                2060

Ile Thr Thr Glu Asn Ile Thr Thr Tyr Val Thr Lys Leu Lys Gly Pro
2065                2070                2075                2080

Lys Ala Ala Ala Leu Phe Ala Lys Thr His Asn Leu Val Pro Leu Gln
            2085                2090                2095

Glu Val Pro Met Asp Arg Phe Thr Val Asp Met Lys Arg Asp Val Lys
        2100                2105                2110

Val Thr Pro Gly Thr Lys His Thr Glu Glu Arg Pro Lys Val Gln Val
    2115                2120                2125

Ile Gln Ala Ala Glu Pro Leu Ala Thr Ala Tyr Leu Cys Gly Ile His
    2130                2135                2140

Arg Glu Leu Val Arg Arg Leu Asn Ala Val Leu Arg Pro Asn Val His
2145                2150                2155                2160

Thr Leu Phe Asp Met Ser Ala Glu Asp Phe Asp Ala Ile Ile Ala Ser
            2165                2170                2175

His Phe His Pro Gly Asp Pro Val Leu Glu Thr Asp Ile Ala Ser Phe
        2180                2185                2190

Asp Lys Ser Gln Asp Asp Ser Leu Ala Leu Thr Gly Leu Met Ile Leu
    2195                2200                2205

Glu Asp Leu Gly Val Asp Gln Tyr Leu Leu Asp Leu Ile Glu Ala Ala
    2210                2215                2220

Phe Gly Glu Ile Ser Ser Cys His Leu Pro Thr Gly Thr Arg Phe Lys
2225                2230                2235                2240

Phe Gly Ala Met Met Lys Ser Gly Met Phe Leu Thr Leu Phe Ile Asn
            2245                2250                2255

Thr Val Leu Asn Ile Thr Ile Ala Ser Arg Val Leu Glu Gln Arg Leu
        2260                2265                2270

Thr Asp Ser Ala Cys Ala Ala Phe Ile Gly Asp Asp Asn Ile Val His
    2275                2280                2285

Gly Val Ile Ser Asp Lys Leu Met Ala Glu Arg Cys Ala Ser Trp Val
    2290                2295                2300

Asn Met Glu Val Lys Ile Ile Asp Ala Val Met Gly Glu Lys Pro Pro
2305                2310                2315                2320
```

-continued

Tyr Phe Cys Gly Gly Phe Ile Val Phe Asp Ser Val Thr Gln Thr Ala
            2325                2330                2335

Cys Arg Val Ser Asp Pro Leu Lys Arg Leu Phe Lys Leu Gly Lys Pro
            2340                2345                2350

Leu Thr Ala Glu Asp Lys Gln Asp Glu Asp Arg Arg Arg Ala Leu Ser
            2355                2360                2365

Asp Glu Val Ser Lys Trp Phe Arg Thr Gly Leu Gly Ala Glu Leu Glu
            2370                2375                2380

Val Ala Leu Thr Ser Arg Tyr Glu Val Glu Gly Cys Lys Ser Ile Leu
2385                2390                2395                2400

Ile Ala Met Ala Thr Leu Ala Arg Asp Ile Lys Ala Phe Lys Lys Leu
            2405                2410                2415

Arg Gly Pro Val Ile His Leu Tyr Gly Gly Pro Arg Leu Val Arg
            2420                2425                2430

<210> SEQ ID NO 9
<211> LENGTH: 2432
<212> TYPE: PRT
<213> ORGANISM: Artificial Sequence
<220> FEATURE:
<223> OTHER INFORMATION: Description of Artificial Sequence: Synthetic
      pJY1099.1 amino acid sequence

<400> SEQUENCE: 9

Met Ala Ala Lys Val His Val Asp Ile Glu Ala Asp Ser Pro Phe Ile
1               5                   10                  15

Lys Ser Leu Gln Lys Ala Phe Pro Ser Phe Glu Val Glu Ser Leu Gln
            20                  25                  30

Val Thr Pro Asn Asp His Ala Asn Ala Arg Ala Phe Ser His Leu Ala
        35                  40                  45

Thr Lys Leu Ile Glu Gln Glu Thr Asp Lys Asp Thr Leu Ile Leu Asp
    50                  55                  60

Ile Gly Ser Ala Pro Ser Arg Arg Met Met Ser Thr His Lys Tyr His
65                  70                  75                  80

Cys Val Cys Pro Met Arg Ser Ala Glu Asp Pro Glu Arg Leu Val Cys
                85                  90                  95

Tyr Ala Lys Lys Leu Ala Ala Ala Ser Gly Lys Val Leu Asp Arg Glu
            100                 105                 110

Ile Ala Gly Lys Ile Thr Asp Leu Gln Thr Val Met Ala Thr Pro Asp
        115                 120                 125

Ala Glu Ser Pro Thr Phe Cys Leu His Thr Asp Val Thr Cys Arg Thr
    130                 135                 140

Ala Ala Glu Val Ala Val Tyr Gln Asp Val Tyr Ala Val His Ala Pro
145                 150                 155                 160

Thr Ser Leu Tyr His Gln Ala Met Lys Gly Val Arg Thr Ala Tyr Trp
                165                 170                 175

Ile Gly Phe Asp Thr Thr Pro Phe Met Phe Asp Ala Leu Ala Gly Ala
            180                 185                 190

Tyr Pro Thr Tyr Ala Thr Asn Trp Ala Asp Glu Gln Val Leu Gln Ala
        195                 200                 205

Arg Asn Ile Gly Leu Cys Ala Ala Ser Leu Thr Glu Gly Arg Leu Gly
    210                 215                 220

Lys Leu Ser Ile Leu Arg Lys Lys Gln Leu Lys Pro Cys Asp Thr Val
225                 230                 235                 240

Met Phe Ser Val Gly Ser Thr Leu Tyr Thr Glu Ser Arg Lys Leu Leu
                245                 250                 255

```
Arg Ser Trp His Leu Pro Ser Val Phe His Leu Lys Gly Lys Gln Ser
            260                 265                 270

Phe Thr Cys Arg Cys Asp Thr Ile Val Ser Cys Glu Gly Tyr Val Val
            275                 280                 285

Lys Lys Ile Thr Met Cys Pro Gly Leu Tyr Gly Lys Thr Val Gly Tyr
            290                 295                 300

Ala Val Thr Tyr His Ala Glu Gly Phe Leu Val Cys Lys Thr Thr Asp
305                 310                 315                 320

Thr Val Lys Gly Glu Arg Val Ser Phe Pro Val Cys Thr Tyr Val Pro
                325                 330                 335

Ser Thr Ile Cys Asp Gln Met Thr Gly Ile Leu Ala Thr Asp Val Thr
            340                 345                 350

Pro Glu Asp Ala Gln Lys Leu Leu Val Gly Leu Asn Gln Arg Ile Val
            355                 360                 365

Val Asn Gly Arg Thr Gln Arg Asn Thr Asn Thr Met Lys Asn Tyr Leu
    370                 375                 380

Leu Pro Ile Val Ala Val Ala Phe Ser Lys Trp Ala Arg Glu Tyr Lys
385                 390                 395                 400

Ala Asp Leu Asp Asp Glu Lys Pro Leu Gly Val Arg Glu Arg Ser Leu
                405                 410                 415

Thr Cys Cys Cys Leu Trp Ala Phe Lys Thr Arg Lys Met His Thr Met
            420                 425                 430

Tyr Lys Lys Pro Asp Thr Gln Thr Ile Val Lys Val Pro Ser Glu Phe
            435                 440                 445

Asn Ser Phe Val Ile Pro Ser Leu Trp Ser Thr Gly Leu Ala Ile Pro
    450                 455                 460

Val Arg Ser Arg Ile Lys Met Leu Leu Ala Lys Lys Thr Lys Arg Glu
465                 470                 475                 480

Leu Ile Pro Val Leu Asp Ala Ser Ser Ala Arg Asp Ala Glu Gln Glu
                485                 490                 495

Glu Lys Glu Arg Leu Glu Ala Glu Leu Thr Arg Glu Ala Leu Pro Pro
            500                 505                 510

Leu Val Pro Ile Ala Pro Ala Glu Thr Gly Val Val Asp Val Asp Val
            515                 520                 525

Glu Glu Leu Glu Tyr His Ala Gly Ala Gly Val Val Glu Thr Pro Arg
530                 535                 540

Ser Ala Leu Lys Val Thr Ala Gln Pro Asn Asp Val Leu Leu Gly Asn
545                 550                 555                 560

Tyr Val Val Leu Ser Pro Gln Thr Val Leu Lys Ser Ser Lys Leu Ala
                565                 570                 575

Pro Val His Pro Leu Ala Glu Gly Val Lys Ile Ile Thr His Asn Gly
            580                 585                 590

Arg Ala Gly Arg Tyr Gln Val Asp Gly Tyr Asp Gly Arg Val Leu Leu
            595                 600                 605

Pro Cys Gly Ser Ala Ile Pro Val Pro Glu Phe Gln Ala Leu Ser Glu
            610                 615                 620

Ser Ala Thr Met Val Tyr Asn Glu Arg Glu Phe Val Asn Arg Lys Leu
625                 630                 635                 640

Tyr His Ile Ala Val His Gly Pro Ser Leu Asn Thr Asp Glu Glu Asn
                645                 650                 655

Tyr Glu Lys Val Arg Ala Glu Arg Thr Asp Ala Glu Tyr Val Phe Asp
            660                 665                 670

Val Asp Lys Lys Cys Cys Val Lys Arg Glu Glu Ala Ser Gly Leu Val
            675                 680                 685
```

-continued

```
Leu Val Gly Glu Leu Thr Asn Pro Phe His Glu Phe Ala Tyr Glu
690                 695                 700

Gly Leu Lys Ile Arg Pro Ser Ala Pro Tyr Lys Thr Thr Val Val Gly
705                 710                 715                 720

Val Phe Gly Val Pro Gly Ser Gly Lys Ser Ala Ile Ile Lys Ser Leu
            725                 730                 735

Val Thr Lys His Asp Leu Val Thr Ser Gly Lys Lys Glu Asn Cys Gln
            740                 745                 750

Glu Ile Val Asn Asp Val Lys Lys His Arg Gly Leu Asp Ile Gln Ala
            755                 760                 765

Lys Thr Val Asp Ser Ile Leu Leu Asn Gly Cys Arg Arg Ala Val Asp
770                 775                 780

Ile Leu Tyr Val Asp Glu Ala Phe Ala Cys His Pro Gly Thr Leu Leu
785                 790                 795                 800

Ala Leu Ile Ala Leu Val Lys Pro Arg Ser Lys Val Val Leu Cys Gly
            805                 810                 815

Asp Pro Lys Gln Cys Gly Phe Phe Asn Met Met Gln Leu Lys Val Asn
            820                 825                 830

Phe Asn His Asn Ile Cys Thr Glu Val Cys His Lys Ser Ile Ser Arg
            835                 840                 845

Arg Cys Thr Arg Pro Val Thr Ala Ile Val Ser Thr Leu His Tyr Gly
850                 855                 860

Gly Lys Met Arg Thr Thr Asn Pro Cys Asn Lys Pro Ile Ile Ile Asp
865                 870                 875                 880

Thr Thr Gly Gln Thr Lys Pro Lys Pro Gly Asp Ile Val Leu Thr Cys
            885                 890                 895

Phe Arg Gly Trp Val Lys Gln Leu Gln Leu Asp Tyr Arg Gly His Glu
            900                 905                 910

Val Met Thr Ala Ala Ala Ser Gln Gly Leu Thr Arg Lys Gly Val Tyr
            915                 920                 925

Ala Val Arg Gln Lys Val Asn Glu Asn Pro Leu Tyr Ala Pro Ala Ser
            930                 935                 940

Glu His Val Asn Val Leu Leu Thr Arg Thr Glu Asp Arg Leu Val Trp
945                 950                 955                 960

Lys Thr Leu Ala Gly Asp Pro Trp Ile Lys Val Leu Ser Asn Ile Pro
            965                 970                 975

Gln Gly Asn Phe Thr Ala Thr Leu Glu Glu Trp Gln Glu Glu His Asp
            980                 985                 990

Lys Ile Met Lys Val Ile Gly Pro Ala Ala Pro Val Asp Ala Phe
            995                 1000                1005

Gln Asn Lys Ala Asn Val Cys Trp Ala Lys Ser Leu Val Pro Val Leu
    1010                1015                1020

Asp Thr Ala Gly Ile Arg Leu Thr Ala Glu Glu Trp Ser Thr Ile Ile
1025                1030                1035                1040

Thr Ala Phe Lys Glu Asp Arg Ala Tyr Ser Pro Val Val Ala Leu Asn
            1045                1050                1055

Glu Ile Cys Thr Lys Tyr Tyr Gly Val Asp Leu Asp Ser Gly Leu Phe
            1060                1065                1070

Ser Ala Pro Lys Val Ser Leu Tyr Tyr Glu Asn Asn His Trp Asp Asn
            1075                1080                1085

Arg Pro Gly Gly Arg Met Tyr Gly Phe Asn Ala Ala Thr Ala Ala Arg
    1090                1095                1100

Leu Glu Ala Arg His Thr Phe Leu Lys Gly Gln Trp His Thr Gly Lys
1105                1110                1115                1120
```

-continued

```
Gln Ala Val Ile Ala Glu Arg Lys Ile Gln Pro Leu Ser Val Leu Asp
            1125                1130                1135

Asn Val Ile Pro Ile Asn Arg Arg Leu Pro His Ala Leu Val Ala Glu
        1140                1145                1150

Tyr Lys Thr Val Lys Gly Ser Arg Val Glu Trp Leu Val Asn Lys Val
    1155                1160                1165

Arg Gly Tyr His Val Leu Leu Val Ser Glu Tyr Asn Leu Ala Leu Pro
 1170                1175                1180

Arg Arg Asp Val Thr Trp Leu Ser Pro Leu Asn Val Thr Gly Ala Asp
1185                1190                1195                1200

Arg Cys Tyr Asp Leu Ser Leu Gly Leu Pro Ala Asp Ala Gly Arg Phe
        1205                1210                1215

Asp Leu Val Phe Val Asn Ile His Thr Glu Phe Arg Ile His His Tyr
    1220                1225                1230

Gln Gln Cys Val Asp His Ala Met Lys Leu Gln Met Leu Gly Gly Asp
 1235                1240                1245

Ala Leu Arg Leu Leu Lys Pro Gly Gly Ser Leu Leu Met Arg Ala Tyr
1250                1255                1260

Gly Tyr Ala Asp Lys Ile Ser Glu Ala Val Val Ser Ser Leu Ser Arg
1265                1270                1275                1280

Lys Phe Ser Ser Ala Arg Val Leu Arg Pro Asp Cys Val Thr Ser Asn
        1285                1290                1295

Thr Glu Val Phe Leu Leu Phe Ser Asn Phe Asp Asn Gly Lys Arg Pro
    1300                1305                1310

Ser Thr Leu His Gln Met Asn Thr Lys Leu Ser Ala Val Tyr Ala Gly
 1315                1320                1325

Glu Ala Met His Thr Ala Gly Cys Ala Pro Ser Tyr Arg Val Lys Arg
1330                1335                1340

Ala Asp Ile Ala Thr Cys Thr Glu Ala Ala Val Val Asn Ala Ala Asn
1345                1350                1355                1360

Ala Arg Gly Thr Val Gly Asp Gly Val Cys Arg Ala Val Ala Lys Lys
        1365                1370                1375

Trp Pro Ser Ala Phe Lys Gly Glu Ala Thr Pro Val Gly Thr Ile Lys
    1380                1385                1390

Thr Val Met Cys Gly Ser Tyr Pro Val Ile His Ala Val Ala Pro Asn
 1395                1400                1405

Phe Ser Ala Thr Thr Glu Ala Glu Gly Asp Arg Glu Leu Ala Ala Val
    1410                1415                1420

Tyr Arg Ala Val Ala Ala Glu Val Asn Arg Leu Ser Leu Ser Ser Val
1425                1430                1435                1440

Ala Ile Pro Leu Leu Ser Thr Gly Val Phe Ser Gly Gly Arg Asp Arg
        1445                1450                1455

Leu Gln Gln Ser Leu Asn His Leu Phe Thr Ala Met Asp Ala Thr Asp
    1460                1465                1470

Ala Asp Val Thr Ile Tyr Cys Arg Asp Lys Ser Trp Glu Lys Lys Ile
 1475                1480                1485

Gln Glu Ala Ile Asp Met Arg Thr Ala Val Glu Leu Leu Asn Asp Asp
    1490                1495                1500

Val Glu Leu Thr Thr Asp Leu Val Arg Val His Pro Asp Ser Ser Leu
1505                1510                1515                1520

Val Gly Arg Lys Gly Tyr Ser Thr Thr Asp Gly Ser Leu Tyr Ser Tyr
        1525                1530                1535

Phe Glu Gly Thr Lys Phe Asn Gln Ala Ala Ile Asp Met Ala Glu Ile
    1540                1545                1550
```

Leu Thr Leu Trp Pro Arg Leu Gln Glu Ala Asn Glu Gln Ile Cys Leu
            1555                1560                1565

Tyr Ala Leu Gly Glu Thr Met Asp Asn Ile Arg Ser Lys Cys Pro Val
        1570                1575                1580

Asn Asp Ser Asp Ser Ser Thr Pro Pro Arg Thr Val Pro Cys Leu Cys
1585                1590                1595                1600

Arg Tyr Ala Met Thr Ala Glu Arg Ile Ala Arg Leu Arg Ser His Gln
            1605                1610                1615

Val Lys Ser Met Val Val Cys Ser Ser Phe Pro Leu Pro Lys Tyr His
        1620                1625                1630

Val Asp Gly Val Gln Lys Val Lys Cys Glu Lys Val Leu Leu Phe Asp
    1635                1640                1645

Pro Thr Val Pro Ser Val Val Ser Pro Arg Lys Tyr Ala Ala Ser Thr
        1650                1655                1660

Thr Asp His Ser Asp Arg Ser Leu Arg Gly Phe Asp Leu Asp Trp Thr
1665                1670                1675                1680

Thr Asp Ser Ser Ser Thr Ala Ser Asp Thr Met Ser Leu Pro Ser Leu
            1685                1690                1695

Gln Ser Cys Asp Ile Asp Ser Ile Tyr Glu Pro Met Ala Pro Ile Val
        1700                1705                1710

Val Thr Ala Asp Val His Pro Glu Pro Ala Gly Ile Ala Asp Leu Ala
    1715                1720                1725

Ala Asp Val His Pro Glu Pro Ala Asp His Val Asp Leu Glu Asn Pro
    1730                1735                1740

Ile Pro Pro Pro Arg Pro Lys Arg Ala Ala Tyr Leu Ala Ser Arg Ala
1745                1750                1755                1760

Ala Glu Arg Pro Val Pro Ala Pro Arg Lys Pro Thr Pro Ala Pro Arg
            1765                1770                1775

Thr Ala Phe Arg Asn Lys Leu Pro Leu Thr Phe Gly Asp Phe Asp Glu
        1780                1785                1790

His Glu Val Asp Ala Leu Ala Ser Gly Ile Thr Phe Gly Asp Phe Asp
    1795                1800                1805

Asp Val Leu Arg Leu Gly Arg Ala Gly Ala Tyr Ile Phe Ser Ser Asp
    1810                1815                1820

Thr Gly Ser Gly His Leu Gln Gln Lys Ser Val Arg Gln His Asn Leu
1825                1830                1835                1840

Gln Cys Ala Gln Leu Asp Ala Val Glu Glu Glu Lys Met Tyr Pro Pro
            1845                1850                1855

Lys Leu Asp Thr Glu Arg Glu Lys Leu Leu Leu Leu Lys Met Gln Met
        1860                1865                1870

His Pro Ser Glu Ala Asn Lys Ser Arg Tyr Gln Ser Arg Lys Val Glu
    1875                1880                1885

Asn Met Lys Ala Thr Val Val Asp Arg Leu Thr Ser Gly Ala Arg Leu
    1890                1895                1900

Tyr Thr Gly Ala Asp Val Gly Arg Ile Pro Thr Tyr Ala Val Arg Tyr
1905                1910                1915                1920

Pro Arg Pro Val Tyr Ser Pro Thr Val Ile Glu Arg Phe Ser Ser Pro
            1925                1930                1935

Asp Val Ala Ile Ala Ala Cys Asn Glu Tyr Leu Ser Arg Asn Tyr Pro
        1940                1945                1950

Thr Val Ala Ser Tyr Gln Ile Thr Asp Glu Tyr Asp Ala Tyr Leu Asp
    1955                1960                1965

Met Val Asp Gly Ser Asp Ser Cys Leu Asp Arg Ala Thr Phe Cys Pro
1970                1975                1980

-continued

```
Ala Lys Leu Arg Cys Tyr Pro Lys His His Ala Tyr His Gln Pro Thr
1985                1990                1995                2000

Val Arg Ser Ala Val Pro Ser Pro Phe Gln Asn Thr Leu Gln Asn Val
            2005                2010                2015

Leu Ala Ala Ala Thr Lys Arg Asn Cys Asn Val Thr Gln Met Arg Glu
        2020                2025                2030

Leu Pro Thr Met Asp Ser Ala Val Phe Asn Val Glu Cys Phe Lys Arg
        2035                2040                2045

Tyr Ala Cys Ser Gly Glu Tyr Trp Glu Glu Tyr Ala Lys Gln Pro Ile
    2050                2055                2060

Arg Ile Thr Thr Glu Asn Ile Thr Thr Tyr Val Thr Lys Leu Lys Gly
2065                2070                2075                2080

Pro Lys Ala Ala Ala Leu Phe Ala Lys Thr His Asn Leu Val Pro Leu
            2085                2090                2095

Gln Glu Val Pro Met Asp Arg Phe Thr Val Asp Met Lys Arg Asp Val
                2100                2105                2110

Lys Val Thr Pro Gly Thr Lys His Thr Glu Glu Arg Pro Lys Val Gln
        2115                2120                2125

Val Ile Gln Ala Ala Glu Pro Leu Ala Thr Ala Tyr Leu Cys Gly Ile
    2130                2135                2140

His Arg Glu Leu Val Arg Arg Leu Asn Ala Val Leu Arg Pro Asn Val
2145                2150                2155                2160

His Thr Leu Phe Asp Met Ser Ala Glu Asp Phe Asp Ala Ile Ile Ala
            2165                2170                2175

Ser His Phe His Pro Gly Asp Pro Val Leu Glu Thr Asp Ile Ala Ser
            2180                2185                2190

Phe Asp Lys Ser Gln Asp Asp Ser Leu Ala Leu Thr Gly Leu Met Ile
        2195                2200                2205

Leu Glu Asp Leu Gly Val Asp Gln Tyr Leu Leu Asp Leu Ile Glu Ala
        2210                2215                2220

Ala Phe Gly Glu Ile Ser Ser Cys His Leu Pro Thr Gly Thr Arg Phe
2225                2230                2235                2240

Lys Phe Gly Ala Met Met Lys Ser Gly Met Phe Leu Thr Leu Phe Ile
            2245                2250                2255

Asn Thr Val Leu Asn Ile Thr Ile Ala Ser Arg Val Leu Glu Gln Arg
        2260                2265                2270

Leu Thr Asp Ser Ala Cys Ala Ala Phe Ile Gly Asp Asp Asn Ile Val
        2275                2280                2285

His Gly Val Ile Ser Asp Lys Leu Met Ala Glu Arg Cys Ala Ser Trp
2290                2295                2300

Val Asn Met Glu Val Lys Ile Ile Asp Ala Val Met Gly Glu Lys Pro
2305                2310                2315                2320

Pro Tyr Phe Cys Gly Gly Phe Ile Val Phe Asp Ser Val Thr Gln Thr
        2325                2330                2335

Ala Cys Arg Val Ser Asp Pro Leu Lys Arg Leu Phe Lys Leu Gly Lys
            2340                2345                2350

Pro Leu Thr Ala Glu Asp Lys Gln Asp Glu Asp Arg Arg Arg Ala Leu
        2355                2360                2365

Ser Asp Glu Val Ser Lys Trp Phe Arg Thr Gly Leu Gly Ala Glu Leu
    2370                2375                2380

Glu Val Ala Leu Thr Ser Arg Tyr Glu Val Glu Gly Cys Lys Ser Ile
2385                2390                2395                2400
```

```
Leu Ile Ala Met Ala Thr Leu Ala Arg Asp Ile Lys Ala Phe Lys Lys
            2405                2410                2415

Leu Arg Gly Pro Val Ile His Leu Tyr Gly Gly Pro Arg Leu Val Arg
        2420                2425                2430

<210> SEQ ID NO 10
<211> LENGTH: 450
<212> TYPE: PRT
<213> ORGANISM: Artificial Sequence
<220> FEATURE:
<223> OTHER INFORMATION: Description of Artificial Sequence: Synthetic
      pJY1099.1 amino acid sequence

<400> SEQUENCE: 10

Met Gly Asn Gly Gln Gly Arg Asp Trp Lys Met Ala Ile Lys Arg Cys
  1               5                  10                  15

Ser Asn Val Ala Val Gly Val Gly Gly Lys Ser Lys Lys Phe Gly Glu
             20                  25                  30

Gly Asn Phe Arg Trp Ala Ile Arg Met Ala Asn Val Ser Thr Gly Arg
         35                  40                  45

Glu Pro Gly Asp Ile Pro Glu Thr Leu Asp Gln Leu Arg Leu Val Ile
 50                  55                  60

Cys Asp Leu Gln Glu Arg Arg Glu Lys Phe Gly Ser Ser Lys Glu Ile
 65                  70                  75                  80

Asp Met Ala Ile Val Thr Leu Lys Val Phe Ala Val Ala Gly Leu Leu
                 85                  90                  95

Asn Met Thr Val Ser Thr Ala Ala Ala Glu Asn Met Tyr Ser Gln
            100                 105                 110

Met Gly Leu Asp Thr Arg Pro Ser Met Lys Glu Ala Gly Gly Lys Glu
        115                 120                 125

Glu Gly Pro Pro Gln Ala Tyr Pro Ile Gln Thr Val Asn Gly Val Pro
    130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Val Gln Leu Trp Phe Thr Ala
                165                 170                 175

Phe Ser Ala Asn Leu Thr Pro Thr Asp Met Ala Thr Leu Ile Met Ala
            180                 185                 190

Ala Pro Gly Cys Ala Ala Asp Lys Glu Ile Leu Asp Glu Ser Leu Lys
        195                 200                 205

Gln Leu Thr Ala Glu Tyr Asp Arg Thr His Pro Pro Asp Ala Pro Arg
    210                 215                 220

Pro Leu Pro Tyr Phe Thr Ala Ala Glu Ile Met Gly Ile Gly Leu Thr
225                 230                 235                 240

Gln Glu Gln Gln Ala Glu Ala Arg Phe Ala Pro Ala Arg Met Gln Cys
                245                 250                 255

Arg Ala Trp Tyr Leu Glu Ala Leu Gly Lys Leu Ala Ala Ile Lys Ala
            260                 265                 270

Lys Ser Pro Arg Ala Val Gln Leu Arg Gln Gly Ala Lys Glu Asp Tyr
        275                 280                 285

Ser Ser Phe Ile Asp Arg Leu Phe Ala Gln Ile Asp Gln Glu Gln Asn
    290                 295                 300

Thr Ala Glu Val Lys Leu Tyr Leu Lys Gln Ser Leu Ser Ile Ala Asn
305                 310                 315                 320

Ala Asn Ala Asp Cys Lys Lys Ala Met Ser His Leu Lys Pro Glu Ser
                325                 330                 335
```

```
Thr Leu Glu Glu Lys Leu Arg Ala Cys Gln Glu Ile Gly Ser Pro Gly
            340                 345                 350

Tyr Lys Met Gln Leu Leu Ala Glu Ala Leu Thr Lys Val Gln Val Val
        355                 360                 365

Gln Ser Lys Gly Ser Gly Pro Val Cys Phe Asn Cys Lys Lys Pro Gly
    370                 375                 380

His Leu Ala Arg Gln Cys Arg Glu Val Lys Lys Cys Asn Lys Cys Gly
385                 390                 395                 400

Lys Pro Gly His Leu Ala Ala Lys Cys Trp Gln Gly Asn Arg Lys Asn
                405                 410                 415

Ser Gly Asn Trp Lys Ala Gly Arg Ala Ala Pro Val Asn Gln Met
            420                 425                 430

Gln Gln Ala Val Met Pro Ser Ala Pro Pro Met Glu Glu Lys Leu Leu
        435                 440                 445

Asp Leu
    450

<210> SEQ ID NO 11
<211> LENGTH: 149
<212> TYPE: PRT
<213> ORGANISM: Artificial Sequence
<220> FEATURE:
<223> OTHER INFORMATION: Description of Artificial Sequence: Synthetic
      pJY1099.1 amino acid sequence

<400> SEQUENCE: 11

Leu Glu Gly Gly Ala Ser Cys Ser Pro Ser Glu Ser Asn Ala Ala Ser
1               5                   10                  15

Ser Asn Ala Ile Cys Thr Ser Asn Gly Gly Glu Thr Ile Gly Phe Ile
            20                  25                  30

Asn Tyr Asn Lys Val Gly Thr Thr Thr Thr Leu Glu Lys Arg Pro Glu
        35                  40                  45

Ile Leu Ile Phe Val Asn Gly Tyr Pro Ile Lys Phe Leu Leu Asp Thr
    50                  55                  60

Gly Ala Asp Ile Thr Ile Leu Asn Arg Arg Asp Phe Gln Val Lys Asn
65                  70                  75                  80

Ser Ile Glu Asn Gly Arg Gln Asn Met Ile Gly Val Gly Gly Gly Lys
                85                  90                  95

Arg Gly Thr Asn Tyr Ile Asn Val His Leu Glu Ile Arg Asp Glu Asn
            100                 105                 110

Tyr Lys Thr Gln Cys Ile Phe Gly Asn Val Cys Val Leu Glu Asp Asn
        115                 120                 125

Ser Leu Ile Gln Pro Leu Leu Gly Arg Asp Asn Met Ile Lys Phe Asn
    130                 135                 140

Ile Arg Leu Val Met
145

<210> SEQ ID NO 12
<211> LENGTH: 2432
<212> TYPE: PRT
<213> ORGANISM: Artificial Sequence
<220> FEATURE:
<223> OTHER INFORMATION: Description of Artificial Sequence: Synthetic
      pJY1302.4 amino acid sequence
```

```
<400> SEQUENCE: 12

Met Ala Ala Lys Val His Val Asp Ile Glu Ala Asp Ser Pro Phe Ile
1               5                   10                  15

Lys Ser Leu Gln Lys Ala Phe Pro Ser Phe Glu Val Glu Ser Leu Gln
            20                  25                  30

Val Thr Pro Asn Asp His Ala Asn Ala Arg Ala Phe Ser His Leu Ala
        35                  40                  45

Thr Lys Leu Ile Glu Gln Glu Thr Asp Lys Asp Thr Leu Ile Leu Asp
    50                  55                  60

Ile Gly Ser Ala Pro Ser Arg Arg Met Met Ser Thr His Lys Tyr His
65                  70                  75                  80

Cys Val Cys Pro Met Arg Ser Ala Glu Asp Pro Glu Arg Leu Val Cys
                85                  90                  95

Tyr Ala Lys Lys Leu Ala Ala Ala Ser Gly Lys Val Leu Asp Arg Glu
            100                 105                 110

Ile Ala Gly Lys Ile Thr Asp Leu Gln Thr Val Met Ala Thr Pro Asp
        115                 120                 125

Ala Glu Ser Pro Thr Phe Cys Leu His Thr Asp Val Thr Cys Arg Thr
    130                 135                 140

Ala Ala Glu Val Ala Val Tyr Gln Asp Val Tyr Ala Val His Ala Pro
145                 150                 155                 160

Thr Ser Leu Tyr His Gln Ala Met Lys Gly Val Arg Thr Ala Tyr Trp
                165                 170                 175

Ile Gly Phe Asp Thr Thr Pro Phe Met Phe Asp Ala Leu Ala Gly Ala
            180                 185                 190

Tyr Pro Thr Tyr Ala Thr Asn Trp Ala Asp Glu Gln Val Leu Gln Ala
        195                 200                 205

Arg Asn Ile Gly Leu Cys Ala Ala Ser Leu Thr Glu Gly Arg Leu Gly
    210                 215                 220

Lys Leu Ser Ile Leu Arg Lys Lys Gln Leu Lys Pro Cys Asp Thr Val
225                 230                 235                 240

Met Phe Ser Val Gly Ser Thr Leu Tyr Thr Glu Ser Arg Lys Leu Leu
                245                 250                 255

Arg Ser Trp His Leu Pro Ser Val Phe His Leu Lys Gly Lys Gln Ser
            260                 265                 270

Phe Thr Cys Arg Cys Asp Thr Ile Val Ser Cys Glu Gly Tyr Val Val
        275                 280                 285

Lys Lys Ile Thr Met Cys Pro Gly Leu Tyr Gly Lys Thr Val Gly Tyr
    290                 295                 300

Ala Val Thr Tyr His Ala Glu Gly Phe Leu Val Cys Lys Thr Thr Asp
305                 310                 315                 320

Thr Val Lys Gly Glu Arg Val Ser Phe Pro Val Cys Thr Tyr Val Pro
                325                 330                 335

Ser Thr Ile Cys Asp Gln Met Thr Gly Ile Leu Ala Thr Asp Val Thr
            340                 345                 350

Pro Glu Asp Ala Gln Lys Leu Leu Val Gly Leu Asn Gln Arg Ile Val
        355                 360                 365

Val Asn Gly Arg Thr Gln Arg Asn Thr Asn Thr Met Lys Asn Tyr Leu
    370                 375                 380

Leu Pro Ile Val Ala Val Ala Phe Ser Lys Trp Ala Arg Glu Tyr Lys
385                 390                 395                 400

Ala Asp Leu Asp Asp Glu Lys Pro Leu Gly Val Arg Glu Arg Ser Leu
                405                 410                 415
```

```
Thr Cys Cys Cys Leu Trp Ala Phe Lys Thr Arg Lys Met His Thr Met
            420                 425                 430

Tyr Lys Lys Pro Asp Thr Gln Thr Ile Val Lys Val Pro Ser Glu Phe
        435                 440                 445

Asn Ser Phe Val Ile Pro Ser Leu Trp Ser Thr Gly Leu Ala Ile Pro
    450                 455                 460

Val Arg Ser Arg Ile Lys Met Leu Leu Ala Lys Lys Thr Lys Arg Glu
465                 470                 475                 480

Leu Ile Pro Val Leu Asp Ala Ser Ser Ala Arg Asp Ala Glu Gln Glu
                485                 490                 495

Glu Lys Glu Arg Leu Glu Ala Glu Leu Thr Arg Glu Ala Leu Pro Pro
                500                 505                 510

Leu Val Pro Ile Ala Pro Ala Glu Thr Gly Val Val Asp Val Asp Val
                515                 520                 525

Glu Glu Leu Glu Tyr His Ala Gly Ala Gly Val Val Glu Thr Pro Arg
530                 535                 540

Ser Ala Leu Lys Val Thr Ala Gln Pro Asn Asp Val Leu Leu Gly Asn
545                 550                 555                 560

Tyr Val Val Leu Ser Pro Gln Thr Val Leu Lys Ser Ser Lys Leu Ala
                565                 570                 575

Pro Val His Pro Leu Ala Glu Gln Val Lys Ile Ile Thr His Asn Gly
                580                 585                 590

Arg Ala Gly Arg Tyr Gln Val Asp Gly Tyr Asp Gly Arg Val Leu Leu
                595                 600                 605

Pro Cys Gly Ser Ala Ile Pro Val Pro Glu Phe Gln Ala Leu Ser Glu
                610                 615                 620

Ser Ala Thr Met Val Tyr Asn Glu Arg Glu Phe Val Asn Arg Lys Leu
625                 630                 635                 640

Tyr His Ile Ala Val His Gly Pro Ser Leu Asn Thr Asp Glu Glu Asn
                645                 650                 655

Tyr Glu Lys Val Arg Ala Glu Arg Thr Asp Ala Glu Tyr Val Phe Asp
                660                 665                 670

Val Asp Lys Lys Cys Cys Val Lys Arg Glu Glu Ala Ser Gly Leu Val
                675                 680                 685

Leu Val Gly Glu Leu Thr Asn Pro Pro Phe His Glu Phe Ala Tyr Glu
                690                 695                 700

Gly Leu Lys Ile Arg Pro Ser Ala Pro Tyr Lys Thr Thr Val Val Gly
705                 710                 715                 720

Val Phe Gly Val Pro Gly Ser Gly Lys Ser Ala Ile Ile Lys Ser Leu
                725                 730                 735

Val Thr Lys His Asp Leu Val Thr Ser Gly Lys Lys Glu Asn Cys Gln
                740                 745                 750

Glu Ile Val Asn Asp Val Lys Lys His Arg Gly Leu Asp Ile Gln Ala
                755                 760                 765

Lys Thr Val Asp Ser Ile Leu Leu Asn Gly Cys Arg Arg Ala Val Asp
                770                 775                 780

Ile Leu Tyr Val Asp Glu Ala Phe Ala Cys His Pro Gly Thr Leu Leu
785                 790                 795                 800

Ala Leu Ile Ala Leu Val Lys Pro Arg Ser Lys Val Val Leu Cys Gly
                805                 810                 815

Asp Pro Lys Gln Cys Gly Phe Phe Asn Met Met Gln Leu Lys Val Asn
                820                 825                 830

Phe Asn His Asn Ile Cys Thr Glu Val Cys His Lys Ser Ile Ser Arg
                835                 840                 845
```

-continued

```
Arg Cys Thr Arg Pro Val Thr Ala Ile Val Ser Thr Leu His Tyr Gly
    850                 855                 860
Gly Lys Met Arg Thr Thr Asn Pro Cys Asn Lys Pro Ile Ile Ile Asp
865                 870                 875                 880
Thr Thr Gly Gln Thr Lys Pro Lys Pro Gly Asp Ile Val Leu Thr Cys
                    885                 890                 895
Phe Arg Gly Trp Val Lys Gln Leu Gln Leu Asp Tyr Arg Gly His Glu
                900                 905                 910
Val Met Thr Ala Ala Ser Gln Gly Leu Thr Arg Lys Gly Val Tyr
            915                 920                 925
Ala Val Arg Gln Lys Val Asn Glu Asn Pro Leu Tyr Ala Pro Ala Ser
    930                 935                 940
Glu His Val Asn Val Leu Leu Thr Arg Thr Glu Asp Arg Leu Val Trp
945                 950                 955                 960
Lys Thr Leu Ala Gly Asp Pro Trp Ile Lys Val Leu Ser Asn Ile Pro
                965                 970                 975
Gln Gly Asn Phe Thr Ala Thr Leu Glu Glu Trp Gln Glu Glu His Asp
                980                 985                 990
Lys Ile Met Lys Val Ile Glu Gly Pro Ala Ala Pro Val Asp Ala Phe
            995                 1000                1005
Gln Asn Lys Ala Asn Val Cys Trp Ala Lys Ser Leu Val Pro Val Leu
    1010                1015                1020
Asp Thr Ala Gly Ile Arg Leu Thr Ala Glu Glu Trp Ser Thr Ile Ile
1025                1030                1035                1040
Thr Ala Phe Lys Glu Asp Arg Ala Tyr Ser Pro Val Val Ala Leu Asn
                1045                1050                1055
Glu Ile Cys Thr Lys Tyr Tyr Gly Val Asp Leu Asp Ser Gly Leu Phe
                1060                1065                1070
Ser Ala Pro Lys Val Ser Leu Tyr Tyr Glu Asn Asn His Trp Asp Asn
            1075                1080                1085
Arg Pro Gly Gly Arg Met Tyr Gly Phe Asn Ala Ala Thr Ala Ala Arg
    1090                1095                1100
Leu Glu Ala Arg His Thr Phe Leu Lys Gly Gln Trp His Thr Gly Lys
1105                1110                1115                1120
Gln Ala Val Ile Ala Glu Arg Lys Ile Gln Pro Leu Ser Val Leu Asp
                1125                1130                1135
Asn Val Ile Pro Ile Asn Arg Arg Leu Pro His Ala Leu Val Ala Glu
                1140                1145                1150
Tyr Lys Thr Val Lys Gly Ser Arg Val Glu Trp Leu Val Asn Lys Val
            1155                1160                1165
Arg Gly Tyr His Val Leu Leu Val Ser Glu Tyr Asn Leu Ala Leu Pro
    1170                1175                1180
Arg Arg Asp Val Thr Trp Leu Ser Pro Leu Asn Val Thr Gly Ala Asp
1185                1190                1195                1200
Arg Cys Tyr Asp Leu Ser Leu Gly Leu Pro Ala Asp Ala Gly Arg Phe
                1205                1210                1215
Asp Leu Val Phe Val Asn Ile His Thr Glu Phe Arg Ile His His Tyr
            1220                1225                1230
Gln Gln Cys Val Asp His Ala Met Lys Leu Gln Met Leu Gly Gly Asp
        1235                1240                1245
Ala Leu Arg Leu Leu Lys Pro Gly Gly Ser Leu Leu Met Arg Ala Tyr
    1250                1255                1260
Gly Tyr Ala Asp Lys Ile Ser Glu Ala Val Val Ser Ser Leu Ser Arg
1265                1270                1275                1280
```

-continued

```
Lys Phe Ser Ser Ala Arg Val Leu Arg Pro Asp Cys Val Thr Ser Asn
            1285                1290                1295

Thr Glu Val Phe Leu Leu Phe Ser Asn Phe Asp Asn Gly Lys Arg Pro
        1300                1305                1310

Ser Thr Leu His Gln Met Asn Thr Lys Leu Ser Ala Val Tyr Ala Gly
    1315                1320                1325

Glu Ala Met His Thr Ala Gly Cys Ala Pro Ser Tyr Arg Val Lys Arg
1330                1335                1340

Ala Asp Ile Ala Thr Cys Thr Glu Ala Ala Val Val Asn Ala Ala Asn
1345                1350                1355                1360

Ala Arg Gly Thr Val Gly Asp Gly Val Cys Arg Ala Val Ala Lys Lys
            1365                1370                1375

Trp Pro Ser Ala Phe Lys Gly Glu Ala Thr Pro Val Gly Thr Ile Lys
        1380                1385                1390

Thr Val Met Cys Gly Ser Tyr Pro Val Ile His Ala Val Ala Pro Asn
    1395                1400                1405

Phe Ser Ala Thr Thr Glu Ala Glu Gly Asp Arg Glu Leu Ala Ala Val
1410                1415                1420

Tyr Arg Ala Val Ala Ala Glu Val Asn Arg Leu Ser Leu Ser Ser Val
1425                1430                1435                1440

Ala Ile Pro Leu Leu Ser Thr Gly Val Phe Ser Gly Gly Arg Asp Arg
            1445                1450                1455

Leu Gln Gln Ser Leu Asn His Leu Phe Thr Ala Met Asp Ala Thr Asp
        1460                1465                1470

Ala Asp Val Thr Ile Tyr Cys Arg Asp Lys Ser Trp Glu Lys Lys Ile
    1475                1480                1485

Gln Glu Ala Ile Asp Met Arg Thr Ala Val Glu Leu Leu Asn Asp Asp
1490                1495                1500

Val Glu Leu Thr Thr Asp Leu Val Arg Val His Pro Asp Ser Ser Leu
1505                1510                1515                1520

Val Gly Arg Lys Gly Tyr Ser Thr Thr Asp Gly Ser Leu Tyr Ser Tyr
            1525                1530                1535

Phe Glu Gly Thr Lys Phe Asn Gln Ala Ala Ile Asp Met Ala Glu Ile
        1540                1545                1550

Leu Thr Leu Trp Pro Arg Leu Gln Glu Ala Asn Glu Gln Ile Cys Leu
    1555                1560                1565

Tyr Ala Leu Gly Glu Thr Met Asp Asn Ile Arg Ser Lys Cys Pro Val
1570                1575                1580

Asn Asp Ser Asp Ser Ser Thr Pro Pro Arg Thr Val Pro Cys Leu Cys
1585                1590                1595                1600

Arg Tyr Ala Met Thr Ala Glu Arg Ile Ala Arg Leu Arg Ser His Gln
            1605                1610                1615

Val Lys Ser Met Val Val Cys Ser Ser Phe Pro Leu Pro Lys Tyr His
        1620                1625                1630

Val Asp Gly Val Gln Lys Val Lys Cys Glu Lys Val Leu Leu Phe Asp
    1635                1640                1645

Pro Thr Val Pro Ser Val Val Ser Pro Arg Lys Tyr Ala Ala Ser Thr
1650                1655                1660

Thr Asp His Ser Asp Arg Ser Leu Arg Gly Phe Asp Leu Asp Trp Thr
1665                1670                1675                1680

Thr Asp Ser Ser Ser Thr Ala Ser Asp Thr Met Ser Leu Pro Ser Leu
            1685                1690                1695

Gln Ser Cys Asp Ile Asp Ser Ile Tyr Glu Pro Met Ala Pro Ile Val
        1700                1705                1710
```

-continued

```
Val Thr Ala Asp Val His Pro Glu Pro Ala Gly Ile Ala Asp Leu Ala
            1715                1720                1725
Ala Asp Val His Pro Glu Pro Ala Asp His Val Asp Leu Glu Asn Pro
        1730                1735                1740
Ile Pro Pro Pro Arg Pro Lys Arg Ala Ala Tyr Leu Ala Ser Arg Ala
1745                1750                1755                1760
Ala Glu Arg Pro Val Pro Ala Pro Arg Lys Pro Thr Pro Ala Pro Arg
            1765                1770                1775
Thr Ala Phe Arg Asn Lys Leu Pro Leu Thr Phe Gly Asp Phe Asp Glu
        1780                1785                1790
His Glu Val Asp Ala Leu Ala Ser Gly Ile Thr Phe Gly Asp Phe Asp
    1795                1800                1805
Asp Val Leu Arg Leu Gly Arg Ala Gly Ala Tyr Ile Phe Ser Ser Asp
    1810                1815                1820
Thr Gly Ser Gly His Leu Gln Gln Lys Ser Val Arg Gln His Asn Leu
1825                1830                1835                1840
Gln Cys Ala Gln Leu Asp Ala Val Glu Glu Lys Met Tyr Pro Pro
        1845                1850                1855
Lys Leu Asp Thr Glu Arg Glu Lys Leu Leu Leu Lys Met Gln Met
            1860                1865                1870
His Pro Ser Glu Ala Asn Lys Ser Arg Tyr Gln Ser Arg Lys Val Glu
        1875                1880                1885
Asn Met Lys Ala Thr Val Val Asp Arg Leu Thr Ser Gly Ala Arg Leu
    1890                1895                1900
Tyr Thr Gly Ala Asp Val Gly Arg Ile Pro Thr Tyr Ala Val Arg Tyr
1905                1910                1915                1920
Pro Arg Pro Val Tyr Ser Pro Thr Val Ile Glu Arg Phe Ser Ser Pro
            1925                1930                1935
Asp Val Ala Ile Ala Ala Cys Asn Glu Tyr Leu Ser Arg Asn Tyr Pro
        1940                1945                1950
Thr Val Ala Ser Tyr Gln Ile Thr Asp Glu Tyr Asp Ala Tyr Leu Asp
    1955                1960                1965
Met Val Asp Gly Ser Asp Ser Cys Leu Asp Arg Ala Thr Phe Cys Pro
    1970                1975                1980
Ala Lys Leu Arg Cys Tyr Pro Lys His His Ala Tyr His Gln Pro Thr
1985                1990                1995                2000
Val Arg Ser Ala Val Pro Ser Pro Phe Gln Asn Thr Leu Gln Asn Val
            2005                2010                2015
Leu Ala Ala Ala Thr Lys Arg Asn Cys Asn Val Thr Gln Met Arg Glu
        2020                2025                2030
Leu Pro Thr Met Asp Ser Ala Val Phe Asn Val Glu Cys Phe Lys Arg
    2035                2040                2045
Tyr Ala Cys Ser Gly Glu Tyr Trp Glu Glu Tyr Ala Lys Gln Pro Ile
    2050                2055                2060
Arg Ile Thr Thr Glu Asn Ile Thr Thr Tyr Val Thr Lys Leu Lys Gly
2065                2070                2075                2080
Pro Lys Ala Ala Ala Leu Phe Ala Lys Thr His Asn Leu Val Pro Leu
            2085                2090                2095
Gln Glu Val Pro Met Asp Arg Phe Thr Val Asp Met Lys Arg Asp Val
        2100                2105                2110
Lys Val Thr Pro Gly Thr Lys His Thr Glu Glu Arg Pro Lys Val Gln
    2115                2120                2125
Val Ile Gln Ala Ala Glu Pro Leu Ala Thr Ala Tyr Leu Cys Gly Ile
    2130                2135                2140
```

-continued

His Arg Glu Leu Val Arg Arg Leu Asn Ala Val Leu Arg Pro Asn Val
2145                2150                2155                2160

His Thr Leu Phe Asp Met Ser Ala Glu Asp Phe Asp Ala Ile Ile Ala
            2165                2170                2175

Ser His Phe His Pro Gly Asp Pro Val Leu Glu Thr Asp Ile Ala Ser
        2180                2185                2190

Phe Asp Lys Ser Gln Asp Asp Ser Leu Ala Leu Thr Gly Leu Met Ile
    2195                2200                2205

Leu Glu Asp Leu Gly Val Asp Gln Tyr Leu Leu Asp Leu Ile Glu Ala
2210                2215                2220

Ala Phe Gly Glu Ile Ser Ser Cys His Leu Pro Thr Gly Thr Arg Phe
2225                2230                2235                2240

Lys Phe Gly Ala Met Met Lys Ser Gly Met Phe Leu Thr Leu Phe Ile
            2245                2250                2255

Asn Thr Val Leu Asn Ile Thr Ile Ala Ser Arg Val Leu Glu Gln Arg
        2260                2265                2270

Leu Thr Asp Ser Ala Cys Ala Ala Phe Ile Gly Asp Asp Asn Ile Val
    2275                2280                2285

His Gly Val Ile Ser Asp Lys Leu Met Ala Glu Arg Cys Ala Ser Trp
2290                2295                2300

Val Asn Met Glu Val Lys Ile Ile Asp Ala Val Met Gly Glu Lys Pro
2305                2310                2315                2320

Pro Tyr Phe Cys Gly Gly Phe Ile Val Phe Asp Ser Val Thr Gln Thr
            2325                2330                2335

Ala Cys Arg Val Ser Asp Pro Leu Lys Arg Leu Phe Lys Leu Gly Lys
        2340                2345                2350

Pro Leu Thr Ala Glu Asp Lys Gln Asp Glu Asp Arg Arg Arg Ala Leu
    2355                2360                2365

Ser Asp Glu Val Ser Lys Trp Phe Arg Thr Gly Leu Gly Ala Glu Leu
2370                2375                2380

Glu Val Ala Leu Thr Ser Arg Tyr Glu Val Glu Gly Cys Lys Ser Ile
2385                2390                2395                2400

Leu Ile Ala Met Ala Thr Leu Ala Arg Asp Ile Lys Ala Phe Lys Lys
            2405                2410                2415

Leu Arg Gly Pro Val Ile His Leu Tyr Gly Gly Pro Arg Leu Val Arg
        2420                2425                2430

<210> SEQ ID NO 13
<211> LENGTH: 450
<212> TYPE: PRT
<213> ORGANISM: Artificial Sequence
<220> FEATURE:
<223> OTHER INFORMATION: Description of Artificial Sequence: Synthetic
      pJY1302.4 amino acid sequence

<400> SEQUENCE: 13

Met Gly Asn Gly Gln Gly Arg Asp Trp Lys Met Ala Ile Lys Arg Cys
1               5                   10                  15

Ser Asn Val Ala Val Gly Val Gly Lys Ser Lys Lys Phe Gly Glu
            20                  25                  30

Gly Asn Phe Arg Trp Ala Ile Arg Met Ala Asn Val Ser Thr Gly Arg
        35                  40                  45

Glu Pro Gly Asp Ile Pro Glu Thr Leu Asp Gln Leu Arg Leu Val Ile
    50                  55                  60

Cys Asp Leu Gln Glu Arg Arg Glu Lys Phe Gly Ser Ser Lys Glu Ile
65                  70                  75                  80

```
Asp Met Ala Ile Val Thr Leu Lys Val Phe Ala Val Ala Gly Leu Leu
                85                  90                  95

Asn Met Thr Val Ser Thr Ala Ala Ala Glu Asn Met Tyr Ser Gln
            100                 105                 110

Met Gly Leu Asp Thr Arg Pro Ser Met Lys Glu Ala Gly Gly Lys Glu
        115                 120                 125

Glu Gly Pro Pro Gln Ala Tyr Pro Ile Gln Thr Val Asn Gly Val Pro
    130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Val Gln Leu Trp Phe Thr Ala
                165                 170                 175

Phe Ser Ala Asn Leu Thr Pro Thr Asp Met Ala Thr Leu Ile Met Ala
                180                 185                 190

Ala Pro Gly Cys Ala Ala Asp Lys Glu Ile Leu Asp Glu Ser Leu Lys
            195                 200                 205

Gln Leu Thr Ala Glu Tyr Asp Arg Thr His Pro Pro Asp Ala Pro Arg
        210                 215                 220

Pro Leu Pro Tyr Phe Thr Ala Ala Glu Ile Met Gly Ile Gly Leu Thr
225                 230                 235                 240

Gln Glu Gln Gln Ala Glu Ala Arg Phe Ala Pro Ala Arg Met Gln Cys
                245                 250                 255

Arg Ala Trp Tyr Leu Glu Ala Leu Gly Lys Leu Ala Ala Ile Lys Ala
                260                 265                 270

Lys Ser Pro Arg Ala Val Gln Leu Arg Gln Gly Ala Lys Glu Asp Tyr
            275                 280                 285

Ser Ser Phe Ile Asp Arg Leu Phe Ala Gln Ile Asp Gln Glu Gln Asn
        290                 295                 300

Thr Ala Glu Val Lys Leu Tyr Leu Lys Gln Ser Leu Ser Ile Ala Asn
305                 310                 315                 320

Ala Asn Ala Asp Cys Lys Lys Ala Met Ser His Leu Lys Pro Glu Ser
                325                 330                 335

Thr Leu Glu Glu Lys Leu Arg Ala Cys Gln Glu Ile Gly Ser Pro Gly
                340                 345                 350

Tyr Lys Met Gln Leu Leu Ala Glu Ala Leu Thr Lys Val Gln Val Val
            355                 360                 365

Gln Ser Lys Gly Ser Gly Pro Val Cys Phe Asn Cys Lys Lys Pro Gly
        370                 375                 380

His Leu Ala Arg Gln Cys Arg Glu Val Lys Lys Cys Asn Lys Cys Gly
385                 390                 395                 400

Lys Pro Gly His Leu Ala Ala Lys Cys Trp Gln Gly Asn Arg Lys Asn
                405                 410                 415

Ser Gly Asn Trp Lys Ala Gly Arg Ala Ala Pro Val Asn Gln Met
                420                 425                 430

Gln Gln Ala Val Met Pro Ser Ala Pro Pro Met Glu Glu Lys Leu Leu
            435                 440                 445

Asp Leu
    450

<210> SEQ ID NO 14
<211> LENGTH: 149
<212> TYPE: PRT
<213> ORGANISM: Artificial Sequence
<220> FEATURE:
<223> OTHER INFORMATION: Description of Artificial Sequence: Synthetic
      pJY1302.4 amino acid sequence
```

-continued

<400> SEQUENCE: 14

Leu Glu Gly Gly Ala Ser Cys Ser Pro Ser Glu Ser Asn Ala Ala Ser
1               5                   10                  15

Ser Asn Ala Ile Cys Thr Ser Asn Gly Gly Glu Thr Ile Gly Phe Ile
            20                  25                  30

Asn Tyr Asn Lys Val Gly Thr Thr Thr Leu Glu Lys Arg Pro Glu
        35                  40                  45

Ile Leu Ile Phe Val Asn Gly Tyr Pro Ile Lys Phe Leu Leu Asp Thr
    50                  55                  60

Gly Ala Asp Ile Thr Ile Leu Asn Arg Arg Asp Phe Gln Val Lys Asn
65                  70                  75                  80

Ser Ile Glu Asn Gly Arg Gln Asn Met Ile Gly Val Gly Gly Lys
                85                  90                  95

Arg Gly Thr Asn Tyr Ile Asn Val His Leu Glu Ile Arg Asp Asn
            100                 105                 110

Tyr Lys Thr Gln Cys Ile Phe Gly Asn Val Cys Val Leu Glu Asp Asn
        115                 120                 125

Ser Leu Ile Gln Pro Leu Leu Gly Arg Asp Asn Met Ile Lys Phe Asn
130                 135                 140

Ile Arg Leu Val Met
145

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cagatgcttg ggggagatgc ggcacgactg ctaaaacccg gcggc        45

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gccgccgggt tttagcagtc gtgccgcatc tcccccaagc atctg        45

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cagatgcttg ggggagatgc gacacgactg ctaaaacccg gcggc        45

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 18
gccgccgggt tttagcagtc gtgtcgcatc tcccccaagc atctg            45

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cagatgcttg ggggagatgc gcaacgactg ctaaaacccg gcggc            45

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gccgccgggt tttagcagtc gttgcgcatc tcccccaagc atctg            45

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cagatgcttg ggggagatgc gtttcgactg ctaaaacccg gcggc            45

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gccgccgggt tttagcagtc gaaacgcatc tcccccaagc atctg            45

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cagatgcttg ggggagatgc gagacgactg ctaaaacccg gcggc            45

<210> SEQ ID NO 24
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 24
gccgccgggt tttagcagtc gtctcgcatc tcccccaagc atctg    45

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gaaaaacccc catatttctg tgggggattc atagtt    36

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aactatgaat cccccacaga aatatggggg tttttc    36

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gacgaataat tggatttata ttttattttg caat    34

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
attgcaaaat aaaatataaa tccaattatt cgtc    34

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gaacgcaatt gctcctgcta ggcct    25

<210> SEQ ID NO 30
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 30
ttctttattc tacttaaa aagtgaaaat aaatacaaag gttcttg                    47

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atggcggatg tgtgacatac acgacgcca                                      29

<210> SEQ ID NO 32
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcgtacacta gtgccgatat ccaagatgag tgtgtctttg tc                       42

<210> SEQ ID NO 33
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgactagtag aaaaactccc ttagccatcc gagtggac                            38

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgactagtag aaaaactccc ttagccatcc gagtggac                            38

<210> SEQ ID NO 35
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggaattctga ttttaattaa cctgcagggt ttaaactaat taattgaatt acatccctac    60
gcaaac                                                               66

<210> SEQ ID NO 36
<211> LENGTH: 104
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 36
ggaattctga ttttaattaa cctgcaggac ctctacggcg gtcctagatt ggtgcgttaa      60
tacacagttt aaactaatta attgaattac atccctacgc aaac                     104

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (11)..(31)

<400> SEQUENCE: 37
ggttaattaa atg ggg aat gga cag ggg cga                                31
            Met Gly Asn Gly Gln Gly Arg
              1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Met Gly Asn Gly Gln Gly Arg
  1               5

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gggtttaaac ttacattact aacctaatat tgaa                                 34

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Phe Asn Ile Arg Leu Val Met
  1               5

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aatggatatc ctataaaatt cttattagat acaggagca                            39
```

```
<210> SEQ ID NO 42
<211> LENGTH: 72
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (10)..(72)

<400> SEQUENCE: 42 agagggtac cac gtc ctg ctg gtg agt gag tac aac ctg gct ttg cct cga      51
          His Val Leu Leu Val Ser Glu Tyr Asn Leu Ala Leu Pro Arg
            1               5                  10 cgc gac gtc act tgg ttg tca                                            72
Arg Asp Val Thr Trp Leu Ser
 15                  20

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

His Val Leu Leu Val Ser Glu Tyr Asn Leu Ala Leu Pro Arg Arg Asp
 1               5                  10                  15

Val Thr Trp Leu Ser
             20

<210> SEQ ID NO 44
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcgtaacgac cgatctgagt ggtccgtcgt agatgc                                36

<210> SEQ ID NO 45
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (1)..(51)

<400> SEQUENCE: 45 gtg gac gag gct ttc gct tgc cat ccc ggt act ctg ctg gcc cta att        48
Val Asp Glu Ala Phe Ala Cys His Pro Gly Thr Leu Leu Ala Leu Ile
 1               5                  10                  15 gct                                                                    51
Ala

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 46

Val Asp Glu Ala Phe Ala Cys His Pro Gly Thr Leu Leu Ala Leu Ile
 1               5                  10                  15

Ala

<210> SEQ ID NO 47
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
agcaattagg gccagcagag tacccccatg gcaagcgaaa gcctcgtcca c            51

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
taatacacag aattctgatt g                                              21

<210> SEQ ID NO 49
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cagactagta gaaaaatttt ttttttttt tttt                                 34

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aaaaagtgaa aataaataca aaggttcttg a                                   31

<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aaaaagtgca aataaataca aaggttcttg a                                   31

<210> SEQ ID NO 52
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 52
aacccgggtt ctttattcta tacttaaaaa gtgcaaataa atacaaaggt            50

<210> SEQ ID NO 53
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gcgtacacta gtgccgatat ccaagatgag tgtgtctttg tc                    42

<210> SEQ ID NO 54
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tcccccggga gaaaaattac attactaacc taat                             34

<210> SEQ ID NO 55
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gggatatccg ttaagtttgt atcgtaatgg ggaatggaca ggggcgagat tgg        53

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
taggatatcc atttacaaat ataagta                                     27

<210> SEQ ID NO 57
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cgtcgcgata tccgttaagt ttgtatcgta aatggggaat ggacaggggc gagattggaa 60
a                                                                 61

<210> SEQ ID NO 58
<211> LENGTH: 47
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 58
gcggtccaga aaaattacat tactaaccta atattgaatt taatcat              47

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gaggaaggcc ctccacaggc atatc                                      25

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (1)..(21)

<400> SEQUENCE: 60 ttc aat att agg tta gta atg taa                                  24
Phe Asn Ile Arg Leu Val Met
 1               5
```